US006706866B1

(12) United States Patent
Thomashow et al.

(10) Patent No.: US 6,706,866 B1
(45) Date of Patent: Mar. 16, 2004

(54) PLANT HAVING ALTERED ENVIRONMENTAL STRESS TOLERANCE

(75) Inventors: Michael Thomashow, East Lansing, MI (US); Sarah Jane Gilmour, Leslie, MI (US); Cai-Zhong Jiang, Fremont, CA (US); Michael Fromm, Kensington, CA (US); Daniel Zarka, Lansing, MI (US); Kirsten Jaglo-Ottosen, East Lansing, MI (US); Eric J. Stockinger, Wooster, OH (US); James Zhang, Palo Alto, CA (US); Volker Haake, Menlo Park, CA (US)

(73) Assignee: Michigan State University, East Lansing, MI (US)

( * ) Notice: Subject to any disclaimer, the term of this patent is extended or adjusted under 35 U.S.C. 154(b) by 0 days.

(21) Appl. No.: 09/601,802

(22) PCT Filed: Aug. 2, 2000

(86) PCT No.: PCT/US99/01895

§ 371 (c)(1),
(2), (4) Date: Sep. 15, 2000

(87) PCT Pub. No.: WO99/38977

PCT Pub. Date: Aug. 5, 1999

Related U.S. Application Data

(63) Continuation-in-part of application No. 09/198,119, filed on Nov. 23, 1998, now Pat. No. 6,417,428, which is a continuation-in-part of application No. 09/018,233, filed on Feb. 3, 1998, now abandoned, which is a continuation-in-part of application No. 09/017,816, filed on Feb. 3, 1998, now abandoned, which is a continuation-in-part of application No. 09/018,235, filed on Feb. 3, 1998, now abandoned, which is a continuation-in-part of application No. 09/017,575, filed on Feb. 3, 1998, now abandoned, which is a continuation-in-part of application No. 09/018,227, filed on Feb. 3, 1998, now abandoned, which is a continuation-in-part of application No. 09/018,234, filed on Feb. 3, 1998, now abandoned, which is a continuation-in-part of application No. 08/706,270, filed on Sep. 4, 1996, now Pat. No. 5,892,009.

(51) Int. Cl.[7] ........................ C07H 21/00; C07H 21/02; C07K 1/00; A01N 37/18

(52) U.S. Cl. ...................... 536/22.1; 536/231; 530/350; 600/277; 600/278

(58) Field of Search ................................ 800/277, 278; 536/22.1, 23.1; 530/350

(56) References Cited

U.S. PATENT DOCUMENTS 6,495,742 B1 12/2002 Shinozaki et al. .......... 800/298

FOREIGN PATENT DOCUMENTS

WO WO 98/26045 6/1998
WO WO 02/16655 2/2002

OTHER PUBLICATIONS

Guy, C. L. "Cold acclimation and freezing stress tolerance: role of protein metabolism" *Annu. Rev. Plant Physiol. Plant Mol. Biol.* 41: 187–223 (1990).

(List continued on next page.)

*Primary Examiner*—Jezia Riley
(74) *Attorney, Agent, or Firm*—Jeffrey M. Libby; Matthew Kaser; Morrison & Foerster, LLP

(57) ABSTRACT

The present invention provides for a non-naturally occurring binding protein comprising an amino acid sequence capable of binding to a CCG regulatory sequence and an amino acid sequence which forms a transcription activation region. In particular the invention comprises a sequence selected from the group consisting of an AP2 domain of SEQ. I.D. Nos. 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95. When these proteins are overexpressed in a plant the plant exhibits increased tolerance to environmental stresses such as cold, freezing, drought or high salinity.

27 Claims, 45 Drawing Sheets

OTHER PUBLICATIONS

Lang, A., in *Encyclopedia of Plant Physiology*, vol. 15–1, ed. Ruhland, W. (Springer, Berlin), pp. 1489–1536 (1965).

Berry, J. A. and J. K. Raison, in *Encyclopedia of Plant Physiology*, vol. 12A, eds. Lange, O. L., Nobel, P. S., Osmond, C. B. and Ziegler, H. (Springer, Berlin), pp. 277–338 (1981).

Monroy, A. F. et al. "Cold–Induced Changes in Freezing Tolerance, Protein Phosphorylation, and Gene Expression" *Plant Physiol.* 102: 1227–1235 (1993).

Monroy, A. F. and R. S. Dhindsa. "Low–Temperature Signal transduction: Induction of Cold Acclimation–Specfic Genes of Alfalfa by Calcium at 25°C" *The Plant Cell* 7: 321–331 (1995).

Knight H. et al. "Cold Calcium Signaling in Arabidopsis Involves Two Cellular Pools and a Change in Calcium Signature after Acclimation" *The Plant Cell* 8:489–503 (1996).

Knight, M. R. et al. "Transgenic plant aequorin reports the effects of touch and cold–shock and elicitors on cytoplasmic calcium" *Nature* 352: 524–526 (1991).

Knight H. et al. "Cold Calcium Signaling in Arabidopsis Involves Two Cellular Pools and a Change in Calcium Signature after Acclimation" *The Plant Cell* 8: 489–503 (1996).

Ding, J. P. and B. G. Pickard. "Modulation of mechanosensitive calcium–selective cation channels by temperature" *Plant J.* 3: 713–720 (1993).

Yamaguchi–Shinozaki, K. et al. "A Novel cis–Acting Element in an Arabidopsis gene Is Involved in Responsiveness to Drought, Low–Temperature, or High–Salt Stress" *The Plant Cell* 6:251–264 (1994).

Baker, S. S. et al. "The 5'–region of *Arabidopsis thaliana cor 15a* has cis–acting elements that confer cold–, drought–and ABA–regulated gene expression" *Plant. Mol. Biol.* 24: 701–713 (1994).

Jiang, C. et al. "Requirement of a CCGAC cis–acting element for cold induction of the *BN115* gene from winter *Brassica napus*" *Plant Mol. Biol.* 30: 679–684 (1996).

Horvath, D. P. et al. "Regulation of *Arabidopsis thaliana* L. (Heyn) *cor78* in Response to Low Temperature" *Plant Physiol.* 103: 1047–1053 (1993).

Wang, H. et al. "Promoters from *kinl* and *cor6.6*, two homologous *Arabidopsis thaliana* genes: transcriptional regulation and gene expression induced by low temperature, ABA, osmoticum and dehydration" *Plant Mol. Biol.* 28: 605–617 (1995).

White, T. C. et al. "Regulation of *BN115*, a Low–Temperature–Responsive Gene from Winter *Brassica napus*" *Plant Physiol.* 106: 917–928 (1994).

Ohme–Takagi, M. et al. "Ethylene–Inducible DNA Binding Proteins That Interact with an Ethylene–Responsive Element" The Plant Cell 7: 173–182 (1995).

Klucher, K. M. et al. "The AINTEGUMENTA Gene of Arabidopsis Required for Ovule and Female Gametophyte Development Is Related to the Floral Homeotic Gene *APELALA2*" *The Plant Cell* 8: 137–153 (1996).

Wilson, K. et al. "A Dissociation Insertion Causes a Semi-dominant Mutation That Increases Expression of *Tiny*, an Arabidopsis Gene Related to *APETALA2*" *The Plant Cell* 8:659–671 (1996).

Raikhel, N. "Nuclear Targeting in Plants" *Plant Physiol.* 100: 1627–1632 (1992).

Hahn, S. "Structure(?) and Function of Acidic Transcription Activators" *Cell* 72: 481–483 (1993).

Jofuku, K. D. et al. "Control of Arabidopsis Flower and Seed Development by the Homeotic Gene *APETALA2*" *The Plant Cell* 6: 1211–1225 (1994).

Elliot, R. C. et al. "*AINTEGUMENTA*, and *APETALA2*–like Gene of Arabidopsis with Pleitropic Roles in Ovule Development and Floral Organ Growth" *The Plant Cell* 8: 155–168 (1996).

Weigel, D. "The APETALA2 Domain Is Related to a Novel Type of DNA Binding Domain" *The Plant Cell* 7: 388–389 (1995).

Foster et al. "Plant bZIP proteins gather at ACGT elements" *FASEB J.* 8: 192–200 (1994).

Ma, J. and M. Ptashne. "A New Class of Yeast Transcriptional Activators" *Cell* 51: 113–199 (1987).

Ma, J. et al. "Yeast activators stimulate plant gene expression" *Nature* 334: 631–633 (1988).

McCarty, D. R. et al. "The *Viviparous–1* Developmental Gene of Maize Encodes a novel Transcriptional Activator" *Cell* 66: 895–905 (1991).

Guarente, L. "Transcriptional coativators in yeast and beyond" *Trends Biochem. Sci.* 20: 517–521 (1995).

Horiuchi, J. et al. "ADA3, a Putative Transcriptional Adaptor, Consists of Two Seperable Domains and Interacts with ADA2 and GCN5 in a Trimeric Complex" *Mol. Cell Biol.* 15: 1203–1209 (1995).

Wolffe, A. P. "Nucleosome positioning and modification: chromatin structures that potentiate transcription" *Trends Biochem. Sci.* 19: 240–244 (1994).

Brownell, J. E. et al. "Tetrahymena Histone acetyltransferase A; A Homolog to Yeast Gcn5p Linking Histone Acetylation to Gene Activation" *Cell* 84: 843–851 (1996).

Riechmann, J.L. et al. "*Arabidopsis* Transcription factors: Genome–Wide Comparative Analysis Among Eukaryotes" *Science* 290: 2105–2110 (2000).

Gao, M.–J., et al., Plant Mol. Biol. 49:459–471 (2002).

Hsieh, T.–H., et al., Plant Physiol. 129:1086–1094 (2002).

Activity of "positive" plasmids in reporter strains

| UAS Replacement Sequence | | | Yeast colony color on X-gal filters |
|---|---|---|---|
| Oligo | C-repeat/DRE | Inserts | |
| MT50 | *COR15a* | | Blue |
| MT50 | *COR15a* | | Blue |
| MT66 | *COR78* | | Blue |
| MT52 | M1 *COR15a* | | White |

```
SEQ ID NO: 1   AAAAAGAATCTACCTGAAAAGAAAAAAAAGAGAGAGAGATATAAATAGCTTACCAAGACAGATATACTATC   71
SEQ ID NO: 1   TTTTATTAATCCAAAAAGACTGAGAACTCTAGTAACTACGTACTACTTAAACCTTATCCAGTTTCTTGAAA  142
SEQ ID NO: 1   CAGAGTACTCTGATCAATG AAC TCA TTT TCA GCT TTT TCT GAA ATG TTT GGC TCC GAT  200
SEQ ID NO: 2                       M   N   S   F   S   A   F   S   E   M   F   G   S   D    14

SEQ ID NO: 1   TAC GAG CCT CAA GGC GGA GAT TAT TGT CCG ACG TTG GCC ACG AGT TGT CCG AAG  254
SEQ ID NO: 2    Y   E   P   Q   G   G   D   Y   C   P   T   L   A   T   S   C   P   K    32
                                                                                    *
SEQ ID NO: 1   AAA CCG GCG GGC CGT AAG AAG TTT CGT GAG ACT CGT CAC CCA ATT TAC AGA GGA  308
SEQ ID NO: 2    K   P   A   G   R   K   K   F   R   E   T   R   H   P   I   Y   R   G    50
                *               *   *   *       *
SEQ ID NO: 1   GTT CGT CAA AGA AAC TCC GGT AAG TGG GTT TCT GAA GTG AGA GAG CCA AAC AAG  362
SEQ ID NO: 2    V   R   Q   R   N   S   G   K   W   V   S   E   V   R   E   P   N   K    68

SEQ ID NO: 1   AAA ACC AGG ATT TGG CTC GGG ACT TTC CAA ACC GCT GAG ATG GCA GCT CGT GCT  416
SEQ ID NO: 2    K   T   R   I   W   L   G   T   F   Q   T   A   E   M   A   A   R   A    86

SEQ ID NO: 1   CAC GAC GTC GCT GCA TTA GCC CTC CGT GGC CGA TCA GCA TGT CTC AAC TTC GCT  470
SEQ ID NO: 2    H   D   V   A   A   L   A   L   R   G   R   S   A   C   L   N   F   A   104

SEQ ID NO: 1   GAC TCG GCT TGG CGG CTA CGA ATC CCG GAG TCA ACA TGC GCC AAG GAT ATC CAA  524
SEQ ID NO: 2    D   S   A   W   R   L   R   I   P   E   S   T   C   A   K   D   I   Q   122

SEQ ID NO: 1   AAA GCG GCT GCT GAA GCG GCG TTG GCT TTT CAA GAT GAG ACG TGT GAT ACG ACG  578
SEQ ID NO: 2    K   A   A   A   E   A   A   L   A   F   Q   D   E   T   C   D   T   T   140

SEQ ID NO: 1   ACC ACG GAT CAT GGC CTG GAC ATG GAG GAG ACG ATG GTG GAA GCT ATT TAT ACA  632
SEQ ID NO: 2    T   T   D   H   G   L   D   M   E   E   T   M   V   E   A   I   Y   T   158

SEQ ID NO: 1   CCG GAA CAG AGC GAA GGT GCG TTT TAT ATG GAT GAG GAG ACA ATG TTT GGG ATG  686
SEQ ID NO: 2    P   B   Q   S   E   G   A   F   Y   M   D   E   E   T   M   F   G   M   176

SEQ ID NO: 1   CCG ACT TTG TTG GAT AAT ATG GCT GAA GGC ATG CTT TTA CCG CCG CCG TCT GTT  740
SEQ ID NO: 2    P   T   L   L   D   N   M   A   E   G   H   L   L   P   P   P   S   V   194

SEQ ID NO: 1   CAA TGG AAT CAT AAT TAT GAC GGC GAA GGA GAT GGT GAC GTG TCG CTT TGG AGT  794
SEQ ID NO: 2    Q   W   N   H   N   Y   D   G   E   G   D   G   D   V   S   L   W   S   212

SEQ ID NO: 1   TAC TAA TATTCGATAGTCGTTTCCATTTTTGTACTATAGTTTGAAAATATTCTAGTTCCTTTTTTAGAA  863
SEQ ID NO: 2    Y                                                                       213

SEQ ID NO: 1   TGGTTCCTTCATTTTATTTTATTTTATTGTTGTAGAAACGAG                               905
```

FIGURE 2B

```
          **                                     **
CBF1      IYRGVRQRNSGKWVSEVREPNKKT.RIWLGT     76
           |||||||   ||: :|:|:|  |  :  |:||||
EREBP2    HYRGVRQRPWGKFAAEIRDPAKNGARVWLGT     98

              **  ^            *      **
CBF1      FQTAEMAARAHDVAALALRGRSACLNFADS     106
          ::|||  ||  |:|  ||   :||   ||||:
EREBP2    YETAEEAALAYDKAAYRMRGSKALLNFPHR     158
```

| | | |
|---|---|---|
| SEQ ID NO: 12 | ATGAACTCATTTTCTGCCTTTTCTGAAATGTTTGGCTCCGATTACGAGTCTCCGGTTTCC | 60 |
| SEQ ID NO: 13 | Met Asn Ser Phe Ser Ala Phe Ser Glu Met Phe Gly Ser Asp Tyr Glu Ser Pro Val Ser | |
| SEQ ID NO: 12 | TCAGGCGGTGATTACAGTCCGAAGCTTGCCACGAGCTGCCCCAAGAAACCAGCGGGAAGG | 120 |
| SEQ ID NO: 13 | Ser Gly Gly Asp Tyr Ser Pro Lys Leu Ala Thr Ser Cys Pro Lys Lys Pro Ala Gly Arg | |
| SEQ ID NO: 12 | AAGAAGTTTCGTGAGACTCGTCACCCAATTTACAGAGGAGTTCGTCAAAGAAACTCCGGT | 180 |
| SEQ ID NO: 13 | Lys Lys Phe Arg Glu Thr Arg His Pro Ile Tyr Arg Gly Val Arg Gln Arg Asn Ser Gly | |
| SEQ ID NO: 12 | AAGTGGGTGTGTGAGTTGAGAGAGCCAAACAAGAAAACGAGGATTTGGCTCGGGACTTTC | 240 |
| SEQ ID NO: 13 | Lys Trp Val Cys Glu Leu Arg Glu Pro Asn Lys Lys Thr Arg Ile Trp Leu Gly Thr Phe | |
| SEQ ID NO: 12 | CAAACCGCTGAGATGGCAGCTCGTGCTCACGACGTCGCCGCCATAGCTCTCCGTGGCAGA | 300 |
| SEQ ID NO: 13 | Gln Thr Ala Glu Met Ala Ala Arg Ala His Asp Val Ala Ala Ile Ala Leu Arg Gly Arg | |
| SEQ ID NO: 12 | TCTGCCTGTCTCAATTTCGCTGACTCGGCTTGGCGGCTACGAATCCCGGAATCAACCTGT | 360 |
| SEQ ID NO: 13 | Ser Ala Cys Leu Asn Phe Ala Asp Ser Ala Trp Arg Leu Arg Ile Pro Glu Ser Thr Cys | |
| SEQ ID NO: 12 | GCCAAGGAAATCCAAAAGGCGGCGGCTGAAGCCGCGTTGAATTTTCAAGATGAGATGTGT | 420 |
| SEQ ID NO: 13 | Ala Lys Glu Ile Gln Lys Ala Ala Ala Glu Ala Ala Leu Asn Phe Gln Asp Glu Met Cys | |
| SEQ ID NO: 12 | CATATGACGACGGATGCTCATGGTCTTGACATGGAGGAGACCTTGGTGGAGGCTATTTAT | 480 |
| SEQ ID NO: 13 | His Met Thr Thr Asp Ala His Gly Leu Asp Met Glu Glu Thr Leu Val Glu Ala Ile Tyr | |
| SEQ ID NO: 12 | ACGCCGGAACAGAGCCAAGATGCGTTTTATATGGATGAAGAGGCGATGTTGGGGATGTCT | 540 |
| SEQ ID NO: 13 | Thr Pro Glu Gln Ser Gln Asp Ala Phe Tyr Met Asp Glu Glu Ala Met Leu Gly Met Ser | |
| SEQ ID NO: 12 | AGTTTGTTGGATAACATGGCCGAAGGGATGCTTTTACCGTCGCCGTCGGTTCAATGGAAC | 600 |
| SEQ ID NO: 13 | Ser Leu Leu Asp Asn Met Ala Glu Gly Met Leu Leu Pro Ser Pro Ser Val Gln Trp Asn | |
| SEQ ID NO: 12 | TATAATTTTGATGTCGAGGGAGATGATGACGTGTCCTTATGGAGCTATTAA | 651 |
| SEQ ID NO: 13 | Tyr Asn Phe Asp Val Glu Gly Asp Asp Asp Val Ser Leu Trp Ser Tyr * | |

FIGURE 12

| | | |
|---|---|---|
| SEQ ID NO: 14 | ATGAACTCATTTTCTGCTTTTTCTGAAATGTTTGGCTCCGATTACGAGTCTTCGGTTTCC | 60 |
| SEQ ID NO: 15 | Met Asn Ser Phe Ser Ala Phe Ser Glu Met Phe Gly Ser Asp Tyr Glu Ser Ser Val Ser | |
| SEQ ID NO: 14 | TCAGGCGGTGATTATATTCCGACGCTTGCGAGCAGCTGCCCCAAGAAACCGGCGGGTCGT | 120 |
| SEQ ID NO: 15 | Ser Gly Gly Asp Tyr Ile Pro Thr Leu Ala Ser Ser Cys Pro Lys Lys Pro Ala Gly Arg | |
| SEQ ID NO: 14 | AAGAAGTTTCGTGAGACTCGTCACCCAATATACAGAGGAGTTCGTCGGAGAAACTCCGGT | 180 |
| SEQ ID NO: 15 | Lys Lys Phe Arg Glu Thr Arg His Pro Ile Tyr Arg Gly Val Arg Arg Arg Asn Ser Gly | |
| SEQ ID NO: 14 | AAGTGGGTTTGTGAGGTTAGAGAACCAAACAAGAAAACAAGGATTTGGCTCGGAACATTT | 240 |
| SEQ ID NO: 15 | Lys Trp Val Cys Glu Val Arg Glu Pro Asn Lys Lys Thr Arg Ile Trp Leu Gly Thr Phe | |
| SEQ ID NO: 14 | CAAACCGCTGAGATGGCAGCTCGAGCTCACGACGTTGCCGCTTTAGCCCTTCGTGGCCGA | 300 |
| SEQ ID NO: 15 | Gln Thr Ala Glu Met Ala Ala Arg Ala His Asp Val Ala Ala Leu Ala Leu Arg Gly Arg | |
| SEQ ID NO: 14 | TCAGCCTGTCTCAATTTCGCTGACTCGGCTTGGAGACTCCGAATCCCGGAATCAACTTGC | 360 |
| SEQ ID NO: 15 | Ser Ala Cys Leu Asn Phe Ala Asp Ser Ala Trp Arg Leu Arg Ile Pro Glu Ser Thr Cys | |
| SEQ ID NO: 14 | GCTAAGGACATCCAAAAGGCGGCGGCTGAAGCTGCGTTGGCGTTTCAGGATGAGATGTGT | 420 |
| SEQ ID NO: 15 | Ala Lys Asp Ile Gln Lys Ala Ala Ala Glu Ala Ala Leu Ala Phe Gln Asp Glu Met Cys | |
| SEQ ID NO: 14 | GATGCGACGACGGATCATGGCTTCGACATGGAGGAGACGTTGGTGGAGGCTATTTACACG | 480 |
| SEQ ID NO: 15 | Asp Ala Thr Thr Asp His Gly Phe Asp Met Glu Glu Thr Leu Val Glu Ala Ile Tyr Thr | |
| SEQ ID NO: 14 | GCGGAACAGAGCGAAAATGCGTTTTATATGCACGATGAGGCGATGTTTGAGATGCCGAGT | 540 |
| SEQ ID NO: 15 | Ala Glu Gln Ser Glu Asn Ala Phe Tyr Met His Asp Glu Ala Met Phe Glu Met Pro Ser | |
| SEQ ID NO: 14 | TTGTTGGCTAATATGGCAGAAGGGATGCTTTTGCCGCTTCCGTCCGTACAGTGGAATCAT | 600 |
| SEQ ID NO: 15 | Leu Leu Ala Asn Met Ala Glu Gly Met Leu Leu Pro Leu Pro Ser Val Gln Trp Asn His | |
| SEQ ID NO: 14 | AATCATGAAGTCGACGGCGATGATGACGACGTATCGTTATGGAGTTATTAA | 651 |
| SEQ ID NO: 15 | Asn His Glu Val Asp Gly Asp Asp Asp Asp Val Ser Leu Trp Ser Tyr * | |

FIGURE 13

```
               MNSFSAFSEMFGSDYESXVSSGGDYXPTLATSCPKKPAGRKKFRETRHPI
                         |         |         |         |         |
                        10        20        30        40        50
SEQ ID NO: 2   MNSFSAFSEMFGSDYEPQ---GGDYCPTLATSCPKKPAGRKKFRETRHPI    47
SEQ ID NO: 13  MNSFSAFSEMFGSDYESPVSSGGDYSPKLATSCPKKPAGRKKFRETRHPI    50
SEQ ID NO: 15  MNSFSAFSEMFGSDYESSVSSGGDYIPTLASSCPKKPAGRKKFRETRHPI    50

               YRGVRQRNSGKWVCEVREPNKKTRIWLGTFQTAEMAARAHDVAALALRGR
                         |         |         |         |         |
                        60        70        80        90       100
SEQ ID NO: 2   YRGVRQRNSGKWVSEVREPNKKTRIWLGTFQTAEMAARAHDVAALALRGR    97
SEQ ID NO: 13  YRGVRQRNSGKWVCELREPNKKTRIWLGTFQTAEMAARAHDVAAIALRGR   100
SEQ ID NO: 15  YRGVRRRNSGKWVCEVREPNKKTRIWLGTFQTAEMAARAHDVAALALRGR   100

               SACLNFADSAWRLRIPESTCAKDIQKAAAEAALAFQDEMCDXTTDXHGLD
                         |         |         |         |         |
                       110       120       130       140       150
SEQ ID NO: 2   SACLNFADSAWRLRIPESTCAKDIQKAAAEAALAFQDETCDTTTTNHGLD   147
SEQ ID NO: 13  SACLNFADSAWRLRIPESTCAKEIQKAAAEAALNFQDEMCHMTTDAHGLD   150
SEQ ID NO: 15  SACLNFADSAWRLRIPESTCAKDIQKAAAEAALAFQDEMCDATTD-HGFD   149

               MEETLVEAIYTPEQSEXAFYMDEEAMFGMPSLLDNMAEGMLLPXPSVQWN
                         |         |         |         |         |
                       160       170       180       190       200
SEQ ID NO: 2   MEETMVEAIYTPEQSEGAFYMDEETMFGMPTLLDNMAEGMLLPPPSVQWN   197
SEQ ID NO: 13  MEETLVEAIYTPEQSQDAFYMDEEAMLGMSSLLDNMAEGMLLPSPSVQWN   200
SEQ ID NO: 15  MEETLVEAIYTAEQSENAFYMHDEAMFEMPSLLANMAEGMLLPLPSVQWN   199

               HNXDVEGDDD-VSLWSY
                         |
                       210
SEQ ID NO: 2   HNYDGEGDGD-VSLWSY                                    213
SEQ ID NO: 13  YNFDVEGDDD-VSLWSY                                    216
SEQ ID NO: 15  HNHEVDGDDDDVSLWSY                                    216
```

FIGURE 14

```
                1                                                            50
SEQ ID NO: 2    mnsfsafsem fgsdyepqgg dycptlatsc pkkpagrkkf retrHPIYRG
SEQ ID NO: 17   ---------- ---------- ---------- ---------- ----HPIYRG
Consensus       ---------- ---------- ---------- ---------- ----HPIYRG

                51                                                          100
SEQ ID NO: 2    VRqRnSGKWV sEVREPNKKt RIWLGTFqTA EMAARAHDVA ALALRGRsAC
SEQ ID NO: 17   VR1RkSGKHV cEVREPNKKs RIWLGTFkTA KMAARAHDVA ALALRGRgAC
Consensus       VR-R-SGKWV -EVREPNKK- RIWLGTF-TA EMAARAHDVA ALALRGR-AC

                101                                                         150
SEQ ID NO: 2    LNfADSAWRL RIPEsTCaKD IQKAAABAAL Afq....... .......dET
SEQ ID NO: 17   LNyADSAWRL RIPECTChKD IQKAAAEAAL AFeaeksdvt mqngqnmeET
Consensus       LN-ADSAWRL RIPE-TC-KD IQKAAAEAAL AF-------- --------ET

                151                                                         200
SEQ ID NO: 2    c......... DT........ .......... ....TTTDHG lDMEETMVEA
SEQ ID NO: 17   tavasqaevn DTttehgmnm eeatavasqa evndTTTDHG vDMEETMVEA
Consensus       ---------- DT-------- ---------- ----TTTDHG -DMEETMVEA

                201                                                         250
SEQ ID NO: 2    iyTpEQSEG. .......... .........a fYMDEEtMfg MPTLLdnMAE
SEQ ID NO: 17   vfTgEQSEGf nmakestvea avvteepskg sYMDEEwMle MPTLLadMAE
Consensus       --T-EQSEG- ---------- ---------- -YMDEE-M-- MPTLL--MAE

                251                         278
SEQ ID NO: 2    GMLLpppsvq wnhnydegd gdvalwsy
SEQ ID NO: 17   GMLL------ --------- --------
Consensus       GMLL------ --------- --------
```

FIGURE 16

FIGURE 18A bjCBF1 Species=Brassica juncea Length=577 [SEQ ID No. 38]
TTTCACCCTATCTACCGGGGAGTTCGCCTGAGAAAGTCAGGTAAGTGGGTGTGTGAAGTG
AGGGAGCCAAACAAGAAATCTAGGATTTGGCTTGGAACTTTCAAAACCGCAGAGATCGCT
GCTCGTGCTCACGACGTTGCCGCCTTAGCCCTCCGTGGAAGAGCGGCCTGTCTCAACTTC
GCCGACTCGGCTTGGCGGCTCCGTATCCCGGAGACAACTTGCGCCAAGGATATCCAGAAG
GCTGCTGCTGAAGCTGCGTTGGCTTTTGGGGCCGAAAAGAGTGATACCACGACGAATGAT
CAAGGCATGAACATGGAGGAGATGACGGTGGTGGCTTCTCAGGCTGAGGTGAGCGACACG
ACGACATATCATGGCCTGGACATGGAGGAGACTATGGTGGAGGCTGTTTTTGCTGAGGAA
CAGAGAGAAGGGTTTTACTTGGCGGAGGAGACGACGGTGGAGGGTGTTGTTACGGAGGAA
CAGAGCAAAGGGTTTTATATGTACGAGGAGTGGACGTTCGGGATGCAGTCCTTTTTGGCC
GATATGGCTGAAGGCATGCTCTTTTCAAAGGGCGAAT bjCBF2 Species=Brassica juncea Length=431 [SEQ ID No. 40]
CATCCGATCTACAGGGGAGTTCGTCTGAGAAAATCAGGTAAGTGGGTGTGTGAAGTGAGG
GAACCAAACAAGAGATCTAGGATCTGGCTCGGTACTTTCCTAACCGCCGAGATCGCAGCT
CGCGCTCACGACGTCGCCGCCATAGCCCTCCGTGGCAAATCCGCATGTCTCAATTTCGCT
GACTCGGCTTGGCGGCTCCGTATCTCGGAGACAACATGCCCTAAGGAGATTCAGAAGGCT
GCTGCTGAAGCCGCGGTGGCTTTTCAGGCTGAGCTAAATGATACGACGGCCGATCATGGC
CTTGACGTGGAGGAGACGATCGTGGAGGCTATTTTCACGGAGGAAAGCAGCGAAGGGTTT
TATATGGACGAGGAGTTCATGTTCGGGATGCCGACCTTGTGGGCTAGTATGGCAGAAGGG
ATGCTTCTTCC bjCBF3 Species=Brassica juncea Length=431 [SEQ ID No. 42]
CATCCAATTTACCGTGGAGTTCGTCTGAGAAAATCAGGTAAGTGGGTGTGTGAAGTGAGG
GAGCCAAACAAGAAATCTAGGATCTGGCCCGGTACTTTCCTAACCGCCGAGATCGCAGCT
CGCGCTCACGACGTCGCCGCCATAGCCCTCCGTGGCAAATCCGCATGTCTCAATTTCGCT
GACTCGGCTTGGCGGCTCCGTATCCCGGAGACAACATGCCCTAAGGAGATTCAGAAGGCT
GCTGCTGAAGCCGCGGTGGCTTTTCAGGCTGAGCTAAATGATACGACGGCCGATCATGGC
CTTGACGTGGAGGAGACGATCGTGGAGGCTATTTTCACGGAGGAAAGCAGCGAAGGGTTT
TATATGGACGAGGAGTTCATGTTCGGGATGCCGACCTTGTGGGCTAGTATGGCGGAGGGC
ATGCTCCTTCC bjCBF4 Species=Brassica juncea Length=425 [SEQ ID No. 44]
CATCCAATCTACCGGGGTGTTCGACAGAGAAACTCAGGGAAATGGGTTTGTGAAGTTAGG
GAGCCTAATAAGAAATCTAGGATCTGGTTAGGGACTTTTCCGACCGTCGAAATGGCCGCT
CGTGCTCACGACGTCGCCGCTTTAGCCCTTCGTGGCCGCTCCGCTTGTCTTAATTTCGCC
GACTCGGCGTGGTGTCTACGGATTCCCGAGTCTACTTGTCCTAAAGAGATTCAGAAAGCT
GCGGCCGAAGCTGCAATGGCGTTTCAGAACGAGACGGCTACGACTGAGACGACTATGGTT
GAGGGAGTCATACCGGCGGAGGAGACGGTGGGGCAGACGCGTGTGGAGACAGCAGAGGAG
AACGGTGTGTTTTATATGGACGATCCAAGGTTTCTTGAGAATATGGCAGAGGGCATGTTC
CTACC bnCBF1 Species=Brassica napus Length=632 [SEQ ID No. 46]
CACCCGATATACCGGGGAGTTCGTCTGAGAAAGTCAGGTAAGTGGGTGTGTGAAGTGAGG
GAACCAAACAAGAAATCTAGAATTTGGCTTGGAACTTTCAAAACAGCTGAGATGGCAGCT
CGTGCTCACGACGTCGCTGCCCTAGCCCTCCGTGGAAGAGGCGCCTGCCTCAATTATGCG
GACTCGGCTTGGCGGCTCCGCATCCCGGAGACAACCTGCCACAAGGATATCCAGAAGGCT
GCTGCTGAAGCCGCATTGGCTTTTGAGGCTGAGAAAAGTGATGTGACGATGCAAAATGGC
CAGAACATGGAGGAGACGACGGCGGTGGCTTCTCAGGCTGAAGTGAATGACACGACGACA
GAACATGGCATGAACATGGAGGAGGCAACGGCAGTGGCTTCTCAGGCTGAGGTGAATGAC
ACGACGACGGATCATGGCGTAGACATGGAGGAGACAATGGTGGAGGCTGTTTTTACTGGG
GAACAAAGTGAAGGGTTTAACATGGCGAAGGAGTCGACGGTGGAGGCTGCTGTTGTTACG
GAGGAACCGAGCAAAGGATCTTACATGGACGAGGAGTGGATGCTCGAGATGCCGACCTTG
TTGGCTGATATGGCAGAAGGGATGCTCCTGCC bnCBF2 Species=Brassica napus Length=876 [SEQ ID No. 48]
ACCGCTCGAGCAACAATGAACACATTCCCTGCTTCCACTGAAATGGTTGGCTCCGAGAAC
GAGTCTCCGGTTACTACGGTAGTAGGAGGTGATTATTATCCCATGTTGGCGGCAAGCTGT
CCGAAGAAGCCAGCGGGTAGGAAGAAGTTTCAGGAGACACGTCACCCCATTTACCGAGGA
GTTCGTCTGAGAAAGTCAGGTAAGTGGGTGTGTGAAGTGAGGGAACCAAACAAGAAATC

FIGURE 18A-continued

AGAATTTGGCCCGGAACTTTCAAAACAGCTGAGATGGCAGCTCGTGCTCACGACGTCGCT
GCCCTAGCCCTCCGTGGAAGAGGCGCCTGCCTCAATTATGCGGACTCGGCTTGGCGGCTC
CGCATCCCGGAAACAACCTGCCACAAGGATATCCAGAAGGCTGCTGCTGAAGCCGCATTG
GCTTTTGAGGCTGAGAAAAGTGATGTGACGATGCAAAATGGCCTGAACATGGAGGAGACG
ACGGCGGTGGCTTCTCAGGCTGAAGTGAATGACACGACGACAGAACATGGCATGAACATG
GAGGAGGCAACAGCGGTGGCTTCTCAGGCTGAGGTGAATGACACGACGACAGATCATGGC
GTAGACATGGAGGAGACGATGGTGGAGGCTGTTTTTACGGAGGAACAAAGTGAAGGGTTC
AACATGGCGGAGGAGTCGACGGTGGAGGCTGCTGTTGTTACGGATGAACTGAGCAAAGGA
TTTTACATGGACGAGGAGTGGACGTACGAGATGCCGACCTTGTTGGCTGATATGGCGGCA
GGGATGCTTTTGCCGCCACCATCTGTACAATGGGGACATAATGATGACTTGGAAGGAGAT
GCGGACATGAACCTCTGGAGTTATTAAGGATCCGCG bnCBF3 Species=Brassica napus Length=884 [SEQ ID No. 50]
ACTACACTCAGCCTTATCCAGTTTTTTTCAAAAGATTTTTCAACAATGAACACATTCCCT
GCGTCCACTGAAATGGTTGGCTCCGAGAACGAGTCTCCGGTTACTACGGTAGCAGGAGGT
GATTATTATCCCATGTTGGCGGCAAGCTGTCCGAAGAAGCCAGCAGGTAGGAAGAAGTTT
CAGGAGACACGTCACCCCATTTACCGAGGAGTTCGTCTGAGAAAGTCAGGTAAGTGGGTG
TGTGAAGTGAGGGAACCAAACAAGAAATCTAGAATTTGGCCCGGAACTTTCAAAACAGCT
GAGATGGCAGCTCGTGCTCACGACGTCGCTGCCCTAGCCCTCCGTGGAAGAGGCGCCTGC
CTCAATTATGCGGACTCGGCTTGGCGGCTCCGCATCCCGGAGACAACCTGCCACAAGGAT
ATCCAGAAGGCTGCTGCTGAAGCCGCATTGGCTTTTGAGGCTGAGAAAAGTGATGTGACG
ATGCAAAATGGCCTGAACATGGAGGAGACGACGGCGGTGGCTTCTCAGGCTGAAGTGAAT
GACACGACGACAGAACATGGCATGAACATGGAGGAGGCAACGGCAGTGGCTTCTCAGGCT
GAGGTGAATGACACGACGACGGATCATGGCGTAGACATGGAGGAGACAATGGTGGAGGCT
GTTTTTACTGGGGAACAAAGTGAAGGGTTTAACATGGCGAAGGAGTCGACGGTGGAGGCT
GCTGTTGTTACGGAGGAACCGAGCAAAGGATCTTACATGGACGAGGAGTGGATGCTCGAG
ATGCCGACCTTGTTGGCTGATATGGCGGAAGGGATGCTTTTGCCGCCGCCGTCCGTACAA
TGGGGACAGAATGATGACTTCGAAGGAGATGCTGACATGAACCT bnCBF4 Species=Brassica napus Length=874 [SEQ ID No. 52]
GTAATTCGATTACCGCTCGAGTACTTACTATACTACACTCAGCCTTATCCAGTTTTTCAA
AAGAAGTTTTCAACTATGAACTCAGTCTCTACTTTTTCTGAACTTCTTGGCTCTGAGAAC
GAGTCTCCGGTAGGTGGTGATTACTGTCCCATGTTGGCGGCGAGCTGTCCGAAGAAGCCG
GCGGGTAGGAAGAAGTTTCGGGAGACACGTCACCCCATTTACCGAGGAGTTCGCCTTAGA
AAATCAGGTAAGTGGGTGTGTGAAGTGAGGGAACCAAACAAAAAATCTAGGATTTGGCTC
GGAACTTTCAAAACAGCTGAGATCGCAGCTCGTGCTCACGACGTCGCCGCCTTAGCTCTC
CGTGGAAGAGGCGCCTGCCTCAACTTCGCCGACTCGGCTTGGCGGCTCCGTATCCCGGAG
ACAACCTGCGCCAAGGATATCCAGAAGGCTGCTGCTGAAGCCGCATTGGCTTTTGAGGCC
GAGAAGAGTGATACCACGACGAATGATCATGGCATGAACATGGCTTCTCAGGCCGAGGTT
AATGACACAACGGATCATGGCCTGGACATGGAGGAGACGATGGTGGAGGCTGTTTTTACT
GAGGAGCAGAGAGACGGGTTTTACATGGCGGAGGAGACGACGGTGGAGGGTGTTGTTCCG
GAGGAACAGATGAGCAAAGGGTTTTACATGGACGAGGAGTGGATGTTCGGGATGCCGACC
TTGTTGGCTGATATGGCGGCAGGGATGCTCTTACCGCCGCCGTCCGTACAATGGGGACAT
AATGATGACTTCGAAGGAGATGTTGACATGAACCTCTGGAATTATTAGTACTCATATTTT
TTTAAATTATTTTTTGAACGAATAATATTTTATT bnCBF1 Species=Brassica napus Length=898 [SEQ ID No. 54]
AATAAATATCTTATCAAACCAGTCAGAACAGAGATCTTGTTACTTACTATACTACACTCA
GCCTTATCCAGTTTTCAAAAAAAGTATTCAACGATGAACTCAGTCTCTACTTTTTCTGAA
CTGCTCCGCTCCGAGAACGAGTCTCCGGTTAATACGGAAGGTGGTGATTACATTTTGGCG
GCGAGCTGTCCCAAGAAACCTGCTGGTAGGAAGAAGTTTCAGGAGACACGCCACCCCATT
TACAGAGGAGTTCGTCTGAGGAAGTCAGGTAAGTGGGTGTGTGAAGTGAGGGAACCAAAC
AAGAAATCTAGAATTTGGCTCGGAACTTTCAAAACAGCTGAGATCGCAGCTCGTGCTCAC
GACGTTGCCGCCTTAGCTCTCCGTGGAAGAGGCGCCTGCCTCAACTTCGCCGACTCGGCT
TGGCGGCTCCGTATCCCGGAGACGACCTGCGCCAAGGATATCCAGAAGGCTGCTGCTGAA
GCCGCATTGGCTTTTGAGGCCGAGAAGAGTGATACCACGACGAATGATCATGGCATGAAC
ATGGCTTCTCAGGTTGAGGTTAATGACACGACGGATCATGACCTGGACATGGAGGAGACG
ATAGTGGAGGCTGTTTTTAGGGAGGAACAGAGAGAAGGGTTTTACATGGCGGAGGAGACG
ACGGTTGTGGGTGTTGTTCCGGAGGAACAGATGAGCAAAGGGTTTTACATGGACGAGGAG
TGGATGTTCGGGATGCCGACCTTGTTGGCTGATATGGCGGCAGGGATGCTCTTACCGCTG
CCGTCCGTACAATGGGGACATAATGATGACTTCGAAGGAGATGCTGACATGAACCTCTGG
AATTATTAGTACTCATATTTTTTTAAATTATTTTTTGAACGAATAATATTTTATTGAA bnCBF6 Species=Brassica napus Length=1132 [SEQ ID No. 56]
GATTACCGCTCGAGTACTTACTATACTACACTCAGCCTTATCCAGTTTTTCTCAAAAGAT
TTTTCAACAATGAACACATTCCCTGCTTCCACTGAAATGGTTGGCTCCGAGAACGAGTCT

FIGURE 18A-continued

CCGGTTACTACGGTAGTAGGAGGTGATTATTATCCCATGTTGGCGGCAAGCTGTCCGAAG
AAGCCAGCGGGTAGGAAGAAGTTTCAGGAGACACGTCACCCCATTTACCGAGGAGTTCGT
CTGAGAAAGTCAGGTAAGTGGGTGTGTGAAGTGAGGGAACCAAACAAGAAATCTAGAATT
TGGCTTGGAACTTTCAAAACAGCTGAGATGGCAGCTCGTGCTCACGACGTGGCTGCCCTA
GCCCTCCGTGGAAGAGGCGCCTGCCTCAATTATGCGGACTCGGCTTCGCGGCTCCGCATC
CCGGAGACAACCTGCCACAAGGATATCCAGAAGGCTGCTGCTGAAGCCGCATTGGCTTTT
GAGGCTGAGAAAAGTGATGTGACGATGGAGGAGACGATGGCGGTGGCTTCTCAGGCTGAA
GTGAATGACACGACGACAGATCATGGCATGAACATGGAGGAGGCAACAGCGGTGGCTTCT
CAGGCTGAGGTGAATGACACGACGACAGATCATGGCGTAGACATGGAGGAGACGATGGTG
GAGGCTGTTTTTACGGAGGAACAAAGTGAAGGGTTCAACATGGCGGAGGAGTCGACGGTG
GAGGCTGCTGTTGTTACGGATGAACTGAGCAAAGGATTTTACATGGACGAGGAGTGGACG
TACGAGATGCCGACCTTGTTGGCTGATATGGCGGCAGGGATGCTTTTGCCGCCACCATCT
GTACAATGGGGACATAATGATGACTTGGAAGGAGATGCTGACATGAACCTCTGGAATTAT
TAATACTCGTGTTTTAAAAATTATACATTGTGCAATAATATTTTATCGAATTTCTAATTC
TGCCTTTAACTTTTAATGGGGATCTTTATTAGTGTAGGAAACGAGTGTAAATGTTCCGCC
GTGGTGTTGTCAAAATGCTGATTATTTTTGTGTGCAGCATAATCACGTTTGGTTTCCTT
TACACTCCAAATTTAGTTGAAATACAAATAGAATAGAAAAGTGAAAAAATGT bnCBF7 Species=Brassica napus Length=768 [SEQ ID No. 58]
AGTGATGTTTTTCAAAAGAAGTTTTCAACTATGAACTCAGTCTCTACTTTTTCTGAACTT
CTTGGCTCTGAGAACGAGTCTCCGGTAGGTGGTGATTACTGTCCCATGTTGGCGGCGAGC
TGTCCGAAGAAGCCGGCGGGTAGGAAGAAGTTTCGGGAGACACGTCACCCCATTTACCGA
GGAGTTCGCCTTAGAAAATCAGGTAAGTGGGTGTGTGAAGTGAGGGAGCCAAACAAGAAA
TCTAGGATTTGGCTCGGTACTTTCCTAACAGCCGAGATCGCAGCCCGTGCTCACGACGTC
GCCGCCATAGCCCTCCGCGGCAAATCAGCTTGTCTCAATTTTGCCGACTCCGCTTGGCGG
CTCCGTATCCCGGAGACAACATGCCCCAAGGAGATTCAGAAGGCGGCTGCTGAAGCCGCG
GTGGCTTTTAAGGCTGAGATAAATAATACGACGGCGGATCATGGCATTGACGTGGAGGAG
ACGATCGTTGAGGCTATTTTCACGGAGGAAAACAACGATGGTTTTTATATGGACGAGGAG
GAGTCCATGTTCGGGATGCCGGCCTTGTTGGCTAGTATGGCTGAAGGAATGCTTTTGCCG
CCTCCGTCCGTACAATTCGGACATACCTATGACTTTGACGGAGATGCTGACGTGTCCCTT
TGGAGTTATTAGTACAAAGATTTTTTATTTCCATTTTTGGTATAATACTTCTTTTTGATT
TTCGGATTCTACCTTTTTATGGGTATCATTTTTTTTTTAGGAAACGGG bnCBF8 Species=Brassica napus Length=953 [SEQ ID No. 60]
ACCGCTCGAGCAACAATGAACACATTCCCTGCTTCCACTGAAATGGTTGGCTCCGAGAAC
GAGTCTCCGGTTACTACGGTAGCAGGAGGTGATTATTATCCCATGTTGGCGGCAAGCTGT
CCGAAGAAGCCAGCGGGTAGGAAGAAGTTTCAGGAGACACGTCACCCCATTTACCGAGGA
GTTCGTCTGAGAAAGTCAGGTAAGTGGGTGTGTGAAGTGAGGGAACCAAACAAGAAATCT
AGAATTTGGCTTGGAACTTTCAAAACAGCTGAGATGGCAGCTCGTGCTCACGACGTGGCT
GCCCTAGCCCTCCGTGGAAGAGGCGCCTGCCTCAATTATGCGGACTCGGCTTCGCGGCTC
CGCATCCCGGAGACAACCTGCCACAAGGATATCCAGAAGGCTGCTGCTGAAGCCGCATTG
GCTTTTGAGGCTGAGAAAAGTGATGTGACGATGGAGGAGACGATGGCGGTGGCTTCTCAG
GCTGAAGTGAATGACACGACGACAGATCATGGCATGAACATGGAGGAGGCAACGGCAGTG
GCTTCTCAGGCTGAGGTGAATGACACGACGACGGATCATGGCGTAGACATGGAGGAGACA
ATGGTGGAGGCTGTTTTTACTGGGGAACAAAGTGAAGGGTTTAACATGGCGAAGGAGTCG
ACGGTGGAGGCTGCTGTTGTTACGGAGGAACCGAGCAAAGGATCTTACATGGACGAGGAG
TGGATGCTCGAGATGCCGACCTTGTTGGCTGATATGGCGGAAGGGATGCTTTTGCCGCCG
CCGTCCGTACAATGGGGACAGAATGATGACTTCGAAGGAGATGCGGACATGAACCTCTGG
AGTTATTAATACTCGTATTTTTAAAATTATTTATTGTGCAATAATTTTTTATCGAATTTC
GAATTCTGCCTTTAATTTTTAATGGGGATCTTTATTTGCCAAAAAAAAAAAAA bnCBF9 Species=Brassica napus Length=889 [SEQ ID No. 62]
CTAGTGATTACCGCTCGAGCAACAATGAACACATTCCCTGCTTCCACTGAAATGGTTGGC
TCCGAGAACGAGTCTCCGGTTACTACGGTAGCAGGAGGTGATTATTATCCCATGTTGGCG
GCAAGCTGTCCGAAGAAGCCAGCGGGTAGGAAGAAGTTTCAGGAGACACGTCACCCCATT
TACCGAGGAGTTCGTCTGAGAAAGTCAGGTAAGTGGGTGTGTGAAGTGAGGGAACCAAAC
AAGAAATCTAGAATTTGGCCCGGAACTTTCAAAACAGCTGAGATGGCAGCTCGTGCTCAC
GACGTCGCTGCCCTAGCCCTCCGTGGAAGAGGCGCCCGCCTCAATTATGCGGACTCAGCT
TGGCGGCTCCGCATCCCGGAGACAACCTGCCACAAGGATATCCAGAAGGCTGCTGCTGAA
GCCGCATTGGCTTTTGAGGCTGAGAAAAGTGATGTGACGATGCAAAATGGCCTGAACATG
GAGGAGACGACGGCGGTGGCTTCTCAGGCTGAAGTGAATGACACGACGACAGAACATGGC
ATGAACATGGAGGAGGCAACGGCAGTGGCTTCTCAGGCTGAGGTGAATGACACGACGACG
GATCATGGCGTAGACATGGAGGAGACAATGGTGGAGGCTGTTTTTACTGGGGAACAAAGT
GAAGGGTTTAACATGGCGAAGGAGTCGACGGTGGAGGCTGCTGTTGTTACGGAGGAACCG
AGCAAAGGATCTTACATGGACGAGGAGTGGATGCTCGAGATGCCGACCTTGTTGGCTGAT
ATGGCGGAAGGGATGCTTTTGCCGCCGCCGTCCGTACAATGGGGACAGAATGATGACTTC

FIGURE 18A-continued

GAAGGAGATGCGCACATGAACCTCTGGAGTTATTAAGGATCCGCGAATC boCBF1 Species=Brassica oleracea Length=563 [SEQ ID No. 64]
CACCCTATCTACCGGGGAGTTCGCCTGAGAAAGTCAGGTAAGTGGGTGTGTGAAGTGAGG
GAGCCAAACAAGAAATCTAGGATTTGGCTTGGAACTTTCAAAACCGCAGAGATCGCTGCT
CGTGCTCACGACGTTGCCGCCTTAGCCCTCCGTGGAAGAGCGGCCTGTCTCAACTTCGCC
GACTCGGCTTGGCGGCTCCGTATCCCGGAGACAACTTGCGCCAAGGATATCCAGAAGGCT
GCTGCTGAAGCTGCGTTGGCTTTTGGGGCCGAAAAGAGTGATACCACGACGAATGATCAA
GGCATGAACATGGAGGAGATGACGGTGGTGGCTTCTCAGGCTGAGGTGAGCGACACGACG
ACATATCATGGCCTGGACATGGAGGAGACTATGGTGGAGGCTGTTTTTGCTGAGGAACAG
AGAGAAGGGTTTTACTTGGCGGAGGAGACGACGGTGGAGGGTGTTGTTACGGAGGAACAG
AGCAAAGGGTTTTATATGGACGAGGAGTGGACGTTCGGGATGCAGTCCTTTTTGGCCGAT
ATGGCTGAAGGCATGCTCTTTCC boCBF2 Species=Brassica oleracea Length=533 [SEQ ID No. 66]
GAAACATAGATCTTTGTACTTACTATACTTCACCTTATCCAGTTTTATTTTTTTATTTAT
AAAGAGTTTTCAACAATGACCTCATTTTCTACCTTTTCTGAACTGTTGGGCTCCGAGCAT
GAGTCTCCGGTTACATTAGGCGAAGAGTATTGTCCGAAGCTGGCCGCAAGCTGTCCGAAG
AAACCAGCCGGCCGGAAGAAGTTTCGAGAGACGCGTCACCCAGTTTACAGAGGAGTTCGT
CTGAGAAACTCAGGTAAGTGGGTGTGTGAAGTGAGGGAGCCAAACAAGAAATCTAGGATT
TGGCTCGGTACTTTCCTAACAGCCGAGATCGCAGCCCGTGCTCACGACGTCGCCGCCATA
GCCCTCCGCGGCAAATCAGCTTGTCTCAATTTTGCCGACTCCGCTTGGCGGCTCCGTATC
CCGGAGACAACATGCCCCAAGGAGATTCAGAAGGCGGCTGCTGAAGCCGCGGTGGCTTTT
AAGGCTGAGATAAATAATACGACGGCGGATCACGGCCTCGACATGGAAGAGAC boCBF3 Species=Brassica oleracea Length=887 [SEQ ID No. 68]
ACTCAGCCTTATCCAGTTTTTCTCAAAAGATTTTTCAACAATGAACACATTCCCTGCTTC
CACTGAAATGGTTGGCTCCGAGAACGAGTCTCCGGTTACTACGGTAGTAGGAGGTGATTA
TTATCCCATGTTGGCGGCAAGCTGTCCGAAGAAGCCAGCGGGTAGGAAGAAGTTTCAGGA
GACACGTCACCCCATTTACCGAGGAGTTCGTCTGAGAAAGTCAGGTAAGTGGGTGTGTGA
AGTGAGGGAACCAAACAAGAAATCTAGAATTTGGCTTGGAACTTTCAAAACAGCTGAGAT
GGCAGCTCGTGCTCACGACGTGGCTGCCCTAGCCCTCCGTGGAAGAGGCGCCTGCCTCAA
TTATGCGGACTCGGCTTGGCGGCTCCGCATCCCGGAGACAACCTGCCACAAGGATATCCA
GAAGGCTGCTGCTGAAGCCGCATTGGCTTTTGAGGCTGAGAAAAGTGATGTGACGATGGA
GGAGACGATGGCGGTGGCTTCTCAGGCTGAAGTGAATGACACGACGACAGATCATGGCAT
GAACATGGAGGAGGCAACAGCGGTGGCTTCTCAGGCTGAGGTGAATGACACGACGACAGA
TCATGGCGTAGACATGGAGGAGACGATGGTGGAGGCTGTTTTTACGGAGGAACAAAGTGA
AGGGTTCAACATGGCGGAGGAGTCGACGGTGGAGGCTGCTGTTGTTACGGATGAACTGAG
CAAAGGATTTTACATGGACGAGGAGTGGACGTACGAGATGCCGACCTTGTTGGCTGATAT
GGCGGCAGGGATGCTTTTGCCGCCACCATCTGTACAATGGGGACATAATGATGACTTGGA
AGGAGATGCGGACATGAACCTCTGGAGTTATTAATACTCGTATTTTT boCBF4 Species=Brassica oleracea Length=950 [SEQ ID No. 70]
CTGAAAAGAAGATAAAAGAGAGAGAAATAAATATCTTATCAAACCAGACAGAACAGAGAT
CTTGTTACTTACTATACTACACTCAGCCTTATCCAGTTTTTCAAAAGAAGTTTTCAACTA
TGAACTCAGTCTCTACTTTTTCTGAACTTCTTGGCTCTGAGAACGAGTCTCCGGTAGGTG
GTGATTACTGTCCCATGTTGGCGGCGAGCTGTCCGAAGAAGCCGGCGGGTAGGAAGAAGT
TTCGGGAGACACGTCACCCCATTTACCGAGGAGTTCGCCTTAGAAAATCAGGTAAGTGGG
TGTGTGAAGTGAGGGAACCAAACAAAAAAATCTAGGATTTGGCTCGGAACTTTCAAAACAG
CTGAGATCGCAGCTCGTGCTCACGACGTCGCCGCCTTAGCTCTCCGTGGAAGAGGCGCCT
GCCTCAACTTCGCCGACTCGGCTTGGCGGCTCCGTATCCCGGAGACAACCTGCGCCAAGG
ATATCCAGAAGGCTGCTGCTGAAGCCGCATTGGCTTTTGAGGCCGAGAAGAGTGATACCA
CGACGAATGATCATGGCATGAACATGGCTTCTCAGGCTGAGGTTAATGACACGACGGATC
ATGGCCTGGACATGGAGGAGACGATGGTGGAGGCTGTTTTTACTGAGGAGCAGAGAGACG
GGTTTTACATGGCGGAGGAGACGACGGTGGAGGGTGTTGTTCCGGAGGAACAGATGAGCA
AAGGGTTTTACATGGACGAGGAGTGGATGTTCGGGATGCCGACCTTGTTGGCTGATATGG
CGGCAGGGATGCTCTTACCGCCGCCGTCCGTACAATGGGGACATAATGATGACTTCGAAG
GAGATGCTGACATGAACCTCTGGAATTATTAGTACTCGTATTTTTTTAAATTATTTTTTG
AACGAATAATATTTTATTGAATTCGGATTCTACCTGTTTTTTTAATGGAT boCBF5 Species=Brassica oleracea Length=877 [SEQ ID No. 72]
ACCGCTCGAGCAACAATGAACACATTCCCTGCTTCCACTGAAATGGTTAGCTCCGAGAAC
GAGTCTCCGGTTACTACGGTAGTAGGAGGTGATTATTATCCCATGTTGGCGGCAAGCTGT
CCGAAGAAGCCAGCGGGTAGGAAGAAGTTTCAGGAGACACGTCACCCCATTTACCGAGGA
GTTCGTCTGAGAAAGTCAGGTAAGTGGGTGTGTGAAGTGAGGGAACTAAACAAGAAATCT
AGAATTTGGCTTGGAACTTTCAAAACAGCTGAGATGGCAGCTCGTGCTCACGACGTGGCT

FIGURE 18A-continued

GCCCTAGCCCTCCGTGGAAGAGGCGCCTGCCTCAATTATGCGGACTCGGCTTGGCGGCTC
CGCATCCCGGAGACAACCTGCCACAAGGATATCCAGAAGGCTGCTGCTGAAGCCGCATTG
GCTTTTGAGGCTGAGAAGAGTGATGCGACGATGCAAAATGGCCTGAACATGGAGGAGACG
ACGGCGGCGGCTTCTCAGACTGAAGTGAGTGACACGACGACAGATCATGGCATGAACATG
GAGGAGACAACGGCGGTGGCTTCTCAGGCTGAGGTGAATGACACGACGACAGATCATGGC
GTAGACATGGAGGAGACGATGGTGGAGGCTGTTTTTACTGAGGAACAAAGTGAAGGGTTC
AACATGGCGAAGGAGTCGACGGCGGAGGCTGCTGTTGTTACGGAGGAACTGAGCAAAGGA
GTTTACATGGACGAGGAGTGGACGTACGAGATGCCGACCTTGTTGGCTGATATGGCGGCA
GGGATGCTTTTGCCGCCACCATCTGTACAATGGGGACATAATGATGACTTGGAAGGAGAT
GCGGACATGAACCTACTGGAGTTATTAAGGATCCGCG brCBF1 Species=Brassica rapa Length=374 [SEQ ID No. 74]
CATCCCATTTACAGGGGGGTTCGTTTAAGAAAGTCAGGTAAGTGGGTGTGTGAAGTGAGG
GAACCAAACAAGAAATCTAGGATTTGGCTCGGAACTTTCAAAACCGCTGAGATCGCTGCT
CGTGCTCACGACGTTGCTGCCTTAGCCCTCCGCGGGAGAGGCGCCTGCCTCAACTTCGCC
GACTCGGCTTGGCGGCTCCGTATCCCGGAGACAACCTGCGCCAAGGACATCCAGAAGGCG
GCTGCTGAAGCTGCATTGGCTTTTGAGGCCGAGAAGAGTGATCATGGCATGAACATCAAG
AATACTACGGCGGTGGTTTCTCAGGTTGAGGTGAATGACACGACGACGGACCACGGCTTG
GACATGGAGGAGAC brCBF2 Species=Brassica rapa Length=884 [SEQ ID No. 76]
TACACTCAGCCTTATCCAGTTTTTTTCAAAAGACTTTTCAACAATGAACACATTCCCTGC
GTCCACTGAAATGGTTGGCTCCGAGAACGAGTCTCCGGTTACTACGGTAGCAGGAGGTGA
TTATTATCCCATGTTGGCGGCAAGCTGTCCGAAGAAGCCAGCGGGTAGGAAGAAGTTTCA
GGAGACACGTCACCCCATTTACCGAGGAGTTCGTCTGAGAAAGTCAGGTAAGTGGGTGTG
TGAAGTGAGGGAACCAAACAAGAAATCTAGAATTTGGCTTGGAACTTTCAAAACAGCTGA
GATGGCAGCTCGTGCTCACGACGTCGCTGCCCTAGCCCTCCGTGGAAGAGGCGCCTGCCT
CAATTATGCGGACTCGGCTTGGCGGCTCCGCATCCCGGAGACAACCTGCCACAAGGATAT
CCAGAAGGCTGCTGCTGAAGCCGCATTGGCTTTTGAGGCTGAGAAAAGTGATGTGACGAT
GCAAAATGGCCTGAACATGGAGGAGATGACGGCGGTGGCTTCTCAGGCTGAAGTGAATGA
CACGACGACAGAACATGGCATGAACATGGAGGAGGCAACGGCAGTGGCTTCTCAGGCTGA
GGTGAATGACACGACGACGGATCATGGCGTAGACATGGAGGAGACAATGGTGGAGGCTGT
TTTTACTGAGGAACAAAGTGAAGGGTTTAACATGGCGAAGGAGTCGACGGTGGAGGCTGC
TGTTGTTACGGAGGAACCGAGCAAAGGATCTTACATGGACGAGGAGTGGATGCTCGAGAT
GCCGACCTTGTTGGCTGATATGGCGGAAGGGATGCTTTTGCCGCCGCCGTCCGTACAATG
GGGACAGAATGATGACTTCGAAGGAGATGCTGACATGAACCTCT brCBF3 Species=Brassica rapa Length=806 [SEQ ID No. 78]
ACACTCAGCCTTATCCAGTTTTCAAAAAAAGTATTCAACGATGAACTCAGTCTCTACTTT
TTCTGAACTGCTCTGCTCCGAGAACGAGTCTCCGGTTAATACGGAAGGTGGTGATTACAT
TTTGGCGGCGAGCTGTCCCAAGAAACCTGCTGGTAGGAAGAAGTTTCAGGAGACACGCCA
CCCCATTTACAGAGGAGTTCGTCTGAGGAAGTCAGGTAAGTGGGTGTGTGAAGTGAGGGA
ACCAAACAAGAAATCTAGAATTTGGCTCGGAACTTTCAAAACAGCTGAGATCGCAGCTCG
TGCTCACGACGTTGCCGCCTTAGCTCTCCGTGGAAGAGGCGCCTGCCTCAACTTCGCCGA
CTCGGCTTGGCGGCTCCGTATCCCGGAGACGACCTGCGCCAAGGATATCCAGAAGGCTGC
TGCTGAAGCCGCATTGGCTTTTGAGGCCGAGAAGAGTGATACCACGACGAATGATCGTGG
CATGAACATGGAGGAGACGTCGGCGGTGGCTTCTCCGGCTGAGTTGAATGATACGACGGC
GGATCATGGCCTGGACATGGAGGAGACGATGGTGGAGGCTGTTTTTAGGGAGGAACAGAG
AGAAGGGTTTTACATGGCGGAGGAGACGACGGTGGAGGGTGTTGTTCCGGAGTAACAGAT
GAGCAAAGGGTTTTACATGGACGAGGAGTGGACGTTCGAGATGCCGAGGTTGTTGGCTGA
TATGGCGGAAGGGATGCTTTTGCCGCCCCCGTCCGTACAATGGGGACATAACGATGACTT
CGAAGGAGATGCTGACATGAACCTCT brCBF4 Species=Brassica rapa Length=755 [SEQ ID No. 80]
ACCGCTCGAGTACTTACTATACTACACTCAGCCTTATCCAGTTTTTCTTCCAACGATGGA
CTCAATCTCTACTTTTCCTGAACTGCTTGGCTCAGAGAACGAGTCTCCGGTTACTACGGT
AGTAGGAGGTGATTATTGTCCCAGGTTGGCGGCAAGCTGTCCGAAGAAGCCAGCGGGTAG
GAAGAAGTTTCAGGAGACACGTCACCCCATTTACCGTGGAGTTCGTTTAAGAAAGTCCGG
TAAGTGGGTGTGTGAAGTGAGGGAACCAAACAAGAAATCTAGGATTTGGCTCGGAACTTT
CAAAACCGCTGAGATCGCTGCTCGTGCTCACGACGTTGCTGCCTTAGCCCTCCGCGGAAG
AGGCGCCTGCCTCAACTTCGCCGACTCGGCTTGACGGCTCCGTATCCCGGAGACAACCTG
CGCCAAGGATATCCAGAAGGCTGCTGCTGAAGCTGCATTGGCTTTTGAGGCCGAGAAGAG
TGATCATGGCATGAACATGAAGAATACTACGGCGGTGGCTTCTCAGGTTGAGGTGAATGA
TACGACGACGGACCATGGCGTGGACATGGAGGAGACGAGGGTGGAGGGTGTTGTTACGGA
GGAACAGAACAATTGGTTTTACATGGACGAGGAGTGGATGTTTGGGATGCCGACGTTGTT
GGTTGATATGGCGGAAGGGATGCTTATACCGCGGCAGTCCGTACAATCGGGACACTACGA

FIGURE 18A-continued

TGACTTCGAAGGAGATGCTGACATGAACCTCTGGA brCBF5 Species=Brassica rapa Length=832 [SEQ ID No. 82]
ACCGCTCGAGTACTTACTATACTACACTCAGCCTTATCCAGTTTTTCTTCCAACGATGGA
CTCAATCTCTACTTTTCCTGAACTGCTTGGCTCAGAGAACGAGTCTCCGGTTACTACGGT
AGTAGGAGGTGATTATTGTCCCAGGTTGGCGGCAAGCTGTCCGAAGAAGCCAGCGGGTAG
GAAGAAGTTTCAGGAGACACGTCACCCCATTTACCGTGGAGTTCGTTTAAGAAAGTCCGG
TAAGTGGGTGTGTGAAGTGAGGGAACCAAACAAGAAATCTAGGATTTGGCTCGGAACTTT
CAAAACCGCTGAGATCGCTGCTCGTGCTCACGACGTTGCTGCCTTAGCCCTCCGCGGAAG
AGGCGCCTGCCTCAACTTCGCCGACTCGGCTTGGCGGCTCCGTATCCCGGAGACAACCTG
CGCCAAGGATATCCAGAAGGCTGCTGCTGAAGCTGCTTTGGCTTTTGAGGCCGAGAAGAG
TGATCATGGCATGAACATGAAGAATACTACGGCGGTGGCTTCTCAGGTTGAGGTGAATGA
TACGACGACGGACCATGGCGTGGACATGGAGGAGACGTTGGTGGAGGCTGTTTTTACGGA
GGAACAGAGAGAAGGGTTTTACATGACGGAGGAGACGAGGGTGGAGGGTGTTGTTACGGA
GGAACAGAACAATTGGTTTTACATGGACGAGGAGTGGATGTTTGGGATGCCGACGTTGTT
GGTTGATATGGCGGAAGGGATGCTTATACCGCGGCAGTCCGTACAATCGGGACACTACGA
TGACTTCGAAGGAGATGCTGACATGAACCTCTGGAATTATTAGGGATCCGCG brCBF6 Species=Brassica rapa Length=830 [SEQ ID No. 84]
TACTACACTCAGCCTTATCCAGTTTTCAAAAAAAGTATTCAACTATGAACTCAGTCTCTA
CTTTTTCTGAACTGCTCTGCTCCGAGAACAAGTCTCCGGTTAATACGGAAGGTGGTGATT
ACATTTTGGCGGCGAGCTGTCCCAAGAAACCTGCTGGTAGGAAGAAGTTTCAGGAGACAC
GCCACCCCATTTACAGAGGAGTTCGCCTAAGAAAGTCAGGTAAGTGGGTGTGTGAAGTGA
GGGAACCAAACAAGAAATCTAGAATTTGGCTCGGAACTTTCAAAACAGCTGAGATAGCAG
CTCGTGCTCACGACGTCGCCGCCTTAGCTCTCCGTGGAAGAGGCGCCTGCCTCAACTTCG
CCGACTCGGCTTGGCGGCTCCGTATCCCAGAGACAACCTGCGCCAAGGATATCCAGAAGG
CTGCTGCTGAAGCCGCATTGGCTTTTGAGGCCGAGAAGAGTGATACCACGACGAATGATC
GTGGCATGAACATGGAGGAGACGTCCGCGGTGGCTTCTCCGGCTGAGTTGAATGATACGA
CGGCGGATCATGGCCTGGACATGGAGGAGACGATGGTGGAGGCTGTTTTTAGGGACGAAC
AGAGAGAAGGGTTTTACATGGCGGAGGAGACGACGGTGGAGGGTGTTGTTCCGGAGGAAC
AGATGAGCAAAGGGTTTTACATGGACGAGGAGTGGACGTTCGAGATGCCGAGGTTGTTGG
CTGATATGGCGGAAGGGATGCTTCTGCCTCCCCCGTCCGTACAATGGGGACATAACGATG
ACTTCGAAGGAGATGCTGACATGAACCTCTGGAATTATTAGGGATCCGCG brCBF7 Species=Brassica rapa Length=854 [SEQ ID No. 86]
CTATACTACACACAGCCTTATCCAGCCGCTCGAGTACTTACTATACTACACTCAGCCTTT
TCCAGTTTTTCAAAAGAAGTTTTCAACGATGAACTCAGTCTCTACTCTTTCTGAAGTTCT
TGGCTCCCAGAACGAGTCTCCCGTAGGTGGTGATTACTGTCCCATGTTGGCGGCGAGCTG
TCCGAAGAAGCCGGCGGGTAGGAAGAAGTTTCGGGAGACACGTCACCCCATTTACAGAGG
AGTTCGTCTTAGAAAGTCAGGTAAGTGGGTGTGTGAAGTGAGGGAACCAAACAAGAAATC
TAGGATTTGGCTCGGAACTTTCAAAACAGCTGAGATCGCAGCTCGTGCTCACGACGTTGC
CGCCTTAGCTCTCCGTGGAAGAGGCGCCTGCCTCAACTTCGCCGACTCGGCTTGGCGGCT
CCGTATCCCGGAGACAACCTGCGCCAAGGATATCCAGAAGGCTGCTGCTGAAGCCGCATT
GGCTTTTGAGGCGGAGAAGAGTGATACCACGACGACGAATGATCATGGCATGAACATGGC
TTCTCAGGTTGAGGTTAATGACACGACGGATCATGACCTGGACATGGAGGAGACGATGGT
GGAGGCTGTTTTTAGGGAGGAACAGAGAGAAGGGTTTTACATGGCGGAGGAGACGACGGT
GGAGGGTATTGTTCCGGAGGAACAGATGAGCAAAGGGTTTTACATGGACGAGGAGTGGAT
GTTCGGGATGCCGACCTTGTTGGCTGATATGGCGGCAGGGATGCTCTTACCGCCGCCGTC
CGTACAATGGGGACATAATGATGACTTCGAAGGAGATGCTGACATGAACCTCTGGAATTA
TTAAGGGATCCGCG gmCBF1 Species=Glycine max Length=738 [SEQ ID No. 88]
CATCCGATTTATAGTGGCGTGAGGAGGAGGAACACGGATAAGTGGGTAAGTGAGGTGAGG
GAGCCCAACAAAAAGACCAGGATTTGGCTGGGGACTTTTCCCACGCCGGAGATGGCGGCA
CGGGCCCACGACGTGGCGGCAATGGCCCTGAGGGGCCGGTATGCCTGTCTCAACTTCGCT
GACTCGACGTGGCGGTTACCAATTCCCGCCACTGCTAACGCAAAGGATATACAGAAAGCA
GCAGCAGAGGCTGCCGAGGCTTTCAGACCAAGTCAGACCTTAGAAAATACGAATACAAAG
CAAGAGTGTGTAAAAGTGGTGACGACAACAACGATCACAGAACAAAAACGAGGAATGTTT
TATACGGAGGAAGAAGAGCAAGTGTTAGATATGCCTGAGTTGCTTAGGAATATGGTGCTT
ATGTCCCCAACACATTGCATAGGGTATGAGTATGAAGATGCTGACTTGGATGCTCAAGAT
GCTGAGGTGTCCCTATGGAGTTTCTCAATTTAATAACGTGCTTTTGGTTTGGTTTTTTAT
GTTAGTTTTGGAGTGTGACTGTCTGTACTGGTTTTTTATTAGTAGTACGGATACTAGCTA
TAGGTGGCAGATTGAAAGGGACCAAAAGGAATTTTCTTTTGAAACCCTTTTTGTCAAAGT
AATCAATCGCGTATCATCAAGTGAATCCCTTGATCAAGTTTATGTATGAATTAAATAAAA
GAAGAATCTAGTTTTGGT

FIGURE 18A-continued rsCBF1 Species= Raphanus sativus Length=793 [SEQ ID No. 90]
ACTACACTCAGCCTTATCCAGTTTTTCTTCCAACGATGGACTCAATCTCTACTTTTTCTG
AACTGCTTGGCTCCGAGAACGAGTCTCCGGTTACTACGGTAGTAGGAGGTGATTATTTTC
CCAGGTTGGCGGCAAGCTGTCCGAAGAAGCCAGCGGGTAGGAAGAAGTTTCAGGAGACAC
GTCACCCCATTTACCGCGGAGTTCGTTTAAGAAAGTCAGGTAAGTGGGTGTGTGAAGTGA
GGGAACCAAACAAGAAATCTAGGATTTGGCTCGGAACTTTCAAAACCGCTGAGATCGCTG
CTCGTGCTCACGACGTTGCTGCCTTAGCCCTCCGCGGAAGAGGCGCCTGCCTCAACTTCG
CCGACTCGGCTTGGCGGCTCCGTATCCCGGAGACAACCTGCGCCAAGGATATCCAGAAGG
CTGCTGCTGAAGCTGCATTGGCTTTTGAGGCCGAGAAGAGTGATCATGGCATGAACATGA
AGAATACTACGGCGGTGGCTTCTCAGGTTGAGGTGAATGACACGACGACGGACCATGGCG
TGGACATGGAGGAGACGTTGGTGGAGGCTGTTTTTACGGAGGAACAGAGAGAAGGGTTTT
ACATGACGGAGGAGACGAGGGTGGAGGGTGTTGTTACGGAGGAACAGAACAATTGGTTTT
ACATGGACGAGGAGTGGATGTTTGGGATGCCGACGTTGTTGGTTGATATGGCGGAAGGGA
TGCTTTTACCGCGGCCGTCCGTACAATCGGGACACTACGATGACTTCGAAGGAGATGCTG
ACATGAACCTCTG rsCBF2 Species= Raphanus sativus Length=682 [SEQ ID No. 92]
ACACCTAAACCTTATCCAGGTTTAACTTTTTTTTTCATAAAGAGTTTTCAACAATGACCA
CATTTTCTACCTTTTCCGAAATGTTGGGCTCCGAGTACGAGTCTCCGGTTACATTAGGCG
GAGAGTATTGTCCGAAGCTGGCCGCGAGCTGTCCGAAGAAACCAGCTGGTCGTAAGAAGT
TTCGAGAGACGCGCCACCCAATATACAGAGGAGTTCGTCTGAGAAACTCAGGTAAGTGGG
TGTGTGAAGTGAGGGAGCCAAACAAGAAATCTAGGATTTGGCTCGGTACTTTCCTAACCG
CCGAGATCGCAGCGCGTGCCCACGACGTCGCCGCCATAGCCCTCCGCGGCAAATCCGCAT
GTCTCAATTTCGCTGACTCGGCTTGGCGGCTCCGTATCCCGGAGACAACATGCCCCAAGG
ATATACAGAAGGCGGCTGCTGAAGCCGCGGTGGCTTTTCAGGCTGAGATAAATGATACGA
CGACGGATCATGGCCTGGACTTGGAGGAGACGATCGTGGAGGCTATTTTTACGGAGGTAA
ACAACGATGAGTTTTATATGGACGAGGAGTCCATGTTCGGGATGCCGTCTTTGTTGGCTA
GTATGGCGGAAGGGATGCTTTTGCCGCTGCCGTCCGTACAATCTGAACATAACTGTGACT
TCGACGGAGATGCTGACATGAA zmCBF1 Species=Zea maize Length=349 [SEQ ID No. 94]
CGGAGTCCGCGGACGGCGGCGGCGGCGGCGACGACGAGTACGCGACGGTGCTGTCGGCGC
CACCCAAGCGGCCGGCGGGGCGGACCAAGTTCCGGGAGACGCGGCACCCCGTGTACCGCG
GCGTGCGGCGGCGCGGGCCCGCGGGGCGCTGGGTGTGCGAGGTCCGCGAGCCCAACAAGA
AGTCGCGCATCTGGCTCGGCACCTTCGCCACCCCCGAGGCCGCCGCGCGCGCGCACGACG
TGGCCGCGCTGGCCCTGCGGGGCCGCGCCGCGTGCCTCAACTTCGCCGACTCGGCGCGCC
TGCTCCAAGTCGACCCCGCCACGCTCGCCACCCCCGACGACATCCGCCG

FIGURE 18B

BJCBF1-PEP Species=Brassica juncea length=130 [SEQ ID No. 39]
LPGVRLRKSGKWVCEVREPNKKSRIWLGTFKTAEIAARAHDVAALALRGRAACLNFADSA
WRLRIPETTCAKDIQKAAAEAALAFGAEKSDTTTNDQGMNMEEMTAVASQAEVSDTTTYH
GLDMEETMVD

BJCBF2-PEP Species=Brassica juncea length=143 [SEQ ID No. 41]
HPIYRGVRLRKSGKWVCEVREPNKRSRIWLGTFLTAEIAARAHDVAAIALRGKSACLNFA
DSAWRLRISETTCPKEIQKAAAEAAVAFQAELNDTTADHGLDVEETIVEAIFTEESSEGF
YMDEEFMFGMPTLWASMAEGMLL

BJCBF3-PEP Species=Brassica juncea length=143 [SEQ ID No. 43]
HPIYRGVRLRKSGKWVCEVREPNKKSRIWPGTFLTAEIAARAHDVAAIALRGKSACLNFA
DSAWRLRIPETTCPKEIQKAAAEAAVAFQAELNDTTADHGLDVEETIVEAIFTEESSEGF
YMAEEFMFGMPTLWASVAEGMLL

BJCBF4-PEP Species=Brassica juncea length=142 [SEQ ID No. 45]
HPIYRGVRQRNSGKWVCEVREPNKKSRIWLGTFPTVEMAARAHDVAALALRGRSACLNFA
DSAWCLRIPESTCPKEIQKAAAEAAMAFQNEETATTETTMVEGVIPAEETVGQTRVETAE
ENGVEYMDDPRFLENMAEGMLF

BNCBF1-PEP Species=Brassica napus length=210 [SEQ ID No. 47]
HPIYRGVRLRKSGKWVCEVREPNKKSRIWLGTFKTAEMAARAHDVAALALRGRGACLNYA
DSAWRLRIPETTCHKDIQKAAAEAALAFEAEKSDVTMQNGQNMEETTAVASQAEVNDTTT
EHGMNMEEATAVASQAEVNDTTTDHGVDMEETMVEAVFTGEQSEGFNMAKESTVEAAVVT
EEPSKGSYMDEEWMLEMPTLLADMAEGMLL

BNCBF2-PEP Species=Brassica napus length=283 [SEQ ID No. 49]
MNTFPASTEMVGSENESPVTTVVGGDYYPMLAASCPKKPAGRKKFQETRHPIYRGVRLRK
SGKWVCEVREPNKKSRIWPGTFKTAEMAARAHDVAALALRGRGACLNYADSAWRLRIPET
TCHKDIQKAAAEAALAFEAEKSDVTMQNGLNMEETTAVASQAEVNDTTTEHGMNMEEATA
VASQAEVNDTTTDHGVDMEETMVEAVFTEEQSEGFNMAEESTVEAAVVTDELSKGFYMDE
EWTYEMPTLLADMAAGMLLPPPSVQWGHNDDLEGDADMNLWSY

BNCBF3-PEP Species=Brassica napus length=279 [SEQ ID No. 51]
MNTFPASTEMVGSENESPVTTVAGGDYYPMLAASCPKKPAGRKKFQETRHPIYRGVRLRK
SGKWVCEVREPNKKSRIWPGTFKTAEMAARAHDVAALALRGRGACLNYADSAWRLRIPET
TCHKDIQKAAAEAALAFEAEKSDVTMQNGLNMEETTAVASQAEVNDTTTEHGMNMEEATA
VASQAEVNDTTTDHGVDMEETMVEAVFTGEQSEGFNMAKESTVEAAVVTEEPSKGSYMDE
EWMLEMPTLLADMAEGMLLPPPSVQWGQNDDFEGDADMN

BNCBF4-PEP Species=Brassica napus length=250 [SEQ ID No. 53]
MNSVSTFSELLGSENESPVGGDYCPMLAASCPKKPAGRKKFRETRHPIYRGVRLRKSGKW
VCEVREPNKKSRIWLGTFKTAEIAARAHDVAALALRGRGACLNFADSAWRLRIPETTCAK
DIQKAAAEAALAFEAEKSDTTTNDHGMNMASQAEVNDTTDHGLDMEETMVEAVFTEEQRD
GFYMAEETTVEGVVPEEQMSKGFYMDEEWMFGMPTLLADMAAGMLLPPPSVQWGHNDDFE
GDVDMNLWNY

BNCBF5-PEP Species=Brassica napus length=251 [SEQ ID No. 55]
MNSVSTFSELLRSENESPVNTEGGDYILAASCPKKPAGRKKFQETRHPIYRGVRLRKSGK
WVCEVREPNKKSRIWLGTFKTAEIAARAHDVAALALRGRGACLNFADSAWRLRIPETTCA
KDIQKAAAEAALAFEAEKSDTTTNDHGMNMASQVEVNDTTDHDLDMEETIVEAVFREEQR
EGFYMAEETTVVGVVPEEQMSKGFYMDEEWMFGMPTLLADMAAGMLLPLPSVQWGHNDDF
EGDADMNLWNY

BNCBF6-PEP Species=Brassica napus length=277 [SEQ ID No. 57]
MNTFPASTEMVGSENESPVTTVVGGDYYPMLAASCPKKPAGRKKFQETRHPIYRGVRLRK
SGKWVCEVREPNKKSRIWLGTFKTAEMAARAHDVAALALRGRGACLNYADSASRLRIPET
TCHKDIQKAAAEAALAFEAEKSDVTMEETMAVASQAEVNDTTTDHGMNMEEATAVASQAE
VNDTTTDHGVDMEETMVEAVFTEEQSEGFNMAEESTVEAAVVTDELSKGFYMDEEWTYEM
PTLLADMAAGMLLPPPSVQWGHNDDLEGDADMNLWNY

BNCBF7-PEP Species=Brassica napus length=213 [SEQ ID No. 59]
MNSVSTFSELLGSENESPVGGDYCPMLAASCPKKPAGRKKFRETRHPIYRGVRLRKSGKW
VCEVREPNKKSRIWLGTFLTAEIAARAHDVAAIALRGKSACLNFADSAWRLRIPETTCPK
EIQKAAAEAAVAFKAEINNTTADHGIDVEETIVEAIFTEENNDGFYMDEEESMFGMPALL

FIGURE 18B-continued

ASMAEGMLLPPPSVQFGHTYDFDGDADVSLWSY

BNCBF8-PEP Species=Brassica napus length=277 [SEQ ID No. 61]
MNTFPASTEMVGSENESPVTTVAGGDYYPMLAASCPKKPAGRKKFQETRHPIYRGVRLRK
SGKWVCEVREPNKKSRIWLGTFKTAEMAARAHDVAALALRGRGACLNYADSASRLRIPET
TCHKDIQKAAAEAALAFEAEKSDVTMEETMAVASQAEVNDTTTDHGMNMEEATAVASQAE
VNDTTTDHGVDMEETMVEAVFTGEQSEGFNMAKESTVEAAVVTEEPSKGSYMDEEWMLEM
PTLLADMAEGMLLPPPSVQWGQNDDFEGDADMNLWSY

BNCBF9-PEP Species=Brassica napus length=283 [SEQ ID No. 63]
MNTFPASTEMVGSENESPVTTVAGGDYYPMLAASCPKKPAGRKKFQETRHPIYRGVRLRK
SGKWVCEVREPNKKSRIWPGTFKTAEMAARAHDVAALALRGRGARLNYADSAWRLRIPET
TCHKDIQKAAAEAALAFEAEKSDVTMQNGLNMEETTAVASQAEVNDTTTEHGMNMEEATA
VASQAEVNDTTTDHGVDMEETMVEAVFTGEQSEGFNMAKESTVEAAVVTEEPSKGSYMDE
EWMLEMPTLLADMAEGMLLPPPSVQWGQNDDFEGDAHMNLWSY

BOCBF1-PEP Species=Brassica olercea Length=188 [SEQ ID No. 65]
HPIYRGVRLRKSGKWVCEVREPNKKSRIWLGTFKTAEIAARAHDVAALALRGRAACLNFA
DSAWRLRIPETTCAKDIQKAAAEAALAFGAEKSDTTTNDQGMNMEEMTVVASQAEVSDTT
TYHGLDMEETMVEAVFAEEQREGFYLAEETTVEGVVTEEQSKGFYMDEEWTFGMQSFLAD
MAEGMLFP

BOCBF2-PEP Species=Brassica olercea Length=152 [SEQ ID No. 67]
MTSFSTFSELLGSEHESPVTLGEEYCPKLAASCPKKPAGRKKFRETRHPVYRGVRLRNSG
KWVCEVREPNKKSRIWLGTFLTAEIAARAHDVAAIALRGKSACLNFADSAWRLRIPETTC
PKEIQKAAAEAAVAFKAEINNTTADHGLDMEE

BOCBF3-PEP Species=Brassica olercea Length=277 [SEQ ID No. 69]
MNTFPASTEMVGSENESPVTTVVGGDYYPMLAASCPKKPAGRKKFQETRHPIYRGVRLRK
SGKWVCEVREPNKKSRIWLGTFKTAEMAARAHDVAALALRGRGACLNYADSAWRLRIPET
TCHKDIQKAAAEAALAFEAEKSDVTMEETMAVASQAEVNDTTTDHGMNMEEATAVASQAE
VNDTTTDHGVDMEETMVEAVFTEEQSEGFNMAEESTVEAAVVTDELSKGFYMDEEWTYEM
PTLLADMAAGMLLPPPSVQWGHNDDLEGDADMNLWSY

BOCBF4-PEP Species=Brassica olercea Length=250 [SEQ ID No. 71]
MNSVSTFSELLGSENESPVGGDYCPMLAASCPKKPAGRKKFRETRHPIYRGVRLRKSGKW
VCEVREPNKKSRIWLGTFKTAEIAARAHDVAALALRGRGACLNFADSAWRLRIPETTCAK
DIQKAAAEAALAFEAEKSDTTTNDHGMNMASQAEVNDTTDHGLDMEETMVEAVFTEEQRD
GFYMAEETTVEGVVPEEQMSKGFYMDEEWMFGMPTLLADMAAGMLLPPPSVQWGHNDDFE
GDADMNLWNY

BOCBF5-PEP Species=Brassica olercea Length=287 [SEQ ID No. 73]
MNTFPASTEMVSSENESPVTTVVGGDYYPMLAASCPKKPAGRKKFQETRHPIYRGVRLRK
SGKWVCEVRELNKKSRIWLGTFKTAEMAARAHDVAALALRGRGACLNYADSAWRLRIPET
TCHKDIQKAAAEAALAFEAEKSDATMQNGLNMEETTAAASQTEVSDTTTDHGMNMEETTA
VASQAEVNDTTTDHGVDMEETMVEAVFTEEQSEGFNMAKESTAEAAVVTEELSKGVYMDE
EWTYEMPTLLADMAAGMLLPPPSVQWGHNDDLEGDADMNLLELLRIR

BRCBF1-PEP Species=Brassica rapa Length=124 [SEQ ID No. 75]
HPIYRGVRLRKSGKWVCEVREPNKKSRIWLGTFKTAEIAARAHDVAALALRGRGACLNFA
DSAWRLRIPETTCAKDIQKAAAEAALAFEAEKSDHGMNIKNTTAVVSQVEVNDTTTDHGL
DMEE

BRCBF2-PEP Species=Brassica rapa Length=280 [SEQ ID No. 77]
MNTFPASTEMVGSENESPVTTVAGGDYYPMLAASCPKKPAGRKKFQETRHPIYRGVRLRK
SGKWVCEVREPNKKSRIWLGTFKTAEMAARAHDVAALALRGRGACLNYADSAWRLRIPET
TCHKDIQKAAAEAALAFEAEKSDVTMQNGLNMEEMTAVASQAEVNDTTTEHGMNMEEATA
VASQAEVNDTTTDHGVDMEETMVEAVFTEEQSEGFNMAKESTVEAAVVTEEPSKGSYMDE
EWMLEMPTLLADMAEGMLLPPPSVQWGQNDDFEGDADMNL

BRCBF3-PEP Species=Brassica rapa Length=204 [SEQ ID No. 79]
MNSVSTFSELLCSENESPVNTEGGDYILAASCPKKPAGRKKFQETRHPIYRGVRLRKSGK
WVCEVREPNKKSRIWLGTFKTAEIAARAHDVAALALRGRGACLNFADSAWRLRIPETTCA
KDIQKAAAEAALAFEAEKSDTTTNDRGMNMEETSAVASPAELNDTTADHGLDMEETMVEA
VFREEQREGFYMAEETTVEGVVPE FIGURE 18B-continued

BRCBF4-PEP Species=Brassica rapa Length=112 [SEQ ID No. 81]
MDSISTFPELLGSENESPVTTVVGGDYCPRLAASCPKKPAGRKKFQETRHPIYRGVRLRK
SGKWVCEVREPNKKSRIWLGTFKTAEIAARAHDVAALALRGRGACLNFADSA

BRCBF5-PEP Species=Brassica rapa Length=255 [SEQ ID No. 83]
MDSISTFPELLGSENESPVTTVVGGDYCPRLAASCPKKPAGRKKFQETRHPIYRGVRLRK
SGKWVCEVREPNKKSRIWLGTFKTAEIAARAHDVAALALRGRGACLNFADSAWRLRIPET
TCAKDIQKAAAEAALAFEAEKSDHGMNMKNTTAVASQVEVNDTTTDHGVDMEETLVEAVF
TEEQREGFYMTEETRVEGVVTEEQNNWFYMDEEWMFGMPTLLVDMAEGMLIPRQSVQSGH
YDDFEGDADMNLWNY

BRCBF6-PEP Species=Brassica rapa Length=258 [SEQ ID No. 85]
MNSVSTFSELLCSENKSPVNTEGGDYILAASCPKKPAGRKKFQETRHPIYRGVRLRKSGK
WVCEVREPNKKSRIWLGTFKTAEIAARAHDVAALALRGRGACLNFADSAWRLRIPETTCA
KDIQKAAAEAALAFEAEKSDTTTNDRGMNMEETSAVASPAELNDTTADHGLDMEETMVEA
VFRDEQREGFYMAEETTVEGVVPEEQMSKGFYMDEEWTFEMPRLLADMAEGMLLPPPSVQ
WGHNDDFEGDADMNLWNY

BRCBF7-PEP Species=Brassica rapa Length=251 [SEQ ID No. 87]
MNSVSTLSEVLGSQNESPVGGDYCPMLAASCPKKPAGRKKFRETRHPIYRGVRLRKSGKW
VCEVREPNKKSRIWLGTFKTAEIAARAHDVAALALRGRGACLNFADSAWRLRIPETTCAK
DIQKAAAEAALAFEAEKSDTTTTNDHGMNMASQVEVNDTTDHDLDMEETMVEAVFREEQR
EGFYMAEETTVEGIVPEEQMSKGFYMDEEWMFGMPTLLADMAAGMLLPPPSVQWGHNDDF
EGDADMNLWNY

GMCBF1-PEP Species=Glycine max Length=170 [SEQ ID No. 89]
HPIYSGVRRRNTDKWVSEVREPNKKTRIWLGTFPTPEMAARAHDVAAMALRGRYACLNFA
DSTWRLPIPATANAKDIQKAAAEAAEAFRPSQTLENTNTKQECVKVVTTTTITEQKRGMF
YTEEEEQVLDMPELLRNMVLMSPTHCIGYEYEDADLDAQDAEVSLWSFSI

RSCBF1-PEP Species=Raphanus sativus Length=252 [SEQ ID No. 91]
MDSISTFSELLGSENESPVTTVVGGDYFPRLAASCPKKPAGRKKFQETRHPIYRGVRLRK
SGKWVCEVREPNKKSRIWLGTFKTAEIAARAHDVAALALRGRGACLNFADSAWRLRIPET
TCAKDIQKAAAEAALAFEAEKSDHGMNMKNTTAVASQVEVNDTTTDHGVDMEETLVEAVF
TEEQREGFYMTEETRVEGVVTEEQNNWFYMDEEWMFGMPTLLVDMAEGMLLPRPSVQSGH
YDDFEGDADMNL

RSCBF2-PEP Species=Raphanus sativus Length=209 [SEQ ID No. 93]
MTTFSTFSEMLGSEYESPVTLGGEYCPKLAASCPKKPAGRKKFRETRHPIYRGVRLRNSG
KWVCEVREPNKKSRIWLGTFLTAEIAARAHDVAAIALRGKSACLNFADSAWRLRIPETTC
PKDIQKAAAEAAVAFQAEINDTTTDHGLDLEETIVEAIFTEVNNDEFYMDEESMFGMPSL
LASMAEGMLLPLPSVQSEHNCDFDGDADM

ZMCBF1-PEP Species=Zea maize Length=115 [SEQ ID No. 95]
ESADGGGGGDDEYATVLSAPPKRPAGRTKFRETRHPVYRGVRRRGPAGRWVCEVREPNKK
SRIWLGTFATPEAAARAHDVAALALRGRAACLNFADSARLLQVDPATLATPDDIR

FIGURE 19A

```
                        1                                                         50         64
AP2{SEQ ID NO:103}  HPiYrGVRqR .nsgkWVcEl REpNKk.tRI WIGTFqTaEm AARAHDVAAi ALRGrsAcLN fADS
AP2{SEQ ID NO:104}  HPiYrGVRrR .nsgkWVcEv REpNKk.tRI WIGTFqTaEm AARAHDVAAl ALRGrsAcLN fADS
AP2{SEQ ID NO:105}  HPiYrGVRqR .nsgkWVsEv REpNKk.tRI WIGTFqTaEm AARAHDVAAl ALRGrsAcLN fADS
AP2{SEQ ID NO:106}  HPiYrGVRqR .nsgkWVcEv REpNKk.sRI WIGTFpTvEm AARAHDVAAl ALRGrsAcLN fADS
AP2{SEQ ID NO:107}  HPvYrGVRIR .nsgkWVcEv RepNKk.sRI WIGTFITaEi AARAHDVAAi ALRGksACLN fADS
AP2{SEQ ID NO:108}  HPiYrGVRIR .nsgkWVcEv REpNKk.sRI WIGTFlTaEi AARAHDVAAi ALRGksAcLN fADS
AP2{SEQ ID NO:109}  HPiYrGVRIR .ksgkWVcEv RepNKr.sRI WIGTFITaEi AARAHDVAAi ALRGksAcLN fADS
AP2{SEQ ID NO:110}  HPiYrGVRIR .ksgkWVcEv RepNKk.sRI WIGTFITaEi AARAHDVAAi ALRGksAcLN fADS
AP2{SEQ ID NO:111}  HPiYrGVRIR .ksgkWVcEv RepNKk.sRI WpGTFITaEi AARAHDVAAi ALRGksAcLN fADS
AP2{SEQ ID NO:112}  HPiYrGVRIR .ksgkWVcEv REpNKk.sRI WpGTFkTaEm AARAHDVAAl ALRGrgAcLN yADS
AP2{SEQ ID NO:113}  HPiYrGVRIR .ksgkWVcEv REpNKk.sRI WpGTFkTaEm AARAHDVAAl ALRGrgAcLN yADS
AP2{SEQ ID NO:114}  HPiYrGVRIR .ksgkWVcEv REpNKk.sRI WIGTFkTaEm AARAHDVAAl ALRGrgAcLN yADS
AP2{SEQ ID NO:115}  HPiYrGVRIR .ksgkWVcEv REpNKk.sRI WIGTFkTaEm AARAHDVAAl ALRGrgAcLN yADS
AP2{SEQ ID NO:116}  HPiYrGVRIR .ksgkWVcEv REpNKk.sRI WIGTFkTaEm AARAHDVAAl ALRGrgAcLN yADS
AP2{SEQ ID NO:117}  HPiYrGVRIR .ksgkWVcEv REpNKk.sRI WIGTFkTaEm AARAHDVAAl ALRGrgAcLN yADS
AP2{SEQ ID NO:118}  HPiYrGVRIR .ksgkWVcEv REpNKk.sRI WIGTFkTaEm AARAHDVAAl ALRGrgAcLN yADS
AP2{SEQ ID NO:119}  HPiYrGVRIR .ksgkWVcEv REpNKk.sRI WIGTFkTaEi AARAHDVAAl ALRGrgAcLN fADS
AP2{SEQ ID NO:120}  HPiYrGVRIR .ksgkWVcEv REpNKk.sRI WIGTFkTaEi AARAHDVAAl ALRGrgAcLN fADS
AP2{SEQ ID NO:121}  HPiYrGVRIR .ksgkWVcEv REpNKk.sRI WIGTFkTaEi AARAHDVAAl ALRGrgAcLN fADS
AP2{SEQ ID NO:122}  HPiYrGVRIR .ksgkWVcEv REpNKk.sRI WIGTFkTaEi AARAHDVAAl ALRGrgAcLN fADS
AP2{SEQ ID NO:123}  HPiYrGVRIR .ksgkWVcEv REpNKk.sRI WIGTFkTaEi AARAHDVAAl ALRGrgAcLN fADS
AP2{SEQ ID NO:124}  HPiYrGVRIR .ksgkWVcEv REpNKk.sRI WIGTFkTaEi AARAHDVAAl ALRGrgAcLN fADS
AP2{SEQ ID NO:125}  HPiYrGVRIR .ksgkWVcEv REpNKk.sRI WIGTFkTaEi AARAHDVAAl ALRGrgAcLN fADS
AP2{SEQ ID NO:126}  HPiYrGVRIR .ksgkWVcEv REpNKk.sRI WIGTFkTaEi AARAHDVAAl ALRGrgAcLN fADS
AP2{SEQ ID NO:127}  HPiYrGVRIR .ksgkWVcEv REpNKk.sRI WIGTFkTaEi AARAHDVAAl ALRGrgAcLN fADS
AP2{SEQ ID NO:128}  HPiYrGVRIR .ksgkWVcEv REpNKk.sRI WIGTFkTaEi AARAHDVAAl ALRGrgAcLN fADS
AP2{SEQ ID NO:129}  HPiYrGVRIR .ksgkWVcEv REpNKk.sRI WIGTFkTaEi AARAHDVAAl ALRGraAcLN fADS
AP2{SEQ ID NO:130}  HPiYrGVRIR .ksgkWVcEv REINKk.sRI WIGTFkTaEm AARAHDVAAl ALRGrgAcLN yADS
AP2{SEQ ID NO:131}  HPiYrGVRIR .ksgkWVcEv REpNKk.sRI WpGTFkTaEm AARAHDVAAl ALRGrgArLN yADS
AP2{SEQ ID NO:132}  HpvYrGVRrR gpagrWVcEv REpNKk.sRI WIGTFaTpEa AARAHDVAAl ALRGraAcLN fADS
AP2{SEQ ID NO:133}  HpiYsGVR.R rntdkWVsEv REpNKk.tRI WIGTFpTpEm AARAHDVAAm ALRGryAcLN fADS
Consensus           HP-Y-GVR-R -----WV-E- RE-NK---RI W-GTF-T-E- AARAHDVAA- ALRG--A-LN -ADS

ap2{SEQ ID NO:134}  GrhYrGVRqR p.wgkfaaEi RdpaKngaRv WIGTyeTaEe AAIAyDkAAy rmRGskAILN Fphr
```

FIGURE 19B

```
                      1                                                   50          64
AP2{SEQ ID NO:103}    HPiYrGVRqR .nsgkWVcEl REpNKk.tRI WIGTFqTaEm AARAHDVAAi ALRGrsAcLN fADS
AP2{SEQ ID NO:104}    HPiYrGVRrR .nsgkWVcEv REpNKk.tRI WIGTFqTaEm AARAHDVAAl ALRGrsAcLN fADS
AP2{SEQ ID NO:105}    HPiYrGVRqR .nsgkWVsEv REpNKk.tRI WIGTFqTaEm AARAHDVAAl ALRGrsAcLN fADS
AP2{SEQ ID NO:106}    HPiYrGVRqR .nsgkWVcEv REpNKk.sRI WIGTFpTvEm AARAHDVAAl ALRGrsAcLN fADS
AP2{SEQ ID NO:107}    HPvYrGVRIR .nsgkWVcEv RepNKk.sRI WIGTFITaEi AARAHDVAAi ALRGksACLN fADS
AP2{SEQ ID NO:108}    HPiYrGVRIR .nsgkWVcEv REpNKk.sRI WIGTFlTaEi AARAHDVAAi ALRGksAcLN fADS
AP2{SEQ ID NO:109}    HPiYrGVRIR .ksgkWVcEv RepNKr.sRI WIGTFITaEi AARAHDVAAi ALRGksAcLN fADS
AP2{SEQ ID NO:110}    HPiYrGVRIR .ksgkWVcEv RepNKk.sRI WIGTFITaEi AARAHDVAAi ALRGksAcLN fADS
AP2{SEQ ID NO:111}    HPiYrGVRIR .ksgkWVcEv RepNKk.sRI WpGTFITaEi AARAHDVAAi ALRGksAcLN fADS
AP2{SEQ ID NO:112}    HPiYrGVRIR .ksgkWVcEv REpNKk.sRI WpGTFkTaEm AARAHDVAAl ALRGrgAcLN yADS
AP2{SEQ ID NO:113}    HPiYrGVRIR .ksgkWVcEv REpNKk.sRI WpGTFkTaEm AARAHDVAAl ALRGrgAcLN yADS
AP2{SEQ ID NO:114}    HPiYrGVRIR .ksgkWVcEv REpNKk.sRI WIGTFkTaEm AARAHDVAAl ALRGrgAcLN yADS
AP2{SEQ ID NO:115}    HPiYrGVRIR .ksgkWVcEv REpNKk.sRI WIGTFkTaEm AARAHDVAAl ALRGrgAcLN yADS
AP2{SEQ ID NO:116}    HPiYrGVRIR .ksgkWVcEv REpNKk.sRI WIGTFkTaEm AARAHDVAAl ALRGrgAcLN yADS
AP2{SEQ ID NO:117}    HPiYrGVRIR .ksgkWVcEv REpNKk.sRI WIGTFkTaEm AARAHDVAAl ALRGrgAcLN yADS
AP2{SEQ ID NO:118}    HPiYrGVRIR .ksgkWVcEv REpNKk.sRI WIGTFkTaEm AARAHDVAAl ALRGrgAcLN yADS
AP2{SEQ ID NO:119}    HPiYrGVRIR .ksgkWVcEv REpNKk.sRI WIGTFkTaEi AARAHDVAAl ALRGrgAcLN fADS
AP2{SEQ ID NO:120}    HPiYrGVRIR .ksgkWVcEv REpNKk.sRI WIGTFkTaEi AARAHDVAAl ALRGrgAcLN fADS
AP2{SEQ ID NO:121}    HPiYrGVRIR .ksgkWVcEv REpNKk.sRI WIGTFkTaEi AARAHDVAAl ALRGrgAcLN fADS
AP2{SEQ ID NO:122}    HPiYrGVRIR .ksgkWVcEv REpNKk.sRI WIGTFkTaEi AARAHDVAAl ALRGrgAcLN fADS
AP2{SEQ ID NO:123}    HPiYrGVRIR .ksgkWVcEv REpNKk.sRI WIGTFkTaEi AARAHDVAAl ALRGrgAcLN fADS
AP2{SEQ ID NO:124}    HPiYrGVRIR .ksgkWVcEv REpNKk.sRI WIGTFkTaEi AARAHDVAAl ALRGrgAcLN fADS
AP2{SEQ ID NO:125}    HPiYrGVRIR .ksgkWVcEv REpNKk.sRI WIGTFkTaEi AARAHDVAAl ALRGrgAcLN fADS
AP2{SEQ ID NO:126}    HPiYrGVRIR .ksgkWVcEv REpNKk.sRI WIGTFkTaEi AARAHDVAAl ALRGrgAcLN fADS
AP2{SEQ ID NO:127}    HPiYrGVRIR .ksgkWVcEv REpNKk.sRI WIGTFkTaEi AARAHDVAAl ALRGrgAcLN fADS
AP2{SEQ ID NO:128}    HPiYrGVRIR .ksgkWVcEv REpNKk.sRI WIGTFkTaEi AARAHDVAAl ALRGrgAcLN fADS
AP2{SEQ ID NO:129}    HPiYrGVRIR .ksgkWVcEv REpNKk.sRI WIGTFkTaEi AARAHDVAAl ALRGraAcLN fADS
AP2{SEQ ID NO:130}    HPiYrGVRIR .ksgkWVcEv REINKk.sRI WIGTFkTaEm AARAHDVAAl ALRGrgAcLN yADS
AP2{SEQ ID NO:131}    HPiYrGVRIR .ksgkWVcEv REpNKk.sRI WpGTFkTaEm AARAHDVAAl ALRGrgArLN yADS
AP2{SEQ ID NO:132}    HpvYrGVRrR gpagrWVcEv REpNKk.sRI WIGTFaTpEa AARAHDVAAl ALRGraAcLN fADS
AP2{SEQ ID NO:133}    HpiYsGVR.R rntdkWVsEv REpNKk.tRI WIGTFpTpEm AARAHDVAAm ALRGryAcLN fADS

ap2{SEQ ID NO:135}    rcsfrGVRqR i.wgkWVaEi REpnrg.sRl WIGTFpTaqe AasAyDeAAk AmyGplArLN fprS
ap2{SEQ ID NO:136}    hcsfrGVRqR i.wgkWVaEi REpkig.tRl WIGTFpTaek AAsAyDeAAt AmyGsIArLN fpqS
Consensus             -----GVR-R -----WV-E- RE------RI W-GTF-T--- AA-A-D-AA- A--G--A-LN ---S
```

FIGURE 19C

```
                     1                                                   50          64
AP2{SEQ ID NO:103}   HPiYrGVRqR .nsgkWVcEl REpNKk.tRI WIGTFqTaEm AARAHDVAAi ALRGrsAcLN fADS
AP2{SEQ ID NO:104}   HPiYrGVRrR .nsgkWVcEv REpNKk.tRI WIGTFqTaEm AARAHDVAAl ALRGrsAcLN fADS
AP2{SEQ ID NO:105}   HPiYrGVRqR .nsgkWVsEv REpNKk.tRI WIGTFqTaEm AARAHDVAAl ALRGrsAcLN fADS
AP2{SEQ ID NO:106}   HPiYrGVRqR .nsgkWVcEv REpNKk.sRI WIGTFpTvEm AARAHDVAAl ALRGrsAcLN fADS
AP2{SEQ ID NO:107}   HPvYrGVRIR .nsgkWVcEv RepNKk.sRI WIGTFITaEi AARAHDVAAi ALRGksACLN fADS
AP2{SEQ ID NO:108}   HPiYrGVRIR .nsgkWVcEv REpNKk.sRI WIGTFlTaEi AARAHDVAAi ALRGksAcLN fADS
AP2{SEQ ID NO:109}   HPiYrGVRIR .ksgkWVcEv RepNKr.sRI WIGTFITaEi AARAHDVAAi ALRGksAcLN fADS
AP2{SEQ ID NO:110}   HPiYrGVRIR .ksgkWVcEv RepNKk.sRI WIGTFITaEi AARAHDVAAi ALRGksAcLN fADS
AP2{SEQ ID NO:111}   HPiYrGVRIR .ksgkWVcEv RepNKk.sRI WpGTFITaEi AARAHDVAAi ALRGksAcLN fADS
AP2{SEQ ID NO:112}   HPiYrGVRIR .ksgkWVcEv REpNKk.sRI WpGTFkTaEm AARAHDVAAl ALRGrgAcLN yADS
AP2{SEQ ID NO:113}   HPiYrGVRIR .ksgkWVcEv REpNKk.sRI WpGTFkTaEm AARAHDVAAl ALRGrgAcLN yADS
AP2{SEQ ID NO:114}   HPiYrGVRIR .ksgkWVcEv REpNKk.sRI WIGTFkTaEm AARAHDVAAl ALRGrgAcLN yADS
AP2{SEQ ID NO:115}   HPiYrGVRIR .ksgkWVcEv REpNKk.sRI WIGTFkTaEm AARAHDVAAl ALRGrgAcLN yADS
AP2{SEQ ID NO:116}   HPiYrGVRIR .ksgkWVcEv REpNKk.sRI WIGTFkTaEm AARAHDVAAl ALRGrgAcLN yADS
AP2{SEQ ID NO:117}   HPiYrGVRIR .ksgkWVcEv REpNKk.sRI WIGTFkTaEm AARAHDVAAl ALRGrgAcLN yADS
AP2{SEQ ID NO:118}   HPiYrGVRIR .ksgkWVcEv REpNKk.sRI WIGTFkTaEm AARAHDVAAl ALRGrgAcLN yADS
AP2{SEQ ID NO:119}   HPiYrGVRIR .ksgkWVcEv REpNKk.sRI WIGTFkTaEi AARAHDVAAl ALRGrgAcLN fADS
AP2{SEQ ID NO:120}   HPiYrGVRIR .ksgkWVcEv REpNKk.sRI WIGTFkTaEi AARAHDVAAl ALRGrgAcLN fADS
AP2{SEQ ID NO:121}   HPiYrGVRIR .ksgkWVcEv REpNKk.sRI WIGTFkTaEi AARAHDVAAl ALRGrgAcLN fADS
AP2{SEQ ID NO:122}   HPiYrGVRIR .ksgkWVcEv REpNKk.sRI WIGTFkTaEi AARAHDVAAl ALRGrgAcLN fADS
AP2{SEQ ID NO:123}   HPiYrGVRIR .ksgkWVcEv REpNKk.sRI WIGTFkTaEi AARAHDVAAl ALRGrgAcLN fADS
AP2{SEQ ID NO:124}   HPiYrGVRIR .ksgkWVcEv REpNKk.sRI WIGTFkTaEi AARAHDVAAl ALRGrgAcLN fADS
AP2{SEQ ID NO:125}   HPiYrGVRIR .ksgkWVcEv REpNKk.sRI WIGTFkTaEi AARAHDVAAl ALRGrgAcLN fADS
AP2{SEQ ID NO:126}   HPiYrGVRIR .ksgkWVcEv REpNKk.sRI WIGTFkTaEi AARAHDVAAl ALRGrgAcLN fADS
AP2{SEQ ID NO:127}   HPiYrGVRIR .ksgkWVcEv REpNKk.sRI WIGTFkTaEi AARAHDVAAl ALRGrgAcLN fADS
AP2{SEQ ID NO:128}   HPiYrGVRIR .ksgkWVcEv REpNKk.sRI WIGTFkTaEi AARAHDVAAl ALRGrgAcLN fADS
AP2{SEQ ID NO:129}   HPiYrGVRIR .ksgkWVcEv REpNKk.sRI WIGTFkTaEi AARAHDVAAl ALRGraAcLN fADS
AP2{SEQ ID NO:130}   HPiYrGVRIR .ksgkWVcEv REINKk.sRI WIGTFkTaEm AARAHDVAAl ALRGrgAcLN yADS
AP2{SEQ ID NO:131}   HPiYrGVRIR .ksgkWVcEv REpNKk.sRI WpGTFkTaEm AARAHDVAAl ALRGrgArLN yADS
AP2{SEQ ID NO:132}   HpvYrGVRrR gpagrWVcEv REpNKk.sRI WIGTFaTpEa AARAHDVAAl ALRGraAcLN fADS
AP2{SEQ ID NO:133}   HpiYsGVR.R rntdkWVsEv REpNKk.tRI WIGTFpTpEm AARAHDVAAm ALRGryAcLN fADS

AP2{SEQ ID NO:135}   rcsfrGVRqR i.wgkWVaEi REpnrg.sRl WIGTFpTaqe AasAyDeAAk AmyGplArLN fprS
AP2{SEQ ID NO:136}   hcsfrGVRqR i.wgkWVaEi REpkig.tRl WIGTFpTaek AAsAyDeAAt AmyGsIArLN fpqS
AP2{SEQ ID NO:137}   hPvyrGVRkR .nwgkWVsEi REprKk.sRI.WIGTFpspem AArAhDvAAl sikGasAiLN fpDl
Consensus            -----GVR-R ----WV-E- RE------RI W-GTF----- AA-A-D-AA- ---G--A-LN ----
```

FIGURE 19D

```
                     1                                                                  50            64
AP2{SEQ ID NO:103}   HPiYrGVRqR .nsgkWVcEl REpNKk.tRI WIGTFqTaEm AARAHDVAAi ALRGrsAcLN fADS
AP2{SEQ ID NO:104}   HPiYrGVRrR .nsgkWVcEv REpNKk.tRI WIGTFqTaEm AARAHDVAAl ALRGrsAcLN fADS
AP2{SEQ ID NO:105}   HPiYrGVRqR .nsgkWVsEv REpNKk.tRI WIGTFqTaEm AARAHDVAAl ALRGrsAcLN fADS
AP2{SEQ ID NO:106}   HPiYrGVRqR .nsgkWVcEv REpNKk.sRI WIGTFpTvEm AARAHDVAAl ALRGrsAcLN fADS
AP2{SEQ ID NO:107}   HPvYrGVRIR .nsgkWVcEv RepNKk.sRI WIGTFITaEi AARAHDVAAi ALRGksACLN fADS
AP2{SEQ ID NO:108}   HPiYrGVRIR .nsgkWVcEv REpNKk.sRI WIGTFlTaEi AARAHDVAAi ALRGksAcLN fADS
AP2{SEQ ID NO:109}   HPiYrGVRIR .ksgkWVcEv RepNKr.sRI WIGTFITaEi AARAHDVAAi ALRGksAcLN fADS
AP2{SEQ ID NO:110}   HPiYrGVRIR .ksgkWVcEv RepNKk.sRI WIGTFITaEi AARAHDVAAi ALRGksAcLN fADS
AP2{SEQ ID NO:111}   HPiYrGVRIR .ksgkWVcEv RepNKk.sRI WpGTFITaEi AARAHDVAAi ALRGksAcLN fADS
AP2{SEQ ID NO:112}   HPiYrGVRIR .ksgkWVcEv REpNKk.sRI WpGTFkTaEm AARAHDVAAl ALRGrgAcLN yADS
AP2{SEQ ID NO:113}   HPiYrGVRIR .ksgkWVcEv REpNKk.sRI WpGTFkTaEm AARAHDVAAl ALRGrgAcLN yADS
AP2{SEQ ID NO:114}   HPiYrGVRIR .ksgkWVcEv REpNKk.sRI WIGTFkTaEm AARAHDVAAl ALRGrgAcLN yADS
AP2{SEQ ID NO:115}   HPiYrGVRIR .ksgkWVcEv REpNKk.sRI WIGTFkTaEm AARAHDVAAl ALRGrgAcLN yADS
AP2{SEQ ID NO:116}   HPiYrGVRIR .ksgkWVcEv REpNKk.sRI WIGTFkTaEm AARAHDVAAl ALRGrgAcLN yADS
AP2{SEQ ID NO:117}   HPiYrGVRIR .ksgkWVcEv REpNKk.sRI WIGTFkTaEm AARAHDVAAl ALRGrgAcLN yADS
AP2{SEQ ID NO:118}   HPiYrGVRIR .ksgkWVcEv REpNKk.sRI WIGTFkTaEm AARAHDVAAl ALRGrgAcLN yADS
AP2{SEQ ID NO:119}   HPiYrGVRIR .ksgkWVcEv REpNKk.sRI WIGTFkTaEi AARAHDVAAl ALRGrgAcLN fADS
AP2{SEQ ID NO:120}   HPiYrGVRIR .ksgkWVcEv REpNKk.sRI WIGTFkTaEi AARAHDVAAl ALRGrgAcLN fADS
AP2{SEQ ID NO:121}   HPiYrGVRIR .ksgkWVcEv REpNKk.sRI WIGTFkTaEi AARAHDVAAl ALRGrgAcLN fADS
AP2{SEQ ID NO:122}   HPiYrGVRIR .ksgkWVcEv REpNKk.sRI WIGTFkTaEi AARAHDVAAl ALRGrgAcLN fADS
AP2{SEQ ID NO:123}   HPiYrGVRIR .ksgkWVcEv REpNKk.sRI WIGTFkTaEi AARAHDVAAl ALRGrgAcLN fADS
AP2{SEQ ID NO:124}   HPiYrGVRIR .ksgkWVcEv REpNKk.sRI WIGTFkTaEi AARAHDVAAl ALRGrgAcLN fADS
AP2{SEQ ID NO:125}   HPiYrGVRIR .ksgkWVcEv REpNKk.sRI WIGTFkTaEi AARAHDVAAl ALRGrgAcLN fADS
AP2{SEQ ID NO:126}   HPiYrGVRIR .ksgkWVcEv REpNKk.sRI WIGTFkTaEi AARAHDVAAl ALRGrgAcLN fADS
AP2{SEQ ID NO:127}   HPiYrGVRIR .ksgkWVcEv REpNKk.sRI WIGTFkTaEi AARAHDVAAl ALRGrgAcLN fADS
AP2{SEQ ID NO:128}   HPiYrGVRIR .ksgkWVcEv REpNKk.sRI WIGTFkTaEi AARAHDVAAl ALRGrgAcLN fADS
AP2{SEQ ID NO:129}   HPiYrGVRIR .ksgkWVcEv REpNKk.sRI WIGTFkTaEi AARAHDVAAl ALRGraAcLN fADS
AP2{SEQ ID NO:130}   HPiYrGVRIR .ksgkWVcEv REINKk.sRI WIGTFkTaEm AARAHDVAAl ALRGrgAcLN yADS
AP2{SEQ ID NO:131}   HPiYrGVRIR .ksgkWVcEv REpNKk.sRI WpGTFkTaEm AARAHDVAAl ALRGrgArLN yADS
AP2{SEQ ID NO:132}   HpvYrGVRrR gpagrWVcEv REpNKk.sRI WIGTFaTpEa AARAHDVAAl ALRGraAcLN fADS
AP2{SEQ ID NO:133}   HpiYsGVR.R rntdkWVsEv REpNKk.tRI WIGTFpTpEm AARAHDVAAm ALRGryAcLN fADS
Consensus            HP-Y-GVR-R -----WV-E- RE-NK---RI W-GTF-T-E- AARAHDV~A- ALRG--A-LN -ADS

AP2{SEQ ID NO:137}   hPvyrGVRkR .nwgkWVsEi REprKk.sRI.WIGTFpspem AArAhDvAAl sikGasAiLN fpDl
Consensus
-AP2{SEQ ID NO:137}  ---------- ---------- ---N------ ------T--- ---------- ALR------- -A-S
```

FIGURE 19E

```
                     1                                                        50          64
AP2{SEQ ID NO:103}   HPiYrGVRqR .nsgkWVcEl REpNKk.tRI WIGTFqTaEm AARAHDVAAi ALRGrsAcLN fADS
AP2{SEQ ID NO:104}   HPiYrGVRrR .nsgkWVcEv REpNKk.tRI WIGTFqTaEm AARAHDVAAl ALRGrsAcLN fADS
AP2{SEQ ID NO:105}   HPiYrGVRqR .nsgkWVsEv REpNKk.tRI WIGTFqTaEm AARAHDVAAl ALRGrsAcLN fADS
AP2{SEQ ID NO:106}   HPiYrGVRqR .nsgkWVcEv REpNKk.sRI WIGTFpTvEm AARAHDVAAl ALRGrsAcLN fADS
AP2{SEQ ID NO:107}   HPvYrGVRIR .nsgkWVcEv RepNKk.sRI WIGTFITaEi AARAHDVAAi ALRGksACLN fADS
AP2{SEQ ID NO:108}   HPiYrGVRIR .nsgkWVcEv REpNKk.sRI WIGTFlTaEi AARAHDVAAi ALRGksAcLN fADS
AP2{SEQ ID NO:109}   HPiYrGVRIR .ksgkWVcEv RepNKr.sRI WIGTFITaEi AARAHDVAAi ALRGksAcLN fADS
AP2{SEQ ID NO:110}   HPiYrGVRIR .ksgkWVcEv RepNKk.sRI WIGTFITaEi AARAHDVAAi ALRGksAcLN fADS
AP2{SEQ ID NO:111}   HPiYrGVRIR .ksgkWVcEv RepNKk.sRI WpGTFITaEi AARAHDVAAi ALRGksAcLN fADS
AP2{SEQ ID NO:112}   HPiYrGVRIR .ksgkWVcEv REpNKk.sRI WpGTFkTaEm AARAHDVAAl ALRGrgAcLN yADS
AP2{SEQ ID NO:113}   HPiYrGVRIR .ksgkWVcEv REpNKk.sRI WpGTFkTaEm AARAHDVAAl ALRGrgAcLN yADS
AP2{SEQ ID NO:114}   HPiYrGVRIR .ksgkWVcEv REpNKk.sRI WIGTFkTaEm AARAHDVAAl ALRGrgAcLN yADS
AP2{SEQ ID NO:115}   HPiYrGVRIR .ksgkWVcEv REpNKk.sRI WIGTFkTaEm AARAHDVAAl ALRGrgAcLN yADS
AP2{SEQ ID NO:116}   HPiYrGVRIR .ksgkWVcEv REpNKk.sRI WIGTFkTaEm AARAHDVAAl ALRGrgAcLN yADS
AP2{SEQ ID NO:117}   HPiYrGVRIR .ksgkWVcEv REpNKk.sRI WIGTFkTaEm AARAHDVAAl ALRGrgAcLN yADS
AP2{SEQ ID NO:118}   HPiYrGVRIR .ksgkWVcEv REpNKk.sRI WIGTFkTaEm AARAHDVAAl ALRGrgAcLN yADS
AP2{SEQ ID NO:119}   HPiYrGVRIR .ksgkWVcEv REpNKk.sRI WIGTFkTaEi AARAHDVAAl ALRGrgAcLN fADS
AP2{SEQ ID NO:120}   HPiYrGVRIR .ksgkWVcEv REpNKk.sRI WIGTFkTaEi AARAHDVAAl ALRGrgAcLN fADS
AP2{SEQ ID NO:121}   HPiYrGVRIR .ksgkWVcEv REpNKk.sRI WIGTFkTaEi AARAHDVAAl ALRGrgAcLN fADS
AP2{SEQ ID NO:122}   HPiYrGVRIR .ksgkWVcEv REpNKk.sRI WIGTFkTaEi AARAHDVAAl ALRGrgAcLN fADS
AP2{SEQ ID NO:123}   HPiYrGVRIR .ksgkWVcEv REpNKk.sRI WIGTFkTaEi AARAHDVAAl ALRGrgAcLN fADS
AP2{SEQ ID NO:124}   HPiYrGVRIR .ksgkWVcEv REpNKk.sRI WIGTFkTaEi AARAHDVAAl ALRGrgAcLN fADS
AP2{SEQ ID NO:125}   HPiYrGVRIR .ksgkWVcEv REpNKk.sRI WIGTFkTaEi AARAHDVAAl ALRGrgAcLN fADS
AP2{SEQ ID NO:126}   HPiYrGVRIR .ksgkWVcEv REpNKk.sRI WIGTFkTaEi AARAHDVAAl ALRGrgAcLN fADS
AP2{SEQ ID NO:127}   HPiYrGVRIR .ksgkWVcEv REpNKk.sRI WIGTFkTaEi AARAHDVAAl ALRGrgAcLN fADS
AP2{SEQ ID NO:128}   HPiYrGVRIR .ksgkWVcEv REpNKk.sRI WIGTFkTaEi AARAHDVAAl ALRGrgAcLN fADS
AP2{SEQ ID NO:129}   HPiYrGVRIR .ksgkWVcEv REpNKk.sRI WIGTFkTaEi AARAHDVAAl ALRGraAcLN fADS
AP2{SEQ ID NO:130}   HPiYrGVRIR .ksgkWVcEv REINKk.sRI WIGTFkTaEm AARAHDVAAl ALRGrgAcLN yADS
AP2{SEQ ID NO:131}   HPiYrGVRIR .ksgkWVcEv REpNKk.sRI WpGTFkTaEm AARAHDVAAl ALRGrgArLN yADS
AP2{SEQ ID NO:132}   HpvYrGVRrR gpagrWVcEv REpNKk.sRI WIGTFaTpEa AARAHDVAAl ALRGraAcLN fADS
AP2{SEQ ID NO:133}   HpiYsGVR.R rntdkWVsEv REpNKk.tRI WIGTFpTpEm AARAHDVAAm ALRGryAcLN fADS
AP2{SEQ ID NO:135}   rcsfrGVRqR i.wgkWVaEi REpnrg.sRl WIGTFpTaqe AasAyDeAAk AmyGplArLN fprS
AP2{SEQ ID NO:136}   hcsfrGVRqR i.wgkWVaEi REpkig.tRl WIGTFpTaek AAsAyDeAAt AmyGsIArLN fpqS
Consensus            -----GVR-R -----WV-E- RE------RI W-GTF-T--- AA-A-D-AA- A--G--A-LN ---S
AP2{SEQ ID NO:137}   hPvyrGVRkR .nwgkWVsEi REprKk.sRI.WIGTFpspem AArAhDvAAl sikGasAiLN fpdl
Consensus
-AP2{SEQ ID NO:137}  ---------- ---------- ---------- ------T--- ---------- A--------- ---S
```

FIGURE 20

```
                  1                                                49
N{SEQ ID NO:138} MnsvstfsEl lcSenespvn te.GgdY..i LAaSCPKKPA GRKKFqETR
N{SEQ ID NO:139} MnsvstfsEl lcSenkspvn te.GgdY.:i LAaSCPKKPA GRKKFqETR
N{SEQ ID NO:140} MnsvstfsEl lrSenespvn te.GgdY..i LAaSCPKKPA GRKKFqETR
N{SEQ ID NO:141} MnsfsafsEm fgSdyespvs s..GgdYspk LAtSCPKKPA GRKKFrETR
N{SEQ ID NO:142} MnsfsafsEm fgSdyessvs s..GgdYipt LAsSCPKKPA GRKKFrETR
N{SEQ ID NO:143} MnsfsafsEm fgSdye...p q..GgdYcpt LAtSCPKKPA GRKKFrETR
N{SEQ ID NO:144} MntfpastEm vgSenespvt tvvGgdYypm LAaSCPKKPA GRKKFqETR
N{SEQ ID NO:145} MntfpastEm vgSenespvt tVVGgdYypm LAaSCPKKPA GRKKFqETR
N{SEQ ID NO:146} MntfpastEm vgSenespvt tVVGgdYypm LAaSCPKKPA GRKKFqETR
N{SEQ ID NO:147} MntfpastEm vgSenespvt tvaGgdYypm LAaSCPKKPA GRKKFqETR
N{SEQ ID NO:148} MntfpastEm vgSenespvt tvaGgdYypm LAaSCPKKPA GRKKFqETR
N{SEQ ID NO:149} MntfpastEm vgSenespvt tvaGgdYypm LAaSCPKKPA GRKKFqETR
N{SEQ ID NO:150} MntfpastEm vgSenespvt tvaGgdYypm LAaSCPKKPA GRKKFqETR
N{SEQ ID NO:151} MntfpastEm vsSenespvt tVVGgdYypm LAaSCPKKPA GRKKFqETR
N{SEQ ID NO:152} MtsfstfsEl lgSehespvt ..lGeeYcpk LAaSCPKKPA GRKKFrETR
N{SEQ ID NO:153} MttfstfsEm lgSeyespvt ..lGgeYcpk LAaSCPKKPA GRKKFrETR
N{SEQ ID NO:154} MnsvstfsEl lgSenesp.. ..vGgdYcpm LAaSCPKKPA GRKKFrETR
N{SEQ ID NO:155} MnsvstfsEl lgSenesp.. ..vGgdYcpm LAaSCPKKPA GRKKFrETR
N{SEQ ID NO:156} MnsvstfsEl lgSenesp.. ..vGgdYcpm LAaSCPKKPA GRKKFrETR
N{SEQ ID NO:157} MnsvstlsEv lgSqnesp. ...vGgdYcpm LAaSCPKKPA GRKKFrETR
N{SEQ ID NO:158} MdsistfpEl lgSenespvt tVVGgdYcpr LAaSCPKKPA GRKKFqETR
N{SEQ ID NO:159} MdsistfpEl lgSenespvt tvvGgdYcpr LAaSCPKKPA GRKKFqETR
N{SEQ ID NO:160} MdsistfsEl lgSenespvt tvvGgdYfpr LAaSCPKKPA GRKKFqETR
Consensus        M-------E- --S------- ---G--Y--- LA-SCPKKPA GRKKF-ETR
```

FIGURE 21A

```
                  1                                                   50
C{SEQ ID NO:161}  AwRLRIpEtT ChKdIQKAAA EAAlaFeaek sdvtmqngln meettavasq
C{SEQ ID NO:162}  AwRLRIpEtT ChKdIQKAAA EAAlaFeaek sdvtmqngln meettavasq
C{SEQ ID NO:163}  AwRLRIpEtT ChKdIQKAAA EAAlaFeaek sdvtmqngln meemtavasq
C{SEQ ID NO:164}  AwRLRIpEtT ChKdIQKAAA EAAlaFeaek sdvtmqngqn meettavasq
C{SEQ ID NO:165}  AsRLRIpEtT ChKdIQKAAA EAAlaFeaek sdvt...... meetmavasq
C{SEQ ID NO:166}  AsRLRIpEtT ChKdIQKAAA EAAlaFeaek sdvt...... meetmavasq
C{SEQ ID NO:167}  AwRLRIpEtT ChKdIQKAAA EAAlaFeaek sdvt...... meetmavasq
C{SEQ ID NO:168}  AwRLRIpEtT ChKdIQKAAA EAAlaFeaek sdvtmqngln meettavasq
C{SEQ ID NO:169}  AwRLRIpEtT ChKdIQKAAA EAAlaFeaek sdatmqngln meettaaasq
C{SEQ ID NO:170}  AwRLRIpEtT CaKdIQKAAA EAAlaFeaek s......... ..........
C{SEQ ID NO:171}  AwRLRIpEtT CaKdIQKAAA EAAlaFeaek s......... ..........
C{SEQ ID NO:172}  AwRLRIpEtT CaKdIQKAAA EAAlaFeaek sd.t...... ..........
C{SEQ ID NO:173}  AwRLRIpEtT CaKdIQKAAA EAAlaFeaek sd.t...... ..........
C{SEQ ID NO:174}  AwRLRIpEtT CaKdIQKAAA EAAlaFeaek sd.t...... ..........
C{SEQ ID NO:175}  AwRLRIpEtT CaKdIQKAAA EAAlaFeaek sdtt...... ..........
C{SEQ ID NO:176}  AwRLRIpEtT CaKdIQKAAA EAAlaFeaek sd.t...... ..........
C{SEQ ID NO:177}  AwRLRIpEtT CaKdIQKAAA EAAlaFgaek sd.t...... ..........
C{SEQ ID NO:178}  AwRLRIsEtT CpKeIQKAAA EAAvaF.... .......... ..........
C{SEQ ID NO:179}  AwRLRIpEtT CpKeIQKAAA EAAvaF.... .......... ..........
C{SEQ ID NO:180}  AwRLRIpEtT CpKeIQKAAA EAAvaF.... .......... ..........
C{SEQ ID NO:181}  AwRLRIpEtT CpKdIQKAAA EAAvaF.... .......... ..........
C{SEQ ID NO:182}  AwRLRIpEsT CaKdIQKAAA EAAlaF.... .......... ..........
C{SEQ ID NO:183}  AwRLRIpEsT CaKeIQKAAA EAAlnF.... .......... ..........
C{SEQ ID NO:184}  AwRLRIpEsT CaKdIQKAAA EAAlaF.... .......... ..........
Consensus         A-RLRI-E-T C-K-IQKAAA EAA--F---- ---------- ----------
```

```
                  51                                                  100
C{SEQ ID NO:185}  aevndtttteh gmnmeeatav asqaEvndtt td.HgvDmEE TmVEAvftgE
C{SEQ ID NO:186}  aevndttteh gmnmeeatav asqaEvndtt td.HgvDmEE TmVEAvftgE
C{SEQ ID NO:187}  aevndttteh gmnmeeatav asqaEvndtt td.HgvDmEE TmVEAvfteE
C{SEQ ID NO:188}  aevndttteh gmnmeeatav asqaEvndtt td.HgvDmEE TmVEAvftgE
C{SEQ ID NO:189}  aevndtttdh gmnmeeatav asqaEvndtt td.HgvDmEE TmVEAvftgE
C{SEQ ID NO:190}  aevndtttdh gmnmeeatav asqaEvndtt td.HgvDmEE TmVEAvfteE
C{SEQ ID NO:191}  aevndtttdh gmnmeeatav asqaEvndtt td.HgvDmEE TmVEAvfteE
C{SEQ ID NO:192}  aevndttteh gmnmeeatav asqaEvndtt td.HgvDmEE TmVEAvfteE
C{SEQ ID NO:193}  tevsdtttdh gmnmeettav asqaEvndxx td.HgvDmEE TmVEAvfteE
C{SEQ ID NO:194}  ........dh Gmnmknttav asqvEvndtt td.HgvDmEE TlVEAvfteE
C{SEQ ID NO:195}  ........dh Gmnmknttav asqvEvndtt td.HgvDmEE TlVEAvfteE
C{SEQ ID NO:196}  .....ttndh Gmnm...... asqaEvndtt .d.~glDmEE TmVEAvfteE
C{SEQ ID NO:197}  .....ttndh Gmnm...... asqaEvndtt .d.HgIDmEE TmVEAvfteE
C{SEQ ID NO:198}  .....ttndh Gmnm...... asqvEvndtt .d.HdlDmEE TiVEAvfreE
C{SEQ ID NO:199}  .....ttndh gmnm...... asqvEvndtt .d.HdlDmEE TmVEAvfreE
C{SEQ ID NO:200}  .....ttndr gmnmeetsav aspaElndtt ad.HgIDmEE TmVEAvfrdE
C{SEQ ID NO:201}  .....ttndq gmnmeemtvv asqaEvsdtt ty.HgIDmEE TmVEAvfaeE
C{SEQ ID NO:202}  .......... .......... ..qaElndtt ad.HgIDvEE TiVEAift.E
C{SEQ ID NO:203}  .......... .......... ..qaElndtt ad.HgIDvEE TiVEAift.E
C{SEQ ID NO:204}  .......... .......... ..kaEinntt ad.HgiDvEE TiVEAift.E
C{SEQ ID NO:205}  .......... .......... ..qaEindtt td.HgIDIEE TiVEAift.E
C{SEQ ID NO:206}  .......... .......... ..qdEtcdtt ttdHgIDmEE TmVEAiytpE
C{SEQ ID NO:207}  .......... .......... ..qdEmchmt tdaHgIDmEE TlVEAiytpE
C{SEQ ID NO:208}  .......... .......... ..qdEmcdat td.HgfDmEE TlVEAiytaE
Consensus         ---------- ---------- ----E----- ---H--D-EE T-VEA----E
```

FIGURE 21A-continued

```
                   101                                                150
C{SEQ ID NO:209}  qsegfnmake stveaavvte epskgsYMd. eEwmleMptl ladmAeGMLl
C{SEQ ID NO:210}  qsegfnmake stveaavvte epskgsYMd. eEwmleMptl ladmAeGMLl
C{SEQ ID NO:211}  qsegfnmake stveaavvte epskgsYMd. eEwmleMptl ladmAeGMLl
C{SEQ ID NO:212}  qsegfnmake stveaavvte epskgsYMd. eEwmleMptl ladmAeGMLl
C{SEQ ID NO:213}  qsegfnmake stveaavvte epskgsYMd. eEwmleMptl ladmAeGMLl
C{SEQ ID NO:214}  qsegfnmaee stveaavvtd elskgfYMd. eEwtyeMptl ladmAaGMLl
C{SEQ ID NO:215}  qsegfnmaee stveaavvtd elskgfYMd. eEwtyeMptl ladmAaGMLl
C{SEQ ID NO:216}  qsegfnmaee stveaavvtd elskgfYMd. eEwtyeMptl ladmAaGMLl
C{SEQ ID NO:217}  qsegfnmake staeaavvte elskgvYMd. eEwtyeMptl ladmAaGMLl
C{SEQ ID NO:218}  qregfymtee trvegvvtee q.nnwfYMd. eEwmfgMptl IvdmAeGMLi
C{SEQ ID NO:219}  qregfymtee trvegvvtee q.nnwfYMd. eEwmfgMptl IvdmAeGMLl
C{SEQ ID NO:220}  qrdgfymaee ttvegvvpee qmskgfYMd. eEwmfgMptl ladmAaGMLl
C{SEQ ID NO:221}  qrdgfymaee ttvegvvpee qmskgfYMd. eEwmfgMptl ladmAaGMLl
C{SEQ ID NO:222}  qregfymaee ttvvgvvpee qmskgfYMd. eEwmfgMptl ladmAaGMLl
C{SEQ ID NO:223}  qregfymaee ttvegivpee qmskgfYMd. eEwmfgMptl ladmAaGMLl
C{SEQ ID NO:224}  qregfymaee ttvegvvpee qmskgfYMd. eEwtfeMprl ladmAeGMLl
C{SEQ ID NO:225}  qregfylaee ttvegvvtee q.skgfYMd. eEwtfgMqsf ladmAeGMLf
C{SEQ ID NO:226}  esse...... .......... ....gfYMd. eEfmfgMptl wasmAeGMLl
C{SEQ ID NO:227}  esse...... .......... ....gfYMa. eEfmfgMptl wasvAeGMLl
C{SEQ ID NO:228}  ennd...... .......... ....gfYMde eEsmfgMpal lasmAeGMLl
C{SEQ ID NO:229}  vnnd...... .......... ....efYMd. eEsmfgMpsl lasmAeGMLl
C{SEQ ID NO:230}  qseg...... .......... ....afYMd. eEtmfgMptl IdnmAeGMLl
C{SEQ ID NO:231}  qsqd...... .......... ....afYMd. eEamlgMssl IdnmAeGMLl
C{SEQ ID NO:232}  qsen...... .......... ....afYMh. dEamfeMpsl LanmAeGMLl
Consensus         ---------- ---------- ------YM-- -E----M--- ----A-GML-
```

FIGURE 21B

```
                      1                                                  50
C{SEQ ID NO:233} AwRLRIPETT CHKDIQKAAA EAALAFEAEK SDvTmqngln MEEttAvASQ
C{SEQ ID NO:234} AwRLRIPETT CHKDIQKAAA EAALAFEAEK SDvTmqngln MEEttAvASQ
C{SEQ ID NO:235} AwRLRIPETT CHKDIQKAAA EAALAFEAEK SDvTmqngln MEEmtAvASQ
C{SEQ ID NO:236} AwRLRIPETT CHKDIQKAAA EAALAFEAEK SDvTmqngqn MEEttAvASQ
C{SEQ ID NO:237} AsRLRIPETT CHKDIQKAAA EAALAFEAEK SDvT...... MEEtmAvASQ
C{SEQ ID NO:238} AsRLRIPETT CHKDIQKAAA EAALAFEAEK SDvT...... MEEtmAvASQ
C{SEQ ID NO:239} AwRLRIPETT CHKDIQKAAA EAALAFEAEK SDvT...... MEEtmAvASQ
C{SEQ ID NO:240} AwRLRIPETT CHKDIQKAAA EAALAFEAEK SDvTmqngln MEEttAvASQ
C{SEQ ID NO:241} AwRLRIPETT CHKDIQKAAA EAALAFEAEK SDaTmqngln MEEttAaASQ
Consensus        A-RLRIPETT CHKDIQKAAA EAALAFEAEK SD-T------ MEE--A-ASQ

                 51                                                     100
C{SEQ ID NO:242} aEVnDTTTeH GMNMEEaTAV ASQAEVNDTT TDHGVDMEET MVEAVFTgEQ
C{SEQ ID NO:243} aEVnDTTTeH GMNMEEaTAV ASQAEVNDTT TDHGVDMEET MVEAVFTgEQ
C{SEQ ID NO:244} aEVnDTTTeH GMNMEEaTAV ASQAEVNDTT TDHGVDMEET MVEAVFTeEQ
C{SEQ ID NO:245} aEVnDTTTeH GMNMEEaTAV ASQAEVNDTT TDHGVDMEET MVEAVFTgEQ
C{SEQ ID NO:246} aEVnDTTTdH GMNMEEaTAV ASQAEVNDTT TDHGVDMEET MVEAVFTgEQ
C{SEQ ID NO:247} aEVnDTTTdH GMNMEEaTAV ASQAEVNDTT TDHGVDMEET MVEAVFTeEQ
C{SEQ ID NO:248} aEVnDTTTdH GMNMEEaTAV ASQAEVNDTT TDHGVDMEET MVEAVFTeEQ
C{SEQ ID NO:249} aEVnDTTTeH GMNMEEaTAV ASQAEVNDTT TDHGVDMEET MVEAVFTeEQ
C{SEQ ID NO:250} tEVsDTTTdH GMNMEEtTAV ASQAEVNDTT TDHGVDMEET MVEAVFTeEQ
Consensus        -EV-DTTT-H GMNMEE-TAV ASQAEVNDTT TDHGVDMEET MVEAVFT-EQ

                 101                                                    150
C{SEQ ID NO:251} SEGFNMAkES TvEAAVVTeE pSKGsYMDEE WmlEMPTLLA DMAeGMLLpp
C{SEQ ID NO:252} SEGFNMAkES TvEAAVVTeE pSKGsYMDEE WmlEMPTLLA DMAeGMLLpp
C{SEQ ID NO:253} SEGFNMAkES TvEAAVVTeE pSKGsYMDEE WmlEMPTLLA DMAeGMLLpp
C{SEQ ID NO:254} SEGFNMAkES TvEAAVVTeE pSKGsYMDEE WmlEMPTLLA DMAeGMLL--
C{SEQ ID NO:255} SEGFNMAkES TvEAAVVTeE pSKGsYMDEE WmlEMPTLLA DMAeGMLLpp
C{SEQ ID NO:256} SEGFNMAeES TvEAAVVTdE lSKGfYMDEE WtyEMPTLLA DMAaGMLLpp
C{SEQ ID NO:257} SEGFNMAeES TvEAAVVTdE lSKGfYMDEE WtyEMPTLLA DMAaGMLLpp
C{SEQ ID NO:258} SEGFNMAeES TvEAAVVTdE lSKGfYMDEE WtyEMPTLLA DMAaGMLLpp
C{SEQ ID NO:259} SEGFNMAkES TaEAAVVTeE lSKGvYMDEE WtyEMPTLLA DMAaGMLLpp
Consensus        SEGFNMA-ES T-EAAVVT-E -SKG-YMDEE W--EMPTLLA DMA-GMLL--
```

PLANT HAVING ALTERED ENVIRONMENTAL STRESS TOLERANCE

This application is a 371 of PCT/US99/01895, filed Jan. 28, 1999, which is a CIP of Ser. No. 09/018,233, filed Feb. 3, 1998, now abandoned, which is a CIP of Ser. No. 08/706,270, filed Sep. 4, 1996, now U.S. Pat. No. 5,892,009; a CIP of Ser. No. 09/017,816, filed Feb. 3, 1998, abandoned; a CIP of Ser. No. 09/018,235, Feb. 3, 1998, now abandoned; a CIP of Ser. No. 09/017,575, Feb. 3, 1998, now abandoned; a CIP of Ser. No. 09/018,227, Feb. 3, 1998, now abandoned; a CIP of Ser. No. 09/018,234, Feb. 3, 1998, now abandoned; a CIP of Ser. No. 09/198,119, filed Nov. 23, 1998, now U.S. Pat. No. 6,417,428.

FIELD OF THE INVENTION

The present invention relates to the regulatory response of plants to environmental stresses such as cold and to drought. More specifically, the present invention relates to genes which regulate the response of a plant to environmental stresses such as cold or drought and their use to enhance the stress tolerance of recombinant plants into which these genes are introduced.

BACKGROUND OF THE INVENTION

Environmental factors serve as cues to trigger a number of specific changes in plant growth and development. One such factor is low temperature. Prominent examples of cold-regulated processes include cold acclimation, the increase in freezing tolerance that occurs in response to low non-freezing temperatures (Guy, C. L., Annu. Rev. Plant Physiol. Plant Mol. Biol. 41:187–223 (1990)); vernalization, the shortening of time to flowering induced by low temperature (Lang, A., in Encyclopedia of Plant Physiology, Vol. 15–1, ed. Ruhland, W. (Springer, Berlin), pp. 1489–1536 (1965)); and stratification, the breaking of seed dormancy by low temperature (Berry, J. A. and J. K. Raison, in Encyclopedia of Plant Physiology, Vol. 12A, eds. Lange, O. L., Nobel, P. S., Osmond, C. B. and Ziegler, H. (Springer, Berlin), pp. 277–338 (1981)). Due to the fundamental nature and agronomic importance of these processes, there is interest in understanding how plants sense and respond to low temperature. One approach being taken is to determine the signal transduction pathways and regulatory mechanisms involved in cold-regulated gene expression.

Strong evidence exists for calcium having a role in low temperature signal transduction and regulation of at least some COR (cold-regulated) genes. Dhindsa and colleagues (Monroy, A. F., et al, Plant Physiol. 102:1227–1235 (1993); Monroy, A. F., and R. S., The Plant Cell, 7:321–331 (1995)) have shown that, in alfalfa, calcium chelators and calcium channel blockers prevent low temperature induction of COR genes and that calcium ionophores and calcium channel agonists induce expression of COR genes at normal growth temperatures. Similarly, Knight et al (The Plant Cell 8:489–503 (1996)) have shown that cold-induced expression of the *Arabidopsis thaliana* COR gene KIN1 is inhibited by calcium chelators and calcium channel blockers. These results suggest that low temperature triggers an influx of extracellular calcium that activates a signal transduction pathway that induces the expression of COR genes. Consistent with this notion is the finding that low temperature evokes transient increases in cytosolic calcium levels in plants (Knight, M. R. et al, Nature 352:524–526 (1991); Knight, H., et al., The Plant Cell 8:489–503 (1996)). In addition, low temperatures have been shown to stimulate the activity of mechanosensitive calcium-selective cation channels in plants (Ding, J. P. and B. G. Pickard, Plant J. 3:713–720 (1993)).

Recent efforts have led to the identification of a cis-acting cold-regulatory element in plants, the C-repeat/DRE (Yamaguchi-Shinozaki, et al., The Plant Cell 6:251–264 (1994); Baker, S. S., et al., Plant. Mol. Biol. 24:701–713 (1994); Jiang, C., et al., Plant Mol. Biol. 30:679–684 (1996)). The element, which has a 5 base pair core sequence for CCGAC, is present once to multiple times in all plant cold-regulated promoters that have been described to date; these include the promoters of the COR15a (Baker, S. S., et al, Plant. Mol. Biol. 24:701–713 (1994)), COR78/RD29A (Horvath, D. P., et al, Plant Physiol. 103:1047–1053 (1993); Yamaguchi-Shinozaki, K., et al., The Plant Cell 6:251–264 (1994)), COR6.6 (Wang, H., et al., Plant Mol. Biol. 28:605–617 (1995)) and KIN1 (Wang, H., et al, Plant Mol. Biol. 28:605–617 (1995)) genes of Arabidopsis and the BN115 gene of *Brassica napus* (White, T. C., et al, Plant Physiol. 106:917–928 (1994)). Deletion analysis of the Arabidopsis COR15a gene suggested that the CCGAC sequence, designated the C-repeat, might be part of a cis-acting cold-regulatory element (Baker, S. S., et al., Plant Mol. Biol. 24:701–713 (1994)). That this was the case was first demonstrated by Yamaguchi-Shinozaki and Shinozaki (Yamaguchi-Shinozaki, K., et al., The Plant Cell 6:251–264 (1994)) who showed that two of the C-repeat sequences present in the promoter of COR78/RD29A induced cold-regulated gene expression when fused to a reporter gene. It was also found that these two elements stimulate transcription in response to dehydration and high salinity and thus, was designated the DRE (dehydration, low temperature and high salt regulatory element). Recent studies by Jiang et al (Jiang, C., et al., Plant Mol. Biol. 30:679–684 (1996)) indicate that the C-repeats (referred to as low temperature response elements) present in the promoter of the *B. napus* BN115 gene also impart cold-regulated gene expression.

U.S. Pat. Nos. 5,296,462 and 5,356,816 to Thomashow describe the genes encoding the proteins involved in cold adaptation in *Arabidopsis thaliana.* In particular the DNA encoding the COR15 proteins is described. These proteins are significant in promoting cold tolerance in plants.

A need exists for the identification of genes which regulate the expression of cold tolerance genes and drought tolerance genes. A further need exists for DNA constructs useful for introducing these regulatory genes into a plant in order to cause the plant to begin expressing or enhance their expression of native or non-native cold tolerance genes and drought tolerance genes. These and other needs are provided by the present invention.

SUMMARY OF THE INVENTION

DNA in isolated form is provided which includes a sequence encoding a binding protein capable of selectively binding to a DNA regulatory sequence which regulates expression of one or more environmental stress tolerance genes in a plant. The binding protein is preferably capable of regulating expression of one or more environmental stress tolerance genes in a plant by selectively binding to a DNA regulatory sequence which regulates the one or more environmental stress tolerance genes. In one embodiment, the binding protein is a non-naturally occurring protein formed by combining an amino acid sequence capable of binding to a CCG regulatory sequence, preferably a CCGAC regulatory sequence with an amino acid sequence which forms a transcription activation region which regulates expression of one or more environmental stress tolerance genes in a plant by regulating expression of one or more environmental stress tolerance genes when the binding protein binds to the regulatory region.

DNA in isolated form is also provided which includes a promoter and the sequence encoding the binding protein. In one variation, the promoter causes expression of the binding protein in a manner which is different than how the binding protein is expressed in its native state. For example, the promoter may increase the level at which the binding protein is expressed, express the binding protein without being induced by an environmental stress and/or express the binding protein in response to a different form or degree of environmental stress than would otherwise be needed to induce expression of the binding protein. The promoter may also be inducible by an exogenous agent. The promoter can also be selected with regard to the type or types of plant tissues that the binding protein will be expressed as well as when in the plant's life the promoter will function to regulate expression of the binding protein.

A nucleic acid construct capable of transforming a plant is also provided which includes a sequence encoding a binding protein capable of selectively binding to a DNA regulatory sequence which regulates expression of one or more environmental stress tolerance genes in a plant. The binding protein is preferably capable of regulating expression of one or more environmental stress tolerance genes in a plant by selectively binding to a DNA regulatory sequence which regulates the one or more environmental stress tolerance genes. The nucleic acid construct may be an RNA or DNA construct. Examples of types of constructs include, but are not limited to DNA and RNA viral vectors and plasmids.

A nucleic acid construct capable of transforming a plant is also provided which includes a sequence which when transformed into a plant expresses a binding protein capable of selectively binding to a DNA regulatory sequence which regulates one or more environmental stress tolerance genes in the plant. The binding protein preferably regulates expression of one or more environmental stress tolerance genes in the plant by selectively binding to a DNA regulatory sequence which regulates the one or more environmental stress tolerance genes.

In one variation of the above constructs, the construct also includes a promoter which regulates expression of the binding protein encoding sequence. The promoter may optionally be homologous or heterologous relative to the binding protein encoding sequence. The promoter and binding protein encoding sequence may also optionally be native to the same or a different plant species. In one variation, the promoter causes expression of the binding protein in a manner which is different than how the binding protein is expressed in its native state. For example, the promoter may increase the level at which the binding protein is expressed, express the binding protein without being induced by an environmental stress and/or express the binding protein in response to a different form or degree of environmental stress than would otherwise be needed to induce expression of the binding protein. The promoter may also be inducible by an exogenous agent. The promoter can also be selected with regard to the type or types of plant tissues that the binding protein will be expressed as well as when in the plant's life the promoter will function to regulate expression of the binding protein. For example, flower-, fruit- and seed-specific promoters can be used to regulate the expression of the binding protein in these tissues of the plant, especially when sudden frosts strike in early spring and late fall.

A binding protein in isolated form is also provided which is capable of selectively binding to a DNA regulatory sequence which regulates expression of one or more environmental stress tolerance genes in a plant. The binding protein is preferably capable of regulating expression of one or more environmental stress tolerance genes in the plant by selectively binding to a DNA regulatory sequence which regulates the one or more environmental stress tolerance genes.

A recombinant binding protein expressed within a plant is also provided which is capable of selectively binding to a DNA regulatory sequence in the plant which regulates expression of one or more environmental stress tolerance genes in the plant. The recombinant binding protein is preferably capable of regulating expression of one or more environmental stress tolerance genes in the plant by selectively binding to a DNA regulatory sequence which regulates the one or more environmental stress tolerance genes. The recombinant binding protein may be native or non-native to the plant. Further, the recombinant binding protein may be homologous or heterologous relative to the DNA binding protein present in the plant in which the binding protein is expressed.

A transformed cell of an organism is also provided which includes a recombinant sequence encoding a binding protein capable of selectively binding to a DNA regulatory sequence which regulates expression of one or more environmental stress tolerance genes in a plant. The binding protein is preferably capable of regulating expression of one or more environmental stress tolerance genes in a plant by selectively binding to a DNA regulatory sequence which regulates the one or more environmental stress tolerance genes. The transformed cell may be a unicellular organism such as a bacterium, yeast or virus, or from a multicellular organism such as a fungus or a plant.

A transformed cell is also provided which includes a promoter and a sequence encoding a binding protein where at least one of the promoter and sequence under regulatory control of the promoter is recombinant. Optionally, one or both of the promoter and sequence under regulatory control of the promoter is not native to the cell. In one variation, the promoter causes expression of the binding protein in a manner which is different than how the binding protein is expressed in its native state. For example, the promoter may increase the level at which the binding protein is expressed, express the binding protein without being induced by an environmental stress and/or express the binding protein in response to a different form or degree of environmental stress than would otherwise be needed to induce expression of the binding protein. The promoter may also be inducible by an exogenous agent. The promoter can also be selected with regard to the type or types of plant tissues that the binding protein will be expressed as well as when in the plant's life the promoter will function to regulate expression of the binding protein.

A transformed cell is also provided which includes a recombinant binding protein expressed within the cell which is capable of selectively binding to a DNA regulatory sequence in the plant which regulates expression of one or more environmental stress tolerance genes in the plant. The binding protein is preferably capable of regulating expression of one or more environmental stress tolerance genes in the plant by selectively binding to a DNA regulatory sequence which regulates the one or more environmental stress tolerance genes. The binding protein may be native or non-native to the cell.

A transformed plant with modified environmental stress tolerance gene expression is also provided. In one embodiment, the transformed plant includes one or more environmental stress tolerance genes; a DNA regulatory sequence which regulates expression of the one or more environmental stress tolerance genes; and a recombinant sequence encoding a binding protein capable of selectively binding to the DNA regulatory sequence.

In another embodiment, the transformed plant includes one or more environmental stress tolerance genes; a DNA regulatory sequence which regulates expression of the one or more environmental stress tolerance genes; a sequence encoding a binding protein capable of selectively binding to the DNA regulatory sequence; and a recombinant promoter which regulates expression of the sequence encoding the binding protein.

In yet another embodiment, the transformed plant includes one or more environmental stress tolerance genes; a recombinant DNA regulatory sequence which regulates expression of the one or more environmental stress tolerance genes; and a sequence encoding a binding protein capable of selectively binding to the DNA regulatory sequence.

In yet another embodiment, the transformed plant includes at least one recombinant environmental stress tolerance gene; a DNA regulatory sequence which regulates expression of the at least one environmental stress tolerance gene; and a sequence encoding a binding protein capable of selectively binding to the DNA regulatory sequence.

In yet another embodiment, the transformed plant includes at least one recombinant environmental stress tolerance gene; a DNA regulatory sequence which regulates expression of the at least one environmental stress tolerance gene; and a recombinant binding protein expressed by the plant which is capable of selectively binding to the DNA regulatory sequence.

A method for altering an environmental stress tolerance of a plant is also provided. In one embodiment, the method includes transforming a plant with at least one copy of a gene encoding a binding protein capable of binding to a DNA regulatory sequence which regulates one or more environmental stress tolerance genes in the plant; expressing the binding protein encoded by the gene; and stimulating expression of at least one environmental stress tolerance gene through binding of the binding protein to the DNA regulatory sequence.

In another embodiment, the method includes transforming a plant with a promoter which regulates expression of at least one copy of a gene encoding a binding protein capable of binding to a DNA regulatory sequence which regulates one or more environmental stress tolerance genes in the plant or in specific type or types of plant tissues; expressing the binding protein encoded by the gene; and stimulating expression of at least one environmental stress tolerance gene through binding of the binding protein to the DNA regulatory sequence.

In another embodiment, the method includes transforming a plant with one or more environmental stress tolerance genes whose expression is regulated by a DNA regulatory sequence; and expressing a binding protein capable of binding to the DNA regulatory sequence and activating expression of the one or more environmental stress tolerance genes.

According to any one of the above embodiments of the present invention, the binding protein may optionally be selected such that it selectively binds to a member of a class of DNA regulatory sequences which includes the subsequence CCG or more particularly one of the following subsequences: CCGAA, CCGAT, CCGAC, CCGAG, CCGTA, CCGTT, CCGTC, CCGTG, CCGCA, CCGCT, CCGCG, CCGCC, CCGGA, CCGGT, CCGGC, CCGGG, AACCG, ATCCG, ACCCG, AGCCG, TACCG, TTCCG, TCCCG, TGCCG, CACCG CCCG, GACCG, GTCCG, GCCCG, GGCCG, ACCGA, ACCGT, ACCGC, ACCGG, TCCGA, TCCGT, TCCGC, TCCGG, CCCGA, CCCGT, CCCGC, CCCGG, GCCGA, GCCGT, GCCGC, and GCCGG. The binding protein may also be selected such that the binding protein includes an AP2 domain.

In each of the above embodiments, the level of expression of the binding protein may be the same or different than the level of expression of the binding protein in its native state. Expression of the binding protein in the transformed cell may be regulated by a recombinant promoter which may have the effect of increasing the level at which the binding protein is expressed, expressing the binding protein without being induced by an environmental stress and/or expressing the binding protein in response to a different form or degree of environmental stress than is otherwise needed to induce expression of the binding protein. Expression may also be induced by an exogenous agent. Expression may also be limited to selected types of plant tissues or selected periods in the plant's life based on which promoter is used. By selecting in what tissues and when in a plant's life the binding protein is expressed, in combination with the selecting how the binding protein is expressed (level of expression and/or type of environmental or chemical induction), an incredible range of control over the environmental stress responses of a plant can be achieved by the present invention.

In each of the above embodiments, the binding protein comprises an amino acid sequence which is capable of binding to a DNA regulatory sequence which regulates one or more environmental stress tolerance genes. In a preferred embodiment, the binding protein further comprises a transcription activation region which acts in concert with the binding sequence to regulate expression of one or more environmental stress tolerance genes in the plant by regulating expression of one or more environmental stress tolerance genes. The environmental stress tolerance gene, DNA regulatory sequence, sequence encoding the binding sequence, and the sequence encoding the transcription activation region may each independently be native or non-native to the plant and may each independently be homologous or heterologous relative to each other.

Optionally, the binding protein satisfies one or more of the following requirements:

the binding protein comprises an AP2 domain which comprises a consensus sequence sufficiently homologous to any one of the consensus sequences shown in FIG. 19A, 19B, or 19C that the binding protein is capable of binding to a CCG regulatory sequence, preferably a CCGAC regulatory sequence;

the binding protein comprises an AP2 domain which comprises a consensus sequence shown in FIG. 19A, 19B or 19C;

the binding protein comprises an AP2 domain which comprises the amino acid residues shown in FIG. 19D or 19E;

the binding protein comprises an AP2 domain which is sufficiently homologous to at least one of the AP2 domains shown in the application such that it is capable of binding to a CCG regulatory sequence, preferably a CCGAC regulatory sequence;

the binding protein comprises one of the AP2 domain sequences shown in this application, including, but not limited to SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95;

the binding protein comprises a sequence which comprises one of the amino terminus domains shown in FIG. 20 (it is noted that the sequence need not be at the amino terminus of the binding protein);

the binding protein comprises the consensus sequence for the amino terminus domains shown in FIG. 20, (it is noted that the sequence need not be at the amino terminus of the binding protein);

the binding protein comprises a sequence which comprises one of the carboxy terminus domains shown in FIG. 21A (it is noted that the sequence need not be at the carboxy terminus of the binding protein);

the binding protein comprises the consensus sequence for the carboxy terminus domains shown in FIG. 21A (it is noted that the sequence need not be at the carboxy terminus of the binding protein); and the binding protein comprises the consensus sequence for the carboxy terminus domains shown in FIG. 21B (it is noted that the sequence need not be at the carboxy terminus of the binding protein).

The amino acid sequence encoding the binding protein may be a naturally occurring sequence such as the ones shown in SEQ. ID. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95 or may be a non-naturally occurring sequence. It is noted, however, that binding proteins according to the present invention are intended to encompass non-naturally occurring sequences which are derivatives of the classes of binding proteins taught herein. For example, additional binding proteins may be constructed using one of the AP2 domains taught herein or the consensus sequence of these AP2 domains. It may be desirable to include with the AP2 domain a transcription activation region. The transcription activation region may be native to the plant or non-native to the plant in which the binding protein will be used. For example, the sequence may include a subsequence which encodes a binding domain for the DNA regulatory sequence fused to a transcription activating region, such as the transcription activating region of VP16 or GAL4. Optionally, one can include in the binding protein one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

Optionally, the binding protein can be viewed as comprising one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

A method is also provided for identifying from a cDNA library of at least a portion of a plant genome a gene sequence encoding a protein capable of binding to a target DNA regulatory sequence. In one embodiment, the method comprises taking a microorganism which includes a target DNA regulatory sequence for one or more environmental stress tolerance genes, a transcription activator for activating expression of a reporter gene, and a reporter gene whose expression is activated by a protein which includes a binding domain capable of binding to the target DNA regulatory sequence and an activation domain capable of activating the transcription activator;

fusing sequences from a cDNA library of at least a portion of a plant genome to a sequence which encodes a functional activation domain in the microorganism;

introducing the fused sequences into the microorganism; and selecting microorganisms which express the reporter gene, expression of the reporter gene indicating expression of a fusion protein which includes a binding domain for the target DNA regulatory sequence and the activation domain; and identifying the gene sequence from the cDNA library introduced into the microorganism.

The target DNA regulatory sequence may optionally include the subsequence CCG or the subsequence CCGAC. This embodiment of the invention also relates to DNA in substantially isolated form, nucleic acid constructs capable of transforming a plant, cells, and transformed plants which include a gene sequence identified by this method.

While the present invention is described with regard to the use of binding proteins which can bind to a DNA regulatory sequence that regulates environmental stress tolerance genes in a plant, it is noted that these same binding proteins can also be used to regulate genes other than environmental stress tolerance genes by placing these other genes under the regulatory control of the DNA regulatory sequence. For example, protein kinases that induce cold and drought inducible genes can be regulated by placing a protein kinase gene under the control of a promoter whose expression is regulated by the DNA regulatory sequence. PCT/US97/23019 (Intl Publication Number WO 98/26045) describes protein kinases that when constitutively expressed, induce cold and drought inducible genes. The ATCDPK1a and the ATCDPK1 constitutive protein kinase coding regions (PCT/US97/23019) can be isolated by PCR and inserted into the drought and cold inducible promoters described in Example 8 by one skilled in the art. The expression of these ATCDPK1 constitutive protein kinase coding regions (PCT/US97/23019) from the drought and cold inducible promoters will increase the drought and cold tolerance of plants and should be synergistic with the drought and cold tolerance induced by CBF expression under inducible promoters.

BRIEF DESCRIPTION OF THE DRAWINGS

FIG. 1A is a schematic diagram showing the screening strategy.

FIG. 1B is a chart showing activity of the "positive" cDNA clones in yeast reporter strains.

FIGS. 2A, 2B, 2C and 2D provide an analysis of the pACT-11 cDNA clone.

FIG. 2A is a schematic drawing of the pACT-11 cDNA insert indicating the location and 5' to 3' orientation of the 24 kDa polypeptide and 25s rRNA sequences.

FIG. 2B is a DNA and amino acid sequence of the 24 kDa polypeptide (SEQ ID NO:1 and SEQ ID NO:2).

FIG. 2C is a schematic drawing indicating the relative positions of the potential nuclear localization signal (NLS), the AP2 domain and the acidic region of the 24 kDa polypeptide.

FIG. 2D is a chart showing comparison of the AP2 domain of the 24 kDa polypeptide SEQ ID NO: 10 with that of the tobacco DNA binding protein EREBP2 SEQ ID NO: 11.

FIG. 7A is a photograph of a membrane RNA isolated from Arabidopsis plants that were grown at 22 C or grown at 22 C and transferred to 2.5 C for the indicated times.

FIG. 7B is a graph showing relative transcript levels of CBF1 in control and cold-treated plants.

FIG. 7C is a graph showing relative transcript levels of COR15a in control and cold-treated plants.

FIG. 12 shows the DNA sequence for CBF2 SEQ ID NO: 12 encoding CBF2 SEQ ID NO: 13.

FIG. 13 shows the DNA sequence for CBF3 SEQ ID NO:14 encoding CBF3 SEQ ID NO:15.

FIG. 14 shows the amino acid alignment of proteins CBF1 (SEQ ID NO:2), CBF2 (SEQ ID NO: 13), and CBF3 (SEQ ID NO: 15).

FIG. 16 shows the amino acid sequence of a canola homolog (SEQ ID NO:17) and its alignment to the amino acid sequence of CBF1 (SEQ ID NO:2).

FIG. 18A shows the DNA sequences for the CBF homologs from *Brassica juncea, Brassica napus, Brassica oleracea, Brassica rapa, Glycine max, Raphanus sativus* and *Zea Maize.*

FIG. 18B shows the amino acid sequences (one-letter abbreviations) encoded by the DNA sequences (shown in FIG. 18A) for CBF homologs from *Brassica juncea, Brassica napus, Brassica oleracea, Brassica rapa, Glycine max, Raphanus sativus* and *Zea Maize.*

FIG. 19A shows an amino acid alignment of the AP2 domains of several CBF proteins SEQ ID NO: (103–133) with the consensus sequence between the proteins highlighted as well as a comparison of the AP2 domains with that of the tobacco DNA binding protein EREBp2 (SEQ ID NO: 134).

FIG. 19B shows an amino acid alignment of the AP2 domains of several CBF proteins (SEQ ID NO: 103–133) including dreb2a (SEQ ID NO: 135)(SEQ ID NO: 136) and dreb2b with the consensus sequence between the proteins highlighted.

FIG. 19C shows an amino acid alignment of the AP2 domains of several CBF proteins (SEQ ID NO: 103–133) including dreb2a (SEQ ID NO: 135), dreb2b (SEQ ID NO: 136), and tiny (SEQ ID NO: 137) with the consensus sequence between the proteins highlighted.

FIG. 19D shows a difference between the consensus sequence shown in FIG. 19A (SEQ ID NO: 103–133) and tiny (SEQ ID NO: 137).

FIG. 19E shows a difference between the consensus sequence shown in FIG. 19B (SEQ ID NO: 103–133, 135, 136) and tiny (SEQ ID NO: 137).

FIG. 20 shows an amino acid alignment of the amino terminus of several CBF proteins (SEQ ID NO: 138–160) with their consensus sequence highlighted.

FIGS. 21A (SEQ ID NO: 161–232) and 21B (SEQ ID NO: 233–259) show an amino acid alignment of the carboxy terminus of several CBF proteins, with their consensus sequences highlighted.

DETAILED DESCRIPTION

Figures 1A, 1B:
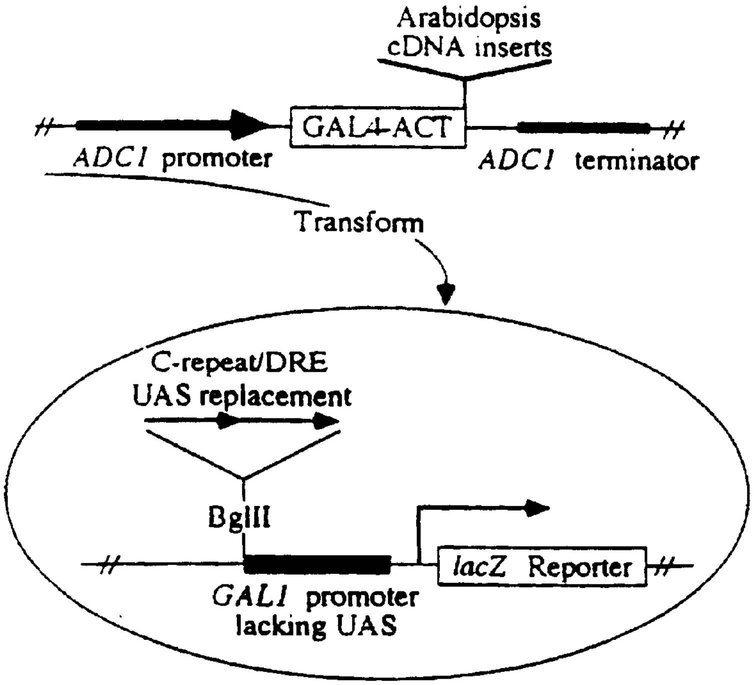
FIGS. 1A and 1B show how the yeast reporter strains were constructed.

The present invention relates to DNA encoding binding proteins capable of binding to a DNA regulatory sequence which regulates expression of one or more environmental stress tolerance genes in a plant. The present invention also relates to the binding proteins encoded by the DNA. The DNA and binding proteins may be native or non-native relative to the DNA regulatory sequence of the plant. The DNA and binding proteins may also be native or non-native relative to environmental stress tolerance genes of the plant which are regulated by the DNA regulatory sequence.

The present invention also relates to methods for using the DNA and binding proteins to regulate expression of one or more native or non-native environmental stress tolerance genes in a plant. These methods may include introducing DNA encoding a binding protein capable of binding to a DNA regulatory sequence into a plant, introducing a promoter into a plant which regulates expression of the binding protein, introducing a DNA regulatory sequence into a plant to which a binding protein can bind, and/or introducing one or more environmental stress tolerance genes into a plant whose expression is regulated by a DNA regulatory sequence.

The present invention also relates to recombinant cells, plants and plant materials (e.g., plant tissue, seeds) into which one or more gene sequences encoding a binding protein have been introduced as well as cells, plants and plant materials within which recombinant binding proteins encoded by these gene sequences are expressed. By introducing a gene sequence encoding a binding protein into a plant, a binding protein can be expressed within the plant which regulates expression of one or more stress tolerance genes in the plant. Regulation of expression can include causing one or more stress tolerance genes to be expressed under different conditions than those genes would be in the plant's native state, increasing a level of expression of one or more stress tolerance genes, and/or causing the expression of one or more stress tolerance genes to be inducible by an exogenous agent. Expression of the binding protein can be under the control of a variety of promoters. For example, promoters can be used to overexpress the binding protein, change the environment conditions under which the binding protein is expressed, or enable the expression of the binding protein to be induced, for example by the addition of an exogenous inducing agent. Promoters can also be used to cause the protein to be expressed at selected times during a plant's life. Tissue-specific promoters can be used to cause the protein to be expressed in selected tissues. For example, flower-, fruit- and seed-specific promoters can be used to cause the protein to be selectively expressed in flowers, fruits or seeds of the plant.

The present invention also relates to cells, recombinant plants and plant materials into which a recombinant promoter is introduced which controls a level of expression of one or more gene sequences encoding a binding protein. The one or more gene sequences may be recombinant native or non-native sequences or may be native, non-recombinant gene sequences whose expression is altered by the introduction of the recombinant promoter.

The present invention also relates to cells, recombinant plants and plant materials into which a recombinant native or non-native DNA regulatory sequence is introduced which regulates expression of one or more native or non-native environmental stress tolerance genes.

Examples of environmental stresses for which stress tolerance genes are known to exist include, but are not limited to, cold tolerance, dehydration tolerance, and salinity tolerance. As used herein, environmental stress tolerance genes refer to genes which function to acclimate a plant to an environment stress. For example, cold tolerance genes, also referred to as COR genes (COld Regulated), refer to genes which function to acclimate a plant to a cold temperature environment. These genes typically are activated when a plant is exposed to cold temperatures. Dehydration tolerance genes refer to genes which function to acclimate a plant to dehydration stress. These genes typically are activated in response to dehydration conditions which can be associated with drought or cold temperatures which cause water in the plant to freeze and thereby dehydrate the plant tissue. It is noted that some cold tolerance genes may function to provide a plant with a degree of dehydration tolerance and visa versa. For example, COR genes are known to also be activated by dehydration stress. This application is intended to encompass genes which regulate one or more environmental stress tolerance genes such as cold tolerance genes, dehydration tolerance genes, and genes which perform a dual function of cold and dehydration tolerance.

One embodiment of the invention relates to a DNA sequence in isolated form which includes a sequence encoding a binding protein capable of selectively binding to a DNA regulatory sequence which regulates expression of one or more environmental stress tolerance genes in a plant. The binding protein is preferably capable of regulating expression of one or more environmental stress tolerance genes in a plant by selectively binding to a DNA regulatory sequence which regulates the one or more environmental stress tolerance genes. In one variation, the binding protein is a non-naturally occurring protein formed by combining an amino acid sequence capable of binding to a CCG regulatory sequence, preferably a CCGAC regulatory sequence with an amino acid sequence which forms a transcription activation region which regulates expression of one or more environmental stress tolerance genes in a plant by regulating expression of one or more environmental stress tolerance genes when the binding protein binds to the regulatory region.

The DNA sequence may exist in a variety of forms including a plasmid or vector and can include sequences unrelated to the gene sequence encoding the binding protein. For example, the DNA sequence can include a promoter which regulates expression of the regulatory gene.

In one variation of this embodiment, the DNA regulatory sequence is a C-repeat cold and drought regulation element (C-repeat/DRE). As will be explained and demonstrated herein, C-repeat/DRE regulatory sequences appear to be conserved in plants with some degree of variability plant to plant. Using the teachings of the present invention, C-repeat/DRE regulatory sequences native to different plants can be identified as well as the native stress tolerance regulatory genes which encode for proteins which bind to the C-repeat/DRE DNA regulatory sequences. Hence, although the examples provided herein to describe the present invention are described with regard to the Arabadopsis C-repeat/DRE DNA regulatory sequence, the present invention is not intended to be limited to the Arabadopsis C-repeat/DRE DNA regulatory sequence. Rather, the Arabadopsis C-repeat/DRE DNA regulatory sequence is believed to be a member of a class of environmental stress response regulatory elements which includes the subsequence CCGAC which in turn is believed to be a member of a class of environmental stress response regulatory elements which includes the subsequence CCG. Other different classes of environmental stress response regulatory elements may also exist. The teachings of the present invention may be used to identify sequences which bind to these and other classes of environmental stress response regulatory elements once they are identified.

In one variation of this embodiment, the gene sequence encodes a binding protein which selectively binds to a member of a class of DNA regulatory sequences which includes the subsequence CCG. In another variation, the gene sequence encodes a binding protein which selectively binds to a member of a class of DNA regulatory sequences which includes the subsequence CCGAC. The CCGAC subsequence has been found to present in the C-repeat/DRE DNA regulatory sequences of Arabadopsis and Brassica and to function in Tobacco based on the ability of the C-repeat/DRE to direct cold and tolerance regulated gene expression.

In yet another variation, the stress tolerance regulatory gene sequence encodes a binding protein which includes an AP2 domain. It is believed that a significant class of environmental stress tolerance regulatory genes encode for binding proteins with an AP2 domain capable of binding to the DNA regulatory sequence. The AP2 domain of the binding protein is preferably a homolog of the AP2 domain of one of the CBF binding proteins described herein. The subsequence encoding the AP2 domain is preferably a homolog of a subsequence of one of the CBF genes described herein which encodes an AP2 domain.

In another variation, the DNA sequence encoding the binding protein satisfies one or more of the following requirements:

- the binding protein comprises an AP2 domain which comprises a consensus sequence sufficiently homologous to any one of the consensus sequences shown in FIG. 19A, 19B, or 19C that the binding protein is capable of binding to a CCG regulatory sequence, preferably a CCGAC regulatory sequence;
- the binding protein comprises an AP2 domain which comprises a consensus sequence shown in FIG. 19A, 19B or 19C;
- the binding protein comprises an AP2 domain which comprises the amino acid residues shown in FIG. 19D or 19E;
- the binding protein comprises an AP2 domain which is sufficiently homologous to at least one of the AP2 domains shown in the application such that it is capable of binding to a CCG regulatory sequence, preferably a CCGAC regulatory sequence;

- the binding protein comprises one of the AP2 domain sequences shown in this application, including, but not limited to SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95;
- the binding protein comprises a sequence which comprises one of the amino terminus domains shown in FIG. 20 (it is noted that the sequence need not be at the amino terminus of the binding protein);
- the binding protein comprises the consensus sequence for the amino terminus domains shown in FIG. 20, (it is noted that the sequence need not be at the amino terminus of the binding protein);
- the binding protein comprises a sequence which comprises one of the carboxy terminus domains shown in FIG. 21A (it is noted that the sequence need not be at the carboxy terminus of the binding protein);
- the binding protein comprises the consensus sequence for the carboxy terminus domains shown in FIG. 21A (it is noted that the sequence need not be at the carboxy terminus of the binding protein);
- the binding protein comprises the consensus sequence for the carboxy terminus domains shown in FIG. 21B (it is noted that the sequence need not be at the carboxy terminus of the binding protein);
- one of SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94; or
- a sequence which has substantially the same degree of homology to SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94 as these sequences have with each other.

The present invention also relates to a method for identifying gene sequences from at least a portion of a plant genome which encode binding proteins capable of binding to a target DNA regulatory sequence which regulates expression of one or more stress tolerance genes in a plant.

In one embodiment, the method includes:

- taking a microorganism which includes a target DNA regulatory sequence for one or more environmental stress tolerance genes, a transcription activator for activating expression of a reporter gene, and a reporter gene whose expression is activated by a protein which includes a binding domain capable of binding to the target DNA regulatory sequence and an activation domain capable of activating the transcription activator;
- fusing sequences from a cDNA library of at least a portion of a plant genome to a sequence which encodes a functional activation domain in the microorganism;
- introducing the fused sequences into the microorganism; and
- selecting microorganisms which express the reporter gene, expression of the reporter gene indicating expression of a fusion protein which includes a binding domain for the target DNA regulatory sequence and the activation domain; and
- identifying the gene sequence from the cDNA library introduced into the microorganism.

In one variation of the method, the target DNA regulatory sequence includes the subsequence CCG and in another embodiment includes the subsequence CCGAC. In yet another variation, the target DNA regulatory sequence is the C-repeat/DRE for Arabadopsis. According to the above method, the target DNA regulatory sequence is preferably native to the plant family and more preferably to the plant species from which the cDNA library is derived.

In another variation of this embodiment, the cDNA library used in the method consists of sequences which encode for a protein having an AP2 domain since it is believed that a significant class of genes encoding binding proteins for stress tolerance genes encode an AP2 domain. As will be explained herein, screening for DNA sequences from a plant genome which exhibit this functional feature has been shown to be effective for isolating gene sequences encoding binding proteins of the present invention.

In another variation of this method, the sequences from the cDNA library are fused to a sequence which includes a selectable marker, the method further including the step of selecting for microorganisms expressing the selectable marker.

While the above methodology of the present invention is described herein with regard to identifying binding protein gene sequences from Arabidopsis cDNA using the C-repeat/DRE regulatory sequence for Arabidopsis, it is noted that this methodology can be readily used to identify regulatory binding protein gene sequences for other plants by using a DNA regulatory sequence native to those plants. Alternatively, different permutations of the CCG subsequence can be used as the target DNA regulatory sequence.

An example of a microorganism which may be used in the above method is yeast. cDNA can be introduced into the microorganism by a variety of mechanisms including plasmids and vectors. In one particular embodiment, the reporter gene is beta-galactosidase.

The present invention also relates to any DNA sequences and binding proteins encoded by those DNA sequences which are identified by the above screening method.

The present invention also relates to a protein expressed by an environmental stress tolerance regulatory gene according to the present invention which can function in vivo in a plant to regulate expression of one or more environmental stress tolerance genes.

According to one embodiment, the protein is a recombinant binding protein expressed by a copy of a recombinant gene which is either not native to the plant or is native to the plant but introduced into the plant by recombinant methodology. For example, one might wish to introduce one or more copies of a regulatory gene which is native to the plant but is under the control of a promoter which overexpresses the binding protein, expresses the binding protein independent of an environmental stress, expresses the binding protein at a higher level in response to the same environmental stress than would a plant in its native state, expresses the binding protein in response to different environmental stress conditions, and/or be induced to express the binding protein by an exogenous agent to which the plant can be exposed. Alternatively, one might wish to introduce one or more copies of a regulatory gene which is not native to the plant. For example, the non-native regulatory gene may be used to alter the way in which native environmental stress tolerance genes are regulated. Alternatively, the non-native regulatory gene may be used to regulate environmental stress tolerance genes which are also not native to the plant. The non-native regulatory gene may be used to bind to a DNA regulatory region which is not native to the plant.

In another embodiment, the proteins have been isolated from a recombinant organism. The organism may be a microorganism (e.g., bacteria, yeast) or a multicellular organism such as a plant. In one variation, the protein is in substantially isolated form.

In yet another embodiment, the protein is a native, non-recombinant binding protein whose expression is regulated within a plant by a recombinant native or non-native promoter. For example, one might wish to replace a native promoter with a recombinant promoter which overexpresses the binding protein, expresses the binding protein independent of an environmental stress, expresses the binding protein at a higher level in response to the same environmental stress than would a plant in its native state, expresses the binding protein in response to different environmental stress conditions, and/or be induced to express the binding protein by an exogenous agent to which the plant can be exposed.

In one variation of the above embodiments, the protein is capable of selectively binding to a DNA regulatory sequence for one or more environmental stress tolerance genes in a plant. In another variation, the protein includes an AP2 domain which is capable of selectively binding to a DNA regulatory sequence for one or more environmental stress tolerance genes in a plant. One method which may be used to determine whether the protein binds selectively to the DNA regulatory sequence is a gel shift assay. The DNA regulatory sequence may optionally include a CCG subsequence, a CCGAC subsequence and optionally the C-repeat/DRE sequence of Arabadopsis.

In another variation of the above embodiments, the binding protein satisfies one or more of the following requirements:

- the binding protein comprises an AP2 domain which comprises a consensus sequence sufficiently homologous to any one of the consensus sequences shown in FIG. 19A, 19B, or 19C that the binding protein is capable of binding to a CCG regulatory sequence, preferably a CCGAC regulatory sequence;
- the binding protein comprises an AP2 domain which comprises a consensus sequence shown in FIG. 19A, 19B or 19C;
- the binding protein comprises an AP2 domain which comprises the amino acid residues shown in FIG. 19D or 19E;
- the binding protein comprises an AP2 domain which is sufficiently homologous to at least one of the AP2 domains shown in the application such that it is capable of binding to a CCG regulatory sequence, preferably a CCGAC regulatory sequence;
- the binding protein comprises one of the AP2 domain sequences shown in this application, including, but not limited to SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95;
- the binding protein comprises a sequence which comprises one of the amino terminus domains shown in FIG. 20 (it is noted that the sequence need not be at the amino terminus of the binding protein);
- the binding protein comprises the consensus sequence for the amino terminus domains shown in FIG. 20, (it is noted that the sequence need not be at the amino terminus of the binding protein);
- the binding protein comprises a sequence which comprises one of the carboxy terminus domains shown in FIG. 21A (it is noted that the sequence need not be at the carboxy terminus of the binding protein);
- the binding protein comprises the consensus sequence for the carboxy terminus domains shown in FIG. 21A (it is noted that the sequence need not be at the carboxy terminus of the binding protein); and
- the binding protein comprises the consensus sequence for the carboxy terminus domains shown in FIG. 21B (it is noted that the sequence need not be at the carboxy terminus of the binding protein).

The sequence of the binding protein may be a naturally occurring sequence such as the ones shown in SEQ. ID. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95 or may be a non-naturally occurring sequence. It is noted, however, that binding proteins according to the present invention are intended to encompass non-naturally occurring sequences which are derivatives of the classes of binding proteins taught herein. For example, additional binding proteins may be constructed using one of the AP2 domains taught herein or the consensus sequence of these AP2 domains. It may be desirable to include with the AP2 domain a transcription activation region. The transcription activation region may be native to the plant or non-native to the plant in which the binding protein will be used. For example, the sequence may include a subsequence which encodes a binding domain for the DNA regulatory sequence fused to a transcription activating region, such as the transcription activating region of VP16 or GAL4. Optionally, one can include in the binding protein one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

Optionally, the binding protein can be viewed as comprising one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

In another embodiment, the binding protein is an isolated protein or a recombinantly produced protein which has a molecular weight of about 26 kDa as measured in an electrophoresis gel and binds to a DNA regulatory sequence which regulates a cold or dehydration regulated gene of *Arabidopsis thaliana.*

The present invention also relates to DNA and RNA constructs, such as plasmids, vectors, and the like, which are capable of transforming a plant. The constructs include a sequence which encodes a binding protein capable of selectively binding to a DNA regulatory sequence which regulates the one or more environmental stress tolerance genes. The binding protein is preferably able to regulate expression of one or more environmental stress tolerance genes in a plant by selectively binding to the DNA regulatory sequence. More preferably, when transformed into a plant, the sequence regulates expression of one or more environmental stress tolerance genes in the plant by expressing the binding protein. In one embodiment, the DNA construct includes a promoter and a regulatory gene sequence whose expression is under the control of the promoter. Different promoters may be used to select the degree of expression or conditions under which the regulatory gene is expressed. For example, the promoter can be used to cause overexpression of the regulatory gene, expression of the regulatory gene independent of an environmental stress, expression of the regulatory gene at a higher level in response to the same environmental stress than would a plant in its native state, expression of the regulatory gene in response to different environmental stress conditions, and/or induction of expression of the regulatory gene by an exogenous agent to which the plant can be exposed. Promoters can also be used to cause the protein to be expressed at selected times during a plant's life. Tissue-specific promoters can be used to cause the protein to be expressed in selected tissues. For example, flower-, fruit- and seed-specific promoters can be used to cause the protein to be selectively expressed in flowers, fruits or seeds of the plant.

In another embodiment, the DNA construct comprises a sequence which encodes:

a binding protein comprising an AP2 domain which comprises a consensus sequence sufficiently homologous to any one of the consensus sequences shown in FIG. 19A, 19B, or 19C that the binding protein is capable of binding to a CCG regulatory sequence, preferably a CCGAC regulatory sequence;

a binding protein comprising an AP2 domain which comprises a consensus sequence shown in FIG. 19A, 19B or 19C;

a binding protein comprising an AP2 domain which comprises the amino acid residues shown in FIG. 19D or 19E;

a binding protein comprising an AP2 domain which is sufficiently homologous to at least one of the AP2 domains shown in the application such that it is capable of binding to a CCG regulatory sequence, preferably a CCGAC regulatory sequence;

a binding protein comprising one of the AP2 domain sequences shown in this application, including, but not limited to SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95;

a binding protein comprising a sequence which comprises one of the amino terminus domains shown in FIG. 20 (it is noted that the sequence need not be at the amino terminus of the binding protein);

a binding protein comprising the consensus sequence for the amino terminus domains shown in FIG. 20, (it is noted that the sequence need not be at the amino terminus of the binding protein);

a binding protein comprising a sequence which comprises one of the carboxy terminus domains shown in FIG. 21A (it is noted that the sequence need not be at the carboxy terminus of the binding protein);

a binding protein comprising the consensus sequence for the carboxy terminus domains shown in FIG. 21A (it is noted that the sequence need not be at the carboxy terminus of the binding protein);

a binding protein comprising the consensus sequence for the carboxy terminus domains shown in FIG. 21B (it is noted that the sequence need not be at the carboxy terminus of the binding protein);

one of SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94; or a sequence which has substantially the same degree of homology to SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94 as these sequences have with each other.

The present invention also relates to plasmids pCBF1 (ATCC 98063), pCBF2, and pCBF3.

The present invention also relates to a recombinant microorganism, such as a bacterium, yeast, fungus, virus, into which at least one copy of a regulatory gene encoding a binding protein of the present invention has been introduced by a recombinant methodology.

The present invention also relates to recombinant plants into which at least one copy of a regulatory gene encoding a binding protein of the present invention has been introduced by a recombinant methodology. The recombinant copy of the regulatory gene may be native or non-native to the plant and express a binding protein which is either native or non-native to the plant. Expression of the recombinant copy of the regulatory gene may be under the control of the promoter. The promoter may increase the level at which the regulatory gene is expressed, express the regulatory gene without being induced by an environmental stress and/or express the regulatory gene in response to a different form or degree of environmental stress than would otherwise be needed to induce expression of the regulatory gene. For example, a promoter can be used which turns on at a temperature that is warmer than the temperature at which the plant normally exhibits cold tolerance. This would enable the cold tolerance thermostat of a plant to be altered. Similarly, a promoter can be used which turns on at a dehydration condition that is wetter than the dehydration condition at which the plant normally exhibits dehydration tolerance. This would enable the level at which a plant responds to dehydration to be altered. A promoter can also be used which causes a higher level of expression to occur at a given environmental condition (e.g. temperature and/or dryness) than the plant would express in its native state. The promoter may also be inducible by an exogenous agent, i.e., express the regulatory gene in response to the presence of an agent to which the promoter is exposed. This would enable stress tolerance to be induced by applying an inducing agent to the plant.

Selection of the promoter can also be used to determine what tissues in the plant express the binding protein as well as when expression occurs in the plant's lifecycle. By selecting a promoter which regulates in what tissues and when in a plant's life the promoter functions to regulate expression of the binding protein, in combination with the selecting how that promoter regulates expression (level of expression and/or type of environmental or chemical induction), an incredible range of control over the environmental stress responses of a plant can be achieved according to the present invention. For example, flower-, fruit- and seed-specific promoters can be used to regulate the expression of the binding protein in these tissues of the plant, especially when sudden frosts strike in early spring and late fall.

The environmental stress tolerance gene regulated by the recombinantly expressed regulatory gene may be native or non-native to the plant. Hence, in one embodiment, the plant includes a recombinant copy of a regulatory gene which is native to the plant and expresses a native protein which functions within the plant to regulate expression of a native environmental stress tolerance gene. In this embodiment, the recombinant plant expresses a higher level of the native regulatory gene than the plant would otherwise.

In another embodiment, at least one of the regulatory genes and the environmental stress tolerance genes is not native to the plant. For example, the regulatory gene can be native and the environmental stress tolerance gene is non-native, or the regulatory gene is non-native and the environmental stress tolerance gene is native to the plant.

In yet another embodiment, the plant can include a recombinant copy of a regulatory gene which is not native to the plant as well as a recombinant copy of one or more environmental stress tolerance genes which also is not native to the plant. According to this embodiment, the non-native regulatory gene expresses a non-native binding protein which functions within the plant to regulate expression of the one or more non-native environmental stress tolerance genes. In this regard, it is envisioned that the present invention can be used to introduce, change and/or augment the environmental stress tolerance of a plant by introducing and causing the expression of environmental stress tolerance which the plant does not have in its native form. Accordingly, plants from warmer climates can be engineered to include one or more cold tolerance genes along with a regulatory gene needed to cause expression of the cold tolerance genes in the plant so that the engineered plant can survive better in a colder climate. Similarly, a plant can be engineered to include one or more dehydration tolerance genes along with a regulatory gene needed to cause expression of the dehydration tolerance gene so that the engineered plant can grow better in a dryer climate. In this regard, it should be possible to take a plant which grows well in a first climate and engineer it to include stress tolerance genes and regulatory genes native to a second climate so that the plant can grow well in the second climate.

The present invention also relates to a method for changing or enhancing the environmental stress tolerance of a plant.

In one embodiment, the method includes introducing at least one copy of a regulatory gene encoding a binding protein of the present invention into a plant; expressing the binding protein encoded by the regulatory gene; and using the expressed binding protein to stimulate expression of at least one environmental stress tolerance gene through binding to a DNA regulatory sequence. According to this embodiment, the regulatory gene may be non-recombinant or recombinant native or non-native to the plant. Similarly, the DNA regulatory sequence and the environmental stress tolerance gene may each independently be native or non-native to the plant. In one variation of this embodiment, the method further includes recombinantly introducing an environmental stress tolerance gene into the plant which is regulated by the recombinant regulatory gene.

In another embodiment, the method includes introducing a recombinant promoter which regulates expression of a regulatory gene encoding a binding protein of the present invention into a plant; expressing the binding protein under the control of the recombinant promoter in the plant; and using the expressed binding protein to stimulate expression of at least one environmental stress tolerance gene through binding to a DNA regulatory sequence.

According to this embodiment, the regulatory gene, the DNA regulatory sequence and the environmental stress tolerance gene may each independently be non-recombinant or recombinant native or non-native to the plant. Also according to this embodiment, the promoter can be a tissue-specific promoter such as a flower-, fruit- and seed-specific promoter. In this instance, expressing the binding protein includes selectively expressing the binding protein in a particular type of tissue, such as flowers, fruits or seeds of the plant.

In yet another embodiment, the method includes introducing at least one recombinant environmental stress tolerance gene into a plant; expressing a binding protein; and using the expressed binding protein to stimulate expression of the recombinant environmental stress tolerance gene through binding to a DNA regulatory sequence. According to this embodiment, the gene encoding the regulatory protein, and the DNA regulatory sequence may each independently be non-recombinant or recombinant native or non-native to the plant. The recombinant environmental stress tolerance gene may be either native or non-native to the plant.

1. Definitions

The term "C-repeat cold and drought regulation element" or "C-repeat/DRE" refers to a sequence which includes CCG and functions as a binding domain in a plant to regulate expression of one or more environmental stress tolerance genes, such as cold or dehydration stress tolerance genes.

The term "cold stress" refers to a decrease in ambient temperature, including a decrease to freezing temperatures, which causes a plant to attempt to acclimate itself to the decreased ambient temperature.

The term "dehydration stress" refers to drought, high salinity and other conditions which cause a decrease in cellular water potential in a plant.

Transformation means the process for changing the genotype of a recipient organism by the stable introduction of DNA by whatever means.

A transgenic plant is a plant containing DNA sequences which were introduced by transformation. Horticultural and crop plants particularly benefit from the present invention.

Translation means the process whereby the genetic information in an mRNA molecule directs the order of specific amino acids during protein synthesis.

The term "essentially homologous" means that the DNA or protein is sufficiently duplicative of that set forth in FIG. 2B to produce the same result. Such DNA can be used as a probe to isolate DNA's in other plants.

A promoter is a DNA fragment which causes transcription of genetic material. For the purposes described herein, promoter is used to denote DNA fragments that permit transcription in plant cells.

A poly-A addition site is a nucleotide sequence which causes certain enzymes to cleave mRNA at a specific site and to add a sequence of adenylic acid residues to the 3'-end of the mRNA.

The phrase "DNA in isolated form" refers to DNA sequence which has been at least partially separated from other DNA present in its native state in an organism. A cDNA library of genomic DNA is not "DNA in isolated form" whereas DNA which has been at least partially purified by gel electrophoresis corresponds to "DNA in isolated form".

2. C-Repeat/DRE Regulatory Elements in Plants

C-repeat cold and drought regulation elements (C-repeat/DRE) are sequences which function as a cis-acting regulatory element that stimulates transcription in response to an environmental stress, such as low temperature (Yamaguchi-Shinozaki, K., et al., The Plant Cell 6:251–264 (1994); and Baker, S. S., et al., Plant Mol. Biol. 24:701–713 (1994); Jiang, C., et al., Plant Mol. Biol. 30:679–684 (1996)) or dehydration stress and high salinity (Yamaguchi-Shinozaki, K., et al., The Plant Cell 6:251–264 (1994)). An object of the research leading to the present invention was the determination of how a C-repeat/DRE stimulates gene expression in response to these environmental factors, and whether cold, dehydration and high salinity affect independent or overlapping regulatory systems.

The first step toward determining how a C-repeat/DRE regulation element stimulates gene expression was the identification of the C-repeat cold and drought regulation element itself. The 5 base pair core sequence, CCGAC, has been found to be present once to multiple times in a variety of plant cold-regulated promoters in Arabidopsis and Brassica including the COR15a (Baker, S. S., et al, Plant. Mol. Biol. 24:701–713 (1994)); COR78/RD29A (Horvath, D. P., et al., Plant Physiol. 103:1047–1053 (1993) and Yamaguchi-Shinozaki, K., et al., The Plant Cell 6:251–264 (1994)); COR6.6 (Wang, H., et al., Plant Mol. biol. 28:605–617 (1995)); and KIN1 (Wang, H., et al, Plant Mol. Biol. 28:605–617 (1995)) genes of Arabidopsis and the BN115 gene of *Brassica napus* (White, T. C., et al, Plant Physiol. 106:917–928 (1994)). As shown in the examples herein, core sequence CCGAC was used to identify proteins encoded by genes within the Arabidopsis genome which bind to this core sequence.

Applicants believe that the CCGAC core sequence is a member of family of core sequences having the common subsequence CCG. The binding of CBF1 to the C-repeat/DRE involves the AP2 domain. In this regard, it is germane to note that the tobacco ethylene response element, AGCCGCC, closely resembles the C-repeat/DRE sequences present in the promoters of the Arabidopsis genes COR15a, GGCCGAC, and COR78/RD29A, TACCGAC. While the specific teachings in the present invention used only a DNA regulatory sequence which includes a CCGAC subsequence as the C-repeat/DRE core regulatory sequence, Applicants believe that other C-repeat/DRE regulatory sequences exist which belong to a broader CCG family of regulatory sequences. By screening plant genomes according to the methodology taught herein using other members of the CCG family, additional regulatory sequences as well as the binding proteins which bind to these regulatory sequences can be identified. For example, plants which are known to exhibit a form of environmental stress tolerance can be screened according to the blue colony assay and other screening methodologies used in the present invention with other members of the CCG family in order to identify other binding proteins and their gene sequences. Examples of other members of the CCG family include, but are not limited to, environmental stress response regulatory elements which include one of the following sequences: CCGAA, CCGAT, CCGAC, CCGAG, CCGTA, CCGTT, CCGTC, CCGTG, CCGCA, CCGCT, CCGCG, CCGCC, CCGGA, CCGGT, CCGGC, CCGGG, AACCG, ATCCG, ACCCG, AGCCG, TACCG, TTCCG, TCCCG, TGCCG, CACCG, CTCCG, CGCCG, CCCCG, GACCG, GTCCG, GCCCG, GGCCG, ACCGA, ACCGT, ACCGC, ACCGG, TCCGA, TCCGT, TCCGC, TCCGG, CCCGA, CCCGT, CCCGC, CCCGG, GCCGA, GCCGT, GCCGC, and GCCGG.

Applicants also believe that other families of environmental stress tolerance DNA regulatory sequences, other than the CCG family may exist. The methodologies of the present invention may be used once such other families are identified in order to identify specific environmental stress tolerance DNA regulatory sequences and associated binding proteins.

3. Identification of Environmental Stress Tolerance Regulatory Gene Sequences Using Target Regulatory Sequence It is possible to take a cDNA library of at least a portion of a plant genome and screen the cDNA library for the presence of regulatory gene sequences which encode binding proteins capable of binding to a target regulatory sequence. As used here, a target DNA regulatory sequence refers to a sequence to which a binding protein for one or more environmental stress tolerance genes binds. Permutations of the CCG and CCGAC families of DNA regulatory sequences represent examples of target DNA regulatory sequences. As detailed in Example 1 herein, this was the approach was used to identify CBF1, a sequence which encodes a binding protein for the Arabadopsis DNA regulatory sequence, from an Arabadopsis cDNA library.

First a target regulatory sequence is selected. The target regulatory sequence is preferably native to the plant from which the cDNA library being screened is derived.

Once a target regulatory sequence is selected, the target regulatory sequence is fused to a reporter gene and introduced into a microorganism. Expression of the reporter gene can be activated by a protein which includes a binding domain capable of binding to the target DNA regulatory sequence and an activation domain capable of activating transcription.

Sequences from a cDNA library of at least a portion of a plant genome are then fused to a sequence which encodes a functional activation domain in the microorganism. The fused sequences are then introduced into the microorganism. It is possible that the sequence from the cDNA library may already encode a functional activation domain, for example as described herein in Example 1.

Microorganisms which express the reporter gene are then selected. Since only those microorganisms which express a fusion protein which includes a binding domain for the target DNA regulatory sequence and an activation domain will stimulate expression of the reporter gene, expression of the reporter gene indicates expression of such a fusion protein.

The gene sequence from the cDNA library introduced into the microorganism which stimulates expression of the reporter gene is then identified.

According to the above method, the target DNA regulatory sequence preferably includes the subsequence CCG and more preferably includes the subsequence CCGAC.

The "one-hybrid" strategy described in Li, J. J. and I. Herskowitz, Science 262:1870–1874 (1993) and used in Example 1 to screen Arabidopsis cDNA is an example of this method. This method can be used to screen any plant species for cDNAs that encode a target regulatory sequence, such as a C-repeat/DRE regulatory sequence. According to the "one hybrid" strategy, yeast strains are constructed that contain a lacZ reporter gene with either wild-type or mutant versions of target regulatory sequences in place of the normal UAS (upstream activator sequence) of the GAL1 promoter. Yeast strains carrying these reporter constructs produce low levels of βbeta-galactosidase and form white colonies on filters containing X-gal. Reporter strains carrying wild-type target regulatory sequences are transformed with a cDNA expression library that contains random cDNA inserts fused to the acidic activator domain of the yeast GAL4 transcription factor "GAL4-ACT". Recombinant plasmids in the expression library that contain a cDNA insert encoding a C-repeat/DRE binding domain fused to GAL4-ACT will express fusion proteins which bind upstream of the lacZ reporter genes carrying the wild-type target regulatory sequence, activate transcription of the lacZ gene, and result in yeast forming blue colonies on X-gal-treated filters. Alternatively, the sequence from the cDNA library introduced into the microorganism may, as was observed in Example 1, include a sequence encoding an activator domain and thus not utilize the acidic activator domain of the yeast GAL4 transcription factor "GAL4-ACT".

Recombinant plasmids from such "blue yeast" are then isolated and transformed back into reporter strains that contain either a wild-type or mutant version of target regulatory sequence fused to the lacZ gene. The plasmids that are desired are those that turn the former strains blue, but not the later, indicating that the cloned DNA binding domain is specific for the target regulatory sequence.

Based on presence of an AP2 binding domain in CBF1, CBF2 and CBF3, Applicants believe that an AP2 binding domain is present in a significant number of the environmental stress tolerance regulatory binding proteins. Accordingly, it is believed that the specificity of the above method for screening for gene sequences encoding a regulatory binding protein can optionally be improved by first selecting cDNA from a plant genome library which includes a potential AP2 domain site. This can be routinely done by selecting probes for selecting sequences in the library which include potential AP2 domain sequences.

4. Screening for Expression of Environmental Stress Tolerance Regulatory Protein Once one or more microorganisms are selected which are believed to express a protein capable of binding to the target regulatory element and activate expression of the reporter gene, further analysis can be performed to identify and isolate full length cDNAs; i.e. cDNAs that encode the entire protein that binds to the target regulatory sequence. The coding sequence for the protein can then cloned into an expression vector, such as the pET bacterial expression vectors (Novagen), and used to produce the protein at high levels. The protein can then be analyzed by gel retardation experiments (See Example 1F) to confirm that it binds specifically to the target regulatory sequence.

Potential sequences can be further screened using known regulatory gene sequences, such as CBF1, CB2, and CBF3, or the presence of an AP2 domain which is believed to be common to a significant class of this genes. Once identified, particular sequences can be transformed into yeast to test for activation of expression of a reporter gene, for example as described in Example 1E.

5. Screening for Binding to Target Regulatory Sequence

Once a regulatory gene sequence is identified, the sequence can be introduced into a microorganism in order to express the protein encoded by the sequence. A gel shift assay, such as the one described in Example 1F, can then be used to test for in vitro binding of the expressed protein to the target DNA regulatory sequence.

Figure 5:
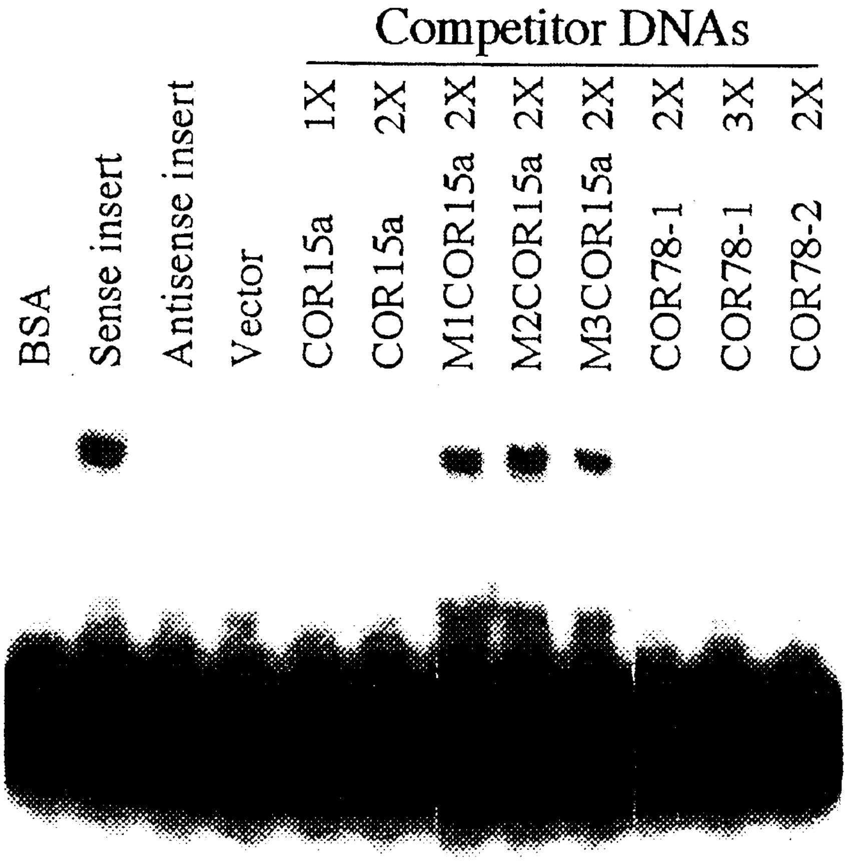
FIG. 5 is a photograph of a gel for shift assays indicating that CBF1 binds to the C-repeat/DRE.

Mutagenesis of the target DNA regulatory sequence can also be performed in order to evaluate the binding selectivity of the expressed protein. It is preferred that the expressed protein selectively bind to the target DNA regulatory sequence over related sequences with one or more base differences from the target DNA regulatory sequence. For example, FIG. 5 is a photograph of a gel from a shift assay in which CBF1 was shown to selectively bind to the wild-type C-repeat/DRE CCGAC.

6. Altering the Environmental Stress Tolerance of a Plant

The present invention also provides a method for recombinant engineered plants with a new or altered response to one or more environmental stresses.

According to one embodiment, a copy of a gene native to a plant which encodes a binding protein according to the present invention is recombinantly introduced into the plant such that the plant expresses a recombinant binding protein encoded by the recombinant copy of the gene.

According to another embodiment, a non-native gene which encodes a binding protein according to the present invention is recombinantly introduced into a plant such that the plant expresses a recombinant binding protein encoded by the recombinant non-native gene.

According to yet another embodiment, a native or non-native DNA regulatory sequence is recombinantly introduced into a plant such that the recombinant DNA regulatory sequence regulates the expression of one or more environmental stress tolerance genes in the plant. The plant includes a gene which encodes a binding protein capable of binding to the recombinant DNA regulatory sequence.

In yet another embodiment, a native or non-native promoter is recombinantly introduced into a plant such that the recombinant promoter regulates the expression of a binding protein which binds to a DNA regulatory sequence.

According to each of the above embodiments, unless otherwise specified, the gene encoding the binding protein, the promoter promoting the expression of the binding protein, the DNA regulatory sequence, and the environmental stress tolerance genes may be non-recombinant or recombinant sequences. The recombinant sequences may be native to the plant or may be non-native to the plant. All the above permutations are intended to fall within the scope of the present invention.

As an example, many plants increase in freezing tolerance in response to low non-freezing temperatures, a process known as cold acclimation. A large number of biochemical changes occur during cold acclimation including the activation of COR (COld Regulated) genes. These genes, which are also expressed in response to dehydration (e.g., drought and high salinity), are thought to help protect plant cells against the potentially deleterious effects of dehydration associated with freezing, drought and high salinity stress. Indeed, expression of the COR15a gene in plants grown at normal temperatures (22° C.) enhances the freezing tolerance of chloroplasts.

By manipulating the expression of COR genes, the stress tolerance of crop and horticultural plants could be improved, e.g., engineer broader climate ranges; target stress resistance to stress-sensitive parts of plants; render plants stress-resistant when a stress condition (frost and drought) is imminent. To bring about these effects, however, the expression of the COR genes must be manipulated. The gene, CBF1, that encodes the transcription factor that binds to the C-repeat/DRE regulatory element present in the promoters of all COR genes described to date has been isolated. CBF1 in yeast activates expression of reporter genes that have been fused to the C-repeat/DRE element. Further, expression of CBF1 in plants has been shown to activate the expression of COR genes.

By introducing modified versions of sequences encoding regulatory binding proteins, such as CBF1, into plants, the expression of COR genes can be modified, and thereby enhance the freezing and dehydration tolerance of plants.

In each of the above embodiments, expression of the recombinant copy of the regulatory gene may be under the control of a promoter. The promoter may be recombinant or non-recombinant. In the case of recombinant promoters, the promoter may be native or non-native to the plant.

When a recombinant promoter is used, the promoter can be selected to cause expression of the binding protein in a manner which is different than how the binding protein is expressed by the plant in its native state. For example, the promoter may increase the level at which the binding protein is expressed, express the binding protein without being induced by an environmental stress and/or express the binding protein in response to a different form or degree of environmental stress than would otherwise be needed to induce expression of the binding protein. The promoter may also be inducible by an exogenous agent. For example, a strong constitutive promoter could be used to cause increased levels of COR gene expression in both non-stress and stressed plants which in turn, results in enhanced freezing and dehydration tolerance. Examples of such strong constitutive promoters-include but are not limited to the nopaline synthase (NOS) and octopine synthase (OCS)

promoters, the cauliflower mosaic virus (CaMV) 19S and 35S (Odell et al., Nature 313: 810–812 (1985)) promoters or the enhanced CaMV 35S promoters (Kay et al., Science 236: 1299–1302 (1987)).

A tissue-specific promoter could also be used to alter COR gene expression in tissues that are highly sensitive to stress such as embryos in the seed, flower and fruit, thereby enhancing the stress tolerance of these tissues. Embryo-active promoters include promoters such as the *B. napus* napin promoter (U.S. Pat. No. 5,420,034), the soybean 7S promoter, the Arabidopsis 12S globulin (cruiferin) promoter (Pang, et al. Plant Molecular Biology 11:805–820 (1988)), or the maize globulin promoter (Kriz et al. Plant Physiol. 91:636 (1989); U.S. Pat. No. 5,773,691) for use in cereal embryos.

Promoters useful in expressing foreign genes in fruits (Cordes et al., Plant Cell 1:1025–1034 (1989); Deikman and Fischer, EMBO J. 7: 3315–3320 (1988); Della Penna et al., Proc. Natl. Acad. Sci. USA 83: 6420–6424 (1986)) could also be used to alter COR gene expression in fruits. Examples include, but are not limited to, the fruit-specific promoter that was used to express an ADP glucose pyrophosphorylase gene in order to increase the solid content of tomato fruit (Kishore, PCT App. WO 91/19806), the promoter from the 2A11 genomic clone (Pear, et al. Plant Mol. Biol. 13: 639–651 (1989); U.S. Pat. No. 4,943,674) that can be used to control expression of ADP glucose pyrophosphorylase in tomato fruit, the E4 and E8promoters (Deikman, et al., EMBO J. 7: 3315–3320 (1988); U.S. Pat. No. 5,545, 815), the promoter for polygalacturonase, the raspberry fruit promoter described in U.S. Pat. No. 5,783,393, fruit-active promoters such as the E8 promoter from tomatoes, and citrus fruit-specific or fruit-active promoters that can be isolated from the CitMT45 cDNA (Moriguchi et al., Gene 12: 221–227 (1998)) and pSPS2 (Komatsu et al., Mol. Gen. Genet. 252:346–351 (1996)).

Promoters known to be expressed in developing flowers, particularly in the carpel or pistil tissues, could also be used to alter COR gene expression in flowers. Examples of such promoters include the DefH9 promoter that was used to make parthenocarpic plants and is expressed in the petals, stamens, carpels and developing ovules (Rotino et al. Nat Biotechnol 15:1398–401(1997)), the SK2-promoter that was shown to express in the pistil (Ficker et al., Plant Mol Biol 35: 425–31 (1997)), and the Agamous promoter and intergenic region that was used to express in early and late flowers, and in the inner two whorls of flowers (Sieburth and Meyerowitz, Plant Cell 9: 355–65 (1997)).

Other tissue-specific promoters that could be used to alter COR gene expression in specific tissues include, but are not limited to, seed-specific promoters for the *B. napus* napin gene (U.S. Pat. No. 5,420,034), the soybean 7S promoter, the Arabidopsis 12S globulin (cruiferin) promoter (Pang, et al. Plant Molecular Biology 11: 805–820 (1988)), the maize 27 kd zein promoter, the rice glutelin 1 promoter and the phytohemaglutinin gene, tuber-specific promoters such as the patatin promoter, and the promoter for the small subunit of ribuloe-1,5-bis-phosphate carboxylase (ssRUBISCO) whose expression is activated in photosynthetic tissues such as leaves. It should be noted that other promoters that are known or found to cause specific expression in flowers, seeds or fruits of plants or express in these or other tissues of the plants to cause transcription in plant cells could also be used to alter COR gene expression in the specific tissues according to the present invention.

Altering COR gene expression in specific tissues of plants such as flowers, fruits or seeds may increase frost tolerance of these tissue and prolong the growing seasons for plants. Examples of the specific tissues of plants according to the present invention include, but not limited to, frost-resistant flowers in strawberries, peaches, blueberries, cherries, apricots, daffodils, apples, and plums; frost-resistant canola or rape seeds for preventing the formation of green seeds at harvest; frost-resistant barley seeds for maintaining malting ability; and frost-resistant fruits including true berries such as tomato, grape, blueberry, cranberry, currant, and eggplant; stone fruits (drupes) such as cherry, plum, apricot, peach, nectarine and avocado; and compound fruits (druplets) such as raspberry and blackberry; in citrus fruits such as oranges, lemons, grapefruit and tangerines; and in melons such watermelon, cantaloupe, honeydew, cucumber, and squash.

In addition, the COR gene expression can also be altered in specific tissues of the following plants according to the present invention: cauliflower (*Brassica oleracea*), artichoke (*Cynara scolymus*), fruits such as apple (*Malus,* e.g. *domesticus*), banana (*Musa,* e.g. *acuminata*), berries (such as the currant, *Ribes,* e.g. *rubrum*), cherries (such as the sweet cherry, *Prunus,* e.g. *avium*), cucumber (*Cucumis,* e.g. *sativus*), grape (*Vitis,* e.g. *vinifera*), lemon (*Citrus limon*), melon (*Cucumis melo*), nuts (such as the walnut, *Juglans,* e.g. *regia;* peanut, *Arachis hypogeae*), orange (*Citrus,* e.g. *maxima*), peach (*Prunus,* e.g. *persica*), pear (*Pyra,* e.g. *communis*), pepper (*Solanum,* e.g. *capsicum*), plum (*Prunus,* e.g. *domestica*), strawberry (*Fragaria,* e.g. *moschata*), tomato (*Lycopersicon,* e.g. *esculentum*), leafs, such as alfalfa (*Medicago,* e.g. *sativa*), cabbages (such as *Brassica oleracea*), endive (*Cichoreum,* e.g. *endivia*), leek (*Allium,* e.g. *porrum*), lettuce (*Lactuca,* e.g. *sativa*), spinach (*Spinacia* e.g. *oleraceae*), tobacco (*Nicotiana,* e.g. *tabacum*), roots, such as arrowroot (*Maranta,* e.g. *arundinacea*), beet (*Beta,* e.g. *vulgaris*), carrot (*Daucus,* e.g. *carota*), cassava (*Manihot,* e.g. *esculenta*), turnip (*Brassica,* e.g. *rapa*), radish (*Raphanus,* e.g. *sativus*), yam (*Dioscorea,* e.g. *esculenta*), sweet potato (*Ipomoea batatas*) and seeds, such as bean (*Phaseolus,* e.g. *vulgaris*), pea (*Pisum,* e.g. *sativum*), soybean (*Glycin,* e.g. *max*), wheat (*Triticum,* e.g. *aestivum*), barley (*Hordeum,* e.g. *vulgare*), corn (*Zea,* e.g. *mays*), rice (*Oryza,* e.g. *sativa*), tubers such as kohlrabi (*Brassica,* e.g. *oleraceae*), and potato (*Solanum,* e.g. *tuberosum*).

Alternatively, an inducible promoter may be used to control the expression of the regulatory binding protein, such as CBF1, in plants. Because, in some cases, constitutive expression of higher levels of CBF proteins may have some detrimental effects on plant growth and development, the controlled expression of CBF genes is especially advantageous. For example, a promoter could be used to induce the expression of CBF proteins only at a proper time, such as prior to a frost that may occur earlier or later in the growing season of a plant, thereby prolonging the growing season of a crop and increasing the productivity of the land. This may be accomplished by applying an exogenous inducer by a grower whenever desired. Alternatively, a promoter could be used which turns on at a temperature that is warmer than the temperature at which the plant normally exhibits cold tolerance. This would enable the cold tolerance thermostat of a plant to be altered. Similarly, a promoter can be used which turns on at a dehydration condition that is wetter than the dehydration condition at which the plant normally exhibits dehydration tolerance. This would enable the level at which a plant responds to dehydration to be altered.

Promoters which are known or are found to cause inducible transcription of the DNA into mRNA in plant cells can be used in the present invention. Such promoters may be obtained from a variety of sources such as plant and inducible microbial sources, and may be activated by a variety of exogenous stimuli, such as cold, heat, dehydration, pathogenesis and chemical treatment. The particular promoter selected is preferably capable of causing sufficient expression of the regulatory binding protein, such as CBF1, to enhance plant tolerance to environmental stresses. Examples of promoters which may be used include, but are not limited to, the promoter for the DRE (C-repeat) binding protein gene dreb2a (Liu, et al. Plant Cell 10: 1391–1406 (1998)) that is activated by dehydration and high-salt stress, the promoter for delta 1-pyrroline-5-carboxylate synthetase (P5CS) whose expression is induced by dehydration, high salt and treatment with plant hormone abscisic acid (ABA) (Yoshiba, et al., Plant J. 7 751–760 (1987)), the promoters for the rd22 gene from Arabidopsis whose transcription is induced under by salt stress, water deficit and endogenous ABA (Yamaguchi-Shinozaki and Shinozaki, Mol Gen Genet 238 17–25 (1993)), the promoter for the rd29b gene (Yamaguchi-Shinizaki and Shinozaki, Plant Physiol., 101 1119–1120 (1993)) whose expression is induced by desiccation, salt stress and exogenous ABA treatment (Ishitani et al., Plant Cell 10 1151–1161 (1998)), the promoter for the rab18 gene from Arabidopsis whose transcripts accumulate in plants exposed to water deficit or exogenous ABA treatment, and the promoter for the pathogenesis-related protein 1a (PR-1a) gene whose expression is induced by pathogenesis organisms or by chemicals such as salicylic acid and polyacrylic acid.

It should be noted that the promoters described above may be further modified to alter their expression characteristics. For example, the drought/ABA inducible promoter for the rab18 gene may be incorporated into seed-specific promoters such that the rab18 promoter is drought/ABA inducible only when developing seeds. Similarly, any number of chimeric promoters can be created by ligating a DNA fragment sufficient to confer environmental stress inducibility from the promoters described above to constitute promoters with other specificities such as tissue-specific promoters, developmentally regulated promoters, light-regulated promoters, hormone-responsive promoters, etc. This should result in the creation of chimeric promoters capable of being used to cause expression of the regulatory binding proteins in any plant tissue or combination of plant tissues. Expression can also be made to occur either at a specific time during a plant's life cycle or throughout the plant's life cycle.

According to the present invention, an expression vector can be constructed to express the regulatory binding protein in the transformed plants to enhance their tolerance to environmental stresses. In one embodiment, the DNA construct may contain (1) an inducible promoter that activates expression of the regulatory binding protein in response to environmental stimuli; (2) a sequence encoding the regulatory binding protein; and (3) a 3' non-translated region which enables 3' transcriptional termination and polyadenylation of the mRNA transcript. The inducible promoter may be any one of the natural or recombinant promoters described above. The gene encoding the regulatory binding protein can be any one disclosed in the present invention. The 3' region downstream from this gene should be capable of providing a polyadenylation signal and other regulatory sequences that may be required for the proper expression and processing of a mRNA may be operably linked to the 3' end of a structural gene to accomplish the invention. This may include the native 3' end of the homologous gene form which the regulatory binding protein and/or the inducible promoter is derived, the 3' end from a heterologous gene encoding the same protein from other species, the 3' end from viral genes such as the 3' end of the 35S or the 19S cauliflower mosaic virus transcripts, the 3' end of the opine synthesis genes of *Agrobacterium tumefaciens,* or the 3' end sequences from any source such that the sequence employed provides the necessary regulatory information within its nucleic acid sequence to result in the proper expression of the promoter/coding region combination to which the 3' end sequence is operably linked.

A variety of expression vectors can be used to transfer the gene encoding the regulatory binding protein as well as the desired promoter into the plant. Examples include but not limited to those derived from a Ti plasmid of *Agrobacterium tumefaciens,* as well as those disclosed by Herrera-Estrella, L., et al., Nature 303: 209(1983), Bevan, M., Nucl. Acids Res. 12: 8711–8721 (1984), Klee, H. J., Bio/Technology 3: 637–642 (1985), and EPO Publication 120,516 (Schilperoort et al.) for dicotyledonous plants. Alternatively, non-Ti vectors can be used to transfer the DNA constructs of this invention into monotyledonous plants and plant cells by using free DNA delivery techniques. Such methods may involve, for example, the use of liposomes, electroporation, microprojectile bombardment, silicon carbide wiskers, viruses and pollen. By using these methods transgenic plants such as wheat, rice (Christou, P., Bio/Technology 9: 957–962 (1991)) and corn (Gordon-Kamm, W., Plant Cell 2: 603–618 (1990)) are produced. An immature embryo can also be a good target tissue for monocots for direct DNA delivery techniques by using the particle gun (Weeks, T. et al., Plant Physiol. 102: 1077–1084 (1993); Vasil, V., Bio/Technology 10: 667–674 (1993); Wan, Y. and Lemeaux, P., Plant Physiol. 104: 37–48 (1994), and for Agrobacterium-mediated DNA transfer (Hiei et al., Plant J. 6: 271–282 (1994); Rashid et al., Plant Cell Rep. 15: 727–730 (1996); Dong, J., et al., Mol. Breeding 2: 267–276 (1996); Aldemita, R. and Hodges, T., Planta 199: 612–617 (1996); Ishida et al., Nature Biotech. 14: 745–750 (1996)).

In one embodiment, the plasmid vector pMEN020 is preferred, which is derived from a Ti plasmid pMON10098 which is the type of binary vector described in U.S. Pat. Nos. 5,773,701 and 5,773,696. PMEN20 differs from pMON10098 by the substitution of a KpnI, SalI, SacI, SacII, NotI, and XbaI restriction sites between the ECaMV 35S promoter and the E9 3' region. Plasmid pMON10098 contains the following DNA segments. Starting at the bottom of the plasmid map is the origin of bacterial replication for maintenance in *E. coli* (ori-322). Moving in a counter-clockwise direction on the map, next is ori-V, which is the vegetative origin of replication (Stalker et al. *Mol. Gen. Genet.* 181:8–12 (1981)). Next is the left border of the T-DNA. Next is the chimeric gene used as the selectable marker. The chimera includes the 0.35 kilobase (kb) of the cauliflower mosaic virus 35S promoter (P-35S) (Odell et al. (1985) *Nature* 313:810–812)., a 0.84 kb neomycin phosphotransferase type II gene (KAN) and a 0.25 kb 3' non-translated region of the nopaline synthase gene (NOS 3') (Fraley et al. (1983) Proc. Natl. Acad. Sci. USA 80:1803–1807). The next sequence contains the enhanced CaMV 35S promoter and E9 3' region gene cassette and restriction sites for inserting genes such as the coding region of CBF genes. This chimeric gene cassette ends with the 0.65 kb of the E9 3' region from the pea small subunit of RUBISCO gene (U.S. Pat. No. 5,773,701). Next is the right border of the T-DNA. Next is the 0.93 kb fragment isolated from transposon Tn7 that encodes the bacterial spectinomycin/streptomycin resistance (Spc/Str), which is a determinant for selection in *E. coli* and *Agrobacterium tumefaciens* (Fling et al., *Nucl. Acids Res.* 13:7095–7106 (1985)).

The pMEN020 plasmid construct is a binary cloning vector that contains both *E. coli* and *Agrobacterium tumefaciens* origins of DNA replication but no vir genes encoding proteins essential for the transfer and integration of the target gene inserted in the T-DNA region. PMEN020 requires the trfA gene product to replicate in Agrobacterium. The strain of Agrobacterium containing this trfA gene is called the ABI strain and is described below and in U.S. Pat. Nos. 5,773,701 and 5,773,696. This cloning vector serves as an *E. coli-Agrobacterium tumefaciens* shuttle vector. All of the cloning steps are carried out in *E. coli* before the vector is introduced into ABI strain of *Agribacterium tumefaciens.*

In another embodiment, pMEN050 is preferred, which is derived from pMEN020 by replacing the NptII kanamycin resistance gene with the Bar gene (U.S. Pat. No. 5,646,024) by using the same cloning method described above for pMEN020.

The recipient ABI strain of Agribacterium carries a modified defective Ti plasmid that serves as a helper plasmid containing a complete set of vir genes but lacks portions or all of the T-DNA region. ABI is the A208 *Agrobacterium tumefaciens* strain carrying the disarmed pTiC58 plasmid pMP90RK (Koncz et al. Mol. Gen. Genet. 204:383–396 (1986)). The disarmed Ti plasmid provides the trfA gene functions that are required for autonomous replication of the binary vectors after transfer into the ABI strain. When plant tissue is incubated with the ABI::binary vector strains, the vectors are transferred to the plant cells by the vir functions encoded by the disarmed pMP90RK Ti plasmid. After the introduction of the binary vector into the recipient Agribacterium, the vir gene products mobilize the T-DNA region of the pMEN020 plasmid to insert the target gene, e.g. the gene encoding the regulatory binding protein, into the plant chromosomal DNA, thus transforming the cell.

It should be noted that methods for transforming a wide variety of different dicots and obtaining transgenic plants are well documented in the literature (See Gasser and Fraley Science 244:1293 (1989); Fisk and Dandekar, Scientia Horticulturae 55: 5–36 (1993); Christou Agro Food Industry Hi Tech March/April: p.17 (1994), and the references cited therein).

Methods for producing transgenic plants among the monocots are also available. Successful transformation and plant regeneration have been achieved in asparagus (*Asparagus officinalis;* Bytebier et al. Proc. Natl. Acad. Sci. USA 84:5345 (1987)); barley (*Hordeum vulgare;* Wan and Lemaux, Plant Physiol 104:37 (1994)); maize (*Zea mays;* Gordon-Kamm et al., Plant Cell 2:603 (1990); Fromm et al. Bio/Technology 8:833 (1990); Koziel et al. Bio/Technology 11: 194 (1993)); oats (*Avena sativa,* Somers et al. Bio/Technology 10: 1589 (1992)); orchardgrass (*Dactylis glomerata;* Horn et al. Plant Cell Rep. 7: 469 (1988)); rice (*Oryza sativa,* including indica and japonica varieties; Toriyama et al. Bio/Technology 6:10 (1988); Zhang et al. Plant Cell Rep. 7: 379 (1988); Luo and Wu Plant Mol. Biol. Rep. 6:165 (1988); Zhang and Wu, Theor. Appl. Genet. 76: 835 (1988); Christou et al. Bio/Technology 9: 957 (1991); rye (*Secale cereale;* De la Pena et al. Nature 325: 274 (1987)); sorghum (*Sorghum bicolor;* Cassas et al. Proc. Natl. Acad. Sci. USA 90:11212 (1993)); sugar cane (Saccharum spp.; Bower and Birch Plant J. 2: 409 (1992)); tall fescue (*Festuca arundinacea;* Wang et al. Bio/Technology 10:691 (1992)); turfgrass (*Agrostis palustris;* Zhong et al. Plant Cell Rep. 13:1 (1993)); wheat (*Triticum aestivum;* Vasil et al. Bio/Technology 10: 667 (1992); Troy Weeks et al. Plant Physiol. 102:1077 (1993); Becker et al. Plant J. 5:299 (1994)).

After transformation of cells or protoplasts, the choice of methods for regenerating fertile plants is not particularly important. Suitable protocols are available for Leguminosae (alfalfa, soybean, clover, etc.), Umbelliferae (Carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops See protocols described in Ammirato et al. (1984) *Handbook of Plant Cell Culture—Crop Species.* Macmillan Publ. Co. Shimamoto et al. Nature 338:274–276 (1989); Fromm et al., *Bio/Technology* 8:833–839 (1990); Vasil et al. *Bio/Technology* 8:429–434 (1990).

It is envisioned that the present invention can be used to introduce, change and/or augment the environmental stress tolerance of a plant by introducing and causing the expression of environmental stress tolerance in a manner which the plant does not exhibit in its native form. For example, by using different promoters in combination with recombinant regulatory genes, native environmental stress tolerance genes can be expressed independent of environmental stress, made responsive to different levels or types of environmental stress, or rendered inducible independent of an environmental stress. Further, selection of the promoter can also be used to determine what tissues in the plant express the binding protein as well as when the expression occurs in the plant's lifecycle. By selecting a promoter which regulates in what tissues and when in a plant's life the promoter functions to regulate expression of the binding protein, in combination with the selecting how that promoter regulates expression (level of expression and/or type of environmental or chemical induction), an incredible range of control over the environmental stress responses of a plant can be achieved using the present invention.

By recombinantly introducing a native environmental stress tolerance gene into a plant in combination with a recombinant regulatory gene under the control of an inducible promoter, a plant can be engineered which includes its native environmental stress tolerance as well as inducible environmental stress tolerance. This might be useful for inducing a cold stress tolerance reaction in anticipation of a frost.

By recombinantly introducing a non-native environmental stress tolerance gene into a plant in combination with a recombinant regulatory gene, a plant can be engineered which includes environmental stress tolerance properties that the plant would not otherwise have. In this regard, plants from warmer climates can be engineered to include one or more cold tolerance genes along with a regulatory gene needed to cause expression of the cold tolerance genes in the plant so that the engineered plant can survive better in a colder climate. Similarly, a plant can be engineered to include one or more dehydration tolerance genes along with a regulatory gene needed to cause expression of the dehydration tolerance gene so that the engineered plant can grow better in a dryer climate. In this regard, it should be possible to take a plant which grows well in a first climate and engineer it to include stress tolerance genes and regulatory genes native to a second climate so that the plant can grow well in the second climate.

By modifying the promoter controlling the expression of the gene encoding a binding protein which regulates the expression of environmental stress tolerance genes, the operation of native, non-recombinant environmental stress tolerance genes and regulatory genes can be changed. For example, the conditions under which the stress tolerance genes are expressed can be changed. Expression can also be rendered inducible by an exogenous agent.

7. Methods for Detecting Stress Tolerance Regulatory Gene Homologs

Once one DNA sequence encoding an environmental stress tolerance regulatory binding protein has been identified, several methods are available for using that sequence and knowledge about the protein it encodes to identify homologs of that sequence from the same plant or different plant species. For example, let us assume that a cDNA encoding a first target binding domain has been isolated from plant species "A." The DNA sequence encoding the first target DNA regulatory sequence could be radiolabeled and used to screen cDNA libraries of plant species "A," or any other plant species, for DNA inserts that encode proteins related to the first target DNA regulatory sequence. This could be done by screening colony or phage "lifts" using either high (Tm of about −10° C.) or low (Tm of about −30° C. or lower) stringency DNA hybridization conditions (Sambrook, J. et al, Molecular Cloning. A Laboratory Manual Cold Spring Harbor Laboratory Press, Cold Spring Harbor, NY., 2nd Ed. (1989)). cDNA inserts that hybridize with the first target DNA regulatory sequence could be sequenced and compared to the original first target DNA regulatory sequence. If the insert is confirmed to encode a polypeptide similar to the first target DNA regulatory sequence, the insert could be cloned into an expression vector to produce the encoded protein. The protein would then be analyzed by gel retardation experiments to confirm that it binds specifically to the first target DNA regulatory sequence.

It is recognized that not all proteins that bind to a first target DNA regulatory sequence will be transcriptional activators. However, a number of routine tests may be performed in order to determine whether a particular protein is in fact a transcriptional activator. One test involves expressing the protein in yeast strains which contain the target DNA regulatory sequence fused to the lacZ reporter gene, as described above. If the protein is a transcriptional activator, it should activate expression of the reporter gene and result in blue colonies.

Another test is a plant transient assay. In this case, a reporter gene, such as GUS, carrying the target DNA regulatory sequence as an upstream activator is introduced into plant cells (e.g. by particle bombardment) with or without a the putative transcriptional activator under control of a constitutive promoter. If the protein is an activator, it will stimulate expression of the reporter (this may be further enhanced if the plant material is placed at low temperature or is subjected to water stress as the C-repeat/DRE is responsive to low temperature and dehydration).

Significantly, once a target DNA regulatory sequence is identified, the sequence can be fused to any potential activator or repressor sequence to modify expression of plant genes that carry the target regulatory sequence as a control element. That is, the DNA regulatory sequence can be used to target "managed" expression of the battery of environmental stress tolerance related genes in a given plant species.

It is possible that the target DNA regulatory sequence of the regulatory element that imparts environmental stress tolerance related gene expression in plant species "A" might be slightly different from the analogous target DNA regulatory element that imparts environmental stress tolerance in species "B." Thus, optimal regulation of the battery of environmental stress tolerance related genes in a given species may require the use of the regulatory binding proteins from that or a closely related plant species. Knowledge of gene sequences which encode for proteins which bind to the DNA regulatory sequence of the regulatory element, in combination with knowledge of the DNA regulatory sequence, greatly simplify the identification of sequences encoding binding proteins native to the plant species.

With the advent of fast and efficient DNA sequencing technologies, the number of plant genomes recorded on computer databases is growing rapidly. These computer databases can be used to search for homologs to CBF sequences identified in this application as well as other sequences which encode binding proteins which regulate cold tolerance genes. As more and more binding protein sequences are identified and the number of computerized plant genome databases increase, searching computer databases for additional sequences encoding binding proteins which regulate cold tolerance genes will become increasingly simplified.

8. Preparation of Binding Proteins Derivatives Using Sequences Identified in This Application According to the present invention, the binding protein is a protein which is capable of binding to a DNA regulatory sequence which regulates expression of one or more environmental stress tolerance genes in a plant. These DNA regulatory sequences are preferably a member of the CCG family of regulatory sequences and more preferably a member of the CCGAC family of regulatory sequences.

Numerous amino acid sequences for CBF binding protein homologs are disclosed in this application including those shown in FIGS. 2B, 14, and 18B and listed in SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95. Nucleic acid sequences encoding these CBF binding protein homologs are disclosed in this application in FIGS. 2B, 12, 13, and 18A and listed in SEQ. I.D. Nos. 1, 12, 14, 40, 42, 44, 46, 48, 50, 52, 54, 56, 58, 60, 62, 64, 66, 68, 70, 72, 74, 76, 78, 80, 82, 84, 86, 88, 90, 92, and 94. These sequences were derived from a variety of different plant species including Arabidopsis, *Brassica juncea, Brassica napus, Brassica oleracea, Brassica rapa, Glycine max, Raphanus sativus* and *Zea Maize.*

The sequences identified in these figures may generally be divided into three regions: AP2 domain, amino terminus domain, and carboxy terminus domain. FIGS. 19A–19E show different AP2 domains from these homologs and consensus sequences between the different AP2 domains shown.

FIG. 19A shows an amino acid alignment of the AP2 domains of several CBF proteins with the consensus sequence between the proteins highlighted as well as a comparison of the AP2 domains with that of the tobacco DNA binding protein EREBp2. FIG. 19B shows an amino acid alignment of the AP2 domains of several CBF proteins including dreb2a and dreb2b with the consensus sequence between the proteins highlighted. FIG. 19C shows an amino acid alignment of the AP2 domains of several CBF proteins including dreb2a, dreb2b, and tiny with the consensus sequence between the proteins highlighted. FIG. 19D shows a consensus sequence corresponding to the difference between the consensus sequence shown in FIG. 19A and tiny. FIG. 19E shows a consensus sequence corresponding to the difference between the consensus sequence shown in FIG. 19B and tiny.

FIGS. 21A and 21B show different carboxy terminus domains from these homologs and consensus sequences between the different carboxy terminus domains shown.

The binding proteins utilized in the present invention include classes of binding proteins which satisfy one or more of the following requirements:

- the binding protein comprises an AP2 domain which comprises a consensus sequence sufficiently homologous to any one of the consensus sequences shown in FIG. 19A, 19B, or 19C that the binding protein is capable of binding to a CCG regulatory sequence, preferably a CCGAC regulatory sequence;
- the binding protein comprises an AP2 domain which comprises a consensus sequence shown in FIG. 19A, 19B or 19C;
- the binding protein comprises an AP2 domain which comprises the amino acid residues shown in FIG. 19D or 19E;
- the binding protein comprises an AP2 domain which is sufficiently homologous to at least one of the AP2 domains shown in the application such that it is capable of binding to a CCG regulatory sequence, preferably a CCGAC regulatory sequence;
- the binding protein comprises one of the AP2 domain sequences shown in this application, including, but not limited to SEQ. I.D. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95;
- the binding protein comprises a sequence which comprises one of the amino terminus domains shown in FIG. 20 (it is noted that the sequence need not be at the amino terminus of the binding protein);
- the binding protein comprises the consensus sequence for the amino terminus domains shown in FIG. 20, (it is noted that the sequence need not be at the amino terminus of the binding protein);
- the binding protein comprises a sequence which comprises one of the carboxy terminus domains shown in FIG. 21A (it is noted that the sequence need not be at the carboxy terminus of the binding protein);
- the binding protein comprises the consensus sequence for the carboxy terminus domains shown in FIG. 21A (it is noted that the sequence need not be at the carboxy terminus of the binding protein); and
- the binding protein comprises the consensus sequence for the carboxy terminus domains shown in FIG. 21B (it is noted that the sequence need not be at the carboxy terminus of the binding protein).

The sequence of the binding protein may be a naturally occurring sequence such as the ones shown in SEQ. ID. Nos. 2, 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95 or may be a non-naturally occurring sequence. It is noted, however, that binding proteins according to the present invention are intended to encompass non-naturally occurring sequences which are derivatives of the classes of binding proteins taught herein.

Additional binding proteins may be constructed using one of the AP2 domains taught herein or the consensus sequence of these AP2 domains. It may be desirable to include with the AP2 domain a transcription activation region. The transcription activation region may be native to the plant or non-native to the plant in which the binding protein will be used. For example, the sequence may include a subsequence which encodes a binding domain for the DNA regulatory sequence fused to a transcription activating region, such as the transcription activating region of VP16 or GAL4. Optionally, one can include in the binding protein one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

Optionally, the binding protein can be viewed as comprising one of the amino terminus domains, the consensus sequence for the amino terminus domain, one of the carboxy terminus domains and/or the consensus sequence for the carboxy terminus domains. It is noted that the amino terminus domain may be positioned away from the amino terminus of the new binding protein and the carboxy terminus domain may be positioned away from the carboxy terminus of the new binding protein.

EXAMPLES

1. Isolation and Analysis of *Arabidopsis Thaliana* cDNA Clone (CBF1) Encoding C-repeat/DRE Binding Factor The following example describes the isolation of an *Arabidopsis thaliana* cDNA clone that encodes a C-repeat/DRE binding factor, CBF1 (C-repeat/DRE Binding Factor 1). Expression of CBF1 in yeast was found to activate transcription of reporter genes containing the C-repeat/DRE (CCGAC) as an upstream activator sequence. Meanwhile, CBF1 did not activate transcription of mutant versions of the CCGAC binding element, indicating that CBF1 is a transcription factor that binds to the C-repeat/DRE. Binding of CBF1 to the C-repeat/DRE was also demonstrated in gel shift assays using recombinant CBF1 protein expressed in *Escherichia coli.* Analysis of the deduced CBF1 amino acid sequence indicated that the protein has a potential nuclear localization sequence, a possible acidic activation domain and an AP2 domain, a DNA-binding motif of about 60 amino acids that is similar to those present in Arabidopsis proteins APETALA2, AINTEGUMENTA and TINY, the tobacco ethylene response element binding proteins, and numerous other plant proteins of unknown function.

A. Materials

Plant material and cold treatment.

*A thaliana* (L.) Heyn. ecotype RLD plants were grown in pots in controlled environment chambers at 22° C. under constant illumination with cool-white fluorescent lamps (100 $\mu$mol $m^{-2}s^{-1}$) essentially as described (Gilmour, S. J., Plant Physiol. 87:745–750 (1988)). Plants were cold-treated by placing pots in a cold room at 2.5° C. under constant illumination with cool-white fluorescent lamps (25 $\mu$mol $m^{-2}s^{-1}$) for the indicated times.

Arabidopsis cDNA expression library. The Arabidopsis pACT cDNA expression library was constructed by John Walker and colleagues (NSF/DOE/USDA Collaborative Research in Plant Biology Program grant USDA 92-37105-7675) and deposited in the Arabidopsis Biological Resource Center (stock #CD4-10).

Yeast reporter strains.

Oligonucleotides (Table 1) (synthesized at the MSU Macromolecular Structure Facility) encoding either wild-type or mutant versions of the C-repeat/DRE were ligated into the BglII site of the lacZ reporter vector pBgl-lacZ (Li, J. J. and I. Herskowitz, Science 262:1870–1874 (1993); kindly provided by Joachim Li). The resulting reported constructs were integrated into the ura3 locus of *Saccharomyces cerevisiae* strain GGY1 (MAT gal4 gal80 ura3 leu2 his3 ade2 tyr) (Li, J. J. and I. Herskowitz, Science 262:1870–1874 (1993); provided by Joachim Li) by transformation and selection for uracil prototrophy.

*E. coli* strains.

*Escherichia coli* strain GM2163 containing plasmid pEJS251 was deposited under the Budapest Treaty on May 17, 1996 with the American Type Culture Collection, Rockville, Md. as ATCC 98063. It is available by name and number pursuant to the provisions of the Budapest Treaty.

TABLE 1

Oligonucleotides encoding wild type and mutant versions of the C-repeat/DRE

| Oligonucleotide | C-repeat/DRE* | Sequence | SEQ ID NO: |
|---|---|---|---|
| MT50 | COR15a | GatcATTTCATGG**CCGAC**CTGCTTTTT | 3 |
| MT52 | M1COR15a | CACAATTTCA**a**GaattcaCTGCTTTTTT | 4 |
| MT80 | M2COR15a | GatcATTTCATGGtatgtCTGCTTTTT | 5 |
| MT125 | M3COR15a | GatcATTTCATGGaatcaCTGCTTTTT | 6 |
| MT68 | COR15b | GatcACTTGATGG**CCGAC**CTCTTTTTT | 7 |
| MT66 | COR78-1 | GatcAATATACTA**CCGAC**ATGAGTTCT | 8 |
| MT86 | COR78-2 | ACTA**CCGAC**ATGAGTTCCAAAAAGC | 9 |

*The C-repeat/DRE sequences tested are either wild-type found in the promoters of COR15a (Baker, S. S., et al., Plant. mol. Biol. 24:701–713 (1994)), COR15b or COR78/RD29A (Horvath, D. P., et al., Plant Physiol. 103:1047–1053 (1993); Yamaguchi-shinozaki, K., et al., The Plant Cell 6:251–264 (1994)) or are mutant versions of the COR15a C-repeat/DRE (M1COR15a, M2COR15a and M3COR15a).

#Uppercase letters designate bases in wild type G-repeat/DRE sequences. The core CCGAC sequence common to the above sequences is indicated in bold type. Lowercase letters at the beginning of a sequence indicate bases added to facilitate cloning. The lowercase letters that are underlined indicate the mutations in the C-repeat/DRE sequence of COR15a.

B. Methods

Screen of Arabidopsis cDNA library.

The Arabidopsis pACT cDNA expression library was screened for clones encoding C-repeat/DRE environmental stress response regulatory elements by the following method. The cDNA library, harbored in *Escherichia coli* BNN132, was amplified by inoculating 0.5 ml of the provided glycerol stock into 1 L of M9 minimal glucose medium (Sambrook, J. et al, Molecular Cloning. A Laboratory Manual (Cold Spring Harbor Laboratory Press, Cold Spring Harbor, N.Y., 2nd Ed. (1989)) and shaking the bacteria for 20 h at 37° C. Plasmid DNA was isolated and purified by cesium chloride density gradient centrifugation (Sambrook et al (1989)) and transformed into the yeast GGY1 reporter strains selecting for leucine prototrophy. Yeast transformants that had been grown for 2 or 3 days at 30° C. were overlaid with either a nitrocellulose membrane filter (Schleicher and Schuell, Keene, N.H.) or Whatman #50 filter paper (Hillsboro, Oreg.) and incubated overnight at 30° C. The yeast impregnated filters were then lifted from the plate and treated with X-gal (5-bromo-4-chloro-3-indolyl-D-galactosidase) to assay colonies for beta-galactosidase activity (Li, J. J. and I. Herskowitz, Science 262:1870–1874 (1993)). Plasmid DNA from "positive" transformants (those forming blue colonies on the X-gal-treated filters) was recovered (Strathern, J. N., and D. R. Higgens, Methods Enzymol. 194:319–329 (1991)), propagated in *E. coli* DH5 and transformed back into the yeast reporter strains to confirm activity.

Yeast transformation and quantitative beta-galactosidase assays.

Yeast were transformed by either electroporation (Becker, D. M., et al., Methods Enzymol. 194:182–187 (1991)) or the lithium acetate/carrier DNA method (Schiestl, R. H., et al., Current Genetics 16:339–346 (1989)). Quantitative in vitro beta-galactosidase assays were done as described (Rose, M., et al., Methods Enzymol. 101:167–180 (1983)).

Expression of CBF1 protein in *E. coli* and yeast.

CBF1 was expressed in *E. coli* using the pET-28a(+) vector (Novagen, Madison, Wis.). The BglII-BclI restriction fragment of pACT-11 encoding CBF1 was ligated into the BamHI site of the vector bringing CBF1 under control of the T7 phage promoter. The construct resulted in a "histidine tag," a thrombin recognition sequence and a "T7 epitope tag" being fused to the amino terminus of CBF1. The construct was transformed into *E. coli* BL21 (DE3) and the recombinant CBF1 protein was expressed as recommended by the supplier (Novagen). Expression of CBF1 in yeast was accomplished by ligating restriction fragments encoding CBF1 (the BclI-BglII and BglII-BglII fragments from pACT-11) into the BglII site of pDB20.1 (Berger, S. L., et al., Cell 70:251–265 (1992); kindly provided by Steve Triezenberg) bringing CBF1 under control of the constitutive ADC1 (alcohol dehydrogenase constitutive 1) promoter.

Gel shift assays.

The presence of expressed protein which binds to a C-repeat/DRE binding domain was evaluated using the following gel shift assay. Total soluble *E. coli* protein (40 ng) was incubated at room temperature in 10 $\mu$l of 1×binding buffer [15 mM HEPES (pH 7.9), 1 mM EDTA, 30 mM KCl, 5% glycerol, 5% BSA, 1 mM DTT) plus 50 ng poly(dI-dC) :poly(dI-dC) (Pharmacia, Piscataway, N.J.) with or without 100 ng competitor DNA. After 10 min, probe DNA (1 ng) that was $^{32}$P-labeled by end-filling (Sambrook et al, 1989) was added and the mixture incubated for an additional 10 min. Samples were loaded onto polyacrylamide gels (4% w/v) and fractionated by electrophoresis at 150V for 2 h (Sambrook et al). Probes and competitor DNAs were prepared from oligonucleotide inserts ligated into the BamHI site of pUC118 (Vieira, J., et al., Methods Enzymol. 153:3–11 (1987)). Orientation and concatenation number of the inserts were determined by dideoxy DNA sequence analysis (Sambrook, et al, (1989)). Inserts were recovered after restriction digestion with EcoRI and HindIII and fractionation on polyacrylamide gels (12% w/v) (Sambrook et al, 1989).

Northern and southern analysis.

Northern and southern analysis was performed as follows. Total RNA was isolated from Arabidopsis (Gilmour, S. J., et al., Plant Physiol. 87:745–750 (1988)) and the poly(A)$^+$ fraction purified using oligo dT cellulose (Sambrook, et al (1989)). Northern transfers were prepared and hybridized as described (Hajela, R. K., et al., Plant Physiol. 93:1246–1252 (1990)) except that high stringency wash conditions were at 50 C. in 0.1×SSPE [×SSPE is 3.6 M NaCl, 20 mM EDTA, 0.2 M $Na_2$—$HPO_4$ (pH7.7)], 0.5% SDS. Membranes were stripped in 0.1×SSPE, 0.5% SDS at 95° C. for 15 min prior to re-probing. Total Arabidopsis genomic DNA was isolated (Stockinger, E. J., et al., J. Heredity, 87:214–218 (1996)) and southern transfers prepared (Sambrook et al 1989) using nylon membranes (MSI, Westborough, Mass.). High stringency hybridization and wash conditions were as described by Walling et al (Walling, L. L., et al., Nucleic Acids Res. 16:10477–10492 (1988)). Low stringency hybridization was in 6×SSPE, 0.5% SDS, 0.25% low fat dried milk at 60° C. Low stringency washes were in 1×SSPE, 0.5% SDS at 50° C. Probes used for the entire CBF1 coding sequence and 3' end of CBF1 were the BclI/BglII and EcoRV/BglII restriction fragments from pACT-11, respectively, that had been gel purified (Sambrook et al (1989)). DNA probes were radiolabeled with $^{32}$P-nucleotides by random priming (Sambrook). Autoradiography was performed using hyperfilm-MP (Amersham, Arlington Heights, Ill.). Radioactivity was quantified using a Betascope 603 blot analyzer (Betagen Corp., Waltham, Mass.).

C. Screen of Arabidopsis cDNA library for sequence encoding a C-repeat/DRE binding domain.

The "one-hybrid" strategy (Li, J. J. and I. Herskowitz, Science 262:1870–1874 (1993)) was used to screen for Arabidopsis cDNA clones encoding a C-repeat/DRE binding domain. In brief, yeast strains were constructed that contained a lacZ reporter gene with either wild-type or mutant C-repeat/DRE sequences in place of the normal UAS (upstream activator sequence) of the GAL1 promoter.

FIGS. 1A and 1B show how the yeast reporter strains were constructed. FIG. 1A is a schematic diagram showing the screening strategy. Yeast reporter strains were constructed that carried C-repeat/DRE sequences as UAS elements fused upstream of a lacZ reporter gene with a minimal GAL1 promoter. The strains were transformed with an Arabidopsis expression library that contained random cDNA inserts fused to the GAL4 activation domain (GAL4-ACT) and screened for blue colony formation on X-gal-treated filters. FIG. 1B is a chart showing activity of the "positive" cDNA clones in yeast reporter strains. The oligonucleotides (oligos) used to make the UAS elements, and their number and direction of insertion, are indicated by the arrows.

Yeast strains carrying these reporter constructs produced low levels of beta-galactosidase and formed white colonies on filters containing X-gal. The reporter strains carrying the wild-type C-repeat/DRE sequences were transformed with a DNA expression library that contained random Arabidopsis cDNA inserts fused to the acidic activator domain of the yeast GAL4 transcription factor, "GAL4-ACT" (FIG. 1A). The notion was that some of the clones might contain a cDNA insert encoding a C-repeat/DRE binding domain fused to GLA4-ACT and that such a hybrid protein could potentially bind upstream of the lacZ reporter genes carrying the wild type C-repeat/DRE sequence, activate transcription of the lacZ gene and result in yeast forming blue colonies on X-gal-treated filters.

Figure 2A:
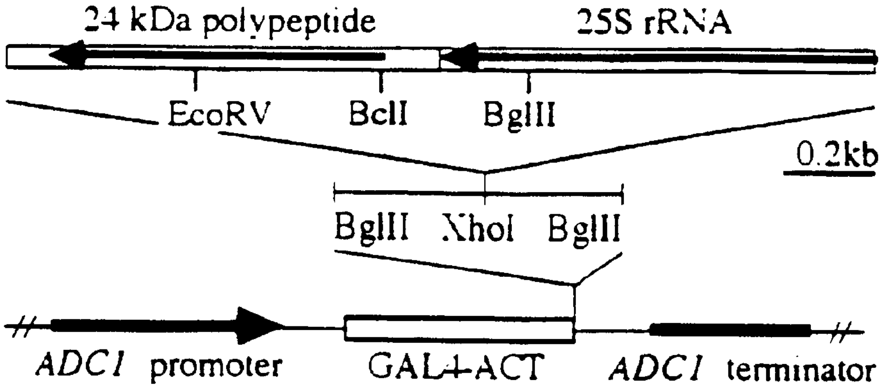

Upon screening about $2\times10^6$ yeast transformants, three "positive" cDNA clones were isolated; i.e., clones that caused yeast strains carrying lacZ reporters fused to wild-type C-repeat/DRE inserts to form blue colonies on X-gal-treated filters (FIG. 1B). The three cDNA clones did not cause a yeast strain carrying a mutant C-repeat/DRE fused to LacZ to turn blue (FIG. 1B). Thus, activation of the reporter genes by the cDNA clones appeared to be dependent on the C-repeat/DRE sequence. Restriction enzyme analysis and DNA sequencing indicated that the three cDNA clones had an identical 1.8 kb insert (FIG. 2A). One of the clones, designated pACT-11, was chosen for further study.

D. Identification of 24 kDa polypeptide with an AP2 domain encoded by pACT-11.

Figures 2C, 2D:
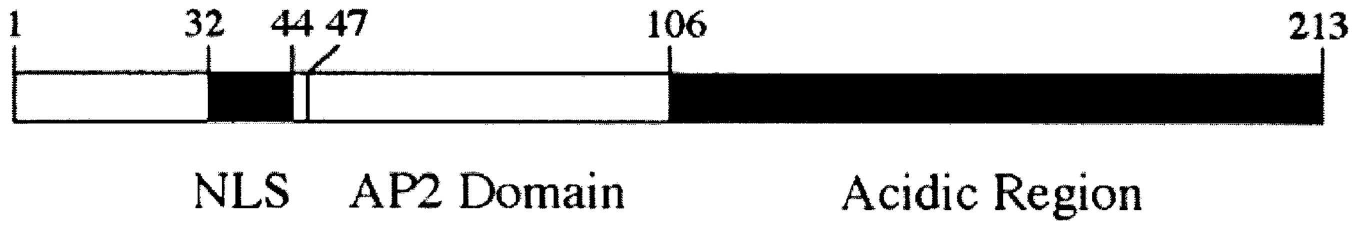

FIGS. 2A, 2B, 2C and 2D provide an analysis of the pACT-11 cDNA clone. FIG. 2A is a schematic drawing of the pACT-11 cDNA insert indicating the location and 5' to 3' orientation of the 24 kDa polypeptide and 25s rRNA sequences. The cDNA insert was cloned into the XhoI site of the pACT vector. FIG. 2B is a DNA and amino acid sequence of the 24 kDa polypeptide (SEQ ID NO:1 and SEQ ID NO:2). The AP2 domain is indicated by a double underline. The basic amino acids that potentially act as a nuclear localization signal are indicated with asterisks. The BclI site immediately upstream of the 24 kDa polypeptide used in subcloning the 24 kDa polypeptide and the EcoRV site used in subcloning the 3' end of CBF1 are indicated by single underlines. FIG. 2C is a schematic drawing indicating the relative positions of the potential nuclear localization signal (NLS), the AP2 domain and the acidic region of the 24 kDa polypeptide. Numbers indicate amino acid residues. FIG. 2D is a chart showing comparison of the AP2 domain of the 24 kDa polypeptide with that of the tobacco DNA binding protein EREBP2 (Okme-Takagi, M., et al., The Plant Cell 7:173–182 (1995) SEQ ID NOS: 10 and 11). Identical amino acids are indicated with single lines; similar amino acids are indicated by double dots; amino acids that are invariant in AP2 domains are indicated with asterisks (Klucher, K. M., et al., The Plant Cell 8:137–153 (1996)); and the histidine residues present in CBF1 and TINY (Wilson, K., et al., The Plant Cell 8:659–671 (1996)) that are tyrosine residues in all other described AP2 domains are indicated with a caret. A single amino acid gap in the CBF1 sequence is indicated by a single dot.

Our expectation was that the cDNA insert in pACT-11 would have a C-repeat/DRE binding domain fused to the yeast GAL4-ACT sequence. However, DNA sequence analysis indicated that an open reading frame of only nine amino acids had been added to the C-terminus of GAL4-ACT. It seemed highly unlikely that such a short amino acid sequence could comprise a DNA binding domain. Also surprising was the fact that about half of the cDNA insert in pACT-11 corresponded to 25s rRNA sequences (FIG. 2A). Further analysis, however, indicated that the insert had an open reading frame, in opposite orientation to the GAL4-ACT sequence, deduced to encode a 24 kDa polypeptide (FIG. 2A–C). The polypeptide has a basic region that could potentially serve as a nuclear localization signal (Raikhel, N., Plant Physiol. 100:1627–1632 (1992)) and an acidic C-terminal half (pI of 3.6) that could potentially act as an acidic transcription activator domain (Hahn, S., Cell 72:481–483 (1993)). A search of the nucleic acid and protein sequence databases indicated that there was no previously described homology of the 24 kDa polypeptide. However, the polypeptide did have an AP2 domain (Jofuku, K. D., et al., The Plant Cell 6:1211–1225 (1994)) (FIGS. 2B, D), a DNA binding motif of about 60 amino acids (Ohme-Takagi, M., et al., The Plant Cell 7:173–182 (1994)) that is present in numerous plant proteins including the APETALA2 (Jofuku, K. D., et al., The Plant Cell 6:1211–1225 (1994)), AINTEGUMENTA (Klucher, K. M., et al., The Plant Cell 8:137–153 (1996); Elliot, R. C., et al., The Plant Cell 8:155–168 (1996)) and TINY (Wilson, K., et al., The Plant Cell 8:659–671 (1996)) proteins of Arabidopsis and the EREBPs (ethylene response element binding proteins) of tobacco (Ohme-Takagi, M., et al., The Plant Cell 7:173–182 (1995)).

E. 24 kDa polypeptide binds to the C-repeat/DRE and activates transcription in yeast.

We hypothesized that the 24 kDa polypeptide was responsible for activating the lacZ reporter genes in yeast. To test this, the BclI-BglII fragment of pACT-11 containing the 24 kDa polypeptide, and the BglII-BglII fragment containing the 24 kDa polypeptide plus a small portion of the 25s rRNA sequence, was inserted into the yeast expression vector pDB20.1

Figure 3:
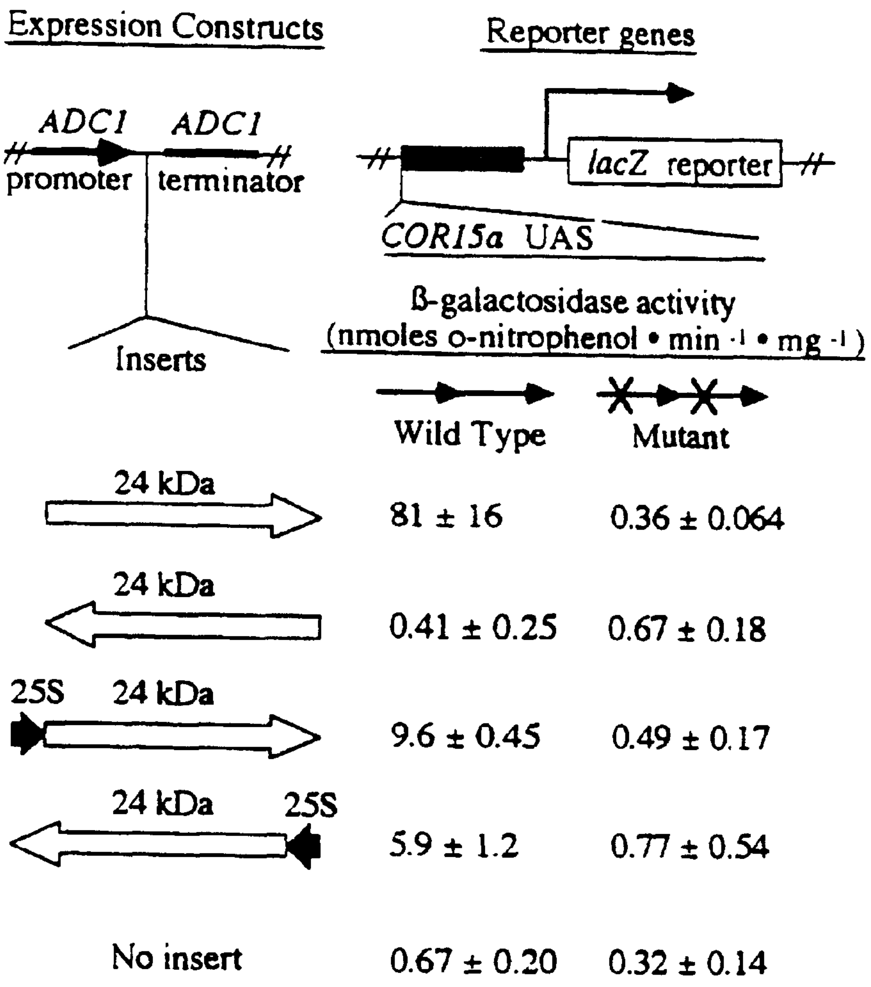
FIG. 3 is a chart showing activation of reporter genes by the 24 kDa polypeptide.

FIG. 3 is a chart showing activation of reporter genes by the 24 kDa polypeptide. Restriction fragments of pACT-11 carrying the 24 kDa polypeptide (BclI-BglII) or the 24 kDa polypeptide plus a small amount of 25s RNA sequence (BglII-BglII) were inserted in both orientations into the yeast expression vector pDB20.1 (see FIG. 2A and 2B for location of BclI and BglII restriction sites). These "expression constructs" were transformed into yeast strains carrying the lacZ reporter gene fused to direct repeat dimers of either the wild-type COR15a C-repeat/DRE (oligonucleotide MT50) or the mutant M2COR15a C-repeat/DRE (oligonucleotide MT80). The specific activity of beta-galactosidase (nmoles o-nitrophenol produced/$min^{-1}$xmg $protein^{-1}$) was determined from cultures grown in triplicate. Standard deviations are indicated. Abbreviations: pADC1, ADC1 promoter; tADC1, ADC1 terminator.

Plasmids containing either insert in the same orientation as the ADC1 promoter stimulated synthesis of beta-galactosidase when transformed into yeast strains carrying the lacZ reporter gene fused to a wild-type COR15a C-repeat/DRE (FIG. 3). The plasmids did not, however, stimulate synthesis of beta-galactosidase when transformed into yeast strains carrying lacZ fused to a mutant version of the COR15a C-repeat/DRE (FIG. 3). These data indicated that the 24 kDa polypeptide could bind to the wild-type C-repeat/DRE and activate expression for the lacZ reporter gene in yeast. Additional experiments indicated that the 24 kDa polypeptide could activate expression of the lacZ reporter gene fused to either a wild-type COR78 C-repeat/DRE (dimer of MT66) or a wild-type COR15b C-repeat/DRE (dimer of MT 68) (not shown). A plasmid containing the BclI-BglII fragment (which encodes only the 24 kDa polypeptide) cloned in opposite orientation to the ADC1 promoter did not stimulate synthesis of beta-galactosidase in reporter strains carrying the wild-type COR15a C-repeat/DRE fused to lacZ (FIG. 3). In contrast, a plasmid carrying the BglII-BglII fragment (containing the 24 kDa polypeptide plus some 25s rRNA sequences) cloned in opposite orientation to the ADC1 promoter produced significant levels of beta-galactosidase in reporter strains carrying the wild-type COR15a C-repeat/DRE (FIG. 3). Thus, a sequence located closely upstream of the 24 kDa polypeptide was able to serve as a cryptic promoter in yeast, a result that offered an explanation for how the 24 kDa polypeptide was expressed in the original pACT-11 clone.

F. Gel shift analysis indicates that the 24 kDa polypeptide binds to the C-repeat/DRE.

Gel shift experiments were conducted to demonstrate further that the 24 kDa polypeptide bound to the C-repeat/DRE. Specifically, the open reading frame for the 24 kDa polypeptide was inserted into the pET-28a(+) bacterial expression vector (see Materials and Methods) and the resulting 28 kDa fusion protein was expressed at high levels in *E. coli.* (FIG. 4).

Figure 4:
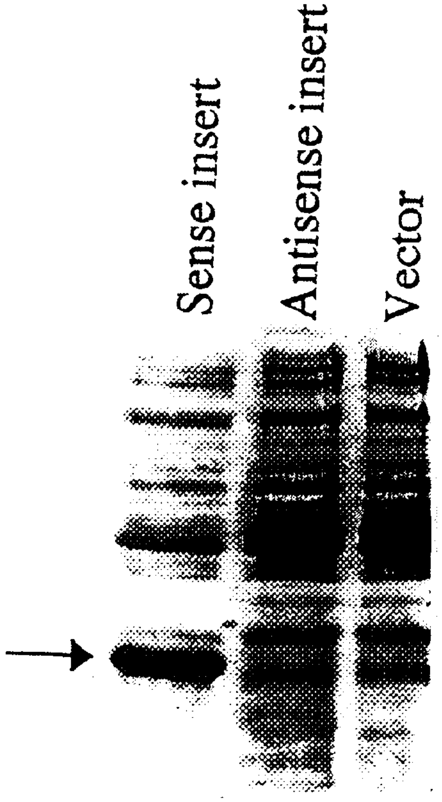
FIG. 4 is a photograph of an electrophoresis gel showing expression of the recombinant 24 kDa polypeptide in *E. coli.*

FIG. 4 is a photograph of an electrophoresis gel showing expression of the recombinant 24 kDa polypeptide in *E. coli.* Shown are the results of SDS-PAGE analysis of protein extracts prepared from *E. coli* harboring either the expression vector alone (vector) or the vector plus an insert encoding the 24 kDa polypeptide in sense (sense insert) or antisense (antisense insert) orientation. The 28 kDa fusion protein (see Materials and Methods) is indicated by an arrow.

FIG. 5 is a photograph of a gel for shift assays indicating that CBF1 binds to the C-repeat/DRE. The C-repeat/DRE probe (1 ng) used in all reactions was a $^{32}P$-labeled dimer of the oligonucleotide MT50 (wild type C-repeat/DRE from COR15a). The protein extracts used in the first four lanes were either bovine serum albumin (BSA) or the indicated CBF1 sense, antisense and vector extracts described in FIG. 4. The eight lanes on the right side of the figure used the CBF1 sense protein extract plus the indicated competitor C-repeat/DRE sequences (100 ng). The numbers 1X, 2X and 3X indicate whether the oligonucleotides were monomers, dimers or trimers, respectively, of the indicated C-repeat/DRE sequences.

Protein extracts prepared from *E. coli* expressing the recombinant protein produced a gel shift when a wild-type COR15a C-repeat/DRE was used as probe (FIG. 5). No shift was detected with BSA or *E. coli* extracts prepared from strains harboring the vector alone, or the vector with an antisense insert for the 24 kDa polypeptide. Oligonucleotides encoding wild-type C-repeat/DRE sequences from COR15a or COR78 competed effectively for binding to the COR15a C-repeat/DRE probe, but mutant version of the COR15a C-repeat/DRE did not (FIG. 5). These in vitro results corroborated the in vivo yeast expression studies indicating that the 24 kDa polypeptide binds to the C-repeat/DRE sequence. The 24 kDa polypeptide was thus designated CBF1 (C-repeat/DRE binding factor 1) and the gene encoding it named CBF1.

G. CBF1 is a unique or low copy number gene.

Figure 6:
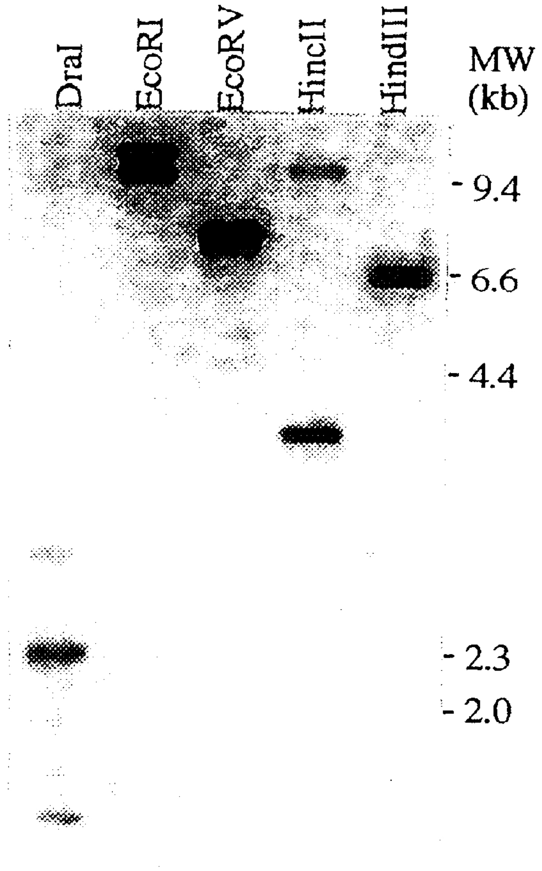
FIG. 6 is a photograph of a southern blot analysis indicating CBF1 is a unique or low copy number gene.

FIG. 6 is a photograph of a southern blot analysis indicating CBF1 is a unique or low copy number gene. Arabidopsis DNA (1 μg) was digested with the indicated restriction endonucleases and southern transfers were prepared and hybridized with a $^{32}P$-labeled probe encoding the entire CBF1 polypeptide.

The hybridization patterns observed in southern analysis of Arabidopsis DNA using the entire CBF1 gene as probe were relatively simple indicating that CBF1 is either a unique or low copy number gene (FIG. 6). The hybridization patterns obtained were not altered if only the 3' end of the gene was used as the probe (the EcoRV/BglII restriction fragment from pACT-11 encoding the acidic region of CBF1, but not the AP2 domain) or if hybridization was carried out at low stringency (not shown).

H. CBF1 transcript level response to low temperature.

FIGS. 7A, 7B and 7C relate to CBF1 transcripts in control and cold-treated Arabidopsis. FIG. 7A is a photograph of a membrane RNA isolated from Arabidopsis plants that were grown at 22° C. or grown at 22° C. and transferred to 2.5° C. for the indicated times. FIGS. 7B and 7C are graphs showing relative transcript levels of CBF1 and COR15a in control and cold-treated plants. The radioactivity present in the samples described in FIG. 7A were quantified using a Betascope 603 blot analyzer and plotted as relative transcript levels (the values for the 22° C. grown plants being arbitrarily set as 1) after adjusting for differences in loading using the values obtained with the pHH25 probe.

Based on FIGS. 7A–7C, northern analysis indicated that the level of CBF1 transcripts increased about 2 to 3 fold in response to low temperature (FIG. 7B). In contrast, the transcript levels for COR15a increased approximately 35 fold in cold-treated plants (FIG. 7C). Only a singly hybridizing band was observed for CBF1 at either high or low stringency with probes for either the entire CBF1 coding sequence or the 3' end of the gene (the EcoRV/BglII fragment of pACT-11) (not shown). The size of the CBF1 transcripts was about 1.0 kb.

I. Discussion Of Experimental Results.

The above example regarding CBF1 represents the first identification of a gene sequence which encodes a protein capable of binding to the C-repeat/DRE sequence CCGAC. The experimental results presented evidence that CBF1 binds to the C-repeat/DRE both in vitro via gel shift assays and in vivo via yeast expression assays. Further, the results demonstrate that CBF1 can activate transcription of reporter genes in yeast that contain the C-repeat/DRE.

The results of the southern analysis indicate that CBF1 is a unique or low copy number gene in Arabidopsis. However, the CBF1 protein contains a 60 amino acid motif, the AP2 domain, that is evolutionary conserved in plants (Weigel, D., The plant Cell 7:388–389 (1995)). It is present in the APETALA2 (Jofuku, K. D., et al., The Plant Cell 6:1211–1225 (1994)), AINTEGUMENTA (Klucher, K. M., et al., the Plant Cell 8:137–153 (1996; and Elliot, R. C., et al., The Plant Cell 8:155–168 (1996)), TINY (Wilson, K., et al., The Plant Cell 8:659–671 (1996)) and cadmium-induced (Choi, S.-Y., et al., Plant Physiol. 108:849 (1995)) proteins of Arabidopsis and the EREBPs of tobacco (Ohme-Takagi, M. et al., The Plant Cell 7:173–182 (1995)). In addition, a search of the GenBank expressed sequence tagged cDNA database indicates that there is one cDNA from *B. napus,* two from *Ricinus communis,* and more than 25 from Arabidopsis and 15 from rice, that are deduced to encode proteins with AP2 domains. The results of Ohme-Takagi and Shinshi (Ohme-Takagi, M., et al., The Plant Cell 7:173–182 (1995)) indicate that the function of the AP2 domain is DNA-binding; this region of the putative tobacco transcription factor EREBP2 is responsible for its binding to the cis-acting ethylene response element referred to as the GCC-repeat. As discussed by Ohme-Takagi and Shinshi (Ohme-Takagi, M., et al., the Plant Cell 7:173–182 (1995)), the DNA-binding domain of EREBP2 (the AP2 domain) contains no significant amino acid sequence similarities or obvious structural similarities with other known transcription factors or DNA binding motifs. Thus, the domain appears to be a novel DNA-binding motif that to date, has only been found in plant proteins.

It is believed that the binding of CBF1 to the C-repeat/DRE involves the AP2 domain. In this regard, it is germane to note that the tobacco ethylene response element, AGCCGCC, closely resembles the C-repeat/DRE sequences present in the promoters of the Arabidopsis genes COR15a, GGCCGAC, and COR78/RD29A, TACCGAC. Applicants believe that CBF1, the EREBPs and other AP2 domain proteins are members of a superfamily of DNA binding proteins that recognize a family of cis-acting regulatory elements having CCG as a common core sequence. Differences in the sequence surrounding the CCG core element could result in recruitment of different AP2 domain proteins which, in turn, could be integrated into signal transduction pathways activated by different environmental, hormonal and developmental cues. Such a scenario is akin to the situation that exists for the ACGT-family of cis-acting elements (Foster et al., FASEB J. 8:192–200 (1994)). In this case, differences in the sequence surrounding the ACGT core element result in the recruitment of different bZIP transcription factors involved in activating transcription in response to a variety of environmental and developmental signals.

The results of the yeast transformation experiments indicate that CBF1 has a domain that can serve as a transcriptional activator. The most likely candidate for this domain is the acidic C-terminal half of the polypeptide. Indeed, random acidic amino acid peptides from *E. coli* have been shown to substitute for the GAL4 acidic activator domain of GAL4 in yeast (Ma, J. and M. Ptashne, Cell 51:113–199 (1987)). Moreover, acidic activator domains have been found to function across kingdoms (Hahn, S., Cell 72:481–483 (1993)); the yeast GAL4 acidic activator, for instance, can activate transcription in tobacco (Ma, J., et al., Nature 334:631–633 (1988)). It has also been shown that certain plant transcription factors, such as Vp1 (McCarty, D. R., et al., Cell 66:895–905 (1991)), have acidic domains that function as transcriptional activators in plants. Significantly, the acidic activation domains of the yeast transcription factors VP16 and GCN4 require the "adaptor" proteins ADA2, ADA3, and GCN5 for full activity (see Guarente, L., Trends Biochem. Sci. 20:517–521 (1995)). These proteins form a heteromeric complex (Horiuchi, J., et al., Mol. Cell Biol. 15:1203–1209 (1995)) that bind to the relevant activation domains. The precise mechanism of transcriptional activation is not known, but appears to involve histone acetylation: there is a wealth of evidence showing a positive correlation between histone acetylation and the transcriptional activity of chromatin (Wolffe, A. P., Trends Biochem. Sci. 19:240–244 (1994)) and recently, the GCN5 protein has been shown to have histone acetyltransferase activity (Brownell, J. E., et al., Cell 84:843–851 (1996)). Genetic studies, indicate that CBF1, like VP16 and GCN4, requires ADA2, ADA3 and GCN5 to function optimally in yeast. The fundamental question thus raised is whether plants have homologs of ADA2, ADA3 and GCN5 and whether these adaptors are required for CBF1 function (and function of other transcription factors with acidic activator regions) in Arabidopsis.

Figure 7:
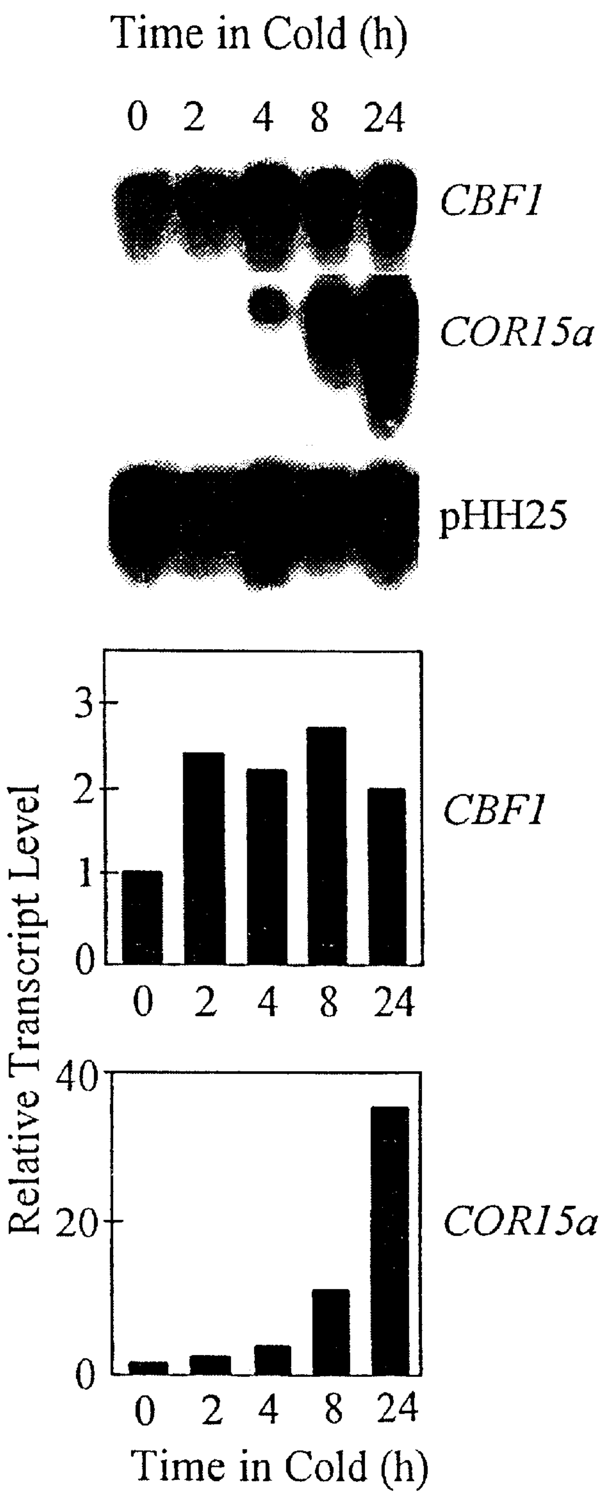
FIGS. 7A, 7B and 7C relate to CBF1 transcripts in control and cold-treated Arabidopsis.

A final point regards regulation of CBF1 activity. The results of the northern analysis indicate that CBF1 transcript levels increase only slightly in response to low temperature, while those for COR15a increase dramatically (FIG. 7). Thus, unlike in yeast, it would appear that transcription of CBF1 in Arabidopsis at warm temperatures is not sufficient to cause appreciable activation of promoters containing the C-repeat/DRE. The molecular basis for this apparent low temperature activation of CBF1 in Arabidopsis is not known. One intriguing possibility, however is that CBF1 might be modified at low temperature in Arabidopsis resulting in either stabilization of the protein, translocation of the protein from the cytoplasm to the nucleus, or activation of either the DNA binding domain or activation domain of the protein. Such modification could involve a signal transduction pathway that is activated by low temperature. Indeed, as already discussed, cold-regulated expression of COR genes in Arabidopsis and alfalfa appears to involve a signal transduction pathway that is activated by low temperature-induced calcium flux (Knight, H., et al., The Plant Cell 8:489–503 (1996); Knight, M. R., et al., Nature 352:524–526 (1991); Monroy, A. F., et al, Plant Physiol. 102:1227–1235 (1993); Monroy, A. F., and R. S., The Plant Cell, 7:321–331 (1995)). It will, therefore, be of interest to determine whether CBF1 is modified at low temperature, perhaps by phosphorylation, and if so, whether this is dependent on calcium-activated signal transduction.

2. Use of CBF1 To Induce Cold Regulated Gene Expression in Nonacclimated Arabidopsis Plants.

The following example demonstrates that increased expression of CBF1 induces COR gene expression in nonacclimated Arabidopsis plants. Transgenic Arabidopsis plants that overexpress CBF1 were created by placing a cDNA encoding CBF1 under the control of the strong cauliflower mosaic virus (CaMV) 35S promoter and transforming the chimeric gene into Arabidopsis ecotype RLD plants (Standard procedures were used for plasmid manipulations (J. Sambrook, et al., Molecular Cloning, A Laboratory Manual (Cold Spring Harbor Laboratory Press, Cold Spring Harbor, ed. 2, (1989)). The CBF1-containing AseI-BglII fragment from pACT-Bgl+ (Stockinger, E. J., et al., Proc. Natl. Acad. Sci. U.S.A. 94:1035 (1997)) was gel-purified, BamHI linkers were ligated to both ends and the fragment was inserted into the BamHI site in pCIB710 (S. Rothstein, et al., Gene 53:153–161 (1987)) which contains the CaMV 35S promoter and terminator. The chimeric plasmid was linearized at the KpnI site and inserted into the KpnI site of the binary vector pCIB10g (Ciba-Geigy, Research Triangle Park, N.C.). The plasmid was transformed into *Agrobacterium tumefaciens* strain C58C1 (pMP90) by electroporation. Arabidopsis plants were transformed by the vacuum infiltration procedure (N. Bechtold, J. Ellis, and G. Pelletier, C. R. Acad. Sci. Paris, Life Sci. 316:1194–1199 (1993)) as modified (A. van Hoof, P. J. Green, Plant Journal 10:415–424 (1996)). Initial screening gave rise to two transgenic lines, A6 and B16, that accumulated CBF1 transcripts at elevated levels.

Figure 8:
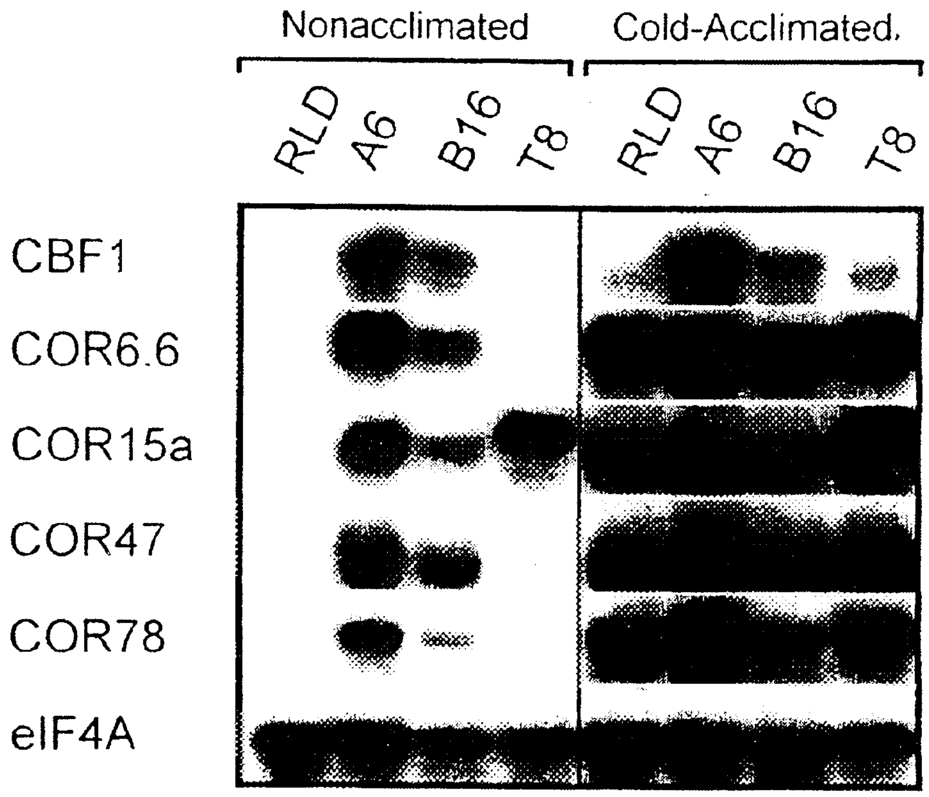
FIG. 8 is a Northern blot showing CBF1 and COR transcript levels in RLD and transgenic Arabidopsis plants.

FIG. 8 is a Northern blot showing CBF1 and COR transcript levels in RLD and transgenic Arabidopsis plants. Leaves from nonacclimated and three-day cold-acclimated plants (*Arabidopsis thaliana* ecotype RLD plants were grown in pots under continuous light (100 $\mu E/m^2/sec$) at 22 C. for 18–25 days as described (Gilmour, S. J., et al., Plant Physiol. 87:735 (1988)). In some cases, plants were then cold-acclimated by placing them at 2.5° C. under continuous light (50 $\mu E/m^2/sec$) for varying amounts of time. Leaves were harvested and total RNA prepared and analyzed for CBF1 and COR transcripts by RNA blot analysis using $^{32}P$-radiolabeled probes (Total RNA was isolated from plant leaves and subjected to RNA blot analysis using high stringency hybridization and wash conditions as described (E. J. Stockinger, et al., Proc. Natl. Acad. Sci. USA 94:1035 (1997); and S. J. Gilmour, et al., Plant Physiol. 87:735 (1988)).

Figure 9:
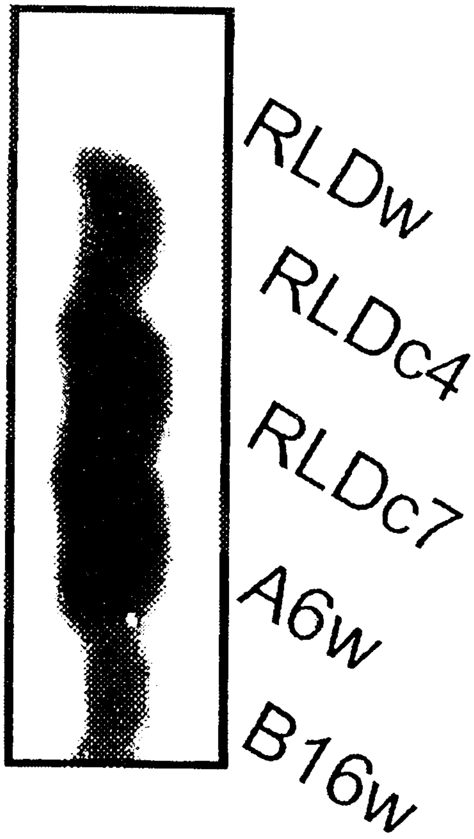
FIG. 9 is an immunoblot showing COR15am protein levels in RLD and transgenic Arabidopsis plants.

FIG. 9 is an immunoblot showing COR15am protein levels in RLD and transgenic Arabidopsis plants. Total soluble protein (100 $\mu g$) was prepared from leaves of the nonacclimated RLD (RLDw), 4-day cold-acclimated RLD (RLDc4), 7-day cold-acclimated RLD (RLDc7) and nonacclimated A6 and B16 plants and the levels of COR15am determined by immunoblot analysis using antiserum raised against the COR15am polypeptide (Total soluble protein was isolated from plant leaves, fractionated by tricine SDS-PAGE and transferred to 0.2 micron nitrocellulose as previously described (N. N. Artus et al., Proc. Natl. Acad. Sci. U.S.A. 93:13404 (1996)). COR15am protein was detected using antiserum raised to purified COR15am and protein A conjugated alkaline phosphatase (Sigma, St. Louis, Mo.) (N. N. Artus et al., Proc. Natl. Acad. Sci. U.S.A. 93:13404 (1996)). No reacting bands were observed with preimmune serum (not shown).

Southern analysis indicated that the A6 line had a single DNA insert while the B16 line had multiple inserts (not shown). Examination of fourth generation homozygous A6 and B16 plants indicated that CBF1 transcript levels were higher in nonacclimated A6 and B16 plants than they were in nonacclimated RLD plants, the levels in A6 being about three fold higher than in B16 (FIG. 8).

CBF1 overexpression resulted in strong induction of COR gene expression (FIG. 8). Specifically, the transcript levels of COR6.6, COR15a, COR47 and COR78 were dramatically elevated in nonacclimated A6 and B16 plants as compared to nonacclimated RLD plants. The effect was greater in the A6 line, where COR transcript levels in nonacclimated plants approximated those found in cold-acclimated RLD plants. The finding that COR gene expression was greater in A6 plants than in B16 plants was consistent with CBF1 transcript levels being higher in the A6 plants (FIG. 7A). Immunoblot analysis indicated that the levels of the COR15am (FIG. 9) and COR6.6 (not shown) polypeptides were also elevated in the A6 and B16 lines, the level of expression again being higher in the A6 line. Attempts to identify the CBF1 protein in either RLD or transgenic plants were unsuccessful. Overexpression of CBF1 had no effect on the transcript levels for eIF4A (eukaryotic initiation factor 4A) (Metz, A. M., et al., Gene 120:313 (1992)), a constitutively expressed gene that is not responsive to low temperature (FIG. 8) and had no obvious effects on plant growth and development.

The results from this example demonstrate that overexpression of the Arabidopsis transcriptional activator CBF1 induces expression of an Arabidopsis COR "regulon" composed of genes carrying the CRT/DRE DNA regulatory element. It appears that CBF1 binds to the CRT/DRE DNA regulatory elements present in the promoters of these genes and activates transcription which is consistent with the notion of CBF1 having a role in COR gene regulation. Significantly, there was a strong correlation between CBF1 transcript levels and the magnitude of COR gene induction in nonacclimated A6, B16, and RLD plants (FIG. 8). However, upon low temperature treatment the level of CBF1 transcripts remained relatively low in RLD plants, while COR gene expression was induced to about the same level as that in nonacclimated A6 plants (FIG. 8). Thus, it appears that CBF1 or an associated protein becomes "activated" in response to low temperature.

3. CBF1 Overexpression Resulted in a Marked Increase in Plant Freezing Tolerance The following example describes a comparison of the freezing tolerance of nonacclimated Arabidopsis plants which overexpress CBF1 to that of cold-acclimated wild-type plants. As described below, the freezing tolerance of nonacclimated Arabidopsis plants overexpressing CBF1 significantly exceeded that of non-acclimated wild-type Arabidopsis plants and approached that of cold-acclimated wild-type plants.

Freezing tolerance was determined using the electrolyte leakage test (Sukumaran, N. P., et al., HortScience 7:467 (1972)). Detached leaves were frozen to various subzero temperatures and, after thawing, cellular damage (due to freeze-induced membrane lesions) was estimated by measuring ion leakage from the tissues.

Figure 10A:
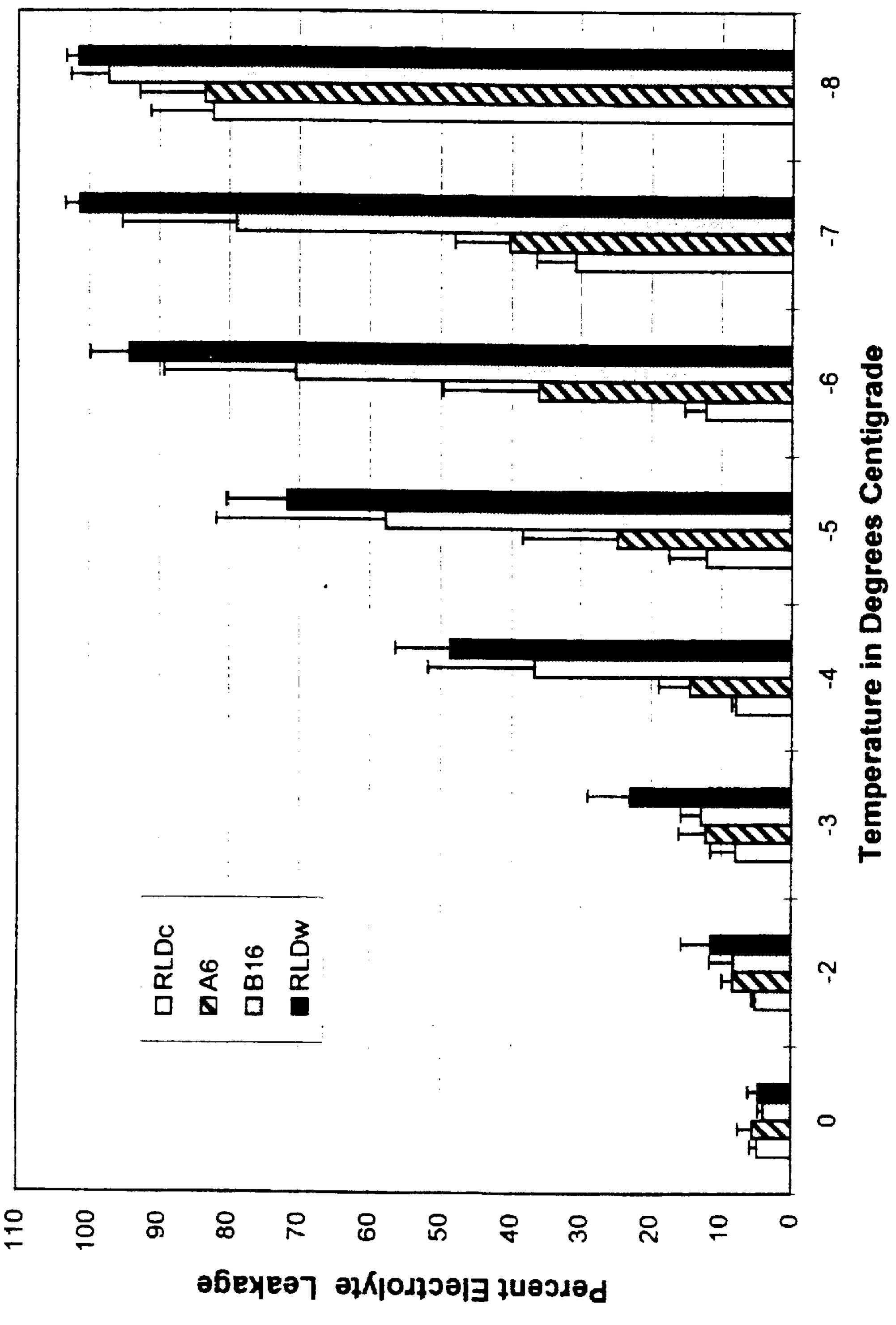
FIGS. 10A and 10B are graphs showing freezing tolerance of leaves from RLD and transgenic Arabidopsis plants.
Figure 10B:
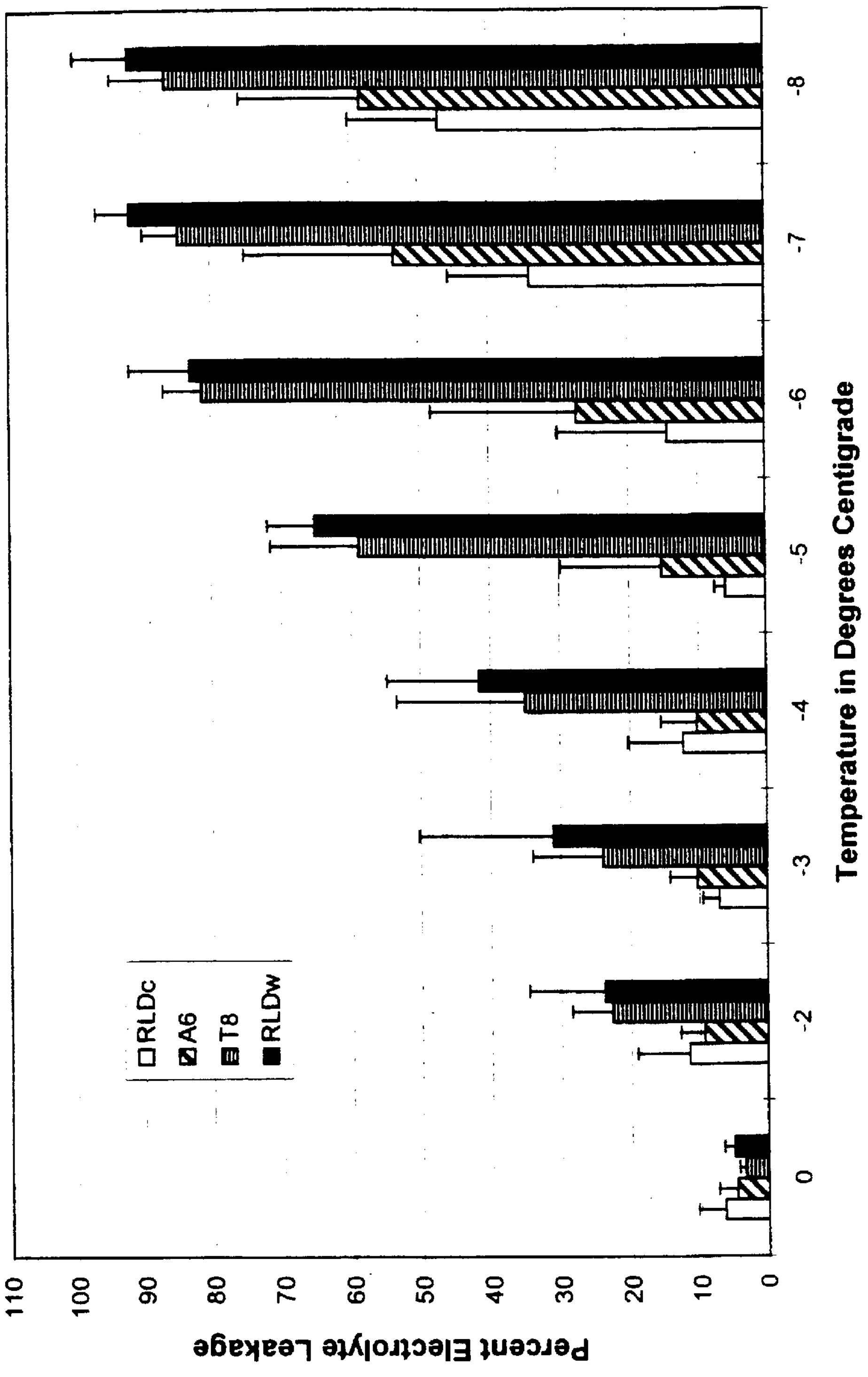

FIGS. 10A and 10B are graphs showing freezing tolerance of leaves from RLD and transgenic Arabidopsis plants. Leaves from nonacclimated RLD (RLDw) plants, cold-acclimated RLD (RLDc) plants and nonacclimated A6, B16 and T8 plants were frozen at the indicated temperatures and the extent of cellular damage was estimated by measuring electrolyte leakage (Electrolyte leakage tests were conducted as described (N. P. Sukumaran, et al., HortScience 7, 467 (1972); and S. J. Gilmour, et al., Plant Physiol. 87:735 (1988)) with the following modifications. Detached leaves (2–4) from nonacclimated or cold-acclimated plants were placed in a test tube and submerged for 1 hour in a −2° C. water-ethylene glycol bath in a completely randomized design, after which ice crystals were added to nucleate freezing. After an additional hour of incubation at −2° C., the samples were cooled in decrements of 1° C. each hour until −8° C. was reached. Samples (five replicates for each data point) were thawed overnight on ice and incubated in 3 ml distilled water with shaking at room temperature for 3 hours. Electrolyte leakage from leaves was measured with a conductivity meter. The solution was then removed, the leaves frozen at −80° C. (for at least one hour), and the solution returned to each tube and incubated for 3 hours to obtain a value for 100% electrolyte leakage. In FIGS. 10A and 10B, the RLDc plants were cold-acclimated for 10 and 11 days, respectively. Error bars indicate standard deviations.

As can be seen from FIGS. 10A and 10B, CBF1 overexpression resulted in a marked increase in plant freezing tolerance. The experiment presented in FIG. 10A indicates that the leaves from both nonacclimated A6 and B16 plants were more freezing tolerant than those from nonacclimated RLD plants. Indeed, the freezing tolerance of leaves from nonacclimated A6 plants approached that of leaves from cold-acclimated RLD plants. The results also indicate that the leaves from nonacclimated A6 plants were more freezing tolerant than those from nonacclimated B16 plants, a result that is consistent with the greater level of CBF1 and COR gene expression in the A6 line.

The results presented in FIG. 10B further demonstrate that the freezing tolerance of leaves from nonacclimated A6 plants was greater than that of leaves from nonacclimated RLD plants and that it approached the freezing tolerance of leaves from cold-acclimated RLD plants. In addition, the results indicate that overexpression of CBF1 increases freezing tolerance to a much greater extent than overexpressing COR15a alone. This conclusion comes from comparing the freezing tolerance of leaves from nonacclimated A6 and T8 plants (FIG. 10B). T8 plants (Artus, N. N., et al., Proc. Natl. Acad. Sci. U.S.A. 93:13404 (1996)) are from a transgenic line that constitutively expresses COR15a (under control of the CaMV 35S promoter) at about the same level as in A6 plants (FIG. 1). However, unlike in A6 plants, other CRT/DRE-regulated COR genes are not constitutively expressed in T8 plants (FIG. 8).

A comparison of $EL_{50}$ values (the freezing temperature that results in release of 50% of tissue electrolytes) of leaves from RLD, A6, B16 and T8 plants is presented in Table 2.

$EL_{50}$ values were calculated and compared by analysis of variance curves fitting up to third order linear polynomial trends were determined for each electrolyte leakage experiment. To insure unbiased predictions of electrolyte leakage, trends significantly improving the model fit at the 0.2 probability level were retained. $EL_{50}$ values were calculated from the fitted models. In Table 2, an unbalanced one-way analysis of variance, adjusted for the different numbers of $EL_{50}$ values for each plant type, was determined using SAS PROC GLM [SAS Institute, Inc. (1989), SAS/STAT User's Guide, Version 6, Cory, N.C.)]. $EL_{50}$ values±SE (n) are presented on the diagonal line for leaves from nonacclimated RLD (RLDw), cold-acclimated (7 to 10 days) RLD (RLDc) and nonacclimated A6, B16 and T8 plants. P values for comparisons of $EL_{50}$ values are indicated in the intersecting cells.

TABLE 2

| | $EL_{50}$ values | | | | |
|---|---|---|---|---|---|
| | RLDw | RLDc | A6 | B16 | T8 |
| RLDw | −3.9 ± 0.21 (8) | P < 0.0001 | P < 0.0001 | P = 0.0014 | P = 0.7406 |
| RLDc | | −7.6 ± 0.30 (4) | P = 0.3261 | P < 0.0001 | P < 0.0001 |
| A6 | | | −7.2 ± 0.25 (6) | P < 0.0001 | P < 0.000i |
| B16 | | | | −5.2 ± 0.27 (5) | P = 0.0044 |
| T8 | | | | | −3.8 ± 0.35 (3) |

The data confirm that: 1) the freezing tolerance of leaves from both nonacclimated A6 and B16 plants is greater than that of leaves from both nonacclimated RLD and T8 plants; and 2) that leaves from nonacclimated A6 plants are more freezing tolerant than leaves from nonacclimated B16 plants. No significant difference was detected in $EL_{50}$ values for leaves from nonacclimated A6 and cold-acclimated RLD plants or from nonacclimated RLD and T8 plants.

Figure 11:
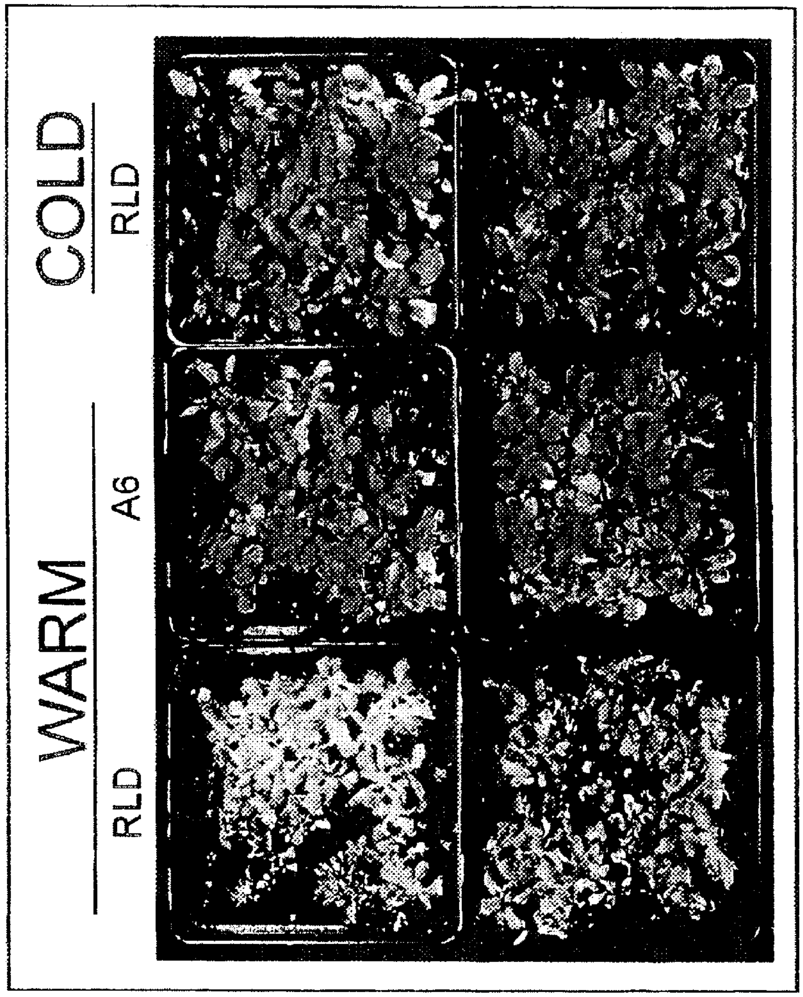
FIG. 11 is a photograph showing freezing survival of RLD and A6 Arabidopsis plants.

The enhancement of freezing tolerance in the A6 line was also apparent at the whole plant level. FIG. 11 is a photograph showing freezing survival of RLD and A6 Arabidopsis plants. Nonacclimated (WARM) RLD and A6 plants and 5-day cold-acclimated (COLD) RLD plants were frozen at −5° C. for 2 days and then returned to a growth chamber at 22° C. (Pots (3.5 inch) containing about 40 nonacclimated Arabidopsis plants (20 day old) and 4 day cold-acclimated plants (25 days old) (*Arabidopsis thaliana* ecotype RLD plants were grown in pots under continuous light (100 $\mu E/m^2/sec$) at 22° C. for 18–25 days as described (S. J. Gilmour, et al., Plant Physiol. 87:735 (1988)). In some cases, plants were then cold-acclimated by placing them at 2.5° C. under continuous light (50 $\mu E/m^2/sec$) for varying amounts of time) were placed in a completely randomized design in a −5° C. cold chamber in the dark. After 1 hour, ice chips were added to each pot to nucleate freezing. Plants were removed after 2 days and returned to a growth chamber at 22° C.). A photograph of the plants after 7 days of regrowth is shown.

Although the magnitude of the difference varied from experiment to experiment, nonacclimated A6 plants consistently displayed greater freezing tolerance in whole plant freeze tests than did nonacclimated RLD plants (FIG. 11). No difference in whole plant freeze survival was detected between nonacclimated B16 and RLD plants or nonacclimated T8 and RLD plants (not shown).

The results of this experiment show that CBF1-induced expression of CRT/DRE-regulated COR genes result in a dramatic increase in freezing tolerance and confirms the belief that COR genes play a major role in plant cold acclimation. The increase in freezing tolerance brought about by expressing the battery of CRT/DRE-regulated COR genes was much greater than that brought about by overexpressing COR15a alone indicating that COR genes in addition to COR15a have roles in freezing tolerance.

Traditional plant breeding approaches have met with limited success in improving the freezing tolerance of agronomic plants (Thomashow, M. F., Adv. Genet 28:99 (1990)). For instance, the freezing tolerance of the best wheat varieties today is essentially the same as the most freezing-tolerance varieties developed in the early part of this century. Thus, in recent years there has been considerable interest that biotechnology might offer new strategies to improve the freezing tolerance of agronomic plants. By the results of the present invention, Applicants demonstrate the ability to enhance the freezing tolerance of nonacclimated Arabidopsis plants by increasing the expressing of the Arabidopsis regulatory gene CBF1. As described throughout this application, the ability of the present invention to modify the expression of environmental stress tolerance genes such as core genes has wide ranging implications since the CRT/DRE DNA regulatory element is not limited to Arabidopsis (Jiang C., et al., Plant Mol. Biol. 30:679 (1996)). Rather, CBF1 and homologous genes can be used to manipulate expression of CRT/DRE-regulated COR genes in important crop species and thereby improve their freezing tolerance. By transforming modified versions of CBF1 (or homologs) into such plants, it will extend their safe growing season, increase yield and expand areas of production.

4. Selection of Promoters to Control Expression of CBF1 in Plants

The following examples describe the isolation of different promoters from plant genomic DNA, construction of the plasmid vectors carrying the CBF1 gene and the inducible promoters, transformation of Arabidoposis cells/plants with these constructs, and regeneration of transgenic plants with increased tolerance to environmental stresses.

A. Isolation of inducible promoters from plant genomic DNAs

Inducible promoters from different plant genomic DNAs were identified and isolated by PCR amplification using primers designed to flank the promoter region and contain suitable restriction sites for cloning into the expression vector. The following genes were used to BLAST search Genbank to find the inducible promoters: Dreb2a; P5CS; Rd22; Rd29a; Rd29b; Rab18; Cor47. Table 3 lists the accession numbers and positions of these promoters. Table 4 lists the forward and reverse primers that were used to isolate the promoters.

TABLE 3

| Gene Name | Accession No. | Position | Length (bps) |
|---|---|---|---|
| Dreb2a | AB010692 | 51901–53955 | 2054 |
| P5Cs | AC003000 | 45472–47460 | 1988 |
| Rd22 | D10703 | 17–1046 | 1029 |
| Rd29a | D13044 | 3870–5511 | 1641 |
| Rd29b | D13044 | 90–1785 | 1695 |
| Rab18 | AB013389 | 8070–9757 | 1887 |
| Cor47 | AB004872 | 1–1370 | 1370 |

TABLE 4

| Promoter name | Primer name | Cloning sites | SEQ. ID. No. |
|---|---|---|---|
| Dreb2a | Dreb2a-reverse | HindIII (AAGCTT) | 19 |
| | Dreb2a-forward | BglII (AGATCT) | 20 |
| P5CS | P5CS-reverse | HindIII (AAGCTT) | 21 |
| | P5CS-forward | BglII (AGATCT) | 22 |
| Rd22 | Rd22-reverse | HindIII (AAGCTT) | 23 |
| | Rd22-forward | KpnI (GGTACC) | 24 |
| Rd29a | Rd29a-reverse | HindIII (AAGCTT) | 25 |
| | Rd29a-forward | KpnI (GGTACC) | 26 |
| Rd29b | Rd29b-reverse | HindIII (AAGCTT) | 27 |
| | Rd29b-forward | KpnI (GGTACC) | 28 |
| Rab18 | Rab18-reverse | HindIII (AAGCTT) | 29 |
| | Rab18-forward | BglII (AGATCT) | 30 |
| Cor47 | Cor47-reverse | HindIII (AAGCTT) | 31 |
| | Cor47-forward | BglII (AGATCT) | 32 |

(1) Dreb2a Promoter

A cDNA encoding DRE (C-repeat) binding protein (DREB2A) has been recently identified (Liu, et al. 1998 Plant Cell 10:1391–1406). The transcription of the DREB2A gene is activated by dehydration and high-salt stress, but not by cold stress. The upstream untranslated region (166 bps) of dreb2a was used to BLAST-search the public database. A region containing the DREB2A promoter was identified in chromosome 5 of Arabidopsis (Accession No. AB010692) between nucleotide positions 51901–53955 (Table 3).

Two PCR primers designed to amplify the promoter region from *Arabidopsis thaliana* genomic DNA are as follows: dreb2a-reverse: 5'-GCCC AAGCTTCAAGTTTAGTGAGCACTATGTGCTCG-3' [SEQ ID No. 19]; and dreb2a-forward: 5'-GGA AGATCTCCTTCCCAGAAACAACACAATCTAC-3' [SEQ. ID. No. 20]. The dre2ba-reverse primer includes a Hind III (AAGCTT) restriction site near the 5'-end of the primer and dreb2a-forward primer has a Bgl II (AGATCT) restriction site at near 5'-end of the primer. These restriction sites may be used to facilitate cloning of the fragment into an expression vector.

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The reaction conditions that may be used in this PCR experiment are as follows: Segment 1: 94° C., 2 minutes; Segment 2: 94° C., 30 seconds; 60° C., 1 minute; 72° C., 3 minutes, for a total of 35 cycles; Segment 3: 72° C. for 10 minutes. A PCR product of 2054 bp is expected.

The PCR products can be subject to electrophoresis in a 0.8% agarose gel and visualized by ethidium bromide staining. The DNA fragments containing the inducible promoter will be excised and purified using a Qiaquick gel extraction kit (Qiagen, Calif.).

(2) P5CS Promoter

A cDNA for delta 1-pyrroline-5-carboxylate synthetase (P5CS) has been isolated and characterized (Yoshiba, et al., 1995, Plant J. 7:751–760). The cDNA encodes an enzyme involved in the biosynthesis of proline under osmotic stress (drought/high salinity). The transcription of the P5CS gene was found to be induced by dehydration, high salt and treatment with plant hormone ABA, while it did not respond to heat or cold treatment.

A genomic DNA containing a promoter region of P5CS was identified by a BLAST search of Genbank using the upstream untranslated region (106 bps) of the P5CS sequence (Accession No. D32138). The sequence for the P5CS promoter is located in the region between from nucleotide positions 45472 to 47460 (Accession No. AC003000; Table 3).

Reverse and forward PCR primers designed to amplify this promoter region from *Arabidopsis thaliana* genomic DNA are P5CS-reverse primer 5'-GCCCAAGCTTGTTT-CATTTTCTCCATGAAGGAGAT-3' [SEQ. ID. No. 21]; and P5CS-forward primer 5'-GGAAGATCTTATCGTCG-TCGTCGTCTACCAAAACCACAC-3' [SEQ. ID. No. 22].

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1988 bps and may be PCR amplified and gel purified following the same protocol described for the dreb2a promoter.

(3) rd22 Promoter

A cDNA clone of rd22 was isolated from Arabidopsis under dehydration conditions (Yamaguchi-Shinozaki and Shinozaki, Mol. Gen. Genet. 238:17–25 (1993)). Transcripts of rd22 were found to be induced by salt stress, water deficit and endogenous abscisic acid (ABA) but not by cold or heat stress. A promoter region was identified from Genebank by using Nucleotide Search WWW Entrez at the NCBI with the rd22 as a search word. The sequence for the rd22 promoter is located in the region between nucleotide positions 17 to 1046 (Accession No. D10703; Table 3).

Reverse and forward PCR primers designed to amplify this promoter region from *Arabidopsis thaliana* genomic DNA are rd22-reverse primer 5'-GCTCT AAGCTTCACAAGGGGTTCGTTTGGTGC-3' [SEQ. ID. No. 23]; and rd22-forward primer 5'-GGGGTACCTTTT-GGGAGTTGGAATAGAAATGGGTTTGATG-3' [SEQ. ID. No. 24]. The rd22-reverse primer includes a Hind III (AAGCTT) restriction site near the 5'-end of primer and rd22-forward primer has a KpnI (GGTACC) restriction site at near 5'-end of primer.

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1029 bps and may be PCR amplified and gel purified following the same protocol described for the dreb2a promoter.

(4) rd29a Promoter

The rd29a and rb29b genes were isolated and characterized by Shinozaki's group in Japan (Yamaguchi-Shinizaki and Shinozaki, Plant Physiol. 101: 1119–1120 (1993)). Both rd29a and rb29b gene expressions were found to be induced by desiccation, salt stress and exogenous ABA treatment (Yamaguchi-Shinizaki and Shinozaki, Plant Physiol. 101: 1119–1120 (1993); Ishitani et al., Plant Cell 10: 1151–1161 (1998)). The rd29a gene expression was induced within 20 min after desiccation, but rd29b mRNA did not accumulate to a detectable level until 3 hours after desiccation. Expression of rd29a could also be induced by cold stress, whereas expression of rd29b could not be induced by low temperature.

A genomic clone carrying the rd29a promoter was identified by using Nucleotide Search WWW Entrez at the NCBI with the rd29a as a search word. The sequence for the rd29a promoter is located in the region between nucieotide positions 3870 to 5511 (Accession No. D13044, Table 3).

Reverse and forward primers designed to amplify this promoter region from Arabidopsis genomic DNA are: rd29a-reverse primer 5'-GCCCAAGCTTAATTTTACTC-AAAATGTTTTGGTTGC-3' [SEQ. ID. No. 25]; and rd29a-forward primer 5'-CCGGTACCTTTCCAAAGATT-TTTTTCTTTCCAATAGAAGTAATC-3' [SEQ. ID. No. 26]. The rd29a-reverse primer includes a Hind III (AAGCTT) restriction site near the 5'-end of primer and rd29a-forward primer has a KpnI (GGTACC) restriction site near 5'-end of primer.

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1641 bps and may be PCR amplified and gel purified following the same protocol described for the dreb2a promoter.

(5) rd29b Promoter

A genomic clone carrying the rd29b promoter was identified by using Nucleotide Search WWW Entrez at the NCBI with the rd29b as a search word. The sequence for the rd29a promoter was located in the region between nucleotide positions 90 to 1785 for rd29b (Accession No. D13044; Table 3).

Reverse and forward PCR primers designed to amplify this promoter region from *Arabidopsis thaliana* genomic DNA are: rd29b-reverse primer 5'-GCGGAAGCTTCAT-TTTCTGCTACAGAAGTG-3' [SEQ. ID. No. 27]; and rd29b-forward primer 5'-CCGGTACCTTTCCAAAGCT-GTGTTTTCTCTTTTTCAAGTG-3' [SEQ. ID. No. 28].

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1695 bps and may be PCR amplified and gel purified following the same protocol described for the dreb2a promoter.

(6) rab18 Promoter

A rab-related (responsive to ABA) gene, rab18 from arabidopsis has been isolated. The gene encodes a hydrophilic, glycine-rich protein with the conserved serine- and lysine-rich domains. The rab18 transcripts accumulate in plants exposed to water deficit or exogenous abscisic acid (ABA) treatment. A weak induction of rab18 mRNA by low temperature was also observed (Ishitani et al., Plant Cell 10: 1151–1161 (1998)).

A genomic DNA containing a promoter region of rab18 was identified by a BLAST search of Genbank using the upstream untranslated region (757 bps) of the rab18 sequence (Accession No. L04173). The sequence of the rab18 promoter is located in the region between nucleotide positions 8070 to 9757 (Accession No. AB013389).

Reverse and forward PCR primers designed and used to amplify this promoter region from *Arabidopsis thaliana* genomic DNA are: rab18-reverse primer 5'-GCCC AAGCTTCAAATTCTGAATATTCACATATCAAAAA-AGTG-3' [SEQ. ID. No. 29]; and rab18-forward primer 5'-GGAAGATCTGTTCTTCTTGTCTTAAGCAAACACT-TTGAGC-3' [SEQ. ID. No. 30]. The rab18-reverse primer includes a Hind III (AAGCTT) restriction site near the 5'-end of the primer and rab18-forward primer has a Bgl II (AGATCT) restriction site near the 5'-end of the primer.

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1687 bps and may be PCR amplified and gel purified following the same protocol described for the dreb2a promoter.

(7) Cor47 Promoter

The DNA sequence of cDNA for cold-regulated (cor47) gene of *Arabidopsis thaliana* was determined. Gilmour et al., Plant Molecular Biology 18: 13–21 (1992)). Expression of cor47 gene was induced by cold stress, dehydration and high NaCl treatment (Ishitani et al., *Plant Cell,* 10. 1151–1161 (1998)). The promoter region of cor47 gene was identified in Genbank by using Nucleotide Search WWW Entrez at the NCBI with the cor47 as a search word. The sequence of the cor47 promoter is located in the region between nucleotide positions 1–1370 (Accession No. AB004872; Table 3).

Reverse and forward PCR primers designed to amplify this promoter region from *Arabidopsis thaliana* genomic DNA are: cor47-reverse primer 5'-GCCCAAGCTTTCG-TCTGTTATCATACAAGGCACAAAACGAC-3' [SEQ. ID. No. 31]; and cor47-forward primer 5'-GGAAGATCT-AGTTAATCTTGATTTGATTAAAAGTTTATATAG-3' [SEQ. ID. No. 32]. The cor47-reverse primer includes a Hind III (AAGCTT) restriction site near the 5'-end of the primer and cor47-forward primer has a Bgl II (AGATCT) restriction site near the 5'-end of the primer.

Total genomic DNA may be isolated from *Arabidopsis thaliana* (ecotype colombia) by using the CTAB method (Ausubel et al. (1992) Current Protocols in Molecular Biology (Greene & Wiley, New York)). Ten nanograms of the genomic DNA can be used as a template in a PCR reaction under conditions suggested by the manufacturer (Boehringer Mannheim). The PCR product is expected to be 1370 bps and may be PCR amplified and gel purified following the same protocol described for the dreb2a promoter.

B. Isolation of seed-specific promoters from plant genomic DNAs

The napin promoter from *Brassica campestris* (genbank accession number M64632) is a seed-specific promoter. A fragment of the napin promoter (between nucleotides 1146 to 2148) is identified and isolated by PCR amplification using a 5' PCR primer containing a HindIII site upstream of the promoter and a 3' PCR primer containing a BamHI site downstream of the promoter. Deletions of the napin promoter to −211 and −152 have been shown to have reduced levels of expression (Ellerstrom et al. Plant Mol Biol 32:1019–27 (1996); Stalberg et al. Planta 199: 515–9 (1996); Stalberg et al. Plant Mol Biol 23: 671–83 (1993)). These 5' deleted promoters are useful to have reduced levels of CBF1 expression for applications where the larger napin promoter fragment is too strong.

Other seed-active promoters or deletions of these promoters can also be isolated from genomic DNA by using the same method described above for the napin promoter. Examples of these promoters include but are not limited to the soybean 7S seed storage protein (Chen et al., Developmental Genetics 10:112–122 (1989), the bean phaseolin promoter (cited in U.S. Pat. No. 5,003,045), the Arabidopsis 12S globulin (cruiferin) promoter (Pang, et al., Plant Mol. Biol. 11:805–820 (1988), the maize globulin1 promoter (Kriz et al. Plant Physiol. 91:636 (1989); U.S. Pat. No. 5,773,691). These promoters may be used for altering COR gene expression in cereals such as corn, barley, wheat, rice and rye seeds.

C. Construction of the plamids containing CBF1 and inducible or tissue-specific promoter The expression binary vector pMEN020 contains a kanamycin resistance gene (neomycin phosphotransferase) for antibiotic selection of the transgenic plants and a Spc/Str gene used for bacterial or agrobacterial selections. The pMEN020 plasmid is digested with restriction enzymes such as HindIII and BglII to remove the 35S promoter. The 35S promoter is then replaced with an inducible promoter.

The expression binary vector pMEN050 is derived from pMEN020 by replacing the NptII kanamycin resistance gene with the Bar gene (U.S. Pat. No. 5,646,024). PMEN050 is digested with HindIII and BamHI restriction enzymes to remove the EcaMV 35S promoter. The EcaMV 35S promoter is then replaced with the seed-specific napin promoter, resulting plasmid pMEN1001. Similarly, the EcaMV 35S promoter is also replaced with the seed-specific napin promoters with −211 and −152 end point deletions to generate plasmid pMEN1002 and pMEN1003, respectively.

(1) Cloning of the Inducible Promoter Into pMEN020

The sequences of the inducible promoters that are PCR amplified and gel purified, as well as the plasmid pMEN020, are subject to restriction digestion with their respective restriction enzymes as listed in Table 4. Both DNA samples are purified by using the Qiaquick purification kit (Qiagen, Calif.) and ligated at a ratio of 3:1 (vector to insert). Ligation reactions using T4 DNA ligase (New England Biolabs, MA) are carried out at 16° C. for 16 hours. The ligated DNAs are transformed into competent cells of the *E. coli* strain DH5 by using the heat shock method. The transformed cells are plated on LB plates containing 100 μg/ml spectinomycin (Sigma). Individual colonies are grown overnight in five milliliters of LB broth containing 100 μg/ml spectinomycin at 37° C.

Plasmid DNAs from transformants are purified by using Qiaquick Mini Prep kits (Qiagen, Calif.) according to the manufacturer's instruction. The presence of the promoter insert is verified by restriction mapping with the respective restriction enzymes as listed in Table 4 to cut out the cloned insert. The plasmid DNA is also subject to double-strand DNA sequencing analysis using a vector primer (E9.1 primer 5'-CAAACTCAGTAGGATTCTGGTGTGT-3' [SEQ. ID. No. 33].

(2) Cloning of the cbf1Gene Into the Plasmids Containing the Inducible Promoters To clone the CBF1 gene into the plasmids, different PCR primers with suitable restriction sites for each plasmid are used to isolate cbf1 gene from *Arabidopsis thaliana* genomic DNA. The primers that may be used are listed in Table 5.

TABLE 5

| Promoter name | Primer name | Cloning sites |
|---|---|---|
| Dreb2a | Cbf1-reverse1 | BglII (AGATCT) |
| | Cbf1-forward1 | BamHI (GGATCC) |
| P5CS | Cbf1-reverse1 | BglII (AGATCT) |
| | Cbf1-forward1 | BamHI (GGATCC) |
| Rd22 | Cbf1-reverse2 | KpnI (GGTACC |
| | Cbf1-forward1 | BamHI (GGATCC) |
| Rd29a | Cbf1-reverse2 | KpnI (GGTACC) |
| | Cbf1-forward1 | BamHI (GGATCC) |
| Rd29b | Cbf1-reverse2 | KpnI (GGTACC) |
| | Cbf1-forward1 | BamHI (GGATCC) |
| Rab18 | Cbf1-reverse1 | BglII (AGATCT) |
| | Cbf1-forward2 | XbaI (TCTAGA |

TABLE 5-continued

| Promoter name | Primer name | Cloning sites |
|---|---|---|
| Cor47 | Cbf1-reverse1<br>Cbf1-forward1 | BglII (AGATCT)<br>BamHI (GGATCC) |

Two of the four available PCR primers (Table 5) are used for cloning the at-cbf1 gene into the expression vectors containing each inducible promoter described above. The four primers have these sequences: cbf1-reverse 1 5'-GGA-AGATCTTGAAACAGAGTACTCTGATCAATGAAC-TC-3' [SEQ. ID. No. 34], cbf1-forward 1 5'-CGCGGAT-CCCTCGTTTCTACAACAATAAAATAAAATAAAA-TG-3' [SEQ. ID. No. 35], cbf1-reverse 2 5'-GGGGTAC-CTGAAACAGAGTACTCTGATCAATGAACTC-3' [SEQ. ID. No. 36], and cbf1-forward 2 5'-GCTCTAGACTCGT-TTCTACAACAATAAAATAAAATAAAATG-3' [SEQ. ID. No. 37]. For example, for the Dreb2a, P5CS, and COR47 promoters that are ligated to a BamHI and BglII flanked insert, the cbf1-reverse 1 and cbf1-forward 1 primers [SEQ. ID. No. 34 and 35, respectively] are used to isolate cbf1 gene from *Arabidopsis thaliana* genomic DNA. The cbf1-reverse primer includes a BglII (AGATCT) restriction site near the 5'-end of the primer and cbf1-forward primer has a BamHI (GGATCC) restriction site near the 5'-end of the primer. A PCR product of 764 bp is expected. The genomic DNA (10 ng) is used as a template in a PCR reaction under conditions suggested by the manufacturer (Boehringer Mannheim). The reaction conditions to be used in this PCR experiment are as follows: Segment 1: 94° C., 2 minutes; Segment 2: 94° C., 30 seconds; 55° C., 1 minute; 72° C., 1 minute, for a total of 35 cycles; Segment 3: 72° C. for 10 minutes.

The PCR products are subject to electrophoresis in a 0.8% agarose gel and visualized by ethidium bromide staining. The DNA fragment containing cbf1 is excised and purified by using a Qiaquick gel extraction kit (Qiagen, Calif.). The purified fragment and the vector pMBI2001 containing the inducible promoter (Table 5) are each digested with BglII and BamHI restriction enzymes at 37° C. for 2 hours. Both DNA samples are purified by using the Qiaquick purification kit (Qiagen, Calif.) and ligated at a ratio of 3:1 (vector to insert). Ligation reactions using T4 DNA ligase (New England Biolabs, MA) are carried out at 16° C. for 16 hours. The ligated DNAs are transformed into competent cells of the *E. coli* strain DH5 by using the heat shock method. The transformation are plated on LB plates containing 100 (g/ml spectinomycin (Sigma).

Individual colonies are grown overnight in five milliliters of LB broth containing 100 g/ml spectinomycin at 37° C. Plasmid DNA are purified by using Qiaquick Mini Prep kits (Qiagen, Calif.). The presence of the cbf1 insert is verified by restriction mapping with BglII and BamHI. The plasmid DNA is also subject to double-strand DNA sequencing analysis by using vector primer E9.1(5'-CAAACTCAGTAGGATTCTGGTGTGT-3') [SEQ. ID. No. 33]. The other primers shown in Table 5 and appropriate restriction enzymes are used in a similar way to clone the Cbf1 gene into plasmids containing the other inducible promoters. The resulting plasmids are listed in Table 6 and shown in FIGS. 17A–17G.

A similar cloning strategy may be used to clone other genes, such as cbf2, cbf3, and the other full length CBF genes listed in Table 9 and shown in FIG. 18 (new CBF gene table) into plasmids containing inducible promoters.

TABLE 6

Figure 17A:
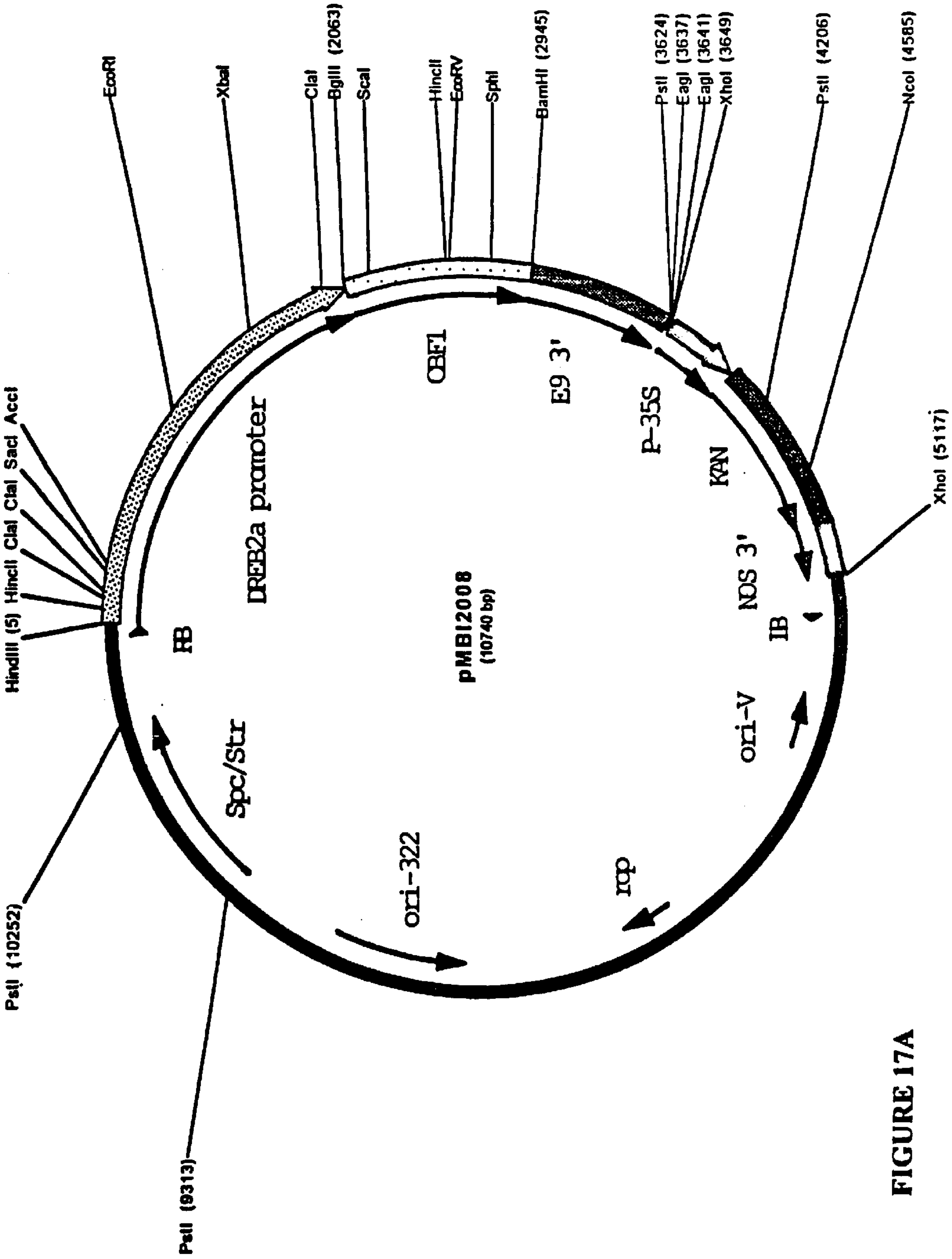
FIGS. 17A, 17B, 17C, 17D, 17E, 17F and 17G show restriction maps of plasmids pMB12008, pMB12009, pMB12010, pMB12011, pMB12012, pMB12013, and pMB12014, respectively.
Figure 17B:
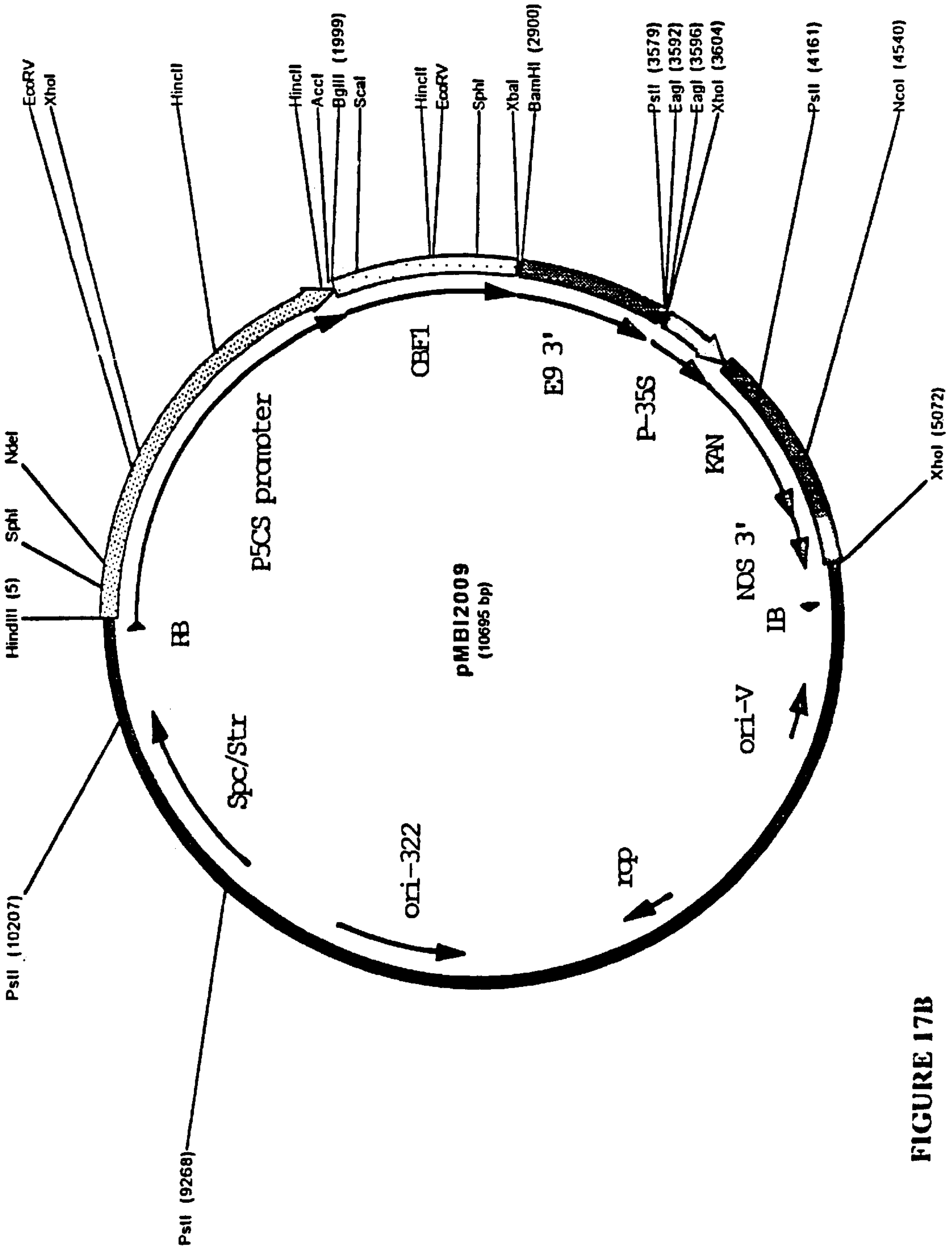
Figure 17C:
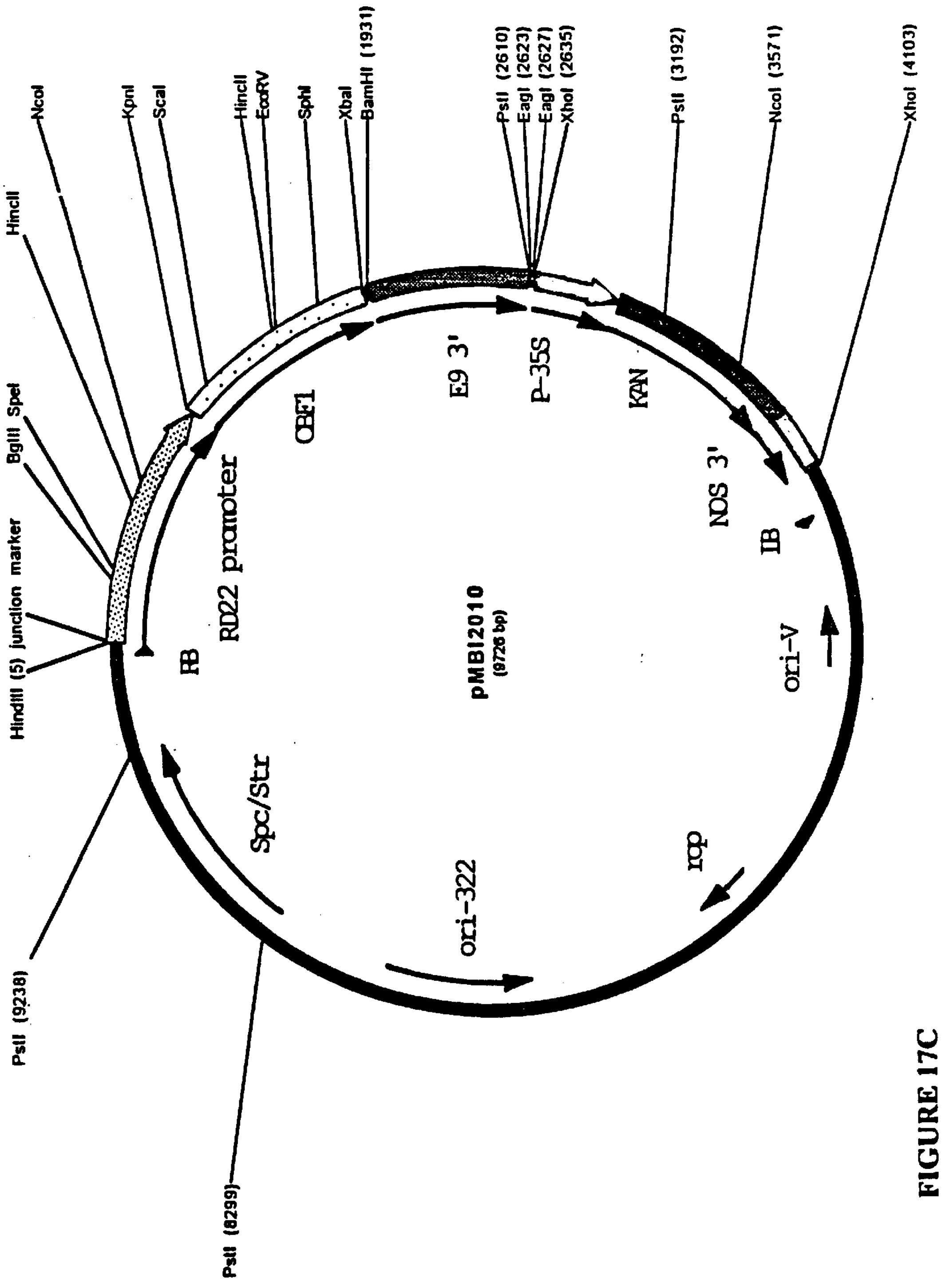
Figure 17D:
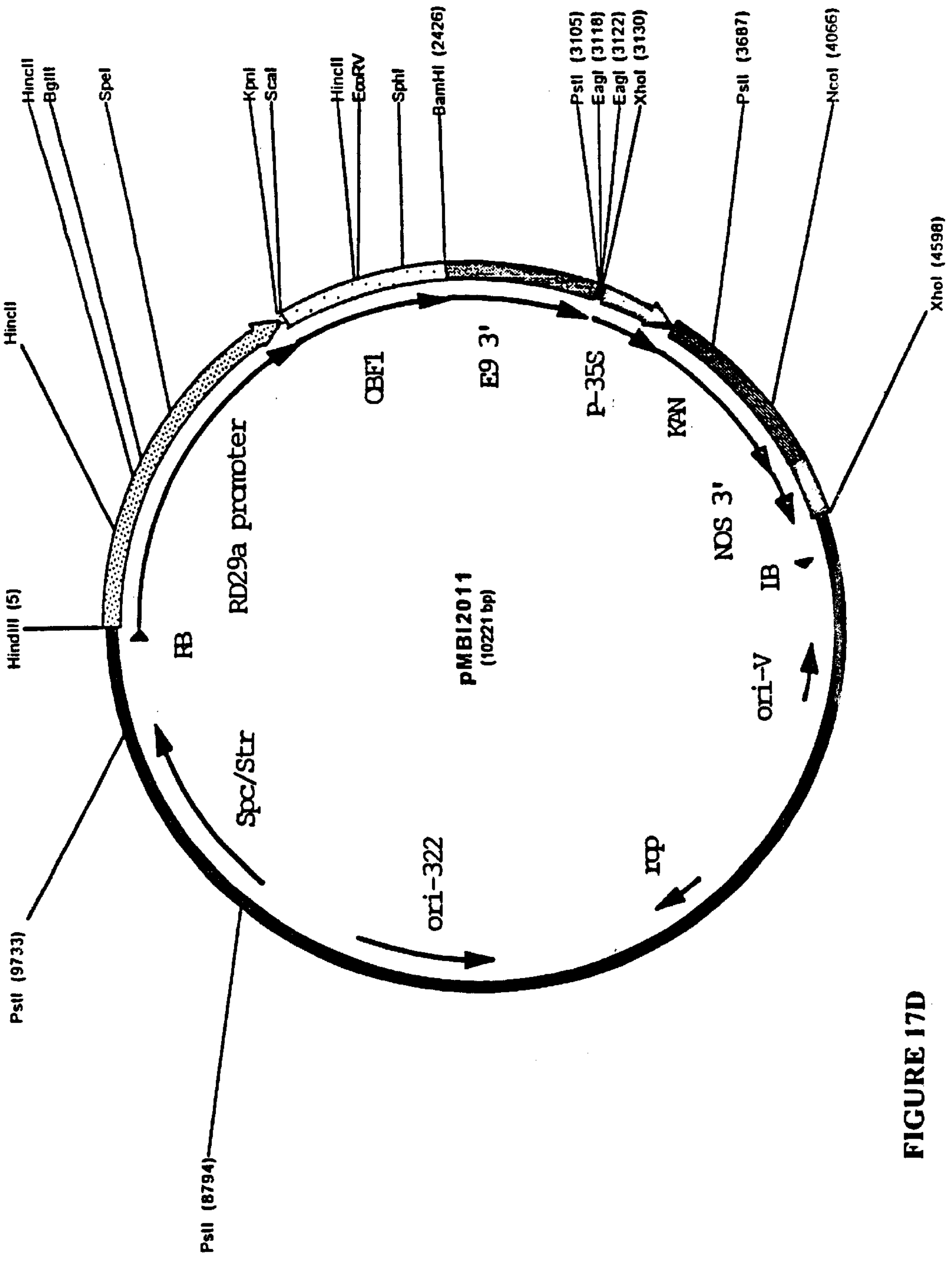
Figure 17E:
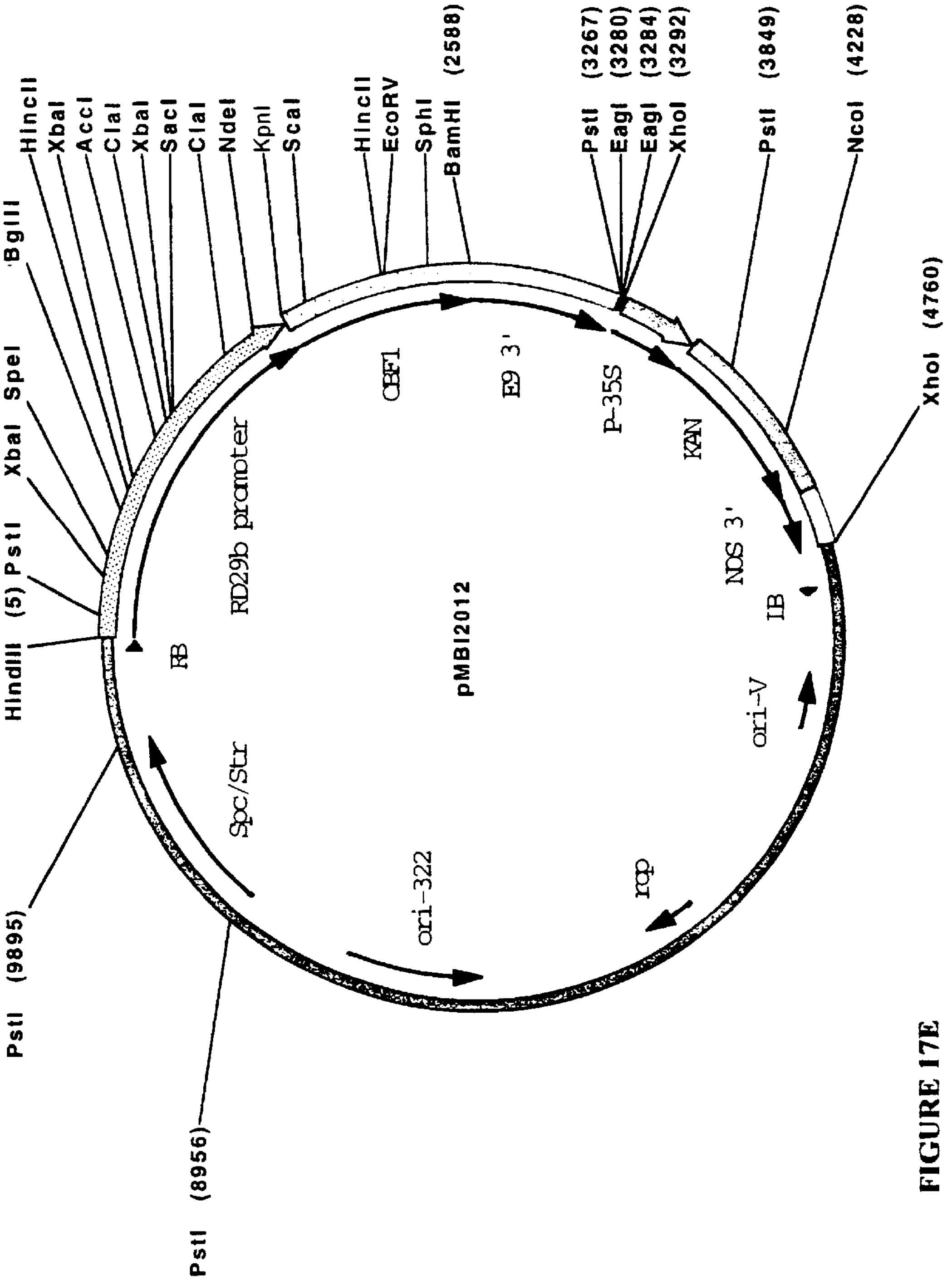
Figure 17F:
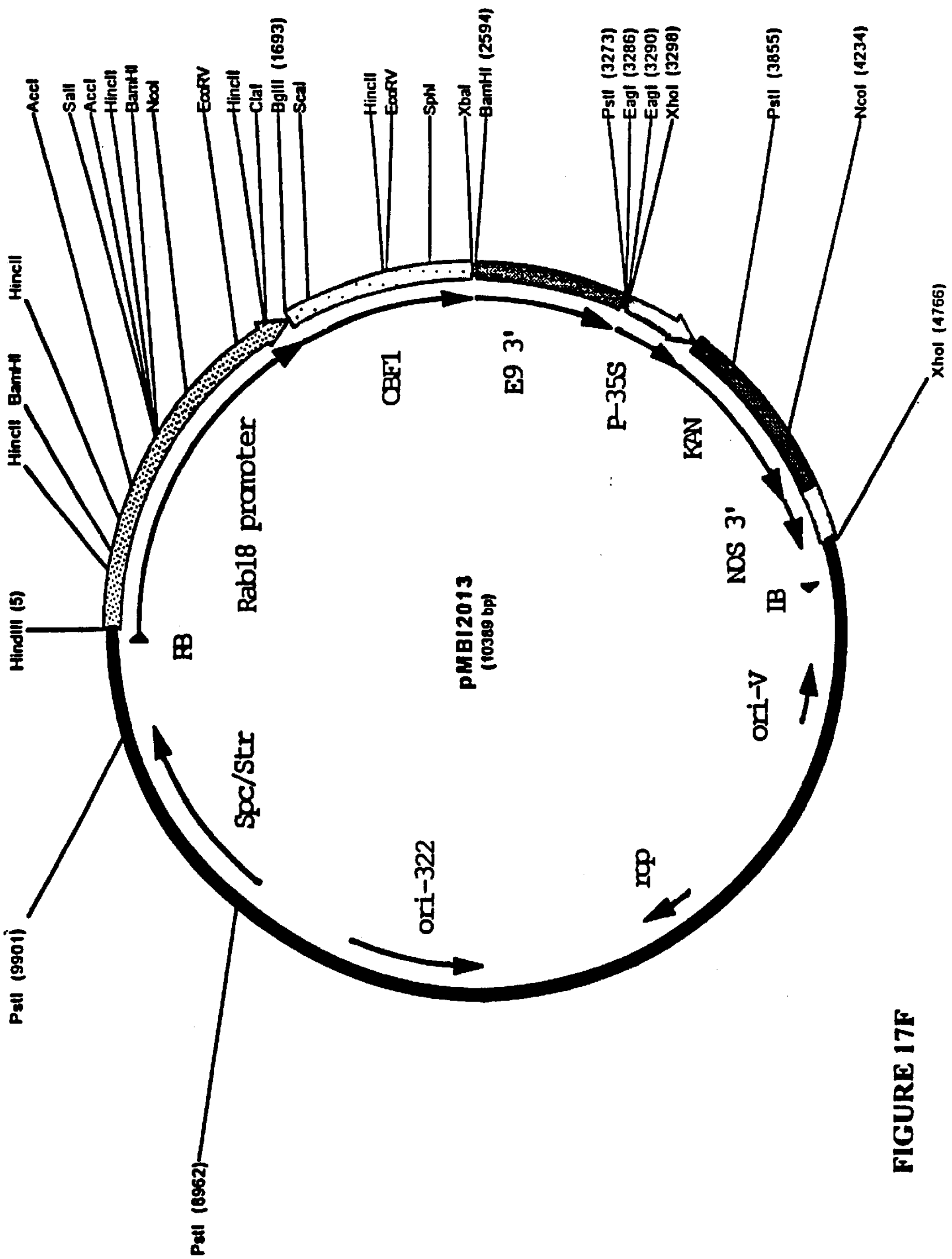
Figure 17G:
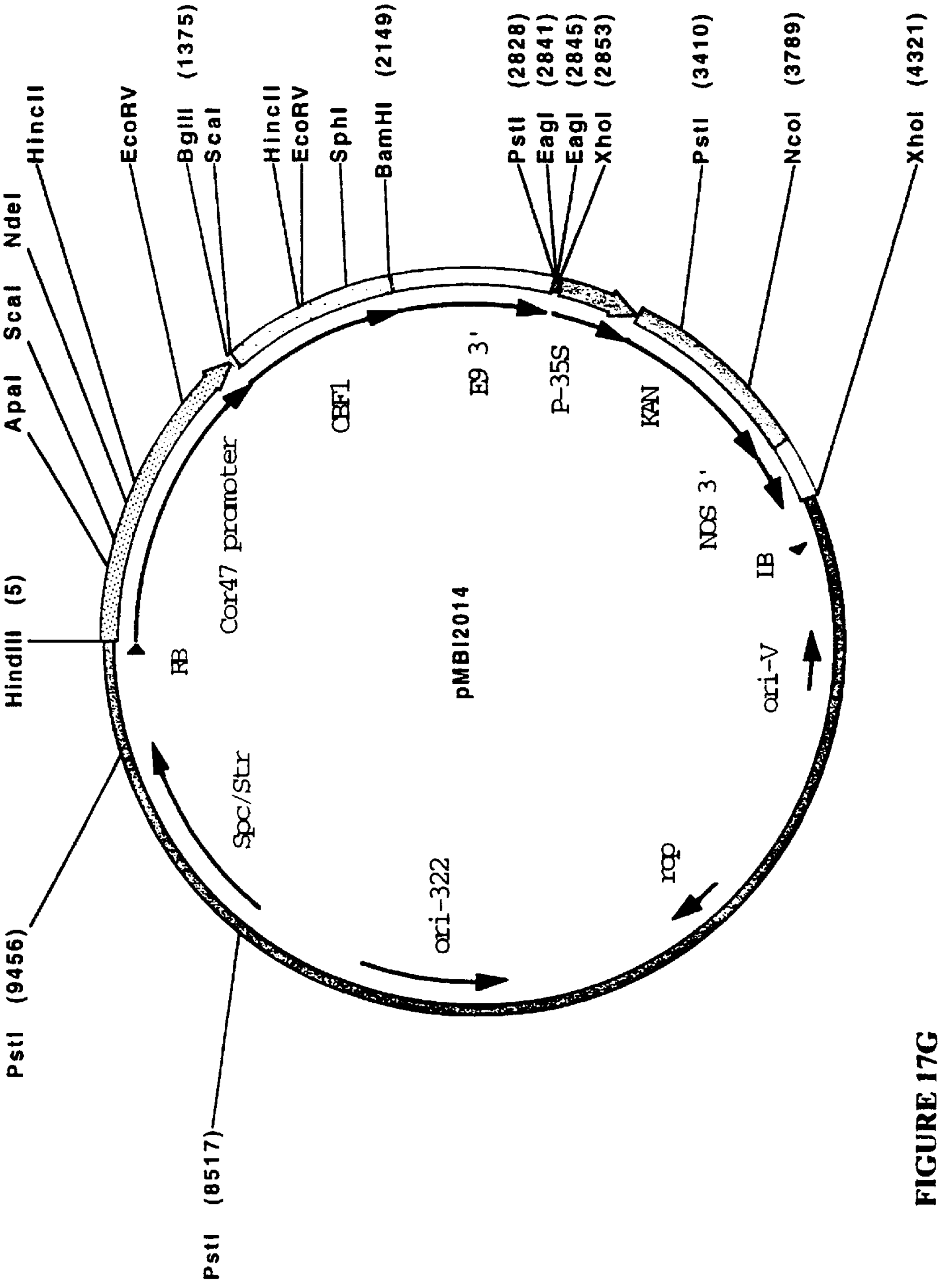

| Construct name | Promoter name | Figure name |
|---|---|---|
| PMBI2008 | Dreb2a | FIG. 17A |
| PMBI2009 | P5CS | FIG. 17B |
| PMBI2010 | Rd22 | FIG. 17C |
| PMBI2011 | Rd29a | FIG. 17D |
| PMBI2012 | Rd29b | FIG. 17E |
| PMBI2013 | Rab18 | FIG. 17F |
| PMBI2014 | Cor47 | FIG. 17G |

(3) Cloning of the cbf1 Gene Into the Plasmids Containing Seed-specific Promoters Several different CBF coding regions with different translational efficiencies in *arabidopsis thaliana* are cloned into expression vectors pMEN1001, pMEN1002, and pMEN1003 to produce different levels of CBF protein in transgenic plants. The 5' and 3' PCR primers used to isolate cbf1 gene from *arabidopsis thaliana* genomic DNA are listed below.

5'-Primer cbf5pri.atg.seq for isolating cbf1. 1 gene [SEQ. ID. No. 96] 5'-ggaagatctatGAAACAGAGTACTCTG-ATCAATGAACTC-3'

5'-Primer cbf5pri.wt.seq for isolating cbf1.2 gene [SEQ. ID. No. 97] 5'-ggaagatctGAAACAGAGTACTCTGA-TCAATGAACTC-3'

5'-Primer cbf5pri.inframeatg.seq for isolating cbf1.3 gene [SEQ. ID. No. 98] 5'-ggaagatctatGMCAGAGTACTCT-GATCAATGAACTC-3'

5-Primer cbf5pri.dbatg.seq for isolating cbf1. 4 gene [SEQ. ID. No. 99] 5'-ggaagatctatGAACAGAGTACTC-TGATgCMTGAACTC-3'

3'-Primer cbf1.long3pri.seq for isolating cbf1. 1–4 genes [SEQ. ID. No. 100] 5'-ggaggatcCTCGTTTCTACAAC-AATAAAATAAAATAAAATGAAGGAACC-3'

The cbf1 gene is cloned into pMEN050 at restriction sites HindIII and BamH1 by using a similar strategy as described in subsection (2) of this section for cloning of the cbf1 gene into the plasmids containing the inducible promoters. The resulting constructs containing cbf1. 1–4 genes are pMEN1001. 1–4 plasmids, pMEN1002. 1–4 plasmids and pMEN1003. 1–4 plasmids, respectively. The presence of the cbf1 gene inserts is verified by restriction mapping with HindIII and BamHI restriction enzymes to cut out the cloned insert. The plasmid DNA is also subject to double-strand DNA sequencing analysis using a vector primer (E9.1 primer 5'-CAAACTCAGTAGGATTCTGGTGTGT-3' [SEQ. ID. No. 33].

D. Transformation of Agrobacterium with Plasmids Containing CBF1 Gene and Inducible or Tissue-Specific Promoters After the plasmid vectors containing cbf1 gene and inducible promoters are constructed, these vectors are used to transform *Agrobacterium tumefaciens* cells expressing the gene products. The stock of *Agrobacterium tumefaciens* cells for transformation are made as described by Nagel et al. FEMS Microbiol Letts 67: 325–328 (1990). Agrobacterium strain ABI is grown in 250 ml LB medium (Sigma) overnight at 28° C. with shaking until an absorbance ($A_{600}$) of 0.5–1.0 is reached. Cells are harvested by centrifugation at 4,000×g for 15 min at 4° C. Cells are then resuspended in 250 μl chilled buffer (1 mM HEPES, pH adjusted to 7.0 with KOH). Cells are centrifuged again as described above and resuspended in 125 μl chilled buffer. Cells are then centrifuged and resuspended two more times in the same HEPES buffer as described above at a volume of 100 μl and 750 μl, respectively. Resuspended cells are then distributed into 40 μl aliquots, quickly frozen in liquid nitrogen, and stored at −80° C.

Agrobacterium cells are transformed with plasmids formed as described above in Section 4B(2) following the protocol described by Nagel et al. FEMS Microbiol Letts 67: 325–328 (1990). For each DNA construct to be transformed, 50–100 ng DNA (generally resuspended in 10 mM Tris-HCl, 1 mM EDTA, pH 8.0) is mixed with 40 $\mu$l of Agrobacterium cells. The DNA/cell mixture is then transferred to a chilled cuvette with a 2 mm electrode gap and subject to a 2.5 kV charge dissipated at 25 $\mu$F and 200 $\mu$F using a Gene Pulser II apparatus (Bio-Rad). After electroporation, cells are immediately resuspended in 1.0 ml LB and allowed to recover without antibiotic selection for 2–4 hours at 28° C. in a shaking incubator. After recovery, cells are plated onto selective medium of LB broth containing 100 $\mu$g/ml spectinomycin (Sigma) and incubated for 24–48 h at 28° C. Single colonies are then picked and inoculated in fresh medium. The presence of the plasmid construct are verified by PCR amplification and sequence analysis.

E. Transformation of Arabidopsis Plants with *Agrobacterium tumefaciens* Carrying Expression Vector for CBF1 Protein After transformation of *Agrobacterium tumefaciens* with plasmid vectors containing cbf1 gene and inducible promoters, single Agrobacterium colonies containing each of pMBI2008-pMBI2014 are identified, propagated, and used to transform Arabidopsis Plants. Briefly, 500 ml cultures of LB medium containing 100 ug/ml spectinomycin are inoculated with the colonies and grown at 28 C. with shaking for 2 days until an absorbance ($A_{600}$) of >2.0 is reached. Cells are then harvested by centrifugation at 4,000×g for 10 min, and resuspended in infiltration medium (1/2×Murashige and Skoog salts (Sigma), 1×Gamborg's B-5 vitamins (Sigma), 5.0% (w/v) sucrose (Sigma), 0.044 $\mu$M benzylamino purine (Sigma), 200 $\mu$l/L Silwet L-77 (Lehle Seeds) until an absorbance ($A_{600}$) of 0.8 is reached.

Prior to transformation, *Arabidopsis thaliana* seeds (ecotype Columbia) are sown at a density of ~10 plants per 4" pot onto Pro-Mix BX potting medium (Hummert International) covered with fiberglass mesh (18 mm×16 mm). Plants are grown under continuous illumination (50–75 $\mu E/m^2/sec$) at 22–23 C. with 65–70% relative humidity. After about 4 weeks, primary inflorescence stems (bolts) are cut off to encourage growth of multiple secondary bolts. After flowering of the mature secondary bolts, plants are prepared for transformation by removal of all siliques and opened flowers.

The pots are then immersed upside down in the mixture of Agrobacterium/infiltration medium as described above for 30 sec, and placed on their sides to allow draining into a 1'×2' flat surface covered with plastic wrap. After 24 h, the plastic wrap is removed and pots are turned upright. The immersion procedure is repeated one week later, for a total of two immersions per pot. Seeds are then collected from each transformation pot and analyzed following the protocol described below.

F. Identification of Arabidopsis Primary Transformants

Seeds collected from the transformation pots are sterilized essentially as follows. Seeds are dispersed into in a solution containing 0.1% (v/v) Triton X-100 (Sigma) and sterile $H_2O$ and washed by shaking the suspension for 20 min. The wash solution is then drained and replaced with fresh wash solution to wash the seeds for 20 min with shaking. After removal of the second wash solution, a solution containing 0.1% (v/v) Triton X-100 and 70% EtOH (Equistar) is added to the seeds and the suspension is shaken for 5 min. After removal of the ethanol/detergent solution, a solution containing 0.1% (v/v) Triton X-100 and 30% (v/v) bleach (Chlorox) is added to the seeds, and the suspension is shaken for 10 min. After removal of the bleach/detergent solution, seeds are then washed five times in sterile distilled $H_2O$. The seeds are stored in the last wash water at 4° C. for 2 days in the dark before being plated onto antibiotic selection medium (1×Murashige and Skoog salts (pH adjusted to 5.7 with 1M KOH), 1×Gamborg's B-5 vitamins, 0.9% phytagar (Life Technologies), and 50 $\mu$g/L kanamycin). Seeds are germinated under continuous illumination (50–75 $\mu E/m^2/sec$) at 22–23° C. After 7–10 days of growth under these conditions, kanamycin resistant primary transformants ($T_1$ generation) are visible and are obtained for each of constructs pMBI2008-pMBI2014. These seedlings are transferred first to fresh selection plates where the seedlings continued to grow for 3–5 more days, and then to soil (Pro-Mix BX potting medium). Progeny seeds ($T_2$) are collected; kanamycin resistant seedlings selected and analyzed as described above.

G. Transformation of Cereal Plants with Plasmid Vectors Containing cbf1 Gene and Inducible Promoters Cereal plants, such as corn, wheat, rice, sorghum and barley, can also be transformed with the plasmid vectors containing the cbf genes and inducible promoters to increase their tolerance to environmental stresses. In these cases, the cloning vector, pMEN020, is modified to replace the NptII coding region with the BAR gene of *Streptomyces hygroscopicus* that confers resistance to phosphinothricin. The KpnI and BglII sites of the Bar gene are removed by site-directed mutagenesis with silent codon changes. After cloning of the inducible promoters into the modified plasmid by the same procedures described above, the at-cbf coding region of cbf1gene is inserted into the plasmid following the same procedures as described above. The resulted plasmids are listed in Table 7.

TABLE 7

| Promoter name | Construct name |
|---|---|
| Dreb2a | PMBI2015 |
| P5CS | PMBI2016 |
| Rd22 | PMBI2017 |
| Rd29a | PMBI2018 |
| Rd29b | PMBI2019 |
| Rab18 | PMBI2020 |
| Cor47 | PMBI2021 |

It is now routine to produce transgenic plants of most cereal crops (Vasil, I., Plant Molec. Biol. 25: 925–937 (1994)) such as corn, wheat, rice, sorghum (Cassas, A. et al., Proc. Natl. Acad Sci USA 90: 11212–11216 (1993) and barley (Wan, Y. and Lemeaux, P. Plant Physiol. 104:37–48 (1994) Other direct DNA transfer methods such as the microprojectile gun or *Agrobacterium tumefaciens*-mediated transformation can be used for corn (Fromm. et al. Bio/Technology 8: 833–839 (1990); Gordon-Kamm et al. Plant Cell 2: 603–618 (1990); Ishida, Y., Nature Biotechnology 14:745–750 (1990)), wheat (Vasil, et al. Bio/Technology 10:667–674 (1992); Vasil et al., Bio/Technology 11:1553–1558 (1993); Weeks et al., Plant Physiol. 102:1077–1084 (1993)), rice (Christou Bio/Technology 9:957–962 (1991); Hiei et al. Plant J. 6:271–282 (1994); Aldemita and Hodges, Planta 199:612–617; Hiei et al., Plant Mol Biol. 35:205–18 (1997)). For most cereal plants, embryogenic cells derived from immature scutellum tissues are the preferred cellular targets for transformation (Hiei et al., Plant Mol Biol. 35:205–18 (1997); Vasil, Plant Molec. Biol. 25: 925–937 (1994)).

Plasmids according to the present invention may be transformed into corn embryogenic cells derived from immature scutellar tissue by using microprojectile bombardment, with the A188XB73 genotype as the preferred genotype (Fromm, et al., Bio/Technology 8: 833–839 (1990); Gordon-Kamm et al., Plant Cell 2: 603–618 (1990)). After microprojectile bombardment the tissues are selected on phosphinothricin to identify the transgenic embryogenic cells (Gordon-Kamm et al., Plant Cell 2: 603–618 (1990)). Transgenic plants are regenerated by standard corn regeneration techniques (Fromm, et al., Bio/Technology 8: 833–839 (1990); Gordon-Kamm et al., Plant Cell 2: 603–618 (1990)).

The plasmids prepared as described above can also be used to produce transgenic wheat and rice plants (Christou, Bio/Technology 9:957–962 (1991); Hiei et al., Plant J. 6:271–282 (1994); Aldemita and Hodges, Planta 199:612–617 (1996); Hiei et al., Plant Mol Biol. 35:205–18 (1997)) by following standard transformation protocols known to those skilled in the art for rice and wheat (Vasil, et al. Bio/Technology 10:667–674 (1992); Vasil et al., Bio/Technology 11:1553–1558 (1993); Weeks et al., Plant Physiol. 102:1077–1084 (1993)), where the BAR gene is used as the selectable marker.

H. Transformation of Plants with Plasmid Vectors Containing cbf1 Gene and Seed-Specific Promoters The binary constructs containing seed-specific napin promoters (pMEN1001.1–4; pMEN1002.1–4; and pMEN1003.1–4) are used to transform canola and rapeseed plants as described (Moloney et al. U.S. Pat. No. 5,750,871), except that the Bar gene selectable marker is used. These constructs are also used to transform regenerable barley cells by microprojectile bombardment (Wan and Lemaux, Plant Physiol. 104: 37–48 (1994)). After bombardment the tissues are selected on phosphinothricin to identify the transgenic embryogenic cells. Transgenic cells are regenerated by standard barley regeneration techniques (Wan and Lemaux Plant Physiol. 104: 37–48 (1994)).

5. Identification of CBF1 Homologs CBF2 and CBF3 Using CBF1

This example describes two homologs of CBF1 from *Arabidopsis thaliana* and named them CBF2 and CBF3.

CBF2 and CBF3 have been cloned and sequenced as described below. The sequences of the DNA and encoded proteins are set forth in SEQ ID NOS: 12, 13, 14 and 15. FIG. 12 shows the DNA sequence for CBF2 encoding CBF2. FIG. 13 shows the DNA sequence for CBF3 encoding CBF3.

A lambda cDNA library prepared from RNA isolated from *Arabidopsis thaliana* ecotype Columbia (Lin and Thomashow, Plant Physiol. 99: 519–525 (1992)) was screened for recombinant clones that carried inserts related to the CBF1 gene (Stockinger, E. J., et al., Proc Natl Acad Sci USA 94:1035–1040 (1997)). CBF1 was $^{32}$P-radiolabeled by random priming (Sambrook et al., Molecular Cloning. A Laboratory Manual, Ed. 2, Cold Spring Harbor Laboratory Press, New York (1989)) and used to screen the library by the plaque-lift technique using standard stringent hybridization and wash conditions (Hajela, R. K., et al., Plant Physiol 93:1246–1252 (1990); Sambrook et al., Molecular Cloning. A Laboratory Manual, Ed 2. Cold Spring Harbor laboratory Press, New York (1989) 6×SSPE buffer, 60° C. for hybridization and 0.1×SSPE buffer and 60° C. for washes). Twelve positively hybridizing clones were obtained and the DNA sequences of the cDNA inserts were determined at the MSU-DOE Plant Research Laboratory sequencing facility. The results indicated that the clones fell into three classes. One class carried inserts corresponding to CBF1. The two other classes carried sequences corresponding to two different homologs of CBF1, designated CBF2 and CBF3. The nucleic acid sequences and predicted protein coding sequences for CBF1, CBF2 and CBF3 appear at FIG. 14.

A comparison of the nucleic acid sequences of CBF1, CBF2 and CBF3 indicate that they are 83 to 85% identical as shown in Table 8. FIG. 14 shows the amino acid alignment of proteins CBF1, CBF2 and CBF3.

TABLE 8

| | Percent identity[a] | |
|---|---|---|
| | DNA[b] | Polypeptide |
| cbf1/cbf2 | 85 | 86 |
| cbf1/cbf3 | 83 | 84 |
| cbf2/cbf3 | 84 | 85 |

[a]Percent identity was determined using the Clustal algorithm from the Megalign program (DNASTAR, Inc.).
[b]Comparisons of the nucleic acid sequences of the open reading frames are shown.

Similarly, the amino acid sequences of the three CBF polypeptides range from 84 to 86% identity. An alignment of the three amino acidic sequences reveals that most of the differences in amino acid sequence occur in the acidic C-terminal half of the polypeptide. This region of CBF1 serves as an activation domain in both yeast and Arabidopsis (not shown).

Residues 47 to 106 of CBF1 correspond to the AP2 domain of the protein, a DNA binding motif that to date, has only been found in plant proteins. A comparison of the AP2 domains of CBF1, CBF2 and CBF3 indicates that there are a few differences in amino acid sequence. These differences in amino acid sequence might have an effect on DNA binding specificity.

6. Activation of Transcription In Yeast Containing C-repeat/DRE Using CBF1, CBF2 and CBF3

This example shows that CBF1, CBF2 and CBF3 activate transcription in yeast containing CRT/DREs upstream of a reporter gene. The CBFs were expressed in yeast under control of the ADC1 promoter on a 2$\mu$ plasmid (pDB20.1; Berger, S. L., et al., Cell 70:251–265 (1992)). Constructs expressing the different CBFs were transformed into yeast reporter strains which had the indicated CRT/DRE upstream of the lacZ reporter gene. Copy number of the CRT/DREs and its orientation relative to the direction of transcription from each promoter is indicated by the direction of the arrow.

Figure 15:
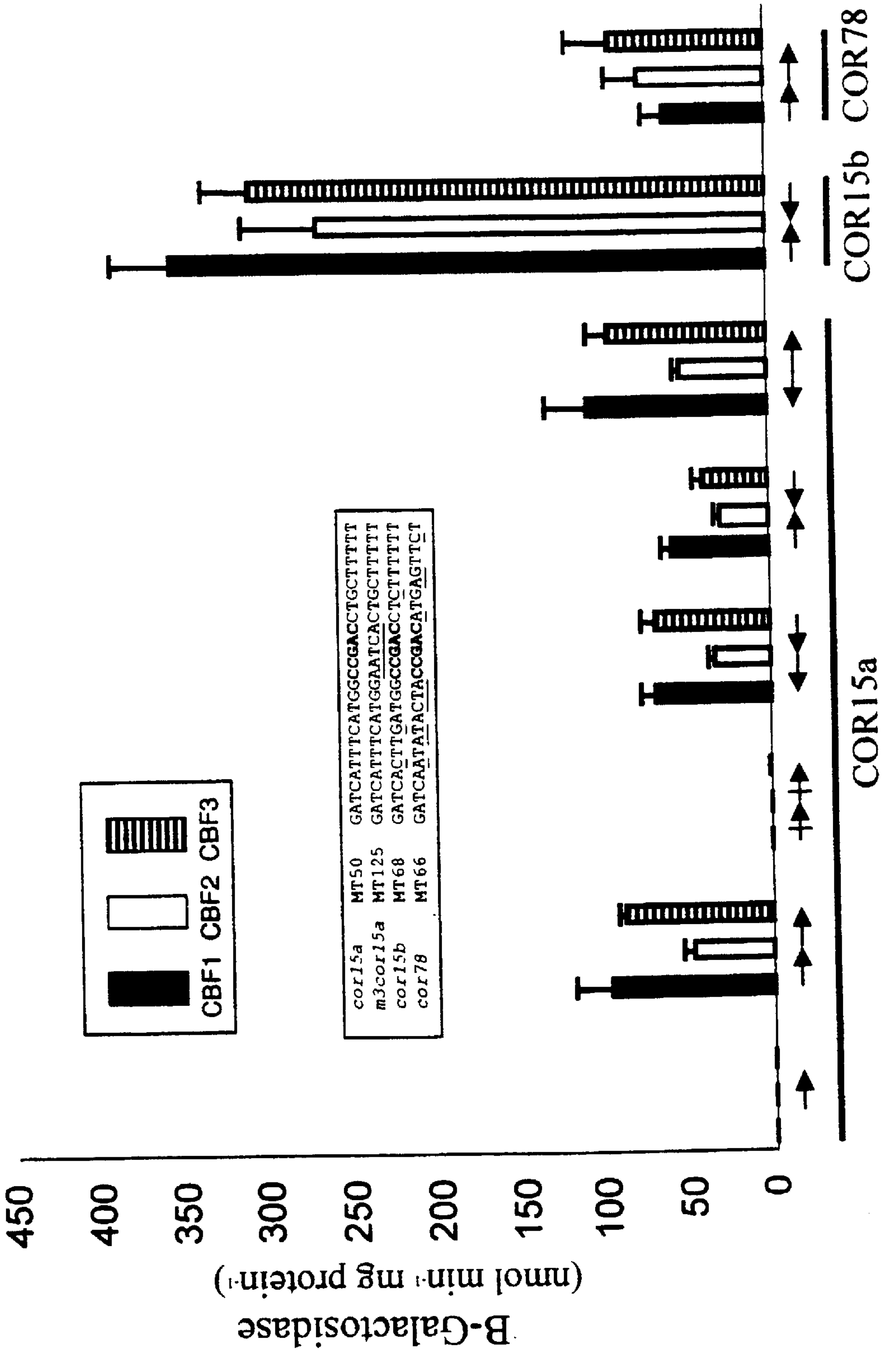
FIG. 15 is a graph showing transcription regulation of COR genes by CBF1, CBF2 and CBF3 genes in yeast.

FIG. 15 is a graph showing transcription regulation of CRT/DRE containing reporter genes by CBF1, CBF2 and CBF3 genes in yeast. In FIG. 15, the vertical lines across the arrows of the COR15a construct represent the m3cor15a mutant CRT/DRE construct. Each CRT/DRE-lacZ construct was integrated into the URA3 locus of yeast. Error bars represent the standard deviation derived from three replicate transformation events with the same CBF activator construct into the respective reporter strain. Quantitative B-gal assays were performed as described by Rose and Botstein (Rose, M., et al., Methods Enzymol. 101:167–180 (1983)).

7. Homologous CBF Encoding Genes in Other Plants

This example shows that homologous sequences to CBF1 are present in other plants. The presence of these homologous sequences suggest that the same or similar cold regulated environmental stress response regulatory elements such as the C-repeat/DRE of Arabidopsis (CCGAC) exist in other plants. This example serves to indicate that genes with significant homology to CBF1, CBF2 and CBF3 exist in a wide range of plant species.

Total plant DNAs from *Arabadopsis thaliana, Nicotiana tabacum, Lycopersicon pimpinellifolium, Prunis avium,*

*Prunus cerasus, Cucumis sativus,* and *Oryza sativa* were isolated according to Stockinger al (Stockinger, E. J., et al., J. Heredity, 87:214–218 (1996)). Approximately 2 to 10 μg of each DNA sample was restriction digested, transferred to nylon membrane (Micron Separations, Westboro, Mass.) and hybridized according to Walling et al. (Walling, L. L., et al., Nucleic Acids Res. 16:10477–10492 (1988)). Hybridization conditions were: 42° C. in 50% formamide, 5×SSC, 20 mM phosphate buffer 1×Denhardt's, 10% dextran sulfate, and 100 μg/ml herring sperm DNA. Four low stringency washes at RT in 2×SSC, 0.05% Na sarcosyl and 0.02% $Na_4$ pyrophosphate were performed prior to high stringency washes at 55° C. in 0.2×SSC, 0.05% Na sarcosyl and 0.01% $Na_4$ pyrophosphate. High stringency washes were performed until no counts were detected in the washout. The BclI-BglII fragment of CBF1 (Stockinger et al., Proc Natl Acad Sci USA 94:1035–1040 (1997)) was gel isolated (Sambrook et al., Molecular Cloning. A Laboratory Manual, Ed 2. Cold Spring Harbor Laboratory Press, New York (1989)) and direct prime labelled (Feinberg and Vogelstein, Anal. Biochem 132: 6–13 (1982)) using the primer MT117 (TTGGCGGCTACGAATCCC; SEQ ID NO:16). Specific activity of the radiolabelled fragment was approximately $4\times\mathbf{10}^8$ cpm/μg. Autoradiography was performed using HYPERFILM-MP (Amersham) at −80° C. with one intensifying screen for 15 hours.

Autoradiography of the gel showed that DNA sequences from *Arabadopsis thaliana, Nicotiana tabacum, Lycopersicon pimpinellifolium, Prunis avium, Prunus cerasus, Cucumis sativus,* and *Oryza sativa* hybridized to the labeled BclI, BglIi fragment of CBF1. These results suggest that homologous CBF encoding genes are present in a variety of other plants.

8. Identification of Homologous Sequence to CBF1 in Canola

This example describes the identification of homologous sequences to CBF1 in canola using PCR. Degenerate primers were designed for regions of AP2 binding domain and outside of the AP2 (carboxyl terminal domain). More specifically, the following degenerate PCR primers were used:

Mol 368 (reverse) 5'-CAY CCN ATH TAY MGN GGN GT-3' (SEQ ID NO: 101)

Mol 378 (forward) 5'-GGN ARN ARC ATN CCY TCN GCC-3' (SEQ ID NO: 102)

(Y: C/T, N: A/C/G/T, H: A/C/T, M: A/C, R: A/G)

Primer Mol 368 is in the AP2 binding domain of CBF1 (amino acid seq: H P I Y R G V) while primer Mol 378 is outside the AP2 domain (carboxyl terminal domain)(amino acid seq: M A E G M L L P).

The genomic DNA isolated from Brassica Napus was PCR amplified by using these primers following these conditions: an initial denaturation step of 2 min at 93° C.; 35 cycles of 93° C. for 1 min, 55° C. for 1 min, and 72° C. for 1 min; and a final incubation of 7 min at 72° C. at the end of cycling.

The PCR products were separated by electrophoresis on a 1.2% agarose gel and, transferred to nylon membrane and hybridized with the AT CBF1 probe prepared from Arabidopsis genomic DNA by PCR amplification. The hybridized products were visualized by colormetric detection system (Boehringer Mannheim) and the corresponding bands from a similar agarose gel were isolated (By Qiagen Extraction Kit). The DNA fragments were ligated into the TA clone vector from TOPO TA Cloning Kit (Invitrogen) and transformed into *E. coli* strain TOP10 (Invitrogen).

Seven colonies were picked and the inserts were sequenced on an ABI 377 machine from both strands of sense and antisense after plasmid DNA isolation. The DNA sequence was edited by sequencer and aligned with the AtCBF1 by GCG software and NCBI blast searching.

FIG. 16 shows an amino acid sequence of a homolog [CAN1; SEQ. ID. No. 17] identified by this process and its alignment to the amino acid sequence of CBF1. The nucleic acid sequence for CAN1 is listed herein as SEQ. ID. No. 18.

As illustrated in FIG. 16, the DNA sequence alignment in four regions of BN-CBF1 shows 82% identity in the AP2 binding domain region and range from 75% to 83% with some alignment gaps due to regions of lesser homology or introns in the genomic sequence. The aligned amino acid sequences show that the BNCBF1 gene has 88% identity in the AP2 domain region and 85% identity outside the AP2 domain when aligned for two insertion sequences that are outside the AP2 domain. The extra amino acids in the 2 insertion regions are either due to the presence of introns in this region of the BNCBF1 gene, as it was derived from genomic DNA, or could be due to extra amino acids in these regions of the BNCBF1 gene. Isolation and sequencing of a cDNA of the BNCBF1 gene using the genomic DNA as a probe will resolve this.

9. Identification of Homologous Sequence to CBF1 in Canola and Other Species

A PCR strategy similar to that described in Example 8 was used to isolate additional CBF homologues from *Brassica juncea, Brassica napus, Brassica oleracea, Brassica rapa, Glycine max, Raphanus sativus* and *Zea Maize.* The nucleotide (e.g. bjCBF1) and peptide sequences (e.g. BJCBF1-PEP) of these isolated CBF homologues are shown in FIGS. 18A and 18B, respectively. Table 9 lists the sequence names and sequence ID Nos. of these isolated CBF homologues. The PCR primers are internal to the gene so partial gene sequences are initially obtained. The full length sequences of some of these genes were further isolated by inverse PCR or ligated linker PCR. One skilled in the art can use the conserved regions in these genes to design PCR primers to isolate additional CBF genes.

TABLE 9

| DNA Seq. Name | Seq. ID No. | Peptide Seq. Name | Seq. ID No. |
|---|---|---|---|
| bjCBF1 | 38 | BJCBF1-PEP | 39 |
| bjCBF2 | 40 | BJCBF2-PEP | 41 |
| bjCBF3 | 42 | BJCBF3-PEP | 43 |
| bjCBF4 | 44 | BJCBF4-PEP | 45 |
| bnCBF1 | 46 | BNCBF1-PEP | 47 |
| bnCBF2 | 48 | BNCBF2-PEP | 49 |
| bnCBF3 | 50 | BNCBF3-PEP | 51 |
| bnCBF4 | 52 | BNCBF4-PEP | 53 |
| bnCBF5 | 54 | BNCBF5-PEP | 55 |
| bnCBF6 | 56 | BNCBF6-PEP | 57 |
| bnCBF7 | 58 | BNCBF7-PEP | 59 |
| bnCBF8 | 60 | BNCBF8-PEP | 61 |
| bnCBF9 | 62 | BNCBF9-PEP | 63 |
| boCBF1 | 64 | BOCBF1-PEP | 65 |
| boCBF2 | 66 | BOCBF2-PEP | 67 |
| boCBF3 | 68 | BOCBF3-PEP | 69 |
| boCBF4 | 70 | BOCBF4-PEP | 71 |
| boCBF5 | 72 | BOCBF5-PEP | 73 |
| brCBF1 | 74 | BRCBF1-PEP | 75 |
| brCBF2 | 76 | BRCBF2-PEP | 77 |
| brCBF3 | 78 | BRCBF3-PEP | 79 |
| brCBF4 | 80 | BRCBF4-PEP | 81 |
| brCBF5 | 82 | BRCBF5-PEP | 83 |
| brCBF6 | 84 | BRCBF6-PEP | 85 |
| brCBF7 | 86 | BRCBF7-PEP | 87 |
| gmCBF1 | 88 | GMCBF1-PEP | 89 |
| rsCBF1 | 90 | RSCBF1-PEP | 91 |

TABLE 9-continued

| DNA Seq. Name | Seq. ID No. | Peptide Seq. Name | Seq. ID No. |
|---|---|---|---|
| rsCBF2 | 92 | RSCBF2-PEP | 93 |
| zmCBF1 | 94 | ZMCBF1-PEP | 95 |

FIG. 19A shows an amino acid alignment of the AP2 domains of the CBF proteins listed in Table 9 with their consensus sequences highlighted. FIG. 19A also provides a comparison of the consensus sequence with that of the tobacco DNA binding protein EREBP2 (Okme-Takagi, M., et al., The Plant Cell 7:173–182 (1995). The sequences of these CBF proteins are BRCBF3-PEP [SEQ. ID. No. 79], BRCBF6-PEP [SEQ. ID. No.85], BNCBF5-PEP [SEQ. ID. No. 55], ATCBF2-PEP [SEQ. ID. No. 13], ATCBF3-PEP [SEQ. ID. No. 15], ATCBF1-PEP [SEQ. ID. No. 2], BNCBF2-PEP [SEQ. ID. No. 49], BNCBF6-PEP [SEQ. ID. No. 57], BOCBF3-PEP [SEQ. ID. No. 69], BNCBF3-PEP [SEQ. ID. No. 51], BNCBF8-PEP [SEQ. ID. No. 61], BNCBF9-PEP [SEQ. ID. No. 63], BRCBF2-PEP [SEQ. ID. No. 77], BOCBF5-PEP [SEQ. ID. No. 73], BOCBF2-PEP [SEQ. ID. No. 67], RSCBF2-PEP [SEQ. ID. No. 93], BNCBF4-PEP [SEQ. ID. No. 53], BNCBF7-PEP [SEQ. ID. No. 59], BOCBF4-PEP [SEQ. ID. No. 71], BRCBF7-PEP [SEQ. ID. No. 87], BRCBF4-PEP [SEQ. ID. No. 81], BRCBF5-PEP [SEQ. ID. No. 83], RSCBF1-PEP [SEQ. ID. No. 91], BJCBF2-PEP [SEQ. ID. No. 41], BJCBF3-PEP [SEQ. ID. No. 43], BNCBF1-PEP [SEQ. ID. No. 47], BOCBF1-PEP [SEQ. ID. No. 65], BRCBF1-PEP [SEQ. ID. No. 75], BJCBF4-PEP [SEQ. ID. No. 45], ZMCBF1-PEP [SEQ. ID. No. 95], and GMCBF1-PEP [SEQ. ID. No. 89].

As can be seen from the consensus sequence shown in FIG. 19A, a significant portion of the AP2 domain is conserved among the different CBF proteins. In view of this data, Applicants use the conserved sequence in the AP2 domain to define a class of AP2 domain proteins comprising this conserved sequence.

FIG. 19B shows an amino acid alignment of the AP2 domains shown in FIG. 19A and dreb2a and dreb2b and a consensus sequence between the proteins highlighted. As can be seen, a very high degree of homology exists between AP2 domains shown in FIG. 19A and dreb2a and dreb2b. Applicants employ the conserved sequence in the AP2 domain shown in FIG. 19B to define a broader class of AP2 domain proteins which are capable of binding to CCG regulatory region.

FIG. 19C shows an amino acid alignment of the AP2 domains shown in FIG. 19B and tiny and a consensus sequence between the proteins highlighted. As can be seen, a very high degree of homology exists between AP2 domains shown in FIG. 19A, dreb2a, dreb2b and tiny. Applicants employ the conserved sequence in the AP2 domain shown in FIG. 19C to define a yet broader class of AP2 domain proteins which are capable of binding to CCG regulatory region.

FIG. 19D shows a consensus sequence corresponding to the difference between the consensus sequence shown in FIGS. 19A and tiny. Applicants employ the highlighted portion of the conserved sequence shown in FIG. 19D to define a group of amino acid residues which may be critical to binding to a CCG regulatory region.

FIG. 19E shows a consensus sequence corresponding to the difference between the consensus sequence shown in FIG. 19B and tiny. Applicants employ the highlighted portion of the conserved sequence shown in FIG. 19E to define another group of amino acid residues which may be critical to binding to a CCG regulatory region.

FIG. 20 shows the amino acid alignment of the amino terminus of the CBF proteins with their consensus sequence highlighted. The sequences of these CBF proteins are: BRCBF3-PEP [SEQ. ID. No. 79], BRCBF6-PEP [SEQ. ID. No.85], BNCBF5-PEP [SEQ. ID. No. 55], ATCBF2-PEP [SEQ. ID. No. 13], ATCBF3-PEP [SEQ. ID. No. 15], ATCBF1-PEP [SEQ. ID. No. 2], BNCBF2-PEP [SEQ. ID. No. 49], BNCBF6-PEP [SEQ. ID. No. 57], BOCBF3-PEP [SEQ. ID. No. 69], BNCBF3-PEP [SEQ. ID. No. 51], BNCBF8-PEP [SEQ. ID. No. 61], BNCBF9-PEP [SEQ. ID. No. 63], BRCBF2-PEP [SEQ. ID. No. 77], BOCBF5-PEP [SEQ. ID. No. 73], BOCBF2-PEP [SEQ. ID. No. 67], RSCBF2-PEP [SEQ. ID. No. 93], BNCBF4-PEP [SEQ. ID. No. 53 ], BNCBF7-PEP [SEQ. ID. No. 59], BOCBF4-PEP [SEQ. ID. No. 71], BRCBF7-PEP [SEQ. ID. No. 87], BRCBF4-PEP [SEQ. ID. No. 81], BRCBF5-PEP [SEQ. ID. No. 83], and RSCBF1-PEP [SEQ. ID. No. 91].

As can be seen from the consensus sequence shown in FIG. 20, a significant portion of the amino terminus of CBF proteins is conserved among the different CBF proteins. In view of this data, Applicants employ the conserved sequence in the amino terminus domain to define a class of proteins comprising this conserved sequence.

FIG. 21A shows the amino acid alignment of the carboxy terminus of 24 CBF proteins with their consensus sequences highlighted. The sequences of these CBF proteins are: BRCBF6-PEP [SEQ. ID. No.85], BNCBF5-PEP [SEQ. ID. No. 55], ATCBF2-PEP [SEQ. ID. No. 13], ATCBF3-PEP [SEQ. ID. No. 15], ATCBF1-PEP [SEQ. ID. No. 2], BNCBF2-PEP [SEQ. ID. No. 49], BNCBF6-PEP [SEQ. ID. No. 57], BOCBF3-PEP [SEQ. ID. No. 69], BNCBF3-PEP [SEQ. ID. No. 51], BNCBF8-PEP [SEQ. ID. No. 61], BNCBF9-PEP [SEQ. ID. No. 63], BRCBF2-PEP [SEQ. ID. No. 77], BOCBF5-PEP [SEQ. ID. No. 73], RSCBF2-PEP [SEQ. ID. No. 93], BNCBF4-PEP [SEQ. ID. No. 53], BNCBF7-PEP [SEQ. ID. No. 59], BOCBF4-PEP [SEQ. ID. No. 71], BRCBF7-PEP [SEQ. ID. No. 87], BRCBF5-PEP [SEQ. ID. No. 83], RSCBF1-PEP [SEQ. ID. No. 91], BJCBF2-PEP [SEQ. ID. No. 41], BJCBF3-PEP [SEQ. ID. No. 43], BNCBF1-PEP [SEQ. ID. No. 47], and BOCBF1-PEP [SEQ. ID. No. 65].

As can be seen from the consensus sequence shown in FIG. 21A, a significant portion of the carboxy terminus of CBF proteins is conserved among the different CBF proteins. In view of this data, Applicants employ the conserved sequence in the carboxy terminus domain to define a class of proteins comprising this conserved sequence.

FIG. 21B shows the amino acid alignment of the carboxy terminus of 9 CBF proteins with their consensus sequences highlighted. The sequences of these CBF proteins are: BNCBF2-PEP [SEQ. ID. No. 49], BOCBF3-PEP [SEQ. ID. No. 69], BNCBF3-PEP [SEQ. ID. No. 51], BNCBF8-PEP [SEQ. ID. No. 61], BNCBF9-PEP [SEQ. ID. No. 63], BRCBF2-PEP [SEQ. ID. No. 77], BOCBF5-PEP [SEQ. ID. No. 73], BNCBF1-PEP [SEQ. ID. No. 47], and BNCBF6-PEP [SEQ. ID. No. 57].

As can be seen from the consensus sequence shown in FIG. 21B, a greater portion of the carboxy terminus is conserved when these 9 CBF proteins are used. In view of this data, Applicants employ the conserved sequence in the carboxy terminus domain to define another class of proteins comprising this conserved sequence.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

We claim:

1. A binding protein other than SEQ ID NO: 2 in isolated form comprising a consensus sequence sufficiently homologous to the consensus sequence shown in FIG. 19A that the binding protein is capable of binding to a CCG regulatory sequence and that the nucleotide sequence that encodes the binding protein can hybridize to SEQ ID NO:1 under the following conditions: 42° C. in 50% formamide, 5×SSC, 20 mM phosphate buffer 1×Denhardt's, 10% dextran sulfate, and 100 μg/ml herring sperm DNA with low stringency washes at RT in 2×SSC, 0.05% Na sarcosyl and 0.02% $Na_4$ pyrophosphate.

2. A binding protein other than SEQ ID NO:2 in isolated form comprising a consensus sequence sufficiently homologous the consensus sequence shown in FIG. 19B that the binding protein is capable of binding to a CCG regulatory sequence and that the nucleotide sequence that encodes the binding protein can hybridize to SEQ ID NO:1 under the following conditions: 42° C. in 50% formamide, 5×SSC, 20 mM phosphate buffer 1×Denhardt's, 10% dextran sulfate, and 100 $\mu$g/ml herring sperm DNA with low stringency washes at RT in 2×SSC, 0.05% Na sarcosyl and 0.02% $Na_4$ pyrophosphate.

3. A binding protein other than SEQ ID NO:2 in isolated form comprising a consensus sequence sufficiently homologous the consensus sequence shown in FIG. 19C that the binding protein is capable of binding to a CCG regulatory sequence and that the nucleotide sequence that encodes the binding protein can hybridize to SEQ ID NO:1 under the following conditions: 42° C. in 50% formamide, 5×SSC, 20 mM phosphate buffer 1×Denhardt's, 10% dextran sulfate, and 100 $\mu$g/ml herring sperm DNA with low stringency washes at RT in 2×SSC, 0.05% Na sarcosyl and 0.02% $Na_4$ pyrophosphate.

4. A binding protein other than SEQ ID NO: 2 in isolated form comprising a consensus sequence shown in FIG. 19A.

5. A binding protein other than SEQ ID NO: 2 in isolated form comprising a consensus sequence shown in FIG. 19B.

6. A binding protein other than SEQ ID NO: 2 in isolated form comprising a consensus sequence shown in FIG. 19C.

7. A binding protein other than SEQ ID NO:2 in isolated form comprising a sequence selected from the group consisting of an AP2 domain of SEQ ID NOS: 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95.

8. A non-naturally occurring binding protein comprising an amino acid sequence capable of binding to a CCG regulatory sequence and an amino acid sequence which forms a transcription activation region.

9. DNA in isolated form comprising a sequence encoding any one of the binding proteins of claims 1–8.

10. A nucleic acid construct capable of transforming a plant comprising a sequence encoding any one of the binding proteins of claims 1–8.

11. A nucleic acid construct according to claim 10, further comprising a promoter which regulates expression of the binding protein.

12. A nucleic acid construct according to claim 11, wherein the promoter is a tissue specific promoter.

13. A nucleic acid construct according to claim 11, wherein the promoter is a flower, fruit or seed specific promoter.

14. A binding protein according to any one of claims 1–8 wherein the binding protein is a recombinant binding protein expressed within a plant.

15. A binding protein other than SEQ ID NO: 2 comprising an AP2 domain having at least an 88% sequence identity to an AP2 domain selected from the group of sequences consisting of SEQ ID NO:2, SEQ ID NO: 13, SEQ ID NO:15, SEQ ID NO: 17, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, and SEQ ID NO: 95.

16. The binding protein of claim 15, wherein said binding protein comprises an amino acid sequence having at least a 85% sequence identity to a member of the group of sequences consisting of SEQ ID NO: 13, SEQ ID NO:15 and SEQ ID NO: 17.

17. The binding protein of claim 15, wherein said binding protein binds to a cold or dehydration transcription regulating region comprising the sequence CCG.

18. The binding protein of claim 7, further comprising a transcription activating domain.

19. The binding protein of claim 18, further comprising the transcription activating domain selected from the group consisting of VP16 and Gal4.

20. The binding protein of claim 7, comprising a sequence selected from the group consisting of SEQ ID NOS: 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95.

21. The non-naturally occuring binding protein of claim 8 comprising the transcription activating domain selected from the group consisting of VP16 and Gal4.

22. The non-naturally occurring binding protein of claim 8, comprising a sequence selected from the group consisting of an AP2 domain of SEQ ID NOS: 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95.

23. A method for altering the environmental stress of a plant comprising:

(a) increasing the expression levels of a binding protein other than SEQ ID NO: 2 comprising a sequence selected from the group consisting of an AP2 domain of SEQ ID NOS: 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95 within a plant; and (b) selecting a plant with an altered environmental stress response.

24. The method of claim 23, wherein said environmental stress is selected from the group consisting of cold, freezing, drought and salinity.

25. The method of claim 23, wherein said binding protein further comprises a transcription activating domain.

26. The method of claim 25, wherein said binding protein comprises the transcription activating domain selected from the group consisting of VP16 and Gal4.

27. The method of claim 23, wherein said binding protein comprises a sequence selected from the group consisting of SEQ ID NOS: 13, 15, 39, 41, 43, 45, 47, 49, 51, 53, 55, 57, 59, 61, 63, 65, 67, 69, 71, 73, 75, 77, 79, 81, 83, 85, 87, 89, 91, 93, and 95.

* * * * *

SEQUENCE LISTING

<160> NUMBER OF SEQ ID NOS: 259

<210> SEQ ID NO 1
<211> LENGTH: 905
<212> TYPE: DNA
<213> ORGANISM: Arabidopsis thaliana

<400> SEQUENCE: 1

```
aaaaagaatc tacctgaaaa gaaaaaaaag agagagagat ataaatagct taccaagaca     60

gatatactat cttttattaa tccaaaaaga ctgagaactc tagtaactac gtactactta    120

aaccttatcc agtttcttga aacagagtac tctgatcaat gaactcattt tcagcttttt    180

ctgaaatgtt tggctccgat tacgagcctc aaggcggaga ttattgtccg acgttggcca    240

cgagttgtcc gaagaaaccg gcgggccgta agaagtttcg tgagactcgt cacccaattt    300

acagaggagt tcgtcaaaga aactccggta agtgggtttc tgaagtgaga gagccaaaca    360

agaaaaccag gatttggctc gggactttcc aaaccgctga gatggcagct cgtgctcacg    420

acgtcgctgc attagccctc cgtggccgat cagcatgtct caacttcgct gactcggctt    480

ggcggctacg aatcccggag tcaacatgcg ccaaggatat ccaaaaagcg gctgctgaag    540

cggcgttggc ttttcaagat gagacgtgtg atacgacgac cacggatcat ggcctggaca    600

tggaggagac gatggtggaa gctatttata caccggaaca gagcgaaggt gcgttttata    660

tggatgagga gacaatgttt gggatgccga ctttgttgga taatatggct gaaggcatgc    720

ttttaccgcc gccgtctgtt caatggaatc ataattatga cggcgaagga gatggtgacg    780

tgtcgctttg gagttactaa tattcgatag tcgtttccat ttttgtacta tagtttgaaa    840

atattctagt tccttttta gaatggttcc ttcattttat tttattttat tgttgtagaa    900

acgag                                                                905
```

<210> SEQ ID NO 2
<211> LENGTH: 213
<212> TYPE: PRT
<213> ORGANISM: Arabidopsis thaliana

<400> SEQUENCE: 2

```
Met Asn Ser Phe Ser Ala Phe Ser Glu Met Phe Gly Ser Asp Tyr Glu
 1               5                  10                  15

Pro Gln Gly Gly Asp Tyr Cys Pro Thr Leu Ala Thr Ser Cys Pro Lys
            20                  25                  30

Lys Pro Ala Gly Arg Lys Lys Phe Arg Glu Thr Arg His Pro Ile Tyr
        35                  40                  45

Arg Gly Val Arg Gln Arg Asn Ser Gly Lys Trp Val Ser Glu Val Arg
    50                  55                  60

Glu Pro Asn Lys Lys Thr Arg Ile Trp Leu Gly Thr Phe Gln Thr Ala
65                  70                  75                  80

Glu Met Ala Ala Arg Ala His Asp Val Ala Ala Leu Ala Leu Arg Gly
                85                  90                  95

Arg Ser Ala Cys Leu Asn Phe Ala Asp Ser Ala Trp Arg Leu Arg Ile
            100                 105                 110

Pro Glu Ser Thr Cys Ala Lys Asp Ile Gln Lys Ala Ala Ala Glu Ala
        115                 120                 125

Ala Leu Ala Phe Gln Asp Glu Thr Cys Asp Thr Thr Thr Thr Asp His
    130                 135                 140
```

-continued

```
Gly Leu Asp Met Glu Glu Thr Met Val Glu Ala Ile Tyr Thr Pro Glu
145                 150                 155                 160

Gln Ser Glu Gly Ala Phe Tyr Met Asp Glu Glu Thr Met Phe Gly Met
                165                 170                 175

Pro Thr Leu Leu Asp Asn Met Ala Glu Gly Met Leu Leu Pro Pro Pro
            180                 185                 190

Ser Val Gln Trp Asn His Asn Tyr Asp Gly Glu Gly Asp Gly Asp Val
        195                 200                 205

Ser Leu Trp Ser Tyr
    210
```

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
gatcatttca tggccgacct gcttttt 27

<210> SEQ ID NO 4
<211> LENGTH: 28
<212> TYPE: DNA
<213> ORGANISM: Artificial Sequence
<220> FEATURE:
<223> OTHER INFORMATION: Synthetic Construct

<400> SEQUENCE: 4
cacaatttca agaattcact gctttttt 28

<210> SEQ ID NO 5
<211> LENGTH: 27
<212> TYPE: DNA
<213> ORGANISM: Artificial Sequence
<220> FEATURE:
<223> OTHER INFORMATION: Synthetic Construct

<400> SEQUENCE: 5
gatcatttca tggtatgtct gcttttt 27

<210> SEQ ID NO 6
<211> LENGTH: 27
<212> TYPE: DNA
<213> ORGANISM: Artificial Sequence
<220> FEATURE:
<223> OTHER INFORMATION: Synthetic Construct

<400> SEQUENCE: 6
gatcatttca tggaatcact gcttttt 27

<210> SEQ ID NO 7
<211> LENGTH: 27
<212> TYPE: DNA
<213> ORGANISM: Artificial Sequence
<220> FEATURE:
<223> OTHER INFORMATION: Synthetic Construct

<400> SEQUENCE: 7
gatcacttga tggccgacct ctttttt 27

<210> SEQ ID NO 8
<211> LENGTH: 27
<212> TYPE: DNA

-continued

<213> ORGANISM: Artificial Sequence
<220> FEATURE:
<223> OTHER INFORMATION: Synthetic Construct

<400> SEQUENCE: 8
gatcaatata ctaccgacat gagttct 27

<210> SEQ ID NO 9
<211> LENGTH: 25
<212> TYPE: DNA
<213> ORGANISM: Artificial Sequence
<220> FEATURE:
<223> OTHER INFORMATION: Synthetic Construct

<400> SEQUENCE: 9
actaccgaca tgagttccaa aaagc 25

<210> SEQ ID NO 10
<211> LENGTH: 60
<212> TYPE: PRT
<213> ORGANISM: Arabidopsis thaliana

<400> SEQUENCE: 10

```
Ile Tyr Arg Gly Val Arg Gln Arg Asn Ser Gly Lys Trp Val Ser Glu
 1               5                  10                  15

Val Arg Glu Pro Asn Lys Lys Thr Arg Ile Trp Leu Gly Thr Phe Gln
            20                  25                  30

Thr Ala Glu Met Ala Ala Arg Ala His Asp Val Ala Ala Leu Ala Leu
        35                  40                  45

Arg Gly Arg Ser Ala Cys Leu Asn Phe Ala Asp Ser
    50                  55                  60
```

<210> SEQ ID NO 11
<211> LENGTH: 61
<212> TYPE: PRT
<213> ORGANISM: Nicotiana tabacum

<400> SEQUENCE: 11

```
His Tyr Arg Gly Val Arg Gln Arg Pro Trp Gly Lys Phe Ala Ala Glu
 1               5                  10                  15

Ile Arg Asp Pro Ala Lys Asn Gly Ala Arg Val Trp Leu Gly Thr Tyr
            20                  25                  30

Glu Thr Ala Glu Glu Ala Ala Leu Ala Tyr Asp Lys Ala Ala Tyr Arg
        35                  40                  45

Met Arg Gly Ser Lys Ala Leu Leu Asn Phe Pro His Arg
    50                  55                  60
```

<210> SEQ ID NO 12
<211> LENGTH: 651
<212> TYPE: DNA
<213> ORGANISM: Arabidopsis thaliana

<400> SEQUENCE: 12

```
atgaactcat tttctgcctt ttctgaaatg tttggctccg attacgagtc tccggtttcc     60

tcaggcggtg attacagtcc gaagcttgcc acgagctgcc ccaagaaacc agcgggaagg    120

aagaagtttc gtgagactcg tcacccaatt tacagaggag ttcgtcaaag aaactccggt    180

aagtgggtgt gtgagttgag agagccaaac aagaaaacga ggatttggct cgggactttc    240

caaaccgctg agatggcagc tcgtgctcac gacgtcgccg ccatagctct ccgtggcaga    300

tctgcctgtc tcaatttcgc tgactcggct tggcggctac gaatcccgga atcaacctgt    360
```

-continued

```
gccaaggaaa tccaaaaggc ggcggctgaa gccgcgttga attttcaaga tgagatgtgt    420

catatgacga cggatgctca tggtcttgac atggaggaga ccttggtgga ggctatttat    480

acgccggaac agagccaaga tgcgttttat atggatgaag aggcgatgtt ggggatgtct    540

agtttgttgg ataacatggc cgaagggatg cttttaccgt cgccgtcggt tcaatggaac    600

tataattttg atgtcgaggg agatgatgac gtgtccttat ggagctatta a             651
```

<210> SEQ ID NO 13
<211> LENGTH: 216
<212> TYPE: PRT
<213> ORGANISM: Arabidopsis thaliana

<400> SEQUENCE: 13

```
Met Asn Ser Phe Ser Ala Phe Ser Glu Met Phe Gly Ser Asp Tyr Glu
 1               5                  10                  15

Ser Pro Val Ser Ser Gly Gly Asp Tyr Ser Pro Lys Leu Ala Thr Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Gln Arg Asn Ser Gly Lys Trp Val Cys
    50                  55                  60

Glu Leu Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Ile Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Glu Ile Gln Lys Ala Ala
        115                 120                 125

Ala Glu Ala Ala Leu Asn Phe Gln Asp Glu Met Cys His Met Thr Thr
    130                 135                 140

Asp Ala His Gly Leu Asp Met Glu Glu Thr Leu Val Glu Ala Ile Tyr
145                 150                 155                 160

Thr Pro Glu Gln Ser Gln Asp Ala Phe Tyr Met Asp Glu Glu Ala Met
                165                 170                 175

Leu Gly Met Ser Ser Leu Leu Asp Asn Met Ala Glu Gly Met Leu Leu
            180                 185                 190

Pro Ser Pro Ser Val Gln Trp Asn Tyr Asn Phe Asp Val Glu Gly Asp
        195                 200                 205

Asp Asp Val Ser Leu Trp Ser Tyr
    210                 215
```

<210> SEQ ID NO 14
<211> LENGTH: 651
<212> TYPE: DNA
<213> ORGANISM: Arabidopsis thaliana

<400> SEQUENCE: 14

```
atgaactcat tttctgcttt ttctgaaatg tttggctccg attacgagtc ttcggtttcc     60

tcaggcggtg attatattcc gacgcttgcg agcagctgcc ccaagaaacc ggcgggtcgt    120

aagaagtttc gtgagactcg tcacccaata tacagaggag ttcgtcggag aaactccggt    180

aagtgggttt gtgaggttag agaaccaaac aagaaaacaa ggatttggct cggaacattt    240

caaaccgctg agatggcagc tcgagctcac gacgttgccg ctttagccct tcgtggccga    300

tcagcctgtc tcaatttcgc tgactcggct tggagactcc gaatcccgga atcaacttgc    360
```

-continued

```
gctaaggaca tccaaaaggc ggcggctgaa gctgcgttgg cgtttcagga tgagatgtgt    420

gatgcgacga cggatcatgg cttcgacatg gaggagacgt tggtggaggc tatttacacg    480

gcggaacaga gcgaaaatgc gttttatatg cacgatgagg cgatgtttga gatgccgagt    540

ttgttggcta atatggcaga agggatgctt ttgccgcttc cgtccgtaca gtggaatcat    600

aatcatgaag tcgacggcga tgatgacgac gtatcgttat ggagttatta a             651


<210> SEQ ID NO 15
<211> LENGTH: 216
<212> TYPE: PRT
<213> ORGANISM: Arabidopsis thaliana

<400> SEQUENCE: 15

Met Asn Ser Phe Ser Ala Phe Ser Glu Met Phe Gly Ser Asp Tyr Glu
 1               5                  10                  15

Ser Ser Val Ser Ser Gly Gly Asp Tyr Ile Pro Thr Leu Ala Ser Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Arg Arg Asn Ser Gly Lys Trp Val Cys
    50                  55                  60

Glu Val Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Leu Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Asp Ile Gln Lys Ala Ala
        115                 120                 125

Ala Glu Ala Ala Leu Ala Phe Gln Asp Glu Met Cys Asp Ala Thr Thr
    130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
            180                 185                 190

Leu Pro Ser Val Gln Trp Asn His Asn His Glu Val Asp Gly Asp Asp
        195                 200                 205

Asp Asp Val Ser Leu Trp Ser Tyr
    210                 215


<210> SEQ ID NO 16
<211> LENGTH: 18
<212> TYPE: DNA
<213> ORGANISM: Tobacco

<400> SEQUENCE: 16

ttggcggcta cgaatccc                                                   18


<210> SEQ ID NO 17
<211> LENGTH: 210
<212> TYPE: PRT
<213> ORGANISM: Brassica napus
```

-continued

<400> SEQUENCE: 17

```
His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser Ala Trp
    50                  55                  60

Arg Leu Arg Ile Pro Glu Thr Thr Cys His Lys Asp Ile Gln Lys Ala
65                  70                  75                  80

Ala Ala Glu Ala Ala Leu Ala Phe Glu Ala Glu Lys Ser Asp Val Thr
                85                  90                  95

Met Gln Asn Gly Gln Asn Met Glu Glu Thr Thr Ala Val Ala Ser Gln
            100                 105                 110

Ala Glu Val Asn Asp Thr Thr Thr Glu His Gly Met Asn Met Glu Glu
        115                 120                 125

Ala Thr Ala Val Ala Ser Gln Ala Glu Val Asn Asp Thr Thr Thr Asp
    130                 135                 140

His Gly Val Asp Met Glu Glu Thr Met Val Glu Ala Val Phe Thr Gly
145                 150                 155                 160

Glu Gln Ser Glu Gly Phe Asn Met Ala Lys Glu Ser Thr Val Glu Ala
                165                 170                 175

Ala Val Val Thr Glu Glu Pro Ser Lys Gly Ser Tyr Met Asp Glu Glu
            180                 185                 190

Trp Met Leu Glu Met Pro Thr Leu Leu Ala Asp Met Ala Glu Gly Met
        195                 200                 205

Leu Leu
    210
```

<210> SEQ ID NO 18
<211> LENGTH: 632
<212> TYPE: DNA
<213> ORGANISM: Canola

<400> SEQUENCE: 18

```
cacccgatat accggggagt tcgtctgaga aagtcaggta agtgggtgtg tgaagtgagg     60

gaaccaaaca agaaatctag aatttggctt ggaactttca aaacagctga gatggcagct    120

cgtgctcacg acgtcgctgc cctagccctc cgtggaagag gcgcctgcct caattatgcg    180

gactcggctt ggcggctccg catcccggag acaacctgcc acaaggatat ccagaaggct    240

gctgctgaag ccgcattggc ttttgaggct gagaaaagtg atgtgacgat gcaaaatggc    300

cagaacatgg aggagacgac ggcggtggct tctcaggctg aagtgaatga cacgacgaca    360

gaacatggca tgaacatgga ggaggcaacg gcagtggctt ctcaggctga ggtgaatgac    420

acgacgacgg atcatggcgt agacatggag gagacaatgg tggaggctgt ttttactggg    480

gaacaaagtg aagggtttaa catggcgaag gagtcgacgg tggaggctgc tgttgttacg    540

gaggaaccga gcaaaggatc ttacatggac gaggagtgga tgctcgagat gccgaccttg    600

ttggctgata tggcagaagg gatgctcctg cc                                  632
```

<210> SEQ ID NO 19
<211> LENGTH: 36
<212> TYPE: DNA
<213> ORGANISM: Artificial Sequence -continued
<220> FEATURE:
<223> OTHER INFORMATION: Synthetic Construct

<400> SEQUENCE: 19
gcccaagctt caagtttagt gagcactatg tgctcg 36

<210> SEQ ID NO 20
<211> LENGTH: 34
<212> TYPE: DNA
<213> ORGANISM: Artificial Sequence
<220> FEATURE:
<223> OTHER INFORMATION: Synthetic Construct

<400> SEQUENCE: 20
ggaagatctc cttcccagaa acaacacaat ctac 34

<210> SEQ ID NO 21
<211> LENGTH: 35
<212> TYPE: DNA
<213> ORGANISM: Artificial Sequence
<220> FEATURE:
<223> OTHER INFORMATION: Synthetic Construct

<400> SEQUENCE: 21
gcccaagctt gtttcatttt ctccatgaag gagat 35

<210> SEQ ID NO 22
<211> LENGTH: 39
<212> TYPE: DNA
<213> ORGANISM: Artificial Sequence
<220> FEATURE:
<223> OTHER INFORMATION: Synthetic Construct

<400> SEQUENCE: 22
ggaagatctt atcgtcgtcg tcgtctacca aaaccacac 39

<210> SEQ ID NO 23
<211> LENGTH: 32
<212> TYPE: DNA
<213> ORGANISM: Artificial Sequence
<220> FEATURE:
<223> OTHER INFORMATION: Synthetic Construct

<400> SEQUENCE: 23
gctctaagct tcacaagggg ttcgtttggt gc 32

<210> SEQ ID NO 24
<211> LENGTH: 40
<212> TYPE: DNA
<213> ORGANISM: Artificial Sequence
<220> FEATURE:
<223> OTHER INFORMATION: Synthetic Construct

<400> SEQUENCE: 24
ggggtacctt ttgggagttg gaatagaaat gggtttgatg 40

<210> SEQ ID NO 25
<211> LENGTH: 36
<212> TYPE: DNA
<213> ORGANISM: Artificial Sequence
<220> FEATURE:
<223> OTHER INFORMATION: Synthetic Construct

<400> SEQUENCE: 25
gcccaagctt aattttactc aaaatgtttt ggttgc 36

-continued

<210> SEQ ID NO 26
<211> LENGTH: 44
<212> TYPE: DNA
<213> ORGANISM: Artificial Sequence
<220> FEATURE:
<223> OTHER INFORMATION: Synthetic Construct

<400> SEQUENCE: 26
ccggtacctt tccaaagatt tttttctttc caatagaagt aatc 44

<210> SEQ ID NO 27
<211> LENGTH: 30
<212> TYPE: DNA
<213> ORGANISM: Artificial Sequence
<220> FEATURE:
<223> OTHER INFORMATION: Synthetic Construct

<400> SEQUENCE: 27
gcggaagctt cattttctgc tacagaagtg 30

<210> SEQ ID NO 28
<211> LENGTH: 40
<212> TYPE: DNA
<213> ORGANISM: Artificial Sequence
<220> FEATURE:
<223> OTHER INFORMATION: Synthetic Construct

<400> SEQUENCE: 28
ccggtacctt tccaaagctg tgttttctct ttttcaagtg 40

<210> SEQ ID NO 29
<211> LENGTH: 42
<212> TYPE: DNA
<213> ORGANISM: Artificial Sequence
<220> FEATURE:
<223> OTHER INFORMATION: Synthetic Construct

<400> SEQUENCE: 29
gcccaagctt caaattctga atattcacat atcaaaaaag tg 42

<210> SEQ ID NO 30
<211> LENGTH: 40
<212> TYPE: DNA
<213> ORGANISM: Artificial Sequence
<220> FEATURE:
<223> OTHER INFORMATION: Synthetic Construct

<400> SEQUENCE: 30
ggaagatctg ttcttcttgt cttaagcaaa cactttgagc 40

<210> SEQ ID NO 31
<211> LENGTH: 41
<212> TYPE: DNA
<213> ORGANISM: Artificial Sequence
<220> FEATURE:
<223> OTHER INFORMATION: Synthetic Construct

<400> SEQUENCE: 31
gcccaagctt tcgtctgtta tcatacaagg cacaaaacga c 41

<210> SEQ ID NO 32
<211> LENGTH: 42
<212> TYPE: DNA
<213> ORGANISM: Artificial Sequence
<220> FEATURE:
<223> OTHER INFORMATION: Synthetic Construct -continued

<400> SEQUENCE: 32
ggaagatcta gttaatcttg atttgattaa aagtttatat ag 42

<210> SEQ ID NO 33
<211> LENGTH: 25
<212> TYPE: DNA
<213> ORGANISM: Artificial Sequence
<220> FEATURE:
<223> OTHER INFORMATION: Synthetic Construct

<400> SEQUENCE: 33
caaactcagt aggattctgg tgtgt 25

<210> SEQ ID NO 34
<211> LENGTH: 38
<212> TYPE: DNA
<213> ORGANISM: Artificial Sequence
<220> FEATURE:
<223> OTHER INFORMATION: Synthetic Construct

<400> SEQUENCE: 34
ggaagatctt gaaacagagt actctgatca atgaactc 38

<210> SEQ ID NO 35
<211> LENGTH: 42
<212> TYPE: DNA
<213> ORGANISM: Artificial Sequence
<220> FEATURE:
<223> OTHER INFORMATION: Synthetic Construct

<400> SEQUENCE: 35
cgcggatccc tcgtttctac aacaataaaa taaaataaaa tg 42

<210> SEQ ID NO 36
<211> LENGTH: 37
<212> TYPE: DNA
<213> ORGANISM: Artificial Sequence
<220> FEATURE:
<223> OTHER INFORMATION: Synthetic Construct

<400> SEQUENCE: 36
ggggtacctg aaacagagta ctctgatcaa tgaactc 37

<210> SEQ ID NO 37
<211> LENGTH: 41
<212> TYPE: DNA
<213> ORGANISM: Artificial Sequence
<220> FEATURE:
<223> OTHER INFORMATION: Synthetic Construct

<400> SEQUENCE: 37
gctctagact cgtttctaca acaataaaat aaaataaaat g 41

<210> SEQ ID NO 38
<211> LENGTH: 577
<212> TYPE: DNA
<213> ORGANISM: Brassica juncea

<400> SEQUENCE: 38
tttcacccta tctaccgggg agttcgcctg agaaagtcag gtaagtgggt gtgtgaagtg 60
agggagccaa acaagaaatc taggatttgg cttggaactt tcaaaaccgc agagatcgct 120
gctcgtgctc acgacgttgc cgccttagcc ctccgtggaa gagcggcctg tctcaacttc 180
gccgactcgg cttggcggct ccgtatcccg gagacaactt gcgccaagga tatccagaag 240

-continued

```
gctgctgctg aagctgcgtt ggcttttggg gccgaaaaga gtgataccac gacgaatgat    300

caaggcatga acatggagga gatgacggtg gtggcttctc aggctgaggt gagcgacacg    360

acgacatatc atggcctgga catggaggag actatggtgg aggctgtttt tgctgaggaa    420

cagagagaag ggttttactt ggcggaggag acgacggtgg agggtgttgt tacggaggaa    480

cagagcaaag ggttttatat gtacgaggag tggacgttcg ggatgcagtc ctttttggcc    540

gatatggctg aaggcatgct cttttcaaag ggcgaat                             577
```

```
<210> SEQ ID NO 39
<211> LENGTH: 130
<212> TYPE: PRT
<213> ORGANISM: Brassica juncea

<400> SEQUENCE: 39

Leu Pro Gly Val Arg Leu Arg Lys Ser Gly Lys Trp Val Cys Glu Val
 1               5                  10                  15

Arg Glu Pro Asn Lys Lys Ser Arg Ile Trp Leu Gly Thr Phe Lys Thr
            20                  25                  30

Ala Glu Ile Ala Ala Arg Ala His Asp Val Ala Ala Leu Ala Leu Arg
        35                  40                  45

Gly Arg Ala Ala Cys Leu Asn Phe Ala Asp Ser Ala Trp Arg Leu Arg
    50                  55                  60

Ile Pro Glu Thr Thr Cys Ala Lys Asp Ile Gln Lys Ala Ala Ala Glu
65                  70                  75                  80

Ala Ala Leu Ala Phe Gly Ala Glu Lys Ser Asp Thr Thr Thr Asn Asp
                85                  90                  95

Gln Gly Met Asn Met Glu Glu Met Thr Ala Val Ala Ser Gln Ala Glu
            100                 105                 110

Val Ser Asp Thr Thr Thr Tyr His Gly Leu Asp Met Glu Glu Thr Met
        115                 120                 125

Val Asp
    130
```

```
<210> SEQ ID NO 40
<211> LENGTH: 431
<212> TYPE: DNA
<213> ORGANISM: Brassica juncea

<400> SEQUENCE: 40

catccgatct acaggggagt tcgtctgaga aaatcaggta agtgggtgtg tgaagtgagg     60

gaaccaaaca agagatctag gatctggctc ggtactttcc taaccgccga gatcgcagct    120

cgcgctcacg acgtcgccgc catagccctc cgtggcaaat ccgcatgtct caatttcgct    180

gactcggctt ggcggctccg tatctcggag acaacatgcc ctaaggagat tcagaaggct    240

gctgctgaag ccgcggtggc ttttcaggct gagctaaatg atacgacggc cgatcatggc    300

cttgacgtgg aggagacgat cgtggaggct attttcacgg aggaaagcag cgaagggttt    360

tatatggacg aggagttcat gttcgggatg ccgaccttgt gggctagtat ggcagaaggg    420

atgcttcttc c                                                         431
```

```
<210> SEQ ID NO 41
<211> LENGTH: 143
<212> TYPE: PRT
<213> ORGANISM: Brassica juncea
```

-continued

<400> SEQUENCE: 41

```
His Pro Ile Tyr Arg Gly Val Arg Leu Arg Lys Ser Gly Lys Trp Val
 1               5                  10                  15

Cys Glu Val Arg Glu Pro Asn Lys Arg Ser Arg Ile Trp Leu Gly Thr
            20                  25                  30

Phe Leu Thr Ala Glu Ile Ala Ala Arg Ala His Asp Val Ala Ala Ile
        35                  40                  45

Ala Leu Arg Gly Lys Ser Ala Cys Leu Asn Phe Ala Asp Ser Ala Trp
    50                  55                  60

Arg Leu Arg Ile Ser Glu Thr Thr Cys Pro Lys Glu Ile Gln Lys Ala
65                  70                  75                  80

Ala Ala Glu Ala Ala Val Ala Phe Gln Ala Glu Leu Asn Asp Thr Thr
                85                  90                  95

Ala Asp His Gly Leu Asp Val Glu Glu Thr Ile Val Glu Ala Ile Phe
            100                 105                 110

Thr Glu Glu Ser Ser Glu Gly Phe Tyr Met Asp Glu Glu Phe Met Phe
        115                 120                 125

Gly Met Pro Thr Leu Trp Ala Ser Met Ala Glu Gly Met Leu Leu
    130                 135                 140
```

<210> SEQ ID NO 42
<211> LENGTH: 431
<212> TYPE: DNA
<213> ORGANISM: Brassica juncea

<400> SEQUENCE: 42

```
catccaattt accgtggagt tcgtctgaga aaatcaggta agtgggtgtg tgaagtgagg     60

gagccaaaca agaaatctag gatctggccc ggtactttcc taaccgccga gatcgcagct    120

cgcgctcacg acgtcgccgc catagccctc cgtggcaaat ccgcatgtct caatttcgct    180

gactcggctt ggcggctccg tatcccggag acaacatgcc ctaaggagat tcagaaggct    240

gctgctgaag ccgcggtggc ttttcaggct gagctaaatg atacgacggc cgatcatggc    300

cttgacgtgg aggagacgat cgtggaggct attttcacgg aggaaagcag cgaagggttt    360

tatatggacg aggagttcat gttcgggatg ccgaccttgt gggctagtat ggcggagggc    420

atgctccttc c                                                         431
```

<210> SEQ ID NO 43
<211> LENGTH: 143
<212> TYPE: PRT
<213> ORGANISM: Brassica juncea

<400> SEQUENCE: 43

```
His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Pro Gly Thr
            20                  25                  30

Phe Leu Thr Ala Glu Ile Ala Ala Arg Ala His Asp Val Ala Ala Ile
        35                  40                  45

Ala Leu Arg Gly Lys Ser Ala Cys Leu Asn Phe Ala Asp Ser Ala Trp
    50                  55                  60

Arg Leu Arg Ile Pro Glu Thr Thr Cys Pro Lys Glu Ile Gln Lys Ala
65                  70                  75                  80

Ala Ala Glu Ala Ala Val Ala Phe Gln Ala Glu Leu Asn Asp Thr Thr
                85                  90                  95
```

-continued

```
Ala Asp His Gly Leu Asp Val Glu Glu Thr Ile Val Glu Ala Ile Phe
            100                 105                 110

Thr Glu Glu Ser Ser Glu Gly Phe Tyr Met Ala Glu Glu Phe Met Phe
        115                 120                 125

Gly Met Pro Thr Leu Trp Ala Ser Val Ala Glu Gly Met Leu Leu
    130                 135                 140


<210> SEQ ID NO 44
<211> LENGTH: 425
<212> TYPE: DNA
<213> ORGANISM: Brassica juncea

<400> SEQUENCE: 44

catccaatct accggggtgt tcgacagaga aactcaggga aatgggtttg tgaagttagg      60

gagcctaata agaaatctag gatctggtta gggacttttc cgaccgtcga aatggccgct     120

cgtgctcacg acgtcgccgc tttagccctt cgtggccgct ccgcttgtct taatttcgcc     180

gactcggcgt ggtgtctacg gattcccgag tctacttgtc ctaaagagat tcagaaagct     240

gcggccgaag ctgcaatggc gtttcagaac gagacggcta cgactgagac gactatggtt     300

gagggagtca taccggcgga ggagacggtg gggcagacgc gtgtggagac agcagaggag     360

aacggtgtgt tttatatgga cgatccaagg tttcttgaga atatggcaga gggcatgttc     420

ctacc                                                                 425


<210> SEQ ID NO 45
<211> LENGTH: 142
<212> TYPE: PRT
<213> ORGANISM: Brassica juncea

<400> SEQUENCE: 45

His Pro Ile Tyr Arg Gly Val Arg Gln Arg Asn Ser Gly Lys Trp Val
 1               5                  10                  15

Cys Glu Val Arg Glu Pro Asn Lys Lys Ser Arg Ile Trp Leu Gly Thr
            20                  25                  30

Phe Pro Thr Val Glu Met Ala Ala Arg Ala His Asp Val Ala Ala Leu
        35                  40                  45

Ala Leu Arg Gly Arg Ser Ala Cys Leu Asn Phe Ala Asp Ser Ala Trp
    50                  55                  60

Cys Leu Arg Ile Pro Glu Ser Thr Cys Pro Lys Glu Ile Gln Lys Ala
65                  70                  75                  80

Ala Ala Glu Ala Ala Met Ala Phe Gln Asn Glu Glu Thr Ala Thr Thr
                85                  90                  95

Glu Thr Thr Met Val Glu Gly Val Ile Pro Ala Glu Glu Thr Val Gly
            100                 105                 110

Gln Thr Arg Val Glu Thr Ala Glu Glu Asn Gly Val Glu Tyr Met Asp
        115                 120                 125

Asp Pro Arg Phe Leu Glu Asn Met Ala Glu Gly Met Leu Phe
    130                 135                 140


<210> SEQ ID NO 46
<211> LENGTH: 632
<212> TYPE: DNA
<213> ORGANISM: Brassica napus

<400> SEQUENCE: 46

cacccgatat accggggagt tcgtctgaga aagtcaggta agtgggtgtg tgaagtgagg      60

gaaccaaaca agaaatctag aatttggctt ggaactttca aaacagctga gatggcagct     120
```

-continued

```
cgtgctcacg acgtcgctgc cctagccctc cgtggaagag gcgcctgcct caattatgcg    180

gactcggctt ggcggctccg catcccggag acaacctgcc acaaggatat ccagaaggct    240

gctgctgaag ccgcattggc ttttgaggct gagaaaagtg atgtgacgat gcaaaatggc    300

cagaacatgg aggagacgac ggcggtggct tctcaggctg aagtgaatga cacgacgaca    360

gaacatggca tgaacatgga ggaggcaacg gcagtggctt ctcaggctga ggtgaatgac    420

acgacgacgg atcatggcgt agacatggag gagacaatgg tggaggctgt ttttactggg    480

gaacaaagtg aagggtttaa catggcgaag gagtcgacgg tggaggctgc tgttgttacg    540

gaggaaccga gcaaaggatc ttacatggac gaggagtgga tgctcgagat gccgaccttg    600

ttggctgata tggcagaagg gatgctcctg cc                                  632
```

```
<210> SEQ ID NO 47
<211> LENGTH: 210
<212> TYPE: PRT
<213> ORGANISM: Brassica napus

<400> SEQUENCE: 47

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser Ala Trp
    50                  55                  60

Arg Leu Arg Ile Pro Glu Thr Thr Cys His Lys Asp Ile Gln Lys Ala
65                  70                  75                  80

Ala Ala Glu Ala Ala Leu Ala Phe Glu Ala Glu Lys Ser Asp Val Thr
                85                  90                  95

Met Gln Asn Gly Gln Asn Met Glu Glu Thr Thr Ala Val Ala Ser Gln
            100                 105                 110

Ala Glu Val Asn Asp Thr Thr Thr Glu His Gly Met Asn Met Glu Glu
        115                 120                 125

Ala Thr Ala Val Ala Ser Gln Ala Glu Val Asn Asp Thr Thr Thr Asp
    130                 135                 140

His Gly Val Asp Met Glu Glu Thr Met Val Glu Ala Val Phe Thr Gly
145                 150                 155                 160

Glu Gln Ser Glu Gly Phe Asn Met Ala Lys Glu Ser Thr Val Glu Ala
                165                 170                 175

Ala Val Val Thr Glu Glu Pro Ser Lys Gly Ser Tyr Met Asp Glu Glu
            180                 185                 190

Trp Met Leu Glu Met Pro Thr Leu Leu Ala Asp Met Ala Glu Gly Met
        195                 200                 205

Leu Leu
    210
```

```
<210> SEQ ID NO 48
<211> LENGTH: 876
<212> TYPE: DNA
<213> ORGANISM: Brassica napus

<400> SEQUENCE: 48

accgctcgag caacaatgaa cacattccct gcttccactg aaatggttgg ctccgagaac     60

gagtctccgg ttactacggt agtaggaggt gattattatc ccatgttggc ggcaagctgt    120
```

-continued

```
ccgaagaagc cagcgggtag gaagaagttt caggagacac gtcaccccat ttaccgagga    180

gttcgtctga gaaagtcagg taagtgggtg tgtgaagtga gggaaccaaa caagaaatct    240

agaatttggc ccggaacttt caaaacagct gagatggcag ctcgtgctca cgacgtcgct    300

gccctagccc tccgtggaag aggcgcctgc ctcaattatg cggactcggc ttggcggctc    360

cgcatcccgg aaacaacctg ccacaaggat atccagaagg ctgctgctga agccgcattg    420

gcttttgagg ctgagaaaag tgatgtgacg atgcaaaatg gcctgaacat ggaggagacg    480

acggcggtgg cttctcaggc tgaagtgaat gacacgacga cagaacatgg catgaacatg    540

gaggaggcaa cagcggtggc ttctcaggct gaggtgaatg acacgacgac agatcatggc    600

gtagacatgg aggagacgat ggtggaggct gtttttacgg aggaacaaag tgaagggttc    660

aacatggcgg aggagtcgac ggtggaggct gctgttgtta cggatgaact gagcaaagga    720

ttttacatgg acgaggagtg gacgtacgag atgccgacct tgttggctga tatggcggca    780

gggatgcttt tgccgccacc atctgtacaa tggggacata atgatgactt ggaaggagat    840

gcggacatga acctctggag ttattaagga tccgcg                              876
```

```
<210> SEQ ID NO 49
<211> LENGTH: 283
<212> TYPE: PRT
<213> ORGANISM: Brassica napus

<400> SEQUENCE: 49

Met Asn Thr Phe Pro Ala Ser Thr Glu Met Val Gly Ser Glu Asn Glu
 1               5                  10                  15

Ser Pro Val Thr Thr Val Val Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Pro Gly
65                  70                  75                  80

Thr Phe Lys Thr Ala Glu Met Ala Ala Arg Ala His Asp Val Ala Ala
                85                  90                  95

Leu Ala Leu Arg Gly Arg Gly Ala Cys Leu Asn Tyr Ala Asp Ser Ala
            100                 105                 110

Trp Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Val
    130                 135                 140

Thr Met Gln Asn Gly Leu Asn Met Glu Glu Thr Thr Ala Val Ala Ser
145                 150                 155                 160

Gln Ala Glu Val Asn Asp Thr Thr Thr Glu His Gly Met Asn Met Glu
                165                 170                 175

Glu Ala Thr Ala Val Ala Ser Gln Ala Glu Val Asn Asp Thr Thr Thr
            180                 185                 190

Asp His Gly Val Asp Met Glu Glu Thr Met Val Glu Ala Val Phe Thr
        195                 200                 205

Glu Glu Gln Ser Glu Gly Phe Asn Met Ala Glu Glu Ser Thr Val Glu
    210                 215                 220

Ala Ala Val Val Thr Asp Glu Leu Ser Lys Gly Phe Tyr Met Asp Glu
225                 230                 235                 240
```

-continued

```
Glu Trp Thr Tyr Glu Met Pro Thr Leu Leu Ala Asp Met Ala Ala Gly
                245                 250                 255

Met Leu Leu Pro Pro Pro Ser Val Gln Trp Gly His Asn Asp Asp Leu
            260                 265                 270

Glu Gly Asp Ala Asp Met Asn Leu Trp Ser Tyr
        275                 280


<210> SEQ ID NO 50
<211> LENGTH: 884
<212> TYPE: DNA
<213> ORGANISM: Brassica napus

<400> SEQUENCE: 50

actacactca gccttatcca gtttttttca aaagattttt caacaatgaa cacattccct      60

gcgtccactg aaatggttgg ctccgagaac gagtctccgg ttactacggt agcaggaggt     120

gattattatc ccatgttggc ggcaagctgt ccgaagaagc cagcaggtag gaagaagttt     180

caggagacac gtcaccccat ttaccgagga gttcgtctga gaaagtcagg taagtgggtg     240

tgtgaagtga gggaaccaaa caagaaatct agaatttggc ccggaacttt caaaacagct     300

gagatggcag ctcgtgctca cgacgtcgct gccctagccc tccgtggaag aggcgcctgc     360

ctcaattatg cggactcggc ttggcggctc cgcatcccgg agacaacctg ccacaaggat     420

atccagaagg ctgctgctga agccgcattg gcttttgagg ctgagaaaag tgatgtgacg     480

atgcaaaatg gcctgaacat ggaggagacg acggcggtgg cttctcaggc tgaagtgaat     540

gacacgacga cagaacatgg catgaacatg gaggaggcaa cggcagtggc ttctcaggct     600

gaggtgaatg acacgacgac ggatcatggc gtagacatgg aggagacaat ggtggaggct     660

gtttttactg ggaacaaag tgaagggttt aacatggcga aggagtcgac ggtggaggct     720

gctgttgtta cggaggaacc gagcaaagga tcttacatgg acgaggagtg gatgctcgag     780

atgccgacct tgttggctga tatggcggaa gggatgcttt tgccgccgcc gtccgtacaa     840

tggggacaga atgatgactt cgaaggagat gctgacatga acct                      884


<210> SEQ ID NO 51
<211> LENGTH: 279
<212> TYPE: PRT
<213> ORGANISM: Brassica napus

<400> SEQUENCE: 51

Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Pro Gly
65                  70                  75                  80

Thr Phe Lys Thr Ala Glu Met Ala Ala Arg Ala His Asp Val Ala Ala
                85                  90                  95

Leu Ala Leu Arg Gly Arg Gly Ala Cys Leu Asn Tyr Ala Asp Ser Ala
            100                 105                 110

Trp Arg Leu Arg Ile Pro Glu Thr Thr Cys His Lys Asp Ile Gln Lys
        115                 120                 125
```

-continued

```
Ala Ala Ala Glu Ala Ala Leu Ala Phe Glu Ala Glu Lys Ser Asp Val
    130                 135                 140

Thr Met Gln Asn Gly Leu Asn Met Glu Glu Thr Thr Ala Val Ala Ser
145                 150                 155                 160

Gln Ala Glu Val Asn Asp Thr Thr Thr Glu His Gly Met Asn Met Glu
                165                 170                 175

Glu Ala Thr Ala Val Ala Ser Gln Ala Glu Val Asn Asp Thr Thr Thr
            180                 185                 190

Asp His Gly Val Asp Met Glu Glu Thr Met Val Glu Ala Val Phe Thr
        195                 200                 205

Gly Glu Gln Ser Glu Gly Phe Asn Met Ala Lys Glu Ser Thr Val Glu
    210                 215                 220

Ala Ala Val Val Thr Glu Glu Pro Ser Lys Gly Ser Tyr Met Asp Glu
225                 230                 235                 240

Glu Trp Met Leu Glu Met Pro Thr Leu Leu Ala Asp Met Ala Glu Gly
                245                 250                 255

Met Leu Leu Pro Pro Pro Ser Val Gln Trp Gly Gln Asn Asp Asp Phe
            260                 265                 270

Glu Gly Asp Ala Asp Met Asn
        275
```

<210> SEQ ID NO 52
<211> LENGTH: 874
<212> TYPE: DNA
<213> ORGANISM: Brassica napus

<400> SEQUENCE: 52

```
gtaattcgat taccgctcga gtacttacta tactacactc agccttatcc agtttttcaa      60

aagaagtttt caactatgaa ctcagtctct actttttctg aacttcttgg ctctgagaac     120

gagtctccgg taggtggtga ttactgtccc atgttggcgg cgagctgtcc gaagaagccg     180

gcgggtagga agaagtttcg ggagacacgt caccccattt accgaggagt tcgccttaga     240

aaatcaggta agtgggtgtg tgaagtgagg gaaccaaaca aaaaatctag gatttggctc     300

ggaactttca aaacagctga gatcgcagct cgtgctcacg acgtcgccgc cttagctctc     360

cgtggaagag gcgcctgcct caacttcgcc gactcggctt ggcggctccg tatcccggag     420

acaacctgcg ccaaggatat ccagaaggct gctgctgaag ccgcattggc ttttgaggcc     480

gagaagagtg ataccacgac gaatgatcat ggcatgaaca tggcttctca ggccgaggtt     540

aatgacacaa cggatcatgg cctggacatg gaggagacga tggtggaggc tgtttttact     600

gaggagcaga gagacgggtt ttacatggcg gaggagacga cggtggaggg tgttgttccg     660

gaggaacaga tgagcaaagg gttttacatg gacgaggagt ggatgttcgg gatgccgacc     720

ttgttggctg atatggcggc agggatgctc ttaccgccgc cgtccgtaca atggggacat     780

aatgatgact tcgaaggaga tgttgacatg aacctctgga attattagta ctcatatttt     840

tttaaattat tttttgaacg aataatattt tatt                                  874
```

<210> SEQ ID NO 53
<211> LENGTH: 250
<212> TYPE: PRT
<213> ORGANISM: Brassica napus

<400> SEQUENCE: 53

```
Met Asn Ser Val Ser Thr Phe Ser Glu Leu Leu Gly Ser Glu Asn Glu
 1               5                  10                  15
```

-continued

```
Ser Pro Val Gly Gly Asp Tyr Cys Pro Met Leu Ala Ala Ser Cys Pro
            20                  25                  30

Lys Lys Pro Ala Gly Arg Lys Lys Phe Arg Glu Thr Arg His Pro Ile
        35                  40                  45

Tyr Arg Gly Val Arg Leu Arg Lys Ser Gly Lys Trp Val Cys Glu Val
    50                  55                  60

Arg Glu Pro Asn Lys Lys Ser Arg Ile Trp Leu Gly Thr Phe Lys Thr
65                  70                  75                  80

Ala Glu Ile Ala Ala Arg Ala His Asp Val Ala Ala Leu Ala Leu Arg
                85                  90                  95

Gly Arg Gly Ala Cys Leu Asn Phe Ala Asp Ser Ala Trp Arg Leu Arg
            100                 105                 110

Ile Pro Glu Thr Thr Cys Ala Lys Asp Ile Gln Lys Ala Ala Ala Glu
        115                 120                 125

Ala Ala Leu Ala Phe Glu Ala Glu Lys Ser Asp Thr Thr Thr Asn Asp
    130                 135                 140

His Gly Met Asn Met Ala Ser Gln Ala Glu Val Asn Asp Thr Thr Asp
145                 150                 155                 160

His Gly Leu Asp Met Glu Glu Thr Met Val Glu Ala Val Phe Thr Glu
                165                 170                 175

Glu Gln Arg Asp Gly Phe Tyr Met Ala Glu Glu Thr Thr Val Glu Gly
            180                 185                 190

Val Val Pro Glu Glu Gln Met Ser Lys Gly Phe Tyr Met Asp Glu Glu
        195                 200                 205

Trp Met Phe Gly Met Pro Thr Leu Leu Ala Asp Met Ala Ala Gly Met
    210                 215                 220

Leu Leu Pro Pro Pro Ser Val Gln Trp Gly His Asn Asp Asp Phe Glu
225                 230                 235                 240

Gly Asp Val Asp Met Asn Leu Trp Asn Tyr
                245                 250
```

<210> SEQ ID NO 54
<211> LENGTH: 898
<212> TYPE: DNA
<213> ORGANISM: Brassica napus

<400> SEQUENCE: 54

```
aataaatatc ttatcaaacc agtcagaaca gagatcttgt tacttactat actacactca      60

gccttatcca gttttcaaaa aaagtattca acgatgaact cagtctctac tttttctgaa     120

ctgctccgct ccgagaacga gtctccggtt aatacggaag gtggtgatta cattttggcg     180

gcgagctgtc ccaagaaacc tgctggtagg aagaagtttc aggagacacg ccaccccatt     240

tacagaggag ttcgtctgag gaagtcaggt aagtgggtgt gtgaagtgag ggaaccaaac     300

aagaaatcta gaatttggct cggaactttc aaaacagctg agatcgcagc tcgtgctcac     360

gacgttgccg ccttagctct ccgtggaaga ggcgcctgcc tcaacttcgc cgactcggct     420

tggcggctcc gtatcccgga gacgacctgc gccaaggata tccagaaggc tgctgctgaa     480

gccgcattgg cttttgaggc cgagaagagt gataccacga cgaatgatca tggcatgaac     540

atggcttctc aggttgaggt taatgacacg acggatcatg acctggacat ggaggagacg     600

atagtggagg ctgtttttag ggaggaacag agagaagggt tttacatggc ggaggagacg     660

acggttgtgg gtgttgttcc ggaggaacag atgagcaaag ggttttacat ggacgaggag     720

tggatgttcg ggatgccgac cttgttggct gatatggcgg cagggatgct cttaccgctg     780
```

-continued ccgtccgtac aatggggaca taatgatgac ttcgaaggag atgctgacat gaacctctgg 840
aattattagt actcatattt ttttaaatta ttttttgaac gaataatatt ttattgaa 898

<210> SEQ ID NO 55
<211> LENGTH: 251
<212> TYPE: PRT
<213> ORGANISM: Brassica napus

<400> SEQUENCE: 55

Met Asn Ser Val Ser Thr Phe Ser Glu Leu Leu Arg Ser Glu Asn Glu
1 5 10 15

Ser Pro Val Asn Thr Glu Gly Gly Asp Tyr Ile Leu Ala Ala Ser Cys
20 25 30

Pro Lys Lys Pro Ala Gly Arg Lys Lys Phe Gln Glu Thr Arg His Pro
35 40 45

Ile Tyr Arg Gly Val Arg Leu Arg Lys Ser Gly Lys Trp Val Cys Glu
50 55 60

Val Arg Glu Pro Asn Lys Lys Ser Arg Ile Trp Leu Gly Thr Phe Lys
65 70 75 80

Thr Ala Glu Ile Ala Ala Arg Ala His Asp Val Ala Ala Leu Ala Leu
85 90 95

Arg Gly Arg Gly Ala Cys Leu Asn Phe Ala Asp Ser Ala Trp Arg Leu
100 105 110

Arg Ile Pro Glu Thr Thr Cys Ala Lys Asp Ile Gln Lys Ala Ala Ala
115 120 125

Glu Ala Ala Leu Ala Phe Glu Ala Glu Lys Ser Asp Thr Thr Thr Asn
130 135 140

Asp His Gly Met Asn Met Ala Ser Gln Val Glu Val Asn Asp Thr Thr
145 150 155 160

Asp His Asp Leu Asp Met Glu Glu Thr Ile Val Glu Ala Val Phe Arg
165 170 175

Glu Glu Gln Arg Glu Gly Phe Tyr Met Ala Glu Glu Thr Thr Val Val
180 185 190

Gly Val Val Pro Glu Glu Gln Met Ser Lys Gly Phe Tyr Met Asp Glu
195 200 205

Glu Trp Met Phe Gly Met Pro Thr Leu Leu Ala Asp Met Ala Ala Gly
210 215 220

Met Leu Leu Pro Leu Pro Ser Val Gln Trp Gly His Asn Asp Asp Phe
225 230 235 240

Glu Gly Asp Ala Asp Met Asn Leu Trp Asn Tyr
245 250

<210> SEQ ID NO 56
<211> LENGTH: 1132
<212> TYPE: DNA
<213> ORGANISM: Brassica napus

<400> SEQUENCE: 56
gattaccgct cgagtactta ctatactaca ctcagcctta tccagttttt ctcaaaagat 60
ttttcaacaa tgaacacatt ccctgcttcc actgaaatgg ttggctccga gaacgagtct 120
ccggttacta cggtagtagg aggtgattat tatcccatgt tggcggcaag ctgtccgaag 180
aagccagcgg gtaggaagaa gtttcaggag acacgtcacc ccatttaccg aggagttcgt 240
ctgagaaagt caggtaagtg ggtgtgtgaa gtgagggaac caaacaagaa atctagaatt 300
tggcttggaa ctttcaaaac agctgagatg gcagctcgtg ctcacgacgt ggctgcccta 360

-continued

```
gccctccgtg gaagaggcgc ctgcctcaat tatgcggact cggcttcgcg gctccgcatc    420

ccggagacaa cctgccacaa ggatatccag aaggctgctg ctgaagccgc attggctttt    480

gaggctgaga aaagtgatgt gacgatggag gagacgatgg cggtggcttc tcaggctgaa    540

gtgaatgaca cgacgacaga tcatggcatg aacatggagg aggcaacagc ggtggcttct    600

caggctgagg tgaatgacac gacgacagat catggcgtag acatggagga gacgatggtg    660

gaggctgttt ttacggagga acaaagtgaa gggttcaaca tggcggagga gtcgacggtg    720

gaggctgctg ttgttacgga tgaactgagc aaaggatttt acatggacga ggagtggacg    780

tacgagatgc cgaccttgtt ggctgatatg gcggcaggga tgcttttgcc gccaccatct    840

gtacaatggg gacataatga tgacttggaa ggagatgctg acatgaacct ctggaattat    900

taatactcgt gttttaaaaa ttatacattg tgcaataata ttttatcgaa tttctaattc    960

tgcctttaac ttttaatggg gatctttatt agtgtaggaa acgagtgtaa atgttccgcc   1020

gtggtgttgt caaaatgctg attatttttt gtgtgcagca taatcacgtt tggtttcctt   1080

tacactccaa atttagttga aatacaaata gaatagaaaa gtgaaaaaat gt           1132


<210> SEQ ID NO 57
<211> LENGTH: 277
<212> TYPE: PRT
<213> ORGANISM: Brassica napus

<400> SEQUENCE: 57

Met Asn Thr Phe Pro Ala Ser Thr Glu Met Val Gly Ser Glu Asn Glu
 1               5                  10                  15

Ser Pro Val Thr Thr Val Val Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Leu Gly
65                  70                  75                  80

Thr Phe Lys Thr Ala Glu Met Ala Ala Arg Ala His Asp Val Ala Ala
                85                  90                  95

Leu Ala Leu Arg Gly Arg Gly Ala Cys Leu Asn Tyr Ala Asp Ser Ala
            100                 105                 110

Ser Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Val
    130                 135                 140

Thr Met Glu Glu Thr Met Ala Val Ala Ser Gln Ala Glu Val Asn Asp
145                 150                 155                 160

Thr Thr Thr Asp His Gly Met Asn Met Glu Glu Ala Thr Ala Val Ala
                165                 170                 175

Ser Gln Ala Glu Val Asn Asp Thr Thr Thr Asp His Gly Val Asp Met
            180                 185                 190

Glu Glu Thr Met Val Glu Ala Val Phe Thr Glu Glu Gln Ser Glu Gly
        195                 200                 205

Phe Asn Met Ala Glu Glu Ser Thr Val Glu Ala Ala Val Val Thr Asp
    210                 215                 220

Glu Leu Ser Lys Gly Phe Tyr Met Asp Glu Glu Trp Thr Tyr Glu Met
225                 230                 235                 240
```

-continued

Pro Thr Leu Leu Ala Asp Met Ala Ala Gly Met Leu Leu Pro Pro Pro
245 250 255

Ser Val Gln Trp Gly His Asn Asp Asp Leu Glu Gly Asp Ala Asp Met
260 265 270

Asn Leu Trp Asn Tyr
275

<210> SEQ ID NO 58
<211> LENGTH: 768
<212> TYPE: DNA
<213> ORGANISM: Brassica napus

<400> SEQUENCE: 58
agtgatgttt ttcaaaagaa gttttcaact atgaactcag tctctacttt ttctgaactt 60
cttggctctg agaacgagtc tccggtaggt ggtgattact gtcccatgtt ggcggcgagc 120
tgtccgaaga agccggcggg taggaagaag tttcgggaga cacgtcaccc catttaccga 180
ggagttcgcc ttagaaaatc aggtaagtgg gtgtgtgaag tgagggagcc aaacaagaaa 240
tctaggattt ggctcggtac tttcctaaca gccgagatcg cagcccgtgc tcacgacgtc 300
gccgccatag ccctccgcgg caaatcagct tgtctcaatt ttgccgactc cgcttggcgg 360
ctccgtatcc cggagacaac atgcccccaag gagattcaga aggcggctgc tgaagccgcg 420
gtggctttta aggctgagat aaataatacg acggcggatc atggcattga cgtggaggag 480
acgatcgttg aggctatttt cacggaggaa aacaacgatg gtttttatat ggacgaggag 540
gagtccatgt tcgggatgcc ggccttgttg gctagtatgg ctgaaggaat gcttttgccg 600
cctccgtccg tacaattcgg acatacctat gactttgacg gagatgctga cgtgtccctt 660
tggagttatt agtacaaaga ttttttattt ccatttttgg tataatactt ctttttgatt 720
ttcggattct accttttat gggtatcatt tttttttag gaaacggg 768

<210> SEQ ID NO 59
<211> LENGTH: 213
<212> TYPE: PRT
<213> ORGANISM: Brassica napus

<400> SEQUENCE: 59

Met Asn Ser Val Ser Thr Phe Ser Glu Leu Leu Gly Ser Glu Asn Glu
1 5 10 15

Ser Pro Val Gly Gly Asp Tyr Cys Pro Met Leu Ala Ala Ser Cys Pro
20 25 30

Lys Lys Pro Ala Gly Arg Lys Lys Phe Arg Glu Thr Arg His Pro Ile
35 40 45

Tyr Arg Gly Val Arg Leu Arg Lys Ser Gly Lys Trp Val Cys Glu Val
50 55 60

Arg Glu Pro Asn Lys Lys Ser Arg Ile Trp Leu Gly Thr Phe Leu Thr
65 70 75 80

Ala Glu Ile Ala Ala Arg Ala His Asp Val Ala Ala Ile Ala Leu Arg
85 90 95

Gly Lys Ser Ala Cys Leu Asn Phe Ala Asp Ser Ala Trp Arg Leu Arg
100 105 110

Ile Pro Glu Thr Thr Cys Pro Lys Glu Ile Gln Lys Ala Ala Ala Glu
115 120 125

Ala Ala Val Ala Phe Lys Ala Glu Ile Asn Asn Thr Thr Ala Asp His
130 135 140

-continued

```
Gly Ile Asp Val Glu Glu Thr Ile Val Glu Ala Ile Phe Thr Glu Glu
145                 150                 155                 160

Asn Asn Asp Gly Phe Tyr Met Asp Glu Glu Glu Ser Met Phe Gly Met
                165                 170                 175

Pro Ala Leu Leu Ala Ser Met Ala Glu Gly Met Leu Leu Pro Pro Pro
            180                 185                 190

Ser Val Gln Phe Gly His Thr Tyr Asp Phe Asp Gly Asp Ala Asp Val
        195                 200                 205

Ser Leu Trp Ser Tyr
    210


<210> SEQ ID NO 60
<211> LENGTH: 953
<212> TYPE: DNA
<213> ORGANISM: Brassica napus

<400> SEQUENCE: 60

accgctcgag caacaatgaa cacattccct gcttccactg aaatggttgg ctccgagaac      60

gagtctccgg ttactacggt agcaggaggt gattattatc ccatgttggc ggcaagctgt     120

ccgaagaagc cagcgggtag gaagaagttt caggagacac gtcaccccat ttaccgagga     180

gttcgtctga gaaagtcagg taagtgggtg tgtgaagtga gggaaccaaa caagaaatct     240

agaatttggc ttggaacttt caaaacagct gagatggcag ctcgtgctca cgacgtggct     300

gccctagccc tccgtggaag aggcgcctgc ctcaattatg cggactcggc ttcgcggctc     360

cgcatcccgg agacaacctg ccacaaggat atccagaagg ctgctgctga agccgcattg     420

gcttttgagg ctgagaaaag tgatgtgacg atggaggaga cgatggcggt ggcttctcag     480

gctgaagtga atgacacgac gacagatcat ggcatgaaca tggaggaggc aacggcagtg     540

gcttctcagg ctgaggtgaa tgacacgacg acggatcatg gcgtagacat ggaggagaca     600

atggtggagg ctgtttttac tggggaacaa agtgaagggt ttaacatggc gaaggagtcg     660

acggtggagg ctgctgttgt tacggaggaa ccgagcaaag gatcttacat ggacgaggag     720

tggatgctcg agatgccgac cttgttggct gatatggcgg aagggatgct tttgccgccg     780

ccgtccgtac aatggggaca gaatgatgac ttcgaaggag atgcggacat gaacctctgg     840

agttattaat actcgtattt ttaaaattat ttattgtgca ataatttttt atcgaatttc     900

gaattctgcc tttaattttt aatggggatc tttatttgcc aaaaaaaaaa aaa            953


<210> SEQ ID NO 61
<211> LENGTH: 277
<212> TYPE: PRT
<213> ORGANISM: Brassica napus

<400> SEQUENCE: 61

Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Leu Gly
65                  70                  75                  80
```

-continued

Thr Phe Lys Thr Ala Glu Met Ala Ala Arg Ala His Asp Val Ala Ala
                85                  90                  95

Leu Ala Leu Arg Gly Arg Gly Ala Cys Leu Asn Tyr Ala Asp Ser Ala
            100                 105                 110

Ser Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Val
    130                 135                 140

Thr Met Glu Glu Thr Met Ala Val Ala Ser Gln Ala Glu Val Asn Asp
145                 150                 155                 160

Thr Thr Thr Asp His Gly Met Asn Met Glu Glu Ala Thr Ala Val Ala
                165                 170                 175

Ser Gln Ala Glu Val Asn Asp Thr Thr Thr Asp His Gly Val Asp Met
            180                 185                 190

Glu Glu Thr Met Val Glu Ala Val Phe Thr Gly Glu Gln Ser Glu Gly
        195                 200                 205

Phe Asn Met Ala Lys Glu Ser Thr Val Glu Ala Ala Val Val Thr Glu
    210                 215                 220

Glu Pro Ser Lys Gly Ser Tyr Met Asp Glu Glu Trp Met Leu Glu Met
225                 230                 235                 240

Pro Thr Leu Leu Ala Asp Met Ala Glu Gly Met Leu Leu Pro Pro Pro
                245                 250                 255

Ser Val Gln Trp Gly Gln Asn Asp Asp Phe Glu Gly Asp Ala Asp Met
            260                 265                 270

Asn Leu Trp Ser Tyr
        275

<210> SEQ ID NO 62
<211> LENGTH: 889
<212> TYPE: DNA
<213> ORGANISM: Brassica napus

<400> SEQUENCE: 62
ctagtgatta ccgctcgagc aacaatgaac acattccctg cttccactga aatggttggc 60
tccgagaacg agtctccggt tactacggta gcaggaggtg attattatcc catgttggcg 120
gcaagctgtc cgaagaagcc agcgggtagg aagaagtttc aggagacacg tcaccccatt 180
taccgaggag ttcgtctgag aaagtcaggt aagtgggtgt gtgaagtgag ggaaccaaac 240
aagaaatcta gaatttggcc cggaactttc aaaacagctg agatggcagc tcgtgctcac 300
gacgtcgctg ccctagccct ccgtggaaga ggcgcccgcc tcaattatgc ggactcagct 360
tggcggctcc gcatcccgga gacaacctgc cacaaggata tccagaaggc tgctgctgaa 420
gccgcattgg cttttgaggc tgagaaaagt gatgtgacga tgcaaaatgg cctgaacatg 480
gaggagacga cggcggtggc ttctcaggct gaagtgaatg acacgacgac agaacatggc 540
atgaacatgg aggaggcaac ggcagtggct tctcaggctg aggtgaatga cacgacgacg 600
gatcatggcg tagacatgga ggagacaatg gtggaggctg tttttactgg ggaacaaagt 660
gaagggttta acatggcgaa ggagtcgacg gtggaggctg ctgttgttac ggaggaaccg 720
agcaaaggat cttacatgga cgaggagtgg atgctcgaga tgccgacctt gttggctgat 780
atggcggaag ggatgctttt gccgccgccg tccgtacaat ggggacagaa tgatgacttc 840
gaaggagatg cgcacatgaa cctctggagt tattaaggat ccgcgaatc 889

-continued

<210> SEQ ID NO 63
<211> LENGTH: 283
<212> TYPE: PRT
<213> ORGANISM: Brassica napus

<400> SEQUENCE: 63

```
Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Pro Gly
65                  70                  75                  80

Thr Phe Lys Thr Ala Glu Met Ala Ala Arg Ala His Asp Val Ala Ala
                85                  90                  95

Leu Ala Leu Arg Gly Arg Gly Ala Arg Leu Asn Tyr Ala Asp Ser Ala
            100                 105                 110

Trp Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Val
    130                 135                 140

Thr Met Gln Asn Gly Leu Asn Met Glu Glu Thr Thr Ala Val Ala Ser
145                 150                 155                 160

Gln Ala Glu Val Asn Asp Thr Thr Thr Glu His Gly Met Asn Met Glu
                165                 170                 175

Glu Ala Thr Ala Val Ala Ser Gln Ala Glu Val Asn Asp Thr Thr Thr
            180                 185                 190

Asp His Gly Val Asp Met Glu Glu Thr Met Val Glu Ala Val Phe Thr
        195                 200                 205

Gly Glu Gln Ser Glu Gly Phe Asn Met Ala Lys Glu Ser Thr Val Glu
    210                 215                 220

Ala Ala Val Val Thr Glu Glu Pro Ser Lys Gly Ser Tyr Met Asp Glu
225                 230                 235                 240

Glu Trp Met Leu Glu Met Pro Thr Leu Leu Ala Asp Met Ala Glu Gly
                245                 250                 255

Met Leu Leu Pro Pro Pro Ser Val Gln Trp Gly Gln Asn Asp Asp Phe
            260                 265                 270

Glu Gly Asp Ala His Met Asn Leu Trp Ser Tyr
        275                 280
```

<210> SEQ ID NO 64
<211> LENGTH: 563
<212> TYPE: DNA
<213> ORGANISM: Brassica oleracea

<400> SEQUENCE: 64

```
caccctatct accggggagt tcgcctgaga aagtcaggta agtgggtgtg tgaagtgagg      60

gagccaaaca agaaatctag gatttggctt ggaactttca aaaccgcaga gatcgctgct     120

cgtgctcacg acgttgccgc cttagccctc cgtggaagag cggcctgtct caacttcgcc     180

gactcggctt ggcggctccg tatcccggag acaacttgcg ccaaggatat ccagaaggct     240

gctgctgaag ctgcgttggc ttttggggcc gaaaagagtg ataccacgac gaatgatcaa     300
```

-continued

```
ggcatgaaca tggaggagat gacggtggtg gcttctcagg ctgaggtgag cgacacgacg    360

acatatcatg gcctggacat ggaggagact atggtggagg ctgtttttgc tgaggaacag    420

agagaagggt tttacttggc ggaggagacg acggtggagg gtgttgttac ggaggaacag    480

agcaaagggt tttatatgga cgaggagtgg acgttcggga tgcagtcctt tttggccgat    540

atggctgaag gcatgctctt tcc                                            563
```

<210> SEQ ID NO 65
<211> LENGTH: 188
<212> TYPE: PRT
<213> ORGANISM: Brassica oleracea

<400> SEQUENCE: 65

```
His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Ala Ala Cys Leu Asn Phe Ala Asp Ser Ala Trp
    50                  55                  60

Arg Leu Arg Ile Pro Glu Thr Thr Cys Ala Lys Asp Ile Gln Lys Ala
65                  70                  75                  80

Ala Ala Glu Ala Ala Leu Ala Phe Gly Ala Glu Lys Ser Asp Thr Thr
                85                  90                  95

Thr Asn Asp Gln Gly Met Asn Met Glu Glu Met Thr Val Val Ala Ser
            100                 105                 110

Gln Ala Glu Val Ser Asp Thr Thr Thr Tyr His Gly Leu Asp Met Glu
        115                 120                 125

Glu Thr Met Val Glu Ala Val Phe Ala Glu Glu Gln Arg Glu Gly Phe
    130                 135                 140

Tyr Leu Ala Glu Glu Thr Thr Val Glu Gly Val Val Thr Glu Glu Gln
145                 150                 155                 160

Ser Lys Gly Phe Tyr Met Asp Glu Glu Trp Thr Phe Gly Met Gln Ser
                165                 170                 175

Phe Leu Ala Asp Met Ala Glu Gly Met Leu Phe Pro
            180                 185
```

<210> SEQ ID NO 66
<211> LENGTH: 533
<212> TYPE: DNA
<213> ORGANISM: Brassica oleracea

<400> SEQUENCE: 66

```
gaaacataga tctttgtact tactatactt caccttatcc agttttattt ttttatttat     60

aaagagtttt caacaatgac ctcattttct accttttctg aactgttggg ctccgagcat    120

gagtctccgg ttacattagg cgaagagtat tgtccgaagc tggccgcaag ctgtccgaag    180

aaaccagccg gccggaagaa gtttcgagag acgcgtcacc cagtttacag aggagttcgt    240

ctgagaaact caggtaagtg ggtgtgtgaa gtgagggagc caaacaagaa atctaggatt    300

tggctcggta ctttcctaac agccgagatc gcagcccgtg ctcacgacgt cgccgccata    360

gccctccgcg gcaaatcagc ttgtctcaat tttgccgact ccgcttggcg gctccgtatc    420

ccggagacaa catgccccaa ggagattcag aaggcggctg ctgaagccgc ggtggctttt    480

aaggctgaga taaataatac gacggcggat cacggcctcg acatggaaga gac           533
```

-continued

<210> SEQ ID NO 67
<211> LENGTH: 152
<212> TYPE: PRT
<213> ORGANISM: Brassica oleracea

<400> SEQUENCE: 67

```
Met Thr Ser Phe Ser Thr Phe Ser Glu Leu Leu Gly Ser Glu His Glu
 1               5                  10                  15

Ser Pro Val Thr Leu Gly Glu Glu Tyr Cys Pro Lys Leu Ala Ala Ser
            20                  25                  30

Cys Pro Lys Lys Pro Ala Gly Arg Lys Lys Phe Arg Glu Thr Arg His
        35                  40                  45

Pro Val Tyr Arg Gly Val Arg Leu Arg Asn Ser Gly Lys Trp Val Cys
    50                  55                  60

Glu Val Arg Glu Pro Asn Lys Lys Ser Arg Ile Trp Leu Gly Thr Phe
65                  70                  75                  80

Leu Thr Ala Glu Ile Ala Ala Arg Ala His Asp Val Ala Ala Ile Ala
                85                  90                  95

Leu Arg Gly Lys Ser Ala Cys Leu Asn Phe Ala Asp Ser Ala Trp Arg
            100                 105                 110

Leu Arg Ile Pro Glu Thr Thr Cys Pro Lys Glu Ile Gln Lys Ala Ala
        115                 120                 125

Ala Glu Ala Ala Val Ala Phe Lys Ala Glu Ile Asn Asn Thr Thr Ala
    130                 135                 140

Asp His Gly Leu Asp Met Glu Glu
145                 150
```

<210> SEQ ID NO 68
<211> LENGTH: 887
<212> TYPE: DNA
<213> ORGANISM: Brassica oleracea

<400> SEQUENCE: 68

```
actcagcctt atccagtttt tctcaaaaga tttttcaaca atgaacacat tccctgcttc     60
cactgaaatg gttggctccg agaacgagtc tccggttact acggtagtag gaggtgatta    120
ttatcccatg ttggcggcaa gctgtccgaa gaagccagcg ggtaggaaga agtttcagga    180
gacacgtcac cccatttacc gaggagttcg tctgagaaag tcaggtaagt gggtgtgtga    240
agtgagggaa ccaaacaaga aatctagaat ttggcttgga actttcaaaa cagctgagat    300
ggcagctcgt gctcacgacg tggctgccct agccctccgt ggaagaggcg cctgcctcaa    360
ttatgcggac tcggcttggc ggctccgcat cccggagaca acctgccaca aggatatcca    420
gaaggctgct gctgaagccg cattggcttt tgaggctgag aaaagtgatg tgacgatgga    480
ggagacgatg gcggtggctt ctcaggctga agtgaatgac acgacgacag atcatggcat    540
gaacatggag gaggcaacag cggtggcttc tcaggctgag gtgaatgaca cgacgacaga    600
tcatggcgta gacatggagg agacgatggt ggaggctgtt tttacggagg aacaaagtga    660
agggttcaac atggcggagg agtcgacggt ggaggctgct gttgttacgg atgaactgag    720
caaaggattt tacatggacg aggagtggac gtacgagatg ccgaccttgt tggctgatat    780
ggcggcaggg atgcttttgc cgccaccatc tgtacaatgg ggacataatg atgacttgga    840
aggagatgcg gacatgaacc tctggagtta ttaatactcg tatttt                   887
```

<210> SEQ ID NO 69
<211> LENGTH: 277

-continued

<212> TYPE: PRT
<213> ORGANISM: Brassica oleracea

<400> SEQUENCE: 69

Met Asn Thr Phe Pro Ala Ser Thr Glu Met Val Gly Ser Glu Asn Glu
1 5 10 15

Ser Pro Val Thr Thr Val Val Gly Gly Asp Tyr Tyr Pro Met Leu Ala
20 25 30

Ala Ser Cys Pro Lys Lys Pro Ala Gly Arg Lys Lys Phe Gln Glu Thr
35 40 45

Arg His Pro Ile Tyr Arg Gly Val Arg Leu Arg Lys Ser Gly Lys Trp
50 55 60

Val Cys Glu Val Arg Glu Pro Asn Lys Lys Ser Arg Ile Trp Leu Gly
65 70 75 80

Thr Phe Lys Thr Ala Glu Met Ala Ala Arg Ala His Asp Val Ala Ala
85 90 95

Leu Ala Leu Arg Gly Arg Gly Ala Cys Leu Asn Tyr Ala Asp Ser Ala
100 105 110

Trp Arg Leu Arg Ile Pro Glu Thr Thr Cys His Lys Asp Ile Gln Lys
115 120 125

Ala Ala Ala Glu Ala Ala Leu Ala Phe Glu Ala Glu Lys Ser Asp Val
130 135 140

Thr Met Glu Glu Thr Met Ala Val Ala Ser Gln Ala Glu Val Asn Asp
145 150 155 160

Thr Thr Thr Asp His Gly Met Asn Met Glu Glu Ala Thr Ala Val Ala
165 170 175

Ser Gln Ala Glu Val Asn Asp Thr Thr Thr Asp His Gly Val Asp Met
180 185 190

Glu Glu Thr Met Val Glu Ala Val Phe Thr Glu Glu Gln Ser Glu Gly
195 200 205

Phe Asn Met Ala Glu Glu Ser Thr Val Glu Ala Ala Val Val Thr Asp
210 215 220

Glu Leu Ser Lys Gly Phe Tyr Met Asp Glu Glu Trp Thr Tyr Glu Met
225 230 235 240

Pro Thr Leu Leu Ala Asp Met Ala Ala Gly Met Leu Leu Pro Pro Pro
245 250 255

Ser Val Gln Trp Gly His Asn Asp Asp Leu Glu Gly Asp Ala Asp Met
260 265 270

Asn Leu Trp Ser Tyr
275

<210> SEQ ID NO 70
<211> LENGTH: 950
<212> TYPE: DNA
<213> ORGANISM: Brassica oleracea

<400> SEQUENCE: 70
ctgaaaagaa gataaaagag agagaaataa atatcttatc aaaccagaca gaacagagat 60
cttgttactt actatactac actcagcctt atccagtttt tcaaaagaag ttttcaacta 120
tgaactcagt ctctactttt tctgaacttc ttggctctga gaacgagtct ccggtaggtg 180
gtgattactg tcccatgttg gcggcgagct gtccgaagaa gccggcgggt aggaagaagt 240
ttcgggagac acgtcacccc atttaccgag gagttcgcct tagaaaatca ggtaagtggg 300
tgtgtgaagt gagggaacca aacaaaaaat ctaggatttg gctcggaact ttcaaaacag 360

-continued

```
ctgagatcgc agctcgtgct cacgacgtcg ccgccttagc tctccgtgga agaggcgcct    420

gcctcaactt cgccgactcg gcttggcggc tccgtatccc ggagacaacc tgcgccaagg    480

atatccagaa ggctgctgct gaagccgcat tggcttttga ggccgagaag agtgatacca    540

cgacgaatga tcatggcatg aacatggctt ctcaggctga ggttaatgac acgacggatc    600

atggcctgga catggaggag acgatggtgg aggctgtttt tactgaggag cagagagacg    660

ggttttacat ggcggaggag acgacggtgg agggtgttgt tccggaggaa cagatgagca    720

aagggtttta catggacgag gagtggatgt tcgggatgcc gaccttgttg gctgatatgg    780

cggcagggat gctcttaccg ccgccgtccg tacaatgggg acataatgat gacttcgaag    840

gagatgctga catgaacctc tggaattatt agtactcgta tttttttaaa ttatttttttg    900

aacgaataat attttattga attcggattc tacctgtttt tttaatggat              950
```

<210> SEQ ID NO 71
<211> LENGTH: 250
<212> TYPE: PRT
<213> ORGANISM: Brassica oleracea

<400> SEQUENCE: 71

```
Met Asn Ser Val Ser Thr Phe Ser Glu Leu Leu Gly Ser Glu Asn Glu
 1               5                  10                  15

Ser Pro Val Gly Gly Asp Tyr Cys Pro Met Leu Ala Ala Ser Cys Pro
            20                  25                  30

Lys Lys Pro Ala Gly Arg Lys Lys Phe Arg Glu Thr Arg His Pro Ile
        35                  40                  45

Tyr Arg Gly Val Arg Leu Arg Lys Ser Gly Lys Trp Val Cys Glu Val
    50                  55                  60

Arg Glu Pro Asn Lys Lys Ser Arg Ile Trp Leu Gly Thr Phe Lys Thr
65                  70                  75                  80

Ala Glu Ile Ala Ala Arg Ala His Asp Val Ala Ala Leu Ala Leu Arg
                85                  90                  95

Gly Arg Gly Ala Cys Leu Asn Phe Ala Asp Ser Ala Trp Arg Leu Arg
            100                 105                 110

Ile Pro Glu Thr Thr Cys Ala Lys Asp Ile Gln Lys Ala Ala Ala Glu
        115                 120                 125

Ala Ala Leu Ala Phe Glu Ala Glu Lys Ser Asp Thr Thr Thr Asn Asp
    130                 135                 140

His Gly Met Asn Met Ala Ser Gln Ala Glu Val Asn Asp Thr Thr Asp
145                 150                 155                 160

His Gly Leu Asp Met Glu Glu Thr Met Val Glu Ala Val Phe Thr Glu
                165                 170                 175

Glu Gln Arg Asp Gly Phe Tyr Met Ala Glu Glu Thr Thr Val Glu Gly
            180                 185                 190

Val Val Pro Glu Glu Gln Met Ser Lys Gly Phe Tyr Met Asp Glu Glu
        195                 200                 205

Trp Met Phe Gly Met Pro Thr Leu Leu Ala Asp Met Ala Ala Gly Met
    210                 215                 220

Leu Leu Pro Pro Pro Ser Val Gln Trp Gly His Asn Asp Asp Phe Glu
225                 230                 235                 240

Gly Asp Ala Asp Met Asn Leu Trp Asn Tyr
                245                 250
```

<210> SEQ ID NO 72
<211> LENGTH: 877

-continued

<212> TYPE: DNA
<213> ORGANISM: Brassica oleracea

<400> SEQUENCE: 72

```
accgctcgag caacaatgaa cacattccct gcttccactg aaatggttag ctccgagaac     60

gagtctccgg ttactacggt agtaggaggt gattattatc ccatgttggc ggcaagctgt    120

ccgaagaagc cagcgggtag gaagaagttt caggagacac gtcaccccat ttaccgagga    180

gttcgtctga gaaagtcagg taagtgggtg tgtgaagtga gggaactaaa caagaaatct    240

agaatttggc ttggaacttt caaaacagct gagatggcag ctcgtgctca cgacgtggct    300

gccctagccc tccgtggaag aggcgcctgc ctcaattatg cggactcggc ttggcggctc    360

cgcatcccgg agacaacctg ccacaaggat atccagaagg ctgctgctga agccgcattg    420

gcttttgagg ctgagaagag tgatgcgacg atgcaaaatg gcctgaacat ggaggagacg    480

acggcggcgg cttctcagac tgaagtgagt gacacgacga cagatcatgg catgaacatg    540

gaggagacaa cggcggtggc ttctcaggct gaggtgaatg acacgacgac agatcatggc    600

gtagacatgg aggagacgat ggtggaggct gtttttactg aggaacaaag tgaagggttc    660

aacatggcga aggagtcgac ggcggaggct gctgttgtta cggaggaact gagcaaagga    720

gtttacatgg acgaggagtg gacgtacgag atgccgacct tgttggctga tatggcggca    780

gggatgcttt tgccgccacc atctgtacaa tggggacata atgatgactt ggaaggagat    840

gcggacatga acctactgga gttattaagg atccgcg                             877
```

<210> SEQ ID NO 73
<211> LENGTH: 287
<212> TYPE: PRT
<213> ORGANISM: Brassica oleracea

<400> SEQUENCE: 73

```
Met Asn Thr Phe Pro Ala Ser Thr Glu Met Val Ser Ser Glu Asn Glu
 1               5                  10                  15

Ser Pro Val Thr Thr Val Val Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Leu Asn Lys Lys Ser Arg Ile Trp Leu Gly
65                  70                  75                  80

Thr Phe Lys Thr Ala Glu Met Ala Ala Arg Ala His Asp Val Ala Ala
                85                  90                  95

Leu Ala Leu Arg Gly Arg Gly Ala Cys Leu Asn Tyr Ala Asp Ser Ala
            100                 105                 110

Trp Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Ala
    130                 135                 140

Thr Met Gln Asn Gly Leu Asn Met Glu Glu Thr Thr Ala Ala Ala Ser
145                 150                 155                 160

Gln Thr Glu Val Ser Asp Thr Thr Thr Asp His Gly Met Asn Met Glu
                165                 170                 175

Glu Thr Thr Ala Val Ala Ser Gln Ala Glu Val Asn Asp Thr Thr Thr
            180                 185                 190
```

-continued

```
Asp His Gly Val Asp Met Glu Glu Thr Met Val Glu Ala Val Phe Thr
        195                 200                 205

Glu Glu Gln Ser Glu Gly Phe Asn Met Ala Lys Glu Ser Thr Ala Glu
    210                 215                 220

Ala Ala Val Val Thr Glu Glu Leu Ser Lys Gly Val Tyr Met Asp Glu
225                 230                 235                 240

Glu Trp Thr Tyr Glu Met Pro Thr Leu Leu Ala Asp Met Ala Ala Gly
                245                 250                 255

Met Leu Leu Pro Pro Pro Ser Val Gln Trp Gly His Asn Asp Asp Leu
            260                 265                 270

Glu Gly Asp Ala Asp Met Asn Leu Leu Glu Leu Leu Arg Ile Arg
        275                 280                 285


<210> SEQ ID NO 74
<211> LENGTH: 374
<212> TYPE: DNA
<213> ORGANISM: Brassica rapa

<400> SEQUENCE: 74

catcccattt acagggggt tcgtttaaga aagtcaggta agtgggtgtg tgaagtgagg      60

gaaccaaaca agaaatctag gatttggctc ggaactttca aaaccgctga gatcgctgct     120

cgtgctcacg acgttgctgc cttagccctc cgcgggagag gcgcctgcct caacttcgcc     180

gactcggctt ggcggctccg tatcccggag acaacctgcg ccaaggacat ccagaaggcg     240

gctgctgaag ctgcattggc ttttgaggcc gagaagagtg atcatggcat gaacatcaag     300

aatactacgg cggtggtttc tcaggttgag gtgaatgaca cgacgacgga ccacggcttg     360

gacatggagg agac                                                       374


<210> SEQ ID NO 75
<211> LENGTH: 124
<212> TYPE: PRT
<213> ORGANISM: Brassica rapa

<400> SEQUENCE: 75

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Gly Ala Cys Leu Asn Phe Ala Asp Ser Ala Trp
    50                  55                  60

Arg Leu Arg Ile Pro Glu Thr Thr Cys Ala Lys Asp Ile Gln Lys Ala
65                  70                  75                  80

Ala Ala Glu Ala Ala Leu Ala Phe Glu Ala Glu Lys Ser Asp His Gly
                85                  90                  95

Met Asn Ile Lys Asn Thr Thr Ala Val Val Ser Gln Val Glu Val Asn
            100                 105                 110

Asp Thr Thr Thr Asp His Gly Leu Asp Met Glu Glu
        115                 120


<210> SEQ ID NO 76
<211> LENGTH: 884
<212> TYPE: DNA
<213> ORGANISM: Brassica rapa
```

-continued

<400> SEQUENCE: 76

```
tacactcagc cttatccagt ttttttcaaa agacttttca acaatgaaca cattccctgc     60

gtccactgaa atggttggct ccgagaacga gtctccggtt actacggtag caggaggtga    120

ttattatccc atgttggcgg caagctgtcc gaagaagcca gcgggtagga agaagtttca    180

ggagacacgt caccccattt accgaggagt tcgtctgaga aagtcaggta agtgggtgtg    240

tgaagtgagg gaaccaaaca agaaatctag aatttggctt ggaactttca aaacagctga    300

gatggcagct cgtgctcacg acgtcgctgc cctagccctc cgtggaagag gcgcctgcct    360

caattatgcg gactcggctt ggcggctccg catcccggag acaacctgcc acaaggatat    420

ccagaaggct gctgctgaag ccgcattggc ttttgaggct gagaaaagtg atgtgacgat    480

gcaaaatggc ctgaacatgg aggagatgac ggcggtggct tctcaggctg aagtgaatga    540

cacgacgaca gaacatggca tgaacatgga ggaggcaacg gcagtggctt ctcaggctga    600

ggtgaatgac acgacgacgg atcatggcgt agacatggag gagacaatgg tggaggctgt    660

ttttactgag gaacaaagtg aagggtttaa catggcgaag gagtcgacgg tggaggctgc    720

tgttgttacg gaggaaccga gcaaaggatc ttacatggac gaggagtgga tgctcgagat    780

gccgaccttg ttggctgata tggcggaagg gatgcttttg ccgccgccgt ccgtacaatg    840

gggacagaat gatgacttcg aaggagatgc tgacatgaac ctct                    884
```

<210> SEQ ID NO 77
<211> LENGTH: 280
<212> TYPE: PRT
<213> ORGANISM: Brassica rapa

<400> SEQUENCE: 77

```
Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Leu Gly
65                  70                  75                  80

Thr Phe Lys Thr Ala Glu Met Ala Ala Arg Ala His Asp Val Ala Ala
                85                  90                  95

Leu Ala Leu Arg Gly Arg Gly Ala Cys Leu Asn Tyr Ala Asp Ser Ala
            100                 105                 110

Trp Arg Leu Arg Ile Pro Glu Thr Thr Cys His Lys Asp Ile Gln Lys
        115                 120                 125

Ala Ala Ala Glu Ala Ala Leu Ala Phe Glu Ala Glu Lys Ser Asp Val
    130                 135                 140

Thr Met Gln Asn Gly Leu Asn Met Glu Glu Met Thr Ala Val Ala Ser
145                 150                 155                 160

Gln Ala Glu Val Asn Asp Thr Thr Thr Glu His Gly Met Asn Met Glu
                165                 170                 175

Glu Ala Thr Ala Val Ala Ser Gln Ala Glu Val Asn Asp Thr Thr Thr
            180                 185                 190

Asp His Gly Val Asp Met Glu Glu Thr Met Val Glu Ala Val Phe Thr
        195                 200                 205
```

-continued

```
Glu Glu Gln Ser Glu Gly Phe Asn Met Ala Lys Glu Ser Thr Val Glu
    210                 215                 220

Ala Ala Val Val Thr Glu Glu Pro Ser Lys Gly Ser Tyr Met Asp Glu
225                 230                 235                 240

Glu Trp Met Leu Glu Met Pro Thr Leu Leu Ala Asp Met Ala Glu Gly
                245                 250                 255

Met Leu Leu Pro Pro Pro Ser Val Gln Trp Gly Gln Asn Asp Asp Phe
            260                 265                 270

Glu Gly Asp Ala Asp Met Asn Leu
        275                 280


<210> SEQ ID NO 78
<211> LENGTH: 806
<212> TYPE: DNA
<213> ORGANISM: Brassica rapa

<400> SEQUENCE: 78

acactcagcc ttatccagtt ttcaaaaaaa gtattcaacg atgaactcag tctctacttt     60

ttctgaactg ctctgctccg agaacgagtc tccggttaat acggaaggtg gtgattacat    120

tttggcggcg agctgtccca agaaacctgc tggtaggaag aagtttcagg agacacgcca    180

ccccatttac agaggagttc gtctgaggaa gtcaggtaag tgggtgtgtg aagtgaggga    240

accaaacaag aaatctagaa tttggctcgg aactttcaaa acagctgaga tcgcagctcg    300

tgctcacgac gttgccgcct tagctctccg tggaagaggc gcctgcctca acttcgccga    360

ctcggcttgg cggctccgta tcccggagac gacctgcgcc aaggatatcc agaaggctgc    420

tgctgaagcc gcattggctt ttgaggccga gaagagtgat accacgacga atgatcgtgg    480

catgaacatg gaggagacgt cggcggtggc ttctccggct gagttgaatg atacgacggc    540

ggatcatggc ctggacatgg aggagacgat ggtggaggct gtttttaggg aggaacagag    600

agaagggttt tacatggcgg aggagacgac ggtggagggt gttgttccgg agtaacagat    660

gagcaaaggg ttttacatgg acgaggagtg gacgttcgag atgccgaggt tgttggctga    720

tatggcggaa gggatgcttt tgccgccccc gtccgtacaa tggggacata acgatgactt    780

cgaaggagat gctgacatga acctct                                         806


<210> SEQ ID NO 79
<211> LENGTH: 204
<212> TYPE: PRT
<213> ORGANISM: Brassica rapa

<400> SEQUENCE: 79

Met Asn Ser Val Ser Thr Phe Ser Glu Leu Leu Cys Ser Glu Asn Glu
 1               5                  10                  15

Ser Pro Val Asn Thr Glu Gly Gly Asp Tyr Ile Leu Ala Ala Ser Cys
            20                  25                  30

Pro Lys Lys Pro Ala Gly Arg Lys Lys Phe Gln Glu Thr Arg His Pro
        35                  40                  45

Ile Tyr Arg Gly Val Arg Leu Arg Lys Ser Gly Lys Trp Val Cys Glu
    50                  55                  60

Val Arg Glu Pro Asn Lys Lys Ser Arg Ile Trp Leu Gly Thr Phe Lys
65                  70                  75                  80

Thr Ala Glu Ile Ala Ala Arg Ala His Asp Val Ala Ala Leu Ala Leu
                85                  90                  95

Arg Gly Arg Gly Ala Cys Leu Asn Phe Ala Asp Ser Ala Trp Arg Leu
            100                 105                 110
```

-continued

```
Arg Ile Pro Glu Thr Thr Cys Ala Lys Asp Ile Gln Lys Ala Ala Ala
        115                 120                 125

Glu Ala Ala Leu Ala Phe Glu Ala Glu Lys Ser Asp Thr Thr Thr Asn
    130                 135                 140

Asp Arg Gly Met Asn Met Glu Glu Thr Ser Ala Val Ala Ser Pro Ala
145                 150                 155                 160

Glu Leu Asn Asp Thr Thr Ala Asp His Gly Leu Asp Met Glu Glu Thr
                165                 170                 175

Met Val Glu Ala Val Phe Arg Glu Glu Gln Arg Glu Gly Phe Tyr Met
            180                 185                 190

Ala Glu Glu Thr Thr Val Glu Gly Val Val Pro Glu
        195                 200


<210> SEQ ID NO 80
<211> LENGTH: 755
<212> TYPE: DNA
<213> ORGANISM: Brassica rapa

<400> SEQUENCE: 80

accgctcgag tacttactat actacactca gccttatcca gtttttcttc caacgatgga      60

ctcaatctct acttttcctg aactgcttgg ctcagagaac gagtctccgg ttactacggt     120

agtaggaggt gattattgtc ccaggttggc ggcaagctgt ccgaagaagc cagcgggtag     180

gaagaagttt caggagacac gtcaccccat ttaccgtgga gttcgtttaa gaaagtccgg     240

taagtgggtg tgtgaagtga gggaaccaaa caagaaatct aggatttggc tcggaacttt     300

caaaaccgct gagatcgctg ctcgtgctca cgacgttgct gccttagccc tccgcggaag     360

aggcgcctgc ctcaacttcg ccgactcggc ttgacggctc cgtatcccgg agacaacctg     420

cgccaaggat atccagaagg ctgctgctga agctgcattg gcttttgagg ccgagaagag     480

tgatcatggc atgaacatga agaatactac ggcggtggct tctcaggttg aggtgaatga     540

tacgacgacg gaccatggcg tggacatgga ggagacgagg gtggagggtg ttgttacgga     600

ggaacagaac aattggtttt acatggacga ggagtggatg tttgggatgc cgacgttgtt     660

ggttgatatg gcggaaggga tgcttatacc gcggcagtcc gtacaatcgg gacactacga     720

tgacttcgaa ggagatgctg acatgaacct ctgga                                755


<210> SEQ ID NO 81
<211> LENGTH: 112
<212> TYPE: PRT
<213> ORGANISM: Brassica rapa

<400> SEQUENCE: 81

Met Asp Ser Ile Ser Thr Phe Pro Glu Leu Leu Gly Ser Glu Asn Glu
 1               5                  10                  15

Ser Pro Val Thr Thr Val Val Gly Gly Asp Tyr Cys Pro Arg Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Leu Gly
65                  70                  75                  80

Thr Phe Lys Thr Ala Glu Ile Ala Ala Arg Ala His Asp Val Ala Ala
                85                  90                  95
```

-continued

```
Leu Ala Leu Arg Gly Arg Gly Ala Cys Leu Asn Phe Ala Asp Ser Ala
            100                 105                 110


<210> SEQ ID NO 82
<211> LENGTH: 832
<212> TYPE: DNA
<213> ORGANISM: Brassica rapa

<400> SEQUENCE: 82

accgctcgag tacttactat actacactca gccttatcca gtttttcttc caacgatgga      60

ctcaatctct acttttcctg aactgcttgg ctcagagaac gagtctccgg ttactacggt     120

agtaggaggt gattattgtc ccaggttggc ggcaagctgt ccgaagaagc cagcgggtag     180

gaagaagttt caggagacac gtcaccccat ttaccgtgga gttcgtttaa gaaagtccgg     240

taagtgggtg tgtgaagtga gggaaccaaa caagaaatct aggatttggc tcggaacttt     300

caaaaccgct gagatcgctg ctcgtgctca cgacgttgct gccttagccc tccgcggaag     360

aggcgcctgc ctcaacttcg ccgactcggc ttggcggctc cgtatcccgg agacaacctg     420

cgccaaggat atccagaagg ctgctgctga agctgctttg gcttttgagg ccgagaagag     480

tgatcatggc atgaacatga agaatactac ggcggtggct tctcaggttg aggtgaatga     540

tacgacgacg gaccatggcg tggacatgga ggagacgttg gtggaggctg tttttacgga     600

ggaacagaga gaagggtttt acatgacgga ggagacgagg gtggagggtg ttgttacgga     660

ggaacagaac aattggtttt acatggacga ggagtggatg tttgggatgc cgacgttgtt     720

ggttgatatg gcggaaggga tgcttatacc gcggcagtcc gtacaatcgg gacactacga     780

tgacttcgaa ggagatgctg acatgaacct ctggaattat tagggatccg cg             832


<210> SEQ ID NO 83
<211> LENGTH: 255
<212> TYPE: PRT
<213> ORGANISM: Brassica rapa

<400> SEQUENCE: 83

Met Asp Ser Ile Ser Thr Phe Pro Glu Leu Leu Gly Ser Glu Asn Glu
1               5                   10                  15

Ser Pro Val Thr Thr Val Val Gly Gly Asp Tyr Cys Pro Arg Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Leu Gly
65                  70                  75                  80

Thr Phe Lys Thr Ala Glu Ile Ala Ala Arg Ala His Asp Val Ala Ala
                85                  90                  95

Leu Ala Leu Arg Gly Arg Gly Ala Cys Leu Asn Phe Ala Asp Ser Ala
            100                 105                 110

Trp Arg Leu Arg Ile Pro Glu Thr Thr Cys Ala Lys Asp Ile Gln Lys
        115                 120                 125

Ala Ala Ala Glu Ala Ala Leu Ala Phe Glu Ala Glu Lys Ser Asp His
    130                 135                 140

Gly Met Asn Met Lys Asn Thr Thr Ala Val Ala Ser Gln Val Glu Val
145                 150                 155                 160

Asn Asp Thr Thr Thr Asp His Gly Val Asp Met Glu Glu Thr Leu Val
                165                 170                 175
```

-continued

Glu Ala Val Phe Thr Glu Glu Gln Arg Glu Gly Phe Tyr Met Thr Glu
180 185 190

Glu Thr Arg Val Glu Gly Val Val Thr Glu Glu Gln Asn Asn Trp Phe
195 200 205

Tyr Met Asp Glu Glu Trp Met Phe Gly Met Pro Thr Leu Leu Val Asp
210 215 220

Met Ala Glu Gly Met Leu Ile Pro Arg Gln Ser Val Gln Ser Gly His
225 230 235 240

Tyr Asp Asp Phe Glu Gly Asp Ala Asp Met Asn Leu Trp Asn Tyr
245 250 255

<210> SEQ ID NO 84
<211> LENGTH: 830
<212> TYPE: DNA
<213> ORGANISM: Brassica rapa

<400> SEQUENCE: 84
tactacactc agccttatcc agttttcaaa aaaagtattc aactatgaac tcagtctcta 60
ctttttctga actgctctgc tccgagaaca agtctccggt taatacggaa ggtggtgatt 120
acattttggc ggcgagctgt cccaagaaac ctgctggtag gaagaagttt caggagacac 180
gccaccccat ttacagagga gttcgcctaa gaaagtcagg taagtgggtg tgtgaagtga 240
gggaaccaaa caagaaatct agaatttggc tcggaacttt caaaacagct gagatagcag 300
ctcgtgctca cgacgtcgcc gccttagctc tccgtggaag aggcgcctgc ctcaacttcg 360
ccgactcggc ttggcggctc cgtatcccag agacaacctg cgccaaggat atccagaagg 420
ctgctgctga agccgcattg gcttttgagg ccgagaagag tgataccacg acgaatgatc 480
gtggcatgaa catggaggag acgtccgcgg tggcttctcc ggctgagttg aatgatacga 540
cggcggatca tggcctggac atggaggaga cgatggtgga ggctgttttt agggacgaac 600
agagagaagg gttttacatg gcggaggaga cgacggtgga gggtgttgtt ccggaggaac 660
agatgagcaa agggttttac atggacgagg agtggacgtt cgagatgccg aggttgttgg 720
ctgatatggc ggaagggatg cttctgcctc ccccgtccgt acaatgggga cataacgatg 780
acttcgaagg agatgctgac atgaacctct ggaattatta gggatccgcg 830

<210> SEQ ID NO 85
<211> LENGTH: 258
<212> TYPE: PRT
<213> ORGANISM: Brassica rapa

<400> SEQUENCE: 85

Met Asn Ser Val Ser Thr Phe Ser Glu Leu Leu Cys Ser Glu Asn Lys
1 5 10 15

Ser Pro Val Asn Thr Glu Gly Gly Asp Tyr Ile Leu Ala Ala Ser Cys
20 25 30

Pro Lys Lys Pro Ala Gly Arg Lys Lys Phe Gln Glu Thr Arg His Pro
35 40 45

Ile Tyr Arg Gly Val Arg Leu Arg Lys Ser Gly Lys Trp Val Cys Glu
50 55 60

Val Arg Glu Pro Asn Lys Lys Ser Arg Ile Trp Leu Gly Thr Phe Lys
65 70 75 80

Thr Ala Glu Ile Ala Ala Arg Ala His Asp Val Ala Ala Leu Ala Leu
85 90 95

Arg Gly Arg Gly Ala Cys Leu Asn Phe Ala Asp Ser Ala Trp Arg Leu
100 105 110

-continued

Arg Ile Pro Glu Thr Thr Cys Ala Lys Asp Ile Gln Lys Ala Ala Ala
115 120 125

Glu Ala Ala Leu Ala Phe Glu Ala Glu Lys Ser Asp Thr Thr Thr Asn
130 135 140

Asp Arg Gly Met Asn Met Glu Glu Thr Ser Ala Val Ala Ser Pro Ala
145 150 155 160

Glu Leu Asn Asp Thr Thr Ala Asp His Gly Leu Asp Met Glu Glu Thr
165 170 175

Met Val Glu Ala Val Phe Arg Asp Glu Gln Arg Glu Gly Phe Tyr Met
180 185 190

Ala Glu Glu Thr Thr Val Glu Gly Val Val Pro Glu Glu Gln Met Ser
195 200 205

Lys Gly Phe Tyr Met Asp Glu Glu Trp Thr Phe Glu Met Pro Arg Leu
210 215 220

Leu Ala Asp Met Ala Glu Gly Met Leu Leu Pro Pro Pro Ser Val Gln
225 230 235 240

Trp Gly His Asn Asp Asp Phe Glu Gly Asp Ala Asp Met Asn Leu Trp
245 250 255

Asn Tyr

<210> SEQ ID NO 86
<211> LENGTH: 854
<212> TYPE: DNA
<213> ORGANISM: Brassica rapa

<400> SEQUENCE: 86
ctatactaca cacagcctta tccagccgct cgagtactta ctatactaca ctcagccttt 60
tccagttttt caaaagaagt tttcaacgat gaactcagtc tctactcttt ctgaagttct 120
tggctcccag aacgagtctc ccgtaggtgg tgattactgt cccatgttgg cggcgagctg 180
tccgaagaag ccggcgggta ggaagaagtt tcgggagaca cgtcacccca tttacagagg 240
agttcgtctt agaaagtcag gtaagtgggt gtgtgaagtg agggaaccaa acaagaaatc 300
taggatttgg ctcggaactt tcaaaacagc tgagatcgca gctcgtgctc acgacgttgc 360
cgccttagct ctccgtggaa gaggcgcctg cctcaacttc gccgactcgg cttggcggct 420
ccgtatcccg gagacaacct gcgccaagga tatccagaag gctgctgctg aagccgcatt 480
ggcttttgag gcggagaaga gtgataccac gacgacgaat gatcatggca tgaacatggc 540
ttctcaggtt gaggttaatg acacgacgga tcatgacctg gacatggagg agacgatggt 600
ggaggctgtt tttagggagg aacagagaga agggttttac atggcggagg agacgacggt 660
ggagggtatt gttccggagg aacagatgag caaagggttt tacatggacg aggagtggat 720
gttcgggatg ccgaccttgt tggctgatat ggcggcaggg atgctcttac cgccgccgtc 780
cgtacaatgg ggacataatg atgacttcga aggagatgct gacatgaacc tctggaatta 840
ttaagggatc cgcg 854

<210> SEQ ID NO 87
<211> LENGTH: 251
<212> TYPE: PRT
<213> ORGANISM: Brassica rapa

<400> SEQUENCE: 87

Met Asn Ser Val Ser Thr Leu Ser Glu Val Leu Gly Ser Gln Asn Glu
1 5 10 15

-continued

```
Ser Pro Val Gly Gly Asp Tyr Cys Pro Met Leu Ala Ala Ser Cys Pro
            20                  25                  30

Lys Lys Pro Ala Gly Arg Lys Lys Phe Arg Glu Thr Arg His Pro Ile
        35                  40                  45

Tyr Arg Gly Val Arg Leu Arg Lys Ser Gly Lys Trp Val Cys Glu Val
    50                  55                  60

Arg Glu Pro Asn Lys Lys Ser Arg Ile Trp Leu Gly Thr Phe Lys Thr
65                  70                  75                  80

Ala Glu Ile Ala Ala Arg Ala His Asp Val Ala Ala Leu Ala Leu Arg
                85                  90                  95

Gly Arg Gly Ala Cys Leu Asn Phe Ala Asp Ser Ala Trp Arg Leu Arg
            100                 105                 110

Ile Pro Glu Thr Thr Cys Ala Lys Asp Ile Gln Lys Ala Ala Ala Glu
        115                 120                 125

Ala Ala Leu Ala Phe Glu Ala Glu Lys Ser Asp Thr Thr Thr Thr Asn
    130                 135                 140

Asp His Gly Met Asn Met Ala Ser Gln Val Glu Val Asn Asp Thr Thr
145                 150                 155                 160

Asp His Asp Leu Asp Met Glu Glu Thr Met Val Glu Ala Val Phe Arg
                165                 170                 175

Glu Glu Gln Arg Glu Gly Phe Tyr Met Ala Glu Glu Thr Thr Val Glu
            180                 185                 190

Gly Ile Val Pro Glu Glu Gln Met Ser Lys Gly Phe Tyr Met Asp Glu
        195                 200                 205

Glu Trp Met Phe Gly Met Pro Thr Leu Leu Ala Asp Met Ala Ala Gly
    210                 215                 220

Met Leu Leu Pro Pro Pro Ser Val Gln Trp Gly His Asn Asp Asp Phe
225                 230                 235                 240

Glu Gly Asp Ala Asp Met Asn Leu Trp Asn Tyr
                245                 250
```

<210> SEQ ID NO 88
<211> LENGTH: 738
<212> TYPE: DNA
<213> ORGANISM: Glycine max

<400> SEQUENCE: 88

```
catccgattt atagtggcgt gaggaggagg aacacggata agtgggtaag tgaggtgagg      60

gagcccaaca aaaagaccag gatttggctg gggacttttc ccacgccgga gatggcggca     120

cgggcccacg acgtggcggc aatggccctg aggggccggt atgcctgtct caacttcgct     180

gactcgacgt ggcggttacc aattcccgcc actgctaacg caaaggatat acagaaagca     240

gcagcagagg ctgccgaggc tttcagacca agtcagacct tagaaaatac gaatacaaag     300

caagagtgtg taaaagtggt gacgacaaca acgatcacag aacaaaaacg aggaatgttt     360

tatacggagg aagaagagca agtgttagat atgcctgagt tgcttaggaa tatggtgctt     420

atgtccccaa cacattgcat agggtatgag tatgaagatg ctgacttgga tgctcaagat     480

gctgaggtgt ccctatggag tttctcaatt taataacgtg cttttggttt ggttttttat     540

gttagttttg gagtgtgact gtctgtactg gttttttatt agtagtacgg atactagcta     600

taggtggcag attgaaaggg accaaaagga attttctttt gaaacccttt ttgtcaaagt     660

aatcaatcgc gtatcatcaa gtgaatccct tgatcaagtt tatgtatgaa ttaaataaaa     720

gaagaatcta gttttggt                                                   738
```

-continued

<210> SEQ ID NO 89
<211> LENGTH: 170
<212> TYPE: PRT
<213> ORGANISM: Glycine max

<400> SEQUENCE: 89

```
His Pro Ile Tyr Ser Gly Val Arg Arg Arg Asn Thr Asp Lys Trp Val
 1               5                  10                  15

Ser Glu Val Arg Glu Pro Asn Lys Lys Thr Arg Ile Trp Leu Gly Thr
            20                  25                  30

Phe Pro Thr Pro Glu Met Ala Ala Arg Ala His Asp Val Ala Ala Met
        35                  40                  45

Ala Leu Arg Gly Arg Tyr Ala Cys Leu Asn Phe Ala Asp Ser Thr Trp
    50                  55                  60

Arg Leu Pro Ile Pro Ala Thr Ala Asn Ala Lys Asp Ile Gln Lys Ala
65                  70                  75                  80

Ala Ala Glu Ala Ala Glu Ala Phe Arg Pro Ser Gln Thr Leu Glu Asn
                85                  90                  95

Thr Asn Thr Lys Gln Glu Cys Val Lys Val Val Thr Thr Thr Thr Ile
            100                 105                 110

Thr Glu Gln Lys Arg Gly Met Phe Tyr Thr Glu Glu Glu Glu Gln Val
        115                 120                 125

Leu Asp Met Pro Glu Leu Leu Arg Asn Met Val Leu Met Ser Pro Thr
    130                 135                 140

His Cys Ile Gly Tyr Glu Tyr Glu Asp Ala Asp Leu Asp Ala Gln Asp
145                 150                 155                 160

Ala Glu Val Ser Leu Trp Ser Phe Ser Ile
                165                 170
```

<210> SEQ ID NO 90
<211> LENGTH: 793
<212> TYPE: DNA
<213> ORGANISM: Raphanus sativus

<400> SEQUENCE: 90

```
actacactca gccttatcca gtttttcttc caacgatgga ctcaatctct acttttttctg     60

aactgcttgg ctccgagaac gagtctccgg ttactacggt agtaggaggt gattattttc    120

ccaggttggc ggcaagctgt ccgaagaagc cagcgggtag gaagaagttt caggagacac    180

gtcaccccat ttaccgcgga gttcgtttaa gaaagtcagg taagtgggtg tgtgaagtga    240

gggaaccaaa caagaaatct aggatttggc tcggaacttt caaaaccgct gagatcgctg    300

ctcgtgctca cgacgttgct gccttagccc tccgcggaag aggcgcctgc ctcaacttcg    360

ccgactcggc ttggcggctc cgtatcccgg agacaacctg cgccaaggat atccagaagg    420

ctgctgctga agctgcattg gcttttgagg ccgagaagag tgatcatggc atgaacatga    480

agaatactac ggcggtggct tctcaggttg aggtgaatga cacgacgacg gaccatggcg    540

tggacatgga ggagacgttg gtggaggctg tttttacgga ggaacagaga gaagggtttt    600

acatgacgga ggagacgagg gtggagggtg ttgttacgga ggaacagaac aattggtttt    660

acatggacga ggagtggatg tttgggatgc cgacgttgtt ggttgatatg gcggaaggga    720

tgcttttacc gcggccgtcc gtacaatcgg gacactacga tgacttcgaa ggagatgctg    780

acatgaacct ctg                                                        793
```

-continued

<210> SEQ ID NO 91
<211> LENGTH: 252
<212> TYPE: PRT
<213> ORGANISM: Raphanus sativus

<400> SEQUENCE: 91

```
Met Asp Ser Ile Ser Thr Phe Ser Glu Leu Leu Gly Ser Glu Asn Glu
 1               5                  10                  15

Ser Pro Val Thr Thr Val Val Gly Gly Asp Tyr Phe Pro Arg Leu Ala
            20                  25                  30

Ala Ser Cys Pro Lys Lys Pro Ala Gly Arg Lys Lys Phe Gln Glu Thr
        35                  40                  45

Arg His Pro Ile Tyr Arg Gly Val Arg Leu Arg Lys Ser Gly Lys Trp
    50                  55                  60

Val Cys Glu Val Arg Glu Pro Asn Lys Lys Ser Arg Ile Trp Leu Gly
65                  70                  75                  80

Thr Phe Lys Thr Ala Glu Ile Ala Ala Arg Ala His Asp Val Ala Ala
                85                  90                  95

Leu Ala Leu Arg Gly Arg Gly Ala Cys Leu Asn Phe Ala Asp Ser Ala
            100                 105                 110

Trp Arg Leu Arg Ile Pro Glu Thr Thr Cys Ala Lys Asp Ile Gln Lys
        115                 120                 125

Ala Ala Ala Glu Ala Ala Leu Ala Phe Glu Ala Glu Lys Ser Asp His
    130                 135                 140

Gly Met Asn Met Lys Asn Thr Thr Ala Val Ala Ser Gln Val Glu Val
145                 150                 155                 160

Asn Asp Thr Thr Thr Asp His Gly Val Asp Met Glu Glu Thr Leu Val
                165                 170                 175

Glu Ala Val Phe Thr Glu Glu Gln Arg Glu Gly Phe Tyr Met Thr Glu
            180                 185                 190

Glu Thr Arg Val Glu Gly Val Val Thr Glu Glu Gln Asn Asn Trp Phe
        195                 200                 205

Tyr Met Asp Glu Glu Trp Met Phe Gly Met Pro Thr Leu Leu Val Asp
    210                 215                 220

Met Ala Glu Gly Met Leu Leu Pro Arg Pro Ser Val Gln Ser Gly His
225                 230                 235                 240

Tyr Asp Asp Phe Glu Gly Asp Ala Asp Met Asn Leu
                245                 250
```

<210> SEQ ID NO 92
<211> LENGTH: 682
<212> TYPE: DNA
<213> ORGANISM: Raphanus sativus

<400> SEQUENCE: 92

```
acacctaaac cttatccagg tttaactttt tttttcataa agagttttca acaatgacca     60

cattttctac cttttccgaa atgttgggct ccgagtacga gtctccggtt acattaggcg    120

gagagtattg tccgaagctg gccgcgagct gtccgaagaa accagctggt cgtaagaagt    180

ttcgagagac gcgccaccca atatacagag gagttcgtct gagaaactca ggtaagtggg    240

tgtgtgaagt gagggagcca aacaagaaat ctaggatttg gctcggtact ttcctaaccg    300

ccgagatcgc agcgcgtgcc cacgacgtcg ccgccatagc cctccgcggc aaatccgcat    360

gtctcaattt cgctgactcg gcttggcggc tccgtatccc ggagacaaca tgccccaagg    420

atatacagaa ggcggctgct gaagccgcgg tggcttttca ggctgagata aatgatacga    480
```

-continued

```
cgacggatca tggcctggac ttggaggaga cgatcgtgga ggctattttt acggaggtaa    540

acaacgatga gttttatatg gacgaggagt ccatgttcgg gatgccgtct ttgttggcta    600

gtatggcgga agggatgctt ttgccgctgc cgtccgtaca atctgaacat aactgtgact    660

tcgacggaga tgctgacatg aa                                             682
```

<210> SEQ ID NO 93
<211> LENGTH: 209
<212> TYPE: PRT
<213> ORGANISM: Raphanus sativus

<400> SEQUENCE: 93

```
Met Thr Thr Phe Ser Thr Phe Ser Glu Met Leu Gly Ser Glu Tyr Glu
 1               5                  10                  15

Ser Pro Val Thr Leu Gly Gly Glu Tyr Cys Pro Lys Leu Ala Ala Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Leu Arg Asn Ser Gly Lys Trp Val Cys
    50                  55                  60

Glu Val Arg Glu Pro Asn Lys Lys Ser Arg Ile Trp Leu Gly Thr Phe
65                  70                  75                  80

Leu Thr Ala Glu Ile Ala Ala Arg Ala His Asp Val Ala Ala Ile Ala
                85                  90                  95

Leu Arg Gly Lys Ser Ala Cys Leu Asn Phe Ala Asp Ser Ala Trp Arg
            100                 105                 110

Leu Arg Ile Pro Glu Thr Thr Cys Pro Lys Asp Ile Gln Lys Ala Ala
        115                 120                 125

Ala Glu Ala Ala Val Ala Phe Gln Ala Glu Ile Asn Asp Thr Thr Thr
    130                 135                 140

Asp His Gly Leu Asp Leu Glu Glu Thr Ile Val Glu Ala Ile Phe Thr
145                 150                 155                 160

Glu Val Asn Asn Asp Glu Phe Tyr Met Asp Glu Glu Ser Met Phe Gly
                165                 170                 175

Met Pro Ser Leu Leu Ala Ser Met Ala Glu Gly Met Leu Leu Pro Leu
            180                 185                 190

Pro Ser Val Gln Ser Glu His Asn Cys Asp Phe Asp Gly Asp Ala Asp
        195                 200                 205

Met
```

<210> SEQ ID NO 94
<211> LENGTH: 349
<212> TYPE: DNA
<213> ORGANISM: Zea maize

<400> SEQUENCE: 94

```
cggagtccgc ggacggcggc ggcggcggcg acgacgagta cgcgacggtg ctgtcggcgc     60

cacccaagcg gccggcgggg cggaccaagt tccgggagac gcggcacccc gtgtaccgcg    120

gcgtgcggcg gcgcgggccc gcggggcgct gggtgtgcga ggtccgcgag cccaacaaga    180

agtcgcgcat ctggctcggc accttcgcca cccccgaggc cgccgcgcgc gcgcacgacg    240

tggccgcgct ggccctgcgg ggccgcgccg cgtgcctcaa cttcgccgac tcggcgcgcc    300

tgctccaagt cgaccccgcc acgctcgcca cccccgacga catccgccg                349
```

-continued

```
<210> SEQ ID NO 95
<211> LENGTH: 115
<212> TYPE: PRT
<213> ORGANISM: Zea maize

<400> SEQUENCE: 95

Glu Ser Ala Asp Gly Gly Gly Gly Gly Asp Asp Glu Tyr Ala Thr Val
 1               5                  10                  15

Leu Ser Ala Pro Pro Lys Arg Pro Ala Gly Arg Thr Lys Phe Arg Glu
            20                  25                  30

Thr Arg His Pro Val Tyr Arg Gly Val Arg Arg Arg Gly Pro Ala Gly
        35                  40                  45

Arg Trp Val Cys Glu Val Arg Glu Pro Asn Lys Lys Ser Arg Ile Trp
    50                  55                  60

Leu Gly Thr Phe Ala Thr Pro Glu Ala Ala Ala Arg Ala His Asp Val
65                  70                  75                  80

Ala Ala Leu Ala Leu Arg Gly Arg Ala Ala Cys Leu Asn Phe Ala Asp
                85                  90                  95

Ser Ala Arg Leu Leu Gln Val Asp Pro Ala Thr Leu Ala Thr Pro Asp
            100                 105                 110

Asp Ile Arg
        115


<210> SEQ ID NO 96
<211> LENGTH: 39
<212> TYPE: DNA
<213> ORGANISM: Artificial Sequence
<220> FEATURE:
<223> OTHER INFORMATION: Synthetic Construct

<400> SEQUENCE: 96

ggaagatcta tgaaacagag tactctgatc aatgaactc                              39


<210> SEQ ID NO 97
<211> LENGTH: 37
<212> TYPE: DNA
<213> ORGANISM: Artificial Sequence
<220> FEATURE:
<223> OTHER INFORMATION: Synthetic Construct

<400> SEQUENCE: 97

ggaagatctg aaacagagta ctctgatcaa tgaactc                                37


<210> SEQ ID NO 98
<211> LENGTH: 38
<212> TYPE: DNA
<213> ORGANISM: Artificial Sequence
<220> FEATURE:
<223> OTHER INFORMATION: Synthetic Construct

<400> SEQUENCE: 98

ggaagatcta tgaacagagt actctgatca atgaactc                               38


<210> SEQ ID NO 99
<211> LENGTH: 39
<212> TYPE: DNA
<213> ORGANISM: Artificial Sequence
<220> FEATURE:
<223> OTHER INFORMATION: Synthetic Construct

<400> SEQUENCE: 99

ggaagatcta tgaacagagt actctgatgc aatgaactc                              39
```

-continued

<210> SEQ ID NO 100
<211> LENGTH: 49
<212> TYPE: DNA
<213> ORGANISM: Artificial Sequence
<220> FEATURE:
<223> OTHER INFORMATION: Synthetic Construct

<400> SEQUENCE: 100
ggaggatcct cgtttctaca acaataaaat aaaataaaat gaaggaacc 49

<210> SEQ ID NO 101
<211> LENGTH: 20
<212> TYPE: DNA
<213> ORGANISM: Artificial Sequence
<220> FEATURE:
<223> OTHER INFORMATION: Degenerate PCR primer
<220> FEATURE:
<221> NAME/KEY: misc_feature
<222> LOCATION: (1)...(20)
<223> OTHER INFORMATION: n = A,T,C or G

<400> SEQUENCE: 101
cayccnatht aymgnggngt 20

<210> SEQ ID NO 102
<211> LENGTH: 21
<212> TYPE: DNA
<213> ORGANISM: Artificial Sequence
<220> FEATURE:
<223> OTHER INFORMATION: Degenerate PCR primer
<220> FEATURE:
<221> NAME/KEY: misc_feature
<222> LOCATION: (1)...(21)
<223> OTHER INFORMATION: n = A,T,C or G

<400> SEQUENCE: 102
ggnarnarca tnccytcngc c 21

<210> SEQ ID NO 103
<211> LENGTH: 62
<212> TYPE: PRT
<213> ORGANISM: Arabidopsis thaliana

<400> SEQUENCE: 103

```
His Pro Ile Tyr Arg Gly Val Arg Gln Arg Asn Ser Gly Lys Trp Val
 1               5                  10                  15

Cys Glu Leu Arg Glu Pro Asn Lys Lys Thr Arg Ile Trp Leu Gly Thr
            20                  25                  30

Phe Gln Thr Ala Glu Met Ala Ala Arg Ala His Asp Val Ala Ala Ile
        35                  40                  45

Ala Leu Arg Gly Arg Ser Ala Cys Leu Asn Phe Ala Asp Ser
    50                  55                  60
```

<210> SEQ ID NO 104
<211> LENGTH: 62
<212> TYPE: PRT
<213> ORGANISM: Arabidopsis thaliana

<400> SEQUENCE: 104

```
His Pro Ile Tyr Arg Gly Val Arg Arg Arg Asn Ser Gly Lys Trp Val
 1               5                  10                  15

Cys Glu Val Arg Glu Pro Asn Lys Lys Thr Arg Ile Trp Leu Gly Thr
            20                  25                  30

Phe Gln Thr Ala Glu Met Ala Ala Arg Ala His Asp Val Ala Ala Leu
        35                  40                  45
```

-continued

```
Ala Leu Arg Gly Arg Ser Ala Cys Leu Asn Phe Ala Asp Ser
    50                  55                  60


<210> SEQ ID NO 105
<211> LENGTH: 62
<212> TYPE: PRT
<213> ORGANISM: Arabidopsis thaliana

<400> SEQUENCE: 105

His Pro Ile Tyr Arg Gly Val Arg Gln Arg Asn Ser Gly Lys Trp Val
 1               5                  10                  15

Ser Glu Val Arg Glu Pro Asn Lys Lys Thr Arg Ile Trp Leu Gly Thr
            20                  25                  30

Phe Gln Thr Ala Glu Met Ala Ala Arg Ala His Asp Val Ala Ala Leu
        35                  40                  45

Ala Leu Arg Gly Arg Ser Ala Cys Leu Asn Phe Ala Asp Ser
    50                  55                  60


<210> SEQ ID NO 106
<211> LENGTH: 62
<212> TYPE: PRT
<213> ORGANISM: Brassica juncea

<400> SEQUENCE: 106

His Pro Ile Tyr Arg Gly Val Arg Gln Arg Asn Ser Gly Lys Trp Val
 1               5                  10                  15

Cys Glu Val Arg Glu Pro Asn Lys Lys Ser Arg Ile Trp Leu Gly Thr
            20                  25                  30

Phe Pro Thr Val Glu Met Ala Ala Arg Ala His Asp Val Ala Ala Leu
        35                  40                  45

Ala Leu Arg Gly Arg Ser Ala Cys Leu Asn Phe Ala Asp Ser
    50                  55                  60


<210> SEQ ID NO 107
<211> LENGTH: 62
<212> TYPE: PRT
<213> ORGANISM: Brassica oleracea

<400> SEQUENCE: 107

His Pro Val Tyr Arg Gly Val Arg Leu Arg Asn Ser Gly Lys Trp Val
 1               5                  10                  15

Cys Glu Val Arg Glu Pro Asn Lys Lys Ser Arg Ile Trp Leu Gly Thr
            20                  25                  30

Phe Leu Thr Ala Glu Ile Ala Ala Arg Ala His Asp Val Ala Ala Ile
        35                  40                  45

Ala Leu Arg Gly Lys Ser Ala Cys Leu Asn Phe Ala Asp Ser
    50                  55                  60


<210> SEQ ID NO 108
<211> LENGTH: 62
<212> TYPE: PRT
<213> ORGANISM: Raphanus sativus

<400> SEQUENCE: 108

His Pro Ile Tyr Arg Gly Val Arg Leu Arg Asn Ser Gly Lys Trp Val
 1               5                  10                  15

Cys Glu Val Arg Glu Pro Asn Lys Lys Ser Arg Ile Trp Leu Gly Thr
            20                  25                  30

Phe Leu Thr Ala Glu Ile Ala Ala Arg Ala His Asp Val Ala Ala Ile
        35                  40                  45
```

-continued

```
Ala Leu Arg Gly Lys Ser Ala Cys Leu Asn Phe Ala Asp Ser
    50                  55                  60


<210> SEQ ID NO 109
<211> LENGTH: 62
<212> TYPE: PRT
<213> ORGANISM: Brassica juncea

<400> SEQUENCE: 109

His Pro Ile Tyr Arg Gly Val Arg Leu Arg Lys Ser Gly Lys Trp Val
 1               5                  10                  15

Cys Glu Val Arg Glu Pro Asn Lys Arg Ser Arg Ile Trp Leu Gly Thr
            20                  25                  30

Phe Leu Thr Ala Glu Ile Ala Ala Arg Ala His Asp Val Ala Ala Ile
        35                  40                  45

Ala Leu Arg Gly Lys Ser Ala Cys Leu Asn Phe Ala Asp Ser
    50                  55                  60


<210> SEQ ID NO 110
<211> LENGTH: 62
<212> TYPE: PRT
<213> ORGANISM: Brassica napus

<400> SEQUENCE: 110

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Leu Thr Ala Glu Ile Ala Ala Arg Ala His Asp Val Ala Ala Ile
        35                  40                  45

Ala Leu Arg Gly Lys Ser Ala Cys Leu Asn Phe Ala Asp Ser
    50                  55                  60


<210> SEQ ID NO 111
<211> LENGTH: 62
<212> TYPE: PRT
<213> ORGANISM: Brassica juncea

<400> SEQUENCE: 111

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Pro Gly Thr
            20                  25                  30

Phe Leu Thr Ala Glu Ile Ala Ala Arg Ala His Asp Val Ala Ala Ile
        35                  40                  45

Ala Leu Arg Gly Lys Ser Ala Cys Leu Asn Phe Ala Asp Ser
    50                  55                  60


<210> SEQ ID NO 112
<211> LENGTH: 62
<212> TYPE: PRT
<213> ORGANISM: Brassica napus

<400> SEQUENCE: 112

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Pro Gly Thr
            20                  25                  30

Phe Lys Thr Ala Glu Met Ala Ala Arg Ala His Asp Val Ala Ala Leu
        35                  40                  45
```

-continued

```
Ala Leu Arg Gly Arg Gly Ala Cys Leu Asn Tyr Ala Asp Ser
    50                  55                  60


<210> SEQ ID NO 113
<211> LENGTH: 62
<212> TYPE: PRT
<213> ORGANISM: Brassica napus

<400> SEQUENCE: 113

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Pro Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser
    50                  55                  60


<210> SEQ ID NO 114
<211> LENGTH: 62
<212> TYPE: PRT
<213> ORGANISM: Brassica napus

<400> SEQUENCE: 114

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser
    50                  55                  60


<210> SEQ ID NO 115
<211> LENGTH: 62
<212> TYPE: PRT
<213> ORGANISM: Brassica napus

<400> SEQUENCE: 115

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser
    50                  55                  60


<210> SEQ ID NO 116
<211> LENGTH: 62
<212> TYPE: PRT
<213> ORGANISM: Brassica napus

<400> SEQUENCE: 116

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45
```

-continued

```
Ala Leu Arg Gly Arg Gly Ala Cys Leu Asn Tyr Ala Asp Ser
    50                  55                  60


<210> SEQ ID NO 117
<211> LENGTH: 62
<212> TYPE: PRT
<213> ORGANISM: Brassica oleracea

<400> SEQUENCE: 117

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser
    50                  55                  60


<210> SEQ ID NO 118
<211> LENGTH: 62
<212> TYPE: PRT
<213> ORGANISM: Brassica rapa

<400> SEQUENCE: 118

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser
    50                  55                  60


<210> SEQ ID NO 119
<211> LENGTH: 62
<212> TYPE: PRT
<213> ORGANISM: Brassica napus

<400> SEQUENCE: 119

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Gly Ala Cys Leu Asn Phe Ala Asp Ser
    50                  55                  60


<210> SEQ ID NO 120
<211> LENGTH: 62
<212> TYPE: PRT
<213> ORGANISM: Brassica napus

<400> SEQUENCE: 120

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45
```

-continued

```
Ala Leu Arg Gly Arg Gly Ala Cys Leu Asn Phe Ala Asp Ser
    50                  55                  60


<210> SEQ ID NO 121
<211> LENGTH: 62
<212> TYPE: PRT
<213> ORGANISM: Brassica oleracea

<400> SEQUENCE: 121

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Gly Ala Cys Leu Asn Phe Ala Asp Ser
    50                  55                  60


<210> SEQ ID NO 122
<211> LENGTH: 62
<212> TYPE: PRT
<213> ORGANISM: Brassica rapa

<400> SEQUENCE: 122

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Gly Ala Cys Leu Asn Phe Ala Asp Ser
    50                  55                  60


<210> SEQ ID NO 123
<211> LENGTH: 62
<212> TYPE: PRT
<213> ORGANISM: Brassica rapa

<400> SEQUENCE: 123

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Gly Ala Cys Leu Asn Phe Ala Asp Ser
    50                  55                  60


<210> SEQ ID NO 124
<211> LENGTH: 62
<212> TYPE: PRT
<213> ORGANISM: Brassica rapa

<400> SEQUENCE: 124

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45
```

-continued

```
Ala Leu Arg Gly Arg Gly Ala Cys Leu Asn Phe Ala Asp Ser
    50                  55                  60
```

<210> SEQ ID NO 125
<211> LENGTH: 62
<212> TYPE: PRT
<213> ORGANISM: Brassica rapa

<400> SEQUENCE: 125

```
His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Gly Ala Cys Leu Asn Phe Ala Asp Ser
    50                  55                  60
```

<210> SEQ ID NO 126
<211> LENGTH: 62
<212> TYPE: PRT
<213> ORGANISM: Brassica rapa

<400> SEQUENCE: 126

```
His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Gly Ala Cys Leu Asn Phe Ala Asp Ser
    50                  55                  60
```

<210> SEQ ID NO 127
<211> LENGTH: 62
<212> TYPE: PRT
<213> ORGANISM: Brassica rapa

<400> SEQUENCE: 127

```
His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Gly Ala Cys Leu Asn Phe Ala Asp Ser
    50                  55                  60
```

<210> SEQ ID NO 128
<211> LENGTH: 62
<212> TYPE: PRT
<213> ORGANISM: Raphanus sativus

<400> SEQUENCE: 128

```
His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45
```

-continued

```
Ala Leu Arg Gly Arg Gly Ala Cys Leu Asn Phe Ala Asp Ser
    50                  55                  60


<210> SEQ ID NO 129
<211> LENGTH: 62
<212> TYPE: PRT
<213> ORGANISM: Brassica oleracea

<400> SEQUENCE: 129

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Leu Gly Thr
            20                  25                  30

Phe Lys Thr Ala Glu Ile Ala Ala Arg Ala His Asp Val Ala Ala Leu
        35                  40                  45

Ala Leu Arg Gly Arg Ala Ala Cys Leu Asn Phe Ala Asp Ser
    50                  55                  60


<210> SEQ ID NO 130
<211> LENGTH: 62
<212> TYPE: PRT
<213> ORGANISM: Brassica oleracea

<400> SEQUENCE: 130

His Pro Ile Tyr Arg Gly Val Arg Leu Arg Lys Ser Gly Lys Trp Val
 1               5                  10                  15

Cys Glu Val Arg Glu Leu Asn Lys Lys Ser Arg Ile Trp Leu Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Cys Leu Asn Tyr Ala Asp Ser
    50                  55                  60


<210> SEQ ID NO 131
<211> LENGTH: 62
<212> TYPE: PRT
<213> ORGANISM: Brassica napus

<400> SEQUENCE: 131

His Pro Ile Tyr Arg Gly Val Arg Leu Arg Lys Ser Gly Lys Trp Val
 1               5                  10                  15

Cys Glu Val Arg Glu Pro Asn Lys Lys Ser Arg Ile Trp Pro Gly Thr
            20                  25                  30

Phe Lys Thr Ala Glu Met Ala Ala Arg Ala His Asp Val Ala Ala Leu
        35                  40                  45

Ala Leu Arg Gly Arg Gly Ala Arg Leu Asn Tyr Ala Asp Ser
    50                  55                  60


<210> SEQ ID NO 132
<211> LENGTH: 63
<212> TYPE: PRT
<213> ORGANISM: Zea mays

<400> SEQUENCE: 132

His Pro Val Tyr Arg Gly Val Arg Arg Arg Gly Pro Ala Gly Arg Trp
 1               5                  10                  15

Val Cys Glu Val Arg Glu Pro Asn Lys Lys Ser Arg Ile Trp Leu Gly
            20                  25                  30

Thr Phe Ala Thr Pro Glu Ala Ala Ala Arg Ala His Asp Val Ala Ala
        35                  40                  45
```

-continued

```
Leu Ala Leu Arg Gly Arg Ala Ala Cys Leu Asn Phe Ala Asp Ser
    50                  55                  60


<210> SEQ ID NO 133
<211> LENGTH: 62
<212> TYPE: PRT
<213> ORGANISM: Glycine max

<400> SEQUENCE: 133

His Pro Ile Tyr Ser Gly Val Arg Arg Arg Asn Thr Asp Lys Trp Val
 1               5                  10                  15

Ser Glu Val Arg Glu Pro Asn Lys Lys Thr Arg Ile Trp Leu Gly Thr
            20                  25                  30

Phe Pro Thr Pro Glu Met Ala Ala Arg Ala His Asp Val Ala Ala Met
        35                  40                  45

Ala Leu Arg Gly Arg Tyr Ala Cys Leu Asn Phe Ala Asp Ser
    50                  55                  60


<210> SEQ ID NO 134
<211> LENGTH: 63
<212> TYPE: PRT
<213> ORGANISM: Nicotiana tabacum

<400> SEQUENCE: 134

Gly Arg His Tyr Arg Gly Val Arg Gln Arg Pro Trp Gly Lys Phe Ala
 1               5                  10                  15

Ala Glu Ile Arg Asp Pro Ala Lys Asn Gly Ala Arg Val Trp Leu Gly
            20                  25                  30

Thr Tyr Glu Thr Ala Glu Glu Ala Ala Leu Ala Tyr Asp Lys Ala Ala
        35                  40                  45

Tyr Arg Met Arg Gly Ser Lys Ala Leu Leu Asn Phe Pro His Arg
    50                  55                  60


<210> SEQ ID NO 135
<211> LENGTH: 62
<212> TYPE: PRT
<213> ORGANISM: Arabidopsis thaliana

<400> SEQUENCE: 135

Arg Cys Ser Phe Arg Gly Val Arg Gln Arg Ile Trp Gly Lys Trp Val
 1               5                  10                  15

Ala Glu Ile Arg Glu Pro Asn Arg Gly Ser Arg Leu Trp Leu Gly Thr
            20                  25                  30

Phe Pro Thr Ala Gln Glu Ala Ala Ser Ala Tyr Asp Glu Ala Ala Lys
        35                  40                  45

Ala Met Tyr Gly Pro Leu Ala Arg Leu Asn Phe Pro Arg Ser
    50                  55                  60


<210> SEQ ID NO 136
<211> LENGTH: 62
<212> TYPE: PRT
<213> ORGANISM: Arabidopsis thaliana

<400> SEQUENCE: 136

His Cys Ser Phe Arg Gly Val Arg Gln Arg Ile Trp Gly Lys Trp Val
 1               5                  10                  15

Ala Glu Ile Arg Glu Pro Lys Ile Gly Thr Arg Leu Trp Leu Gly Thr
            20                  25                  30

Phe Pro Thr Ala Glu Lys Ala Ala Ser Ala Tyr Asp Glu Ala Ala Thr
        35                  40                  45
```

-continued

```
Ala Met Tyr Gly Ser Leu Ala Arg Leu Asn Phe Pro Gln Ser
    50                  55                  60


<210> SEQ ID NO 137
<211> LENGTH: 62
<212> TYPE: PRT
<213> ORGANISM: Arabidopsis thaliana

<400> SEQUENCE: 137

His Pro Val Tyr Arg Gly Val Arg Lys Arg Asn Trp Gly Lys Trp Val
 1               5                  10                  15

Ser Glu Ile Arg Glu Pro Arg Lys Lys Ser Arg Ile Trp Leu Gly Thr
            20                  25                  30

Phe Pro Ser Pro Glu Met Ala Ala Arg Ala His Asp Val Ala Ala Leu
        35                  40                  45

Ser Ile Lys Gly Ala Ser Ala Ile Leu Asn Phe Pro Asp Leu
    50                  55                  60


<210> SEQ ID NO 138
<211> LENGTH: 46
<212> TYPE: PRT
<213> ORGANISM: Brassica rapa

<400> SEQUENCE: 138

Met Asn Ser Val Ser Thr Phe Ser Glu Leu Leu Cys Ser Glu Asn Glu
 1               5                  10                  15

Ser Pro Val Asn Thr Glu Gly Gly Asp Tyr Ile Leu Ala Ala Ser Cys
            20                  25                  30

Pro Lys Lys Pro Ala Gly Arg Lys Lys Phe Gln Glu Thr Arg
        35                  40                  45


<210> SEQ ID NO 139
<211> LENGTH: 46
<212> TYPE: PRT
<213> ORGANISM: Brassica rapa

<400> SEQUENCE: 139

Met Asn Ser Val Ser Thr Phe Ser Glu Leu Leu Cys Ser Glu Asn Lys
 1               5                  10                  15

Ser Pro Val Asn Thr Glu Gly Gly Asp Tyr Ile Leu Ala Ala Ser Cys
            20                  25                  30

Pro Lys Lys Pro Ala Gly Arg Lys Lys Phe Gln Glu Thr Arg
        35                  40                  45


<210> SEQ ID NO 140
<211> LENGTH: 46
<212> TYPE: PRT
<213> ORGANISM: Brassica napus

<400> SEQUENCE: 140

Met Asn Ser Val Ser Thr Phe Ser Glu Leu Leu Arg Ser Glu Asn Glu
 1               5                  10                  15

Ser Pro Val Asn Thr Glu Gly Gly Asp Tyr Ile Leu Ala Ala Ser Cys
            20                  25                  30

Pro Lys Lys Pro Ala Gly Arg Lys Lys Phe Gln Glu Thr Arg
        35                  40                  45


<210> SEQ ID NO 141
<211> LENGTH: 47
<212> TYPE: PRT
<213> ORGANISM: Arabidopsis thaliana
```

-continued

<400> SEQUENCE: 141

```
Met Asn Ser Phe Ser Ala Phe Ser Glu Met Phe Gly Ser Asp Tyr Glu
 1               5                  10                  15

Ser Pro Val Ser Ser Gly Gly Asp Tyr Ser Pro Lys Leu Ala Thr Ser
            20                  25                  30

Cys Pro Lys Lys Pro Ala Gly Arg Lys Lys Phe Arg Glu Thr Arg
        35                  40                  45
```

<210> SEQ ID NO 142
<211> LENGTH: 47
<212> TYPE: PRT
<213> ORGANISM: Arabidopsis thaliana

<400> SEQUENCE: 142

```
Met Asn Ser Phe Ser Ala Phe Ser Glu Met Phe Gly Ser Asp Tyr Glu
 1               5                  10                  15

Ser Ser Val Ser Ser Gly Gly Asp Tyr Ile Pro Thr Leu Ala Ser Ser
            20                  25                  30

Cys Pro Lys Lys Pro Ala Gly Arg Lys Lys Phe Arg Glu Thr Arg
        35                  40                  45
```

<210> SEQ ID NO 143
<211> LENGTH: 44
<212> TYPE: PRT
<213> ORGANISM: Arabidopsis thaliana

<400> SEQUENCE: 143

```
Met Asn Ser Phe Ser Ala Phe Ser Glu Met Phe Gly Ser Asp Tyr Glu
 1               5                  10                  15

Pro Gln Gly Gly Asp Tyr Cys Pro Thr Leu Ala Thr Ser Cys Pro Lys
            20                  25                  30

Lys Pro Ala Gly Arg Lys Lys Phe Arg Glu Thr Arg
        35                  40
```

<210> SEQ ID NO 144
<211> LENGTH: 49
<212> TYPE: PRT
<213> ORGANISM: Brassica napus

<400> SEQUENCE: 144

```
Met Asn Thr Phe Pro Ala Ser Thr Glu Met Val Gly Ser Glu Asn Glu
 1               5                  10                  15

Ser Pro Val Thr Thr Val Val Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg
```

<210> SEQ ID NO 145
<211> LENGTH: 49
<212> TYPE: PRT
<213> ORGANISM: Brassica napus

<400> SEQUENCE: 145

```
Met Asn Thr Phe Pro Ala Ser Thr Glu Met Val Gly Ser Glu Asn Glu
 1               5                  10                  15

Ser Pro Val Thr Thr Val Val Gly Gly Asp Tyr Tyr Pro Met Leu Ala
            20                  25                  30
```

-continued

```
Ala Ser Cys Pro Lys Lys Pro Ala Gly Arg Lys Lys Phe Gln Glu Thr
        35                  40                  45

Arg


<210> SEQ ID NO 146
<211> LENGTH: 49
<212> TYPE: PRT
<213> ORGANISM: Brassica oleracea

<400> SEQUENCE: 146

Met Asn Thr Phe Pro Ala Ser Thr Glu Met Val Gly Ser Glu Asn Glu
 1               5                  10                  15

Ser Pro Val Thr Thr Val Val Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg


<210> SEQ ID NO 147
<211> LENGTH: 49
<212> TYPE: PRT
<213> ORGANISM: Brassica napus

<400> SEQUENCE: 147

Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg


<210> SEQ ID NO 148
<211> LENGTH: 49
<212> TYPE: PRT
<213> ORGANISM: Brassica napus

<400> SEQUENCE: 148

Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg


<210> SEQ ID NO 149
<211> LENGTH: 49
<212> TYPE: PRT
<213> ORGANISM: Brassica napus

<400> SEQUENCE: 149

Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
            20                  25                  30
```

-continued

```
Ala Ser Cys Pro Lys Lys Pro Ala Gly Arg Lys Lys Phe Gln Glu Thr
        35                  40                  45

Arg


<210> SEQ ID NO 150
<211> LENGTH: 49
<212> TYPE: PRT
<213> ORGANISM: Brassica rapa

<400> SEQUENCE: 150

Met Asn Thr Phe Pro Ala Ser Thr Glu Met Val Gly Ser Glu Asn Glu
 1               5                  10                  15

Ser Pro Val Thr Thr Val Ala Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg


<210> SEQ ID NO 151
<211> LENGTH: 49
<212> TYPE: PRT
<213> ORGANISM: Brassica oleracea

<400> SEQUENCE: 151

Met Asn Thr Phe Pro Ala Ser Thr Glu Met Val Ser Ser Glu Asn Glu
 1               5                  10                  15

Ser Pro Val Thr Thr Val Val Gly Gly Asp Tyr Tyr Pro Met Leu Ala
            20                  25                  30

Ala Ser Cys Pro Lys Lys Pro Ala Gly Arg Lys Lys Phe Gln Glu Thr
        35                  40                  45

Arg


<210> SEQ ID NO 152
<211> LENGTH: 47
<212> TYPE: PRT
<213> ORGANISM: Brassica oleracea

<400> SEQUENCE: 152

Met Thr Ser Phe Ser Thr Phe Ser Glu Leu Leu Gly Ser Glu His Glu
 1               5                  10                  15

Ser Pro Val Thr Leu Gly Glu Glu Tyr Cys Pro Lys Leu Ala Ala Ser
            20                  25                  30

Cys Pro Lys Lys Pro Ala Gly Arg Lys Lys Phe Arg Glu Thr Arg
        35                  40                  45


<210> SEQ ID NO 153
<211> LENGTH: 47
<212> TYPE: PRT
<213> ORGANISM: Raphanus sativus

<400> SEQUENCE: 153

Met Thr Thr Phe Ser Thr Phe Ser Glu Met Leu Gly Ser Glu Tyr Glu
 1               5                  10                  15

Ser Pro Val Thr Leu Gly Gly Glu Tyr Cys Pro Lys Leu Ala Ala Ser
            20                  25                  30

Cys Pro Lys Lys Pro Ala Gly Arg Lys Lys Phe Arg Glu Thr Arg
        35                  40                  45
```

-continued

<210> SEQ ID NO 154
<211> LENGTH: 45
<212> TYPE: PRT
<213> ORGANISM: Brassica napus

<400> SEQUENCE: 154

```
Met Asn Ser Val Ser Thr Phe Ser Glu Leu Leu Gly Ser Glu Asn Glu
 1              5                   10                  15

Ser Pro Val Gly Gly Asp Tyr Cys Pro Met Leu Ala Ala Ser Cys Pro
            20                  25                  30

Lys Lys Pro Ala Gly Arg Lys Lys Phe Arg Glu Thr Arg
        35                  40                  45
```

<210> SEQ ID NO 155
<211> LENGTH: 45
<212> TYPE: PRT
<213> ORGANISM: Brassica napus

<400> SEQUENCE: 155

```
Met Asn Ser Val Ser Thr Phe Ser Glu Leu Leu Gly Ser Glu Asn Glu
 1              5                   10                  15

Ser Pro Val Gly Gly Asp Tyr Cys Pro Met Leu Ala Ala Ser Cys Pro
            20                  25                  30

Lys Lys Pro Ala Gly Arg Lys Lys Phe Arg Glu Thr Arg
        35                  40                  45
```

<210> SEQ ID NO 156
<211> LENGTH: 45
<212> TYPE: PRT
<213> ORGANISM: Brassica oleracea

<400> SEQUENCE: 156

```
Met Asn Ser Val Ser Thr Phe Ser Glu Leu Leu Gly Ser Glu Asn Glu
 1              5                   10                  15

Ser Pro Val Gly Gly Asp Tyr Cys Pro Met Leu Ala Ala Ser Cys Pro
            20                  25                  30

Lys Lys Pro Ala Gly Arg Lys Lys Phe Arg Glu Thr Arg
        35                  40                  45
```

<210> SEQ ID NO 157
<211> LENGTH: 45
<212> TYPE: PRT
<213> ORGANISM: Brassica rapa

<400> SEQUENCE: 157

```
Met Asn Ser Val Ser Thr Leu Ser Glu Val Leu Gly Ser Gln Asn Glu
 1              5                   10                  15

Ser Pro Val Gly Gly Asp Tyr Cys Pro Met Leu Ala Ala Ser Cys Pro
            20                  25                  30

Lys Lys Pro Ala Gly Arg Lys Lys Phe Arg Glu Thr Arg
        35                  40                  45
```

<210> SEQ ID NO 158
<211> LENGTH: 49
<212> TYPE: PRT
<213> ORGANISM: Brassica rapa

<400> SEQUENCE: 158

```
Met Asp Ser Ile Ser Thr Phe Pro Glu Leu Leu Gly Ser Glu Asn Glu
 1              5                   10                  15
```

-continued

```
Ser Pro Val Thr Thr Val Val Gly Gly Asp Tyr Cys Pro Arg Leu Ala
            20                  25                  30

Ala Ser Cys Pro Lys Lys Pro Ala Gly Arg Lys Lys Phe Gln Glu Thr
        35                  40                  45

Arg


<210> SEQ ID NO 159
<211> LENGTH: 49
<212> TYPE: PRT
<213> ORGANISM: Brassica rapa

<400> SEQUENCE: 159

Met Asp Ser Ile Ser Thr Phe Pro Glu Leu Leu Gly Ser Glu Asn Glu
 1               5                  10                  15

Ser Pro Val Thr Thr Val Val Gly Gly Asp Tyr Cys Pro Arg Leu Ala
            20                  25                  30

Ala Ser Cys Pro Lys Lys Pro Ala Gly Arg Lys Lys Phe Gln Glu Thr
        35                  40                  45

Arg


<210> SEQ ID NO 160
<211> LENGTH: 49
<212> TYPE: PRT
<213> ORGANISM: Raphanus sativus

<400> SEQUENCE: 160

Met Asp Ser Ile Ser Thr Phe Ser Glu Leu Leu Gly Ser Glu Asn Glu
 1               5                  10                  15

Ser Pro Val Thr Thr Val Val Gly Gly Asp Tyr Phe Pro Arg Leu Ala
            20                  25                  30

Ala Ser Cys Pro Lys Lys Pro Ala Gly Arg Lys Lys Phe Gln Glu Thr
        35                  40                  45

Arg


<210> SEQ ID NO 161
<211> LENGTH: 50
<212> TYPE: PRT
<213> ORGANISM: Brassica napus

<400> SEQUENCE: 161

Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Gln Asn Gly Leu Asn Met Glu Glu Thr Thr Ala Val Ala
        35                  40                  45

Ser Gln
    50


<210> SEQ ID NO 162
<211> LENGTH: 50
<212> TYPE: PRT
<213> ORGANISM: Brassica napus

<400> SEQUENCE: 162

Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30
```

-continued

```
Val Thr Met Gln Asn Gly Leu Asn Met Glu Glu Thr Thr Ala Val Ala
        35                  40                  45

Ser Gln
    50


<210> SEQ ID NO 163
<211> LENGTH: 50
<212> TYPE: PRT
<213> ORGANISM: Brassica rapa

<400> SEQUENCE: 163

Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Gln Asn Gly Leu Asn Met Glu Glu Met Thr Ala Val Ala
        35                  40                  45

Ser Gln
    50


<210> SEQ ID NO 164
<211> LENGTH: 50
<212> TYPE: PRT
<213> ORGANISM: Brassica napus

<400> SEQUENCE: 164

Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Gln Asn Gly Gln Asn Met Glu Glu Thr Thr Ala Val Ala
        35                  40                  45

Ser Gln
    50


<210> SEQ ID NO 165
<211> LENGTH: 44
<212> TYPE: PRT
<213> ORGANISM: Brassica napus

<400> SEQUENCE: 165

Ala Ser Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Glu Glu Thr Met Ala Val Ala Ser Gln
        35                  40


<210> SEQ ID NO 166
<211> LENGTH: 44
<212> TYPE: PRT
<213> ORGANISM: Brassica napus

<400> SEQUENCE: 166

Ala Ser Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Glu Glu Thr Met Ala Val Ala Ser Gln
        35                  40
```

-continued

<210> SEQ ID NO 167
<211> LENGTH: 44
<212> TYPE: PRT
<213> ORGANISM: Brassica oleracea

<400> SEQUENCE: 167

```
Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Glu Glu Thr Met Ala Val Ala Ser Gln
        35                  40
```

<210> SEQ ID NO 168
<211> LENGTH: 50
<212> TYPE: PRT
<213> ORGANISM: Brassica napus

<400> SEQUENCE: 168

```
Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Gln Asn Gly Leu Asn Met Glu Glu Thr Thr Ala Val Ala
        35                  40                  45

Ser Gln
    50
```

<210> SEQ ID NO 169
<211> LENGTH: 50
<212> TYPE: PRT
<213> ORGANISM: Brassica oleracea

<400> SEQUENCE: 169

```
Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Ala Thr Met Gln Asn Gly Leu Asn Met Glu Glu Thr Thr Ala Ala Ala
        35                  40                  45

Ser Gln
    50
```

<210> SEQ ID NO 170
<211> LENGTH: 31
<212> TYPE: PRT
<213> ORGANISM: Brassica rapa

<400> SEQUENCE: 170

```
Ala Trp Arg Leu Arg Ile Pro Glu Thr Thr Cys Ala Lys Asp Ile Gln
 1               5                  10                  15

Lys Ala Ala Ala Glu Ala Ala Leu Ala Phe Glu Ala Glu Lys Ser
            20                  25                  30
```

<210> SEQ ID NO 171
<211> LENGTH: 31
<212> TYPE: PRT
<213> ORGANISM: Raphanus sativus -continued

<400> SEQUENCE: 171

Ala Trp Arg Leu Arg Ile Pro Glu Thr Thr Cys Ala Lys Asp Ile Gln
1 5 10 15

Lys Ala Ala Ala Glu Ala Ala Leu Ala Phe Glu Ala Glu Lys Ser
20 25 30

<210> SEQ ID NO 172
<211> LENGTH: 33
<212> TYPE: PRT
<213> ORGANISM: Brassica napus

<400> SEQUENCE: 172

Ala Trp Arg Leu Arg Ile Pro Glu Thr Thr Cys Ala Lys Asp Ile Gln
1 5 10 15

Lys Ala Ala Ala Glu Ala Ala Leu Ala Phe Glu Ala Glu Lys Ser Asp
20 25 30

Thr

<210> SEQ ID NO 173
<211> LENGTH: 33
<212> TYPE: PRT
<213> ORGANISM: Brassica oleracea

<400> SEQUENCE: 173

Ala Trp Arg Leu Arg Ile Pro Glu Thr Thr Cys Ala Lys Asp Ile Gln
1 5 10 15

Lys Ala Ala Ala Glu Ala Ala Leu Ala Phe Glu Ala Glu Lys Ser Asp
20 25 30

Thr

<210> SEQ ID NO 174
<211> LENGTH: 33
<212> TYPE: PRT
<213> ORGANISM: Brassica napus

<400> SEQUENCE: 174

Ala Trp Arg Leu Arg Ile Pro Glu Thr Thr Cys Ala Lys Asp Ile Gln
1 5 10 15

Lys Ala Ala Ala Glu Ala Ala Leu Ala Phe Glu Ala Glu Lys Ser Asp
20 25 30

Thr

<210> SEQ ID NO 175
<211> LENGTH: 34
<212> TYPE: PRT
<213> ORGANISM: Brassica rapa

<400> SEQUENCE: 175

Ala Trp Arg Leu Arg Ile Pro Glu Thr Thr Cys Ala Lys Asp Ile Gln
1 5 10 15

Lys Ala Ala Ala Glu Ala Ala Leu Ala Phe Glu Ala Glu Lys Ser Asp
20 25 30

Thr Thr

<210> SEQ ID NO 176
<211> LENGTH: 33
<212> TYPE: PRT
<213> ORGANISM: Brassica rapa -continued

<400> SEQUENCE: 176

```
Ala Trp Arg Leu Arg Ile Pro Glu Thr Thr Cys Ala Lys Asp Ile Gln
 1               5                  10                  15

Lys Ala Ala Ala Glu Ala Ala Leu Ala Phe Glu Ala Glu Lys Ser Asp
            20                  25                  30

Thr
```

<210> SEQ ID NO 177
<211> LENGTH: 33
<212> TYPE: PRT
<213> ORGANISM: Brassica oleracea

<400> SEQUENCE: 177

```
Ala Trp Arg Leu Arg Ile Pro Glu Thr Thr Cys Ala Lys Asp Ile Gln
 1               5                  10                  15

Lys Ala Ala Ala Glu Ala Ala Leu Ala Phe Gly Ala Glu Lys Ser Asp
            20                  25                  30

Thr
```

<210> SEQ ID NO 178
<211> LENGTH: 26
<212> TYPE: PRT
<213> ORGANISM: Brassica juncea

<400> SEQUENCE: 178

```
Ala Trp Arg Leu Arg Ile Ser Glu Thr Thr Cys Pro Lys Glu Ile Gln
 1               5                  10                  15

Lys Ala Ala Ala Glu Ala Ala Val Ala Phe
            20                  25
```

<210> SEQ ID NO 179
<211> LENGTH: 26
<212> TYPE: PRT
<213> ORGANISM: Brassica juncea

<400> SEQUENCE: 179

```
Ala Trp Arg Leu Arg Ile Pro Glu Thr Thr Cys Pro Lys Glu Ile Gln
 1               5                  10                  15

Lys Ala Ala Ala Glu Ala Ala Val Ala Phe
            20                  25
```

<210> SEQ ID NO 180
<211> LENGTH: 26
<212> TYPE: PRT
<213> ORGANISM: Brassica napus

<400> SEQUENCE: 180

```
Ala Trp Arg Leu Arg Ile Pro Glu Thr Thr Cys Pro Lys Glu Ile Gln
 1               5                  10                  15

Lys Ala Ala Ala Glu Ala Ala Val Ala Phe
            20                  25
```

<210> SEQ ID NO 181
<211> LENGTH: 26
<212> TYPE: PRT
<213> ORGANISM: Raphanus sativus

<400> SEQUENCE: 181

```
Ala Trp Arg Leu Arg Ile Pro Glu Thr Thr Cys Pro Lys Asp Ile Gln
 1               5                  10                  15
```

-continued

```
Lys Ala Ala Ala Glu Ala Ala Val Ala Phe
            20                  25


<210> SEQ ID NO 182
<211> LENGTH: 26
<212> TYPE: PRT
<213> ORGANISM: Arabidopsis thaliana

<400> SEQUENCE: 182

Ala Trp Arg Leu Arg Ile Pro Glu Ser Thr Cys Ala Lys Asp Ile Gln
 1               5                  10                  15

Lys Ala Ala Ala Glu Ala Ala Leu Ala Phe
            20                  25


<210> SEQ ID NO 183
<211> LENGTH: 26
<212> TYPE: PRT
<213> ORGANISM: Arabidopsis thaliana

<400> SEQUENCE: 183

Ala Trp Arg Leu Arg Ile Pro Glu Ser Thr Cys Ala Lys Glu Ile Gln
 1               5                  10                  15

Lys Ala Ala Ala Glu Ala Ala Leu Asn Phe
            20                  25


<210> SEQ ID NO 184
<211> LENGTH: 26
<212> TYPE: PRT
<213> ORGANISM: Arabidopsis thaliana

<400> SEQUENCE: 184

Ala Trp Arg Leu Arg Ile Pro Glu Ser Thr Cys Ala Lys Asp Ile Gln
 1               5                  10                  15

Lys Ala Ala Ala Glu Ala Ala Leu Ala Phe
            20                  25


<210> SEQ ID NO 185
<211> LENGTH: 49
<212> TYPE: PRT
<213> ORGANISM: Brassica napus

<400> SEQUENCE: 185

Ala Glu Val Asn Asp Thr Thr Thr Glu His Gly Met Asn Met Glu Glu
 1               5                  10                  15

Ala Thr Ala Val Ala Ser Gln Ala Glu Val Asn Asp Thr Thr Thr Asp
            20                  25                  30

His Gly Val Asp Met Glu Glu Thr Met Val Glu Ala Val Phe Thr Gly
        35                  40                  45

Glu


<210> SEQ ID NO 186
<211> LENGTH: 49
<212> TYPE: PRT
<213> ORGANISM: Brassica napus

<400> SEQUENCE: 186

Ala Glu Val Asn Asp Thr Thr Thr Glu His Gly Met Asn Met Glu Glu
 1               5                  10                  15

Ala Thr Ala Val Ala Ser Gln Ala Glu Val Asn Asp Thr Thr Thr Asp
            20                  25                  30
```

-continued

His Gly Val Asp Met Glu Glu Thr Met Val Glu Ala Val Phe Thr Gly
35 40 45

Glu

<210> SEQ ID NO 187
<211> LENGTH: 49
<212> TYPE: PRT
<213> ORGANISM: Brassica rapa

<400> SEQUENCE: 187

Ala Glu Val Asn Asp Thr Thr Thr Glu His Gly Met Asn Met Glu Glu
1 5 10 15

Ala Thr Ala Val Ala Ser Gln Ala Glu Val Asn Asp Thr Thr Thr Asp
20 25 30

His Gly Val Asp Met Glu Glu Thr Met Val Glu Ala Val Phe Thr Glu
35 40 45

Glu

<210> SEQ ID NO 188
<211> LENGTH: 49
<212> TYPE: PRT
<213> ORGANISM: Brassica napus

<400> SEQUENCE: 188

Ala Glu Val Asn Asp Thr Thr Thr Glu His Gly Met Asn Met Glu Glu
1 5 10 15

Ala Thr Ala Val Ala Ser Gln Ala Glu Val Asn Asp Thr Thr Thr Asp
20 25 30

His Gly Val Asp Met Glu Glu Thr Met Val Glu Ala Val Phe Thr Gly
35 40 45

Glu

<210> SEQ ID NO 189
<211> LENGTH: 49
<212> TYPE: PRT
<213> ORGANISM: Brassica napus

<400> SEQUENCE: 189

Ala Glu Val Asn Asp Thr Thr Thr Asp His Gly Met Asn Met Glu Glu
1 5 10 15

Ala Thr Ala Val Ala Ser Gln Ala Glu Val Asn Asp Thr Thr Thr Asp
20 25 30

His Gly Val Asp Met Glu Glu Thr Met Val Glu Ala Val Phe Thr Gly
35 40 45

Glu

<210> SEQ ID NO 190
<211> LENGTH: 49
<212> TYPE: PRT
<213> ORGANISM: Brassica napus

<400> SEQUENCE: 190

Ala Glu Val Asn Asp Thr Thr Thr Asp His Gly Met Asn Met Glu Glu
1 5 10 15

Ala Thr Ala Val Ala Ser Gln Ala Glu Val Asn Asp Thr Thr Thr Asp
20 25 30

-continued

```
His Gly Val Asp Met Glu Glu Thr Met Val Glu Ala Val Phe Thr Glu
        35                  40                  45

Glu


<210> SEQ ID NO 191
<211> LENGTH: 49
<212> TYPE: PRT
<213> ORGANISM: Brassica oleracea

<400> SEQUENCE: 191

Ala Glu Val Asn Asp Thr Thr Thr Asp His Gly Met Asn Met Glu Glu
 1               5                  10                  15

Ala Thr Ala Val Ala Ser Gln Ala Glu Val Asn Asp Thr Thr Thr Asp
            20                  25                  30

His Gly Val Asp Met Glu Glu Thr Met Val Glu Ala Val Phe Thr Glu
        35                  40                  45

Glu


<210> SEQ ID NO 192
<211> LENGTH: 49
<212> TYPE: PRT
<213> ORGANISM: Brassica napus

<400> SEQUENCE: 192

Ala Glu Val Asn Asp Thr Thr Thr Glu His Gly Met Asn Met Glu Glu
 1               5                  10                  15

Ala Thr Ala Val Ala Ser Gln Ala Glu Val Asn Asp Thr Thr Thr Asp
            20                  25                  30

His Gly Val Asp Met Glu Glu Thr Met Val Glu Ala Val Phe Thr Glu
        35                  40                  45

Glu


<210> SEQ ID NO 193
<211> LENGTH: 49
<212> TYPE: PRT
<213> ORGANISM: Brassica oleracea
<220> FEATURE:
<221> NAME/KEY: VARIANT
<222> LOCATION: (1)...(49)
<223> OTHER INFORMATION: Xaa = Any Amino Acid

<400> SEQUENCE: 193

Thr Glu Val Ser Asp Thr Thr Thr Asp His Gly Met Asn Met Glu Glu
 1               5                  10                  15

Thr Thr Ala Val Ala Ser Gln Ala Glu Val Asn Asp Xaa Xaa Thr Asp
            20                  25                  30

His Gly Val Asp Met Glu Glu Thr Met Val Glu Ala Val Phe Thr Glu
        35                  40                  45

Glu


<210> SEQ ID NO 194
<211> LENGTH: 41
<212> TYPE: PRT
<213> ORGANISM: Brassica rapa

<400> SEQUENCE: 194

Asp His Gly Met Asn Met Lys Asn Thr Thr Ala Val Ala Ser Gln Val
 1               5                  10                  15

Glu Val Asn Asp Thr Thr Thr Asp His Gly Val Asp Met Glu Glu Thr
            20                  25                  30
```

-continued

Leu Val Glu Ala Val Phe Thr Glu Glu
        35                  40

<210> SEQ ID NO 195
<211> LENGTH: 41
<212> TYPE: PRT
<213> ORGANISM: Raphanus sativus

<400> SEQUENCE: 195

Asp His Gly Met Asn Met Lys Asn Thr Thr Ala Val Ala Ser Gln Val
 1               5                  10                  15

Glu Val Asn Asp Thr Thr Thr Asp His Gly Val Asp Met Glu Glu Thr
            20                  25                  30

Leu Val Glu Ala Val Phe Thr Glu Glu
        35                  40

<210> SEQ ID NO 196
<211> LENGTH: 37
<212> TYPE: PRT
<213> ORGANISM: Brassica napus

<400> SEQUENCE: 196

Thr Thr Asn Asp His Gly Met Asn Met Ala Ser Gln Ala Glu Val Asn
 1               5                  10                  15

Asp Thr Thr Asp His Gly Leu Asp Met Glu Glu Thr Met Val Glu Ala
            20                  25                  30

Val Phe Thr Glu Glu
        35

<210> SEQ ID NO 197
<211> LENGTH: 37
<212> TYPE: PRT
<213> ORGANISM: Brassica oleracea

<400> SEQUENCE: 197

Thr Thr Asn Asp His Gly Met Asn Met Ala Ser Gln Ala Glu Val Asn
 1               5                  10                  15

Asp Thr Thr Asp His Gly Leu Asp Met Glu Glu Thr Met Val Glu Ala
            20                  25                  30

Val Phe Thr Glu Glu
        35

<210> SEQ ID NO 198
<211> LENGTH: 37
<212> TYPE: PRT
<213> ORGANISM: Brassica napus

<400> SEQUENCE: 198

Thr Thr Asn Asp His Gly Met Asn Met Ala Ser Gln Val Glu Val Asn
 1               5                  10                  15

Asp Thr Thr Asp His Asp Leu Asp Met Glu Glu Thr Ile Val Glu Ala
            20                  25                  30

Val Phe Arg Glu Glu
        35

<210> SEQ ID NO 199
<211> LENGTH: 37
<212> TYPE: PRT
<213> ORGANISM: Brassica rapa -continued

<400> SEQUENCE: 199

Thr Thr Asn Asp His Gly Met Asn Met Ala Ser Gln Val Glu Val Asn
1 5 10 15
Asp Thr Thr Asp His Asp Leu Asp Met Glu Glu Thr Met Val Glu Ala
20 25 30
Val Phe Arg Glu Glu
35

<210> SEQ ID NO 200
<211> LENGTH: 44
<212> TYPE: PRT
<213> ORGANISM: Brassica rapa

<400> SEQUENCE: 200

Thr Thr Asn Asp Arg Gly Met Asn Met Glu Glu Thr Ser Ala Val Ala
1 5 10 15

Ser Pro Ala Glu Leu Asn Asp Thr Thr Ala Asp His Gly Leu Asp Met
20 25 30

Glu Glu Thr Met Val Glu Ala Val Phe Arg Asp Glu
35 40

<210> SEQ ID NO 201
<211> LENGTH: 44
<212> TYPE: PRT
<213> ORGANISM: Brassica oleracea

<400> SEQUENCE: 201

Thr Thr Asn Asp Gln Gly Met Asn Met Glu Glu Met Thr Val Val Ala
1 5 10 15

Ser Gln Ala Glu Val Ser Asp Thr Thr Thr Tyr His Gly Leu Asp Met
20 25 30

Glu Glu Thr Met Val Glu Ala Val Phe Ala Glu Glu
35 40

<210> SEQ ID NO 202
<211> LENGTH: 26
<212> TYPE: PRT
<213> ORGANISM: Brassica juncea

<400> SEQUENCE: 202

Gln Ala Glu Leu Asn Asp Thr Thr Ala Asp His Gly Leu Asp Val Glu
1 5 10 15

Glu Thr Ile Val Glu Ala Ile Phe Thr Glu
20 25

<210> SEQ ID NO 203
<211> LENGTH: 26
<212> TYPE: PRT
<213> ORGANISM: Brassica juncea

<400> SEQUENCE: 203

Gln Ala Glu Leu Asn Asp Thr Thr Ala Asp His Gly Leu Asp Val Glu
1 5 10 15

Glu Thr Ile Val Glu Ala Ile Phe Thr Glu
20 25

<210> SEQ ID NO 204
<211> LENGTH: 26
<212> TYPE: PRT
<213> ORGANISM: Brassica napus -continued

<400> SEQUENCE: 204

```
Lys Ala Glu Ile Asn Asn Thr Thr Ala Asp His Gly Ile Asp Val Glu
 1               5                  10                  15

Glu Thr Ile Val Glu Ala Ile Phe Thr Glu
            20                  25
```

<210> SEQ ID NO 205
<211> LENGTH: 26
<212> TYPE: PRT
<213> ORGANISM: Raphanus sativus

<400> SEQUENCE: 205

```
Gln Ala Glu Ile Asn Asp Thr Thr Thr Asp His Gly Leu Asp Ile Glu
 1               5                  10                  15

Glu Thr Ile Val Glu Ala Ile Phe Thr Glu
            20                  25
```

<210> SEQ ID NO 206
<211> LENGTH: 28
<212> TYPE: PRT
<213> ORGANISM: Arabidopsis thaliana

<400> SEQUENCE: 206

```
Gln Asp Glu Thr Cys Asp Thr Thr Thr Thr Asp His Gly Leu Asp Met
 1               5                  10                  15

Glu Glu Thr Met Val Glu Ala Ile Tyr Thr Pro Glu
            20                  25
```

<210> SEQ ID NO 207
<211> LENGTH: 28
<212> TYPE: PRT
<213> ORGANISM: Arabidopsis thaliana

<400> SEQUENCE: 207

```
Gln Asp Glu Met Cys His Met Thr Thr Asp Ala His Gly Leu Asp Met
 1               5                  10                  15

Glu Glu Thr Leu Val Glu Ala Ile Tyr Thr Pro Glu
            20                  25
```

<210> SEQ ID NO 208
<211> LENGTH: 27
<212> TYPE: PRT
<213> ORGANISM: Arabidopsis thaliana

<400> SEQUENCE: 208

```
Gln Asp Glu Met Cys Asp Ala Thr Thr Asp His Gly Phe Asp Met Glu
 1               5                  10                  15

Glu Thr Leu Val Glu Ala Ile Tyr Thr Ala Glu
            20                  25
```

<210> SEQ ID NO 209
<211> LENGTH: 49
<212> TYPE: PRT
<213> ORGANISM: Brassica napus

<400> SEQUENCE: 209

```
Gln Ser Glu Gly Phe Asn Met Ala Lys Glu Ser Thr Val Glu Ala Ala
 1               5                  10                  15

Val Val Thr Glu Glu Pro Ser Lys Gly Ser Tyr Met Asp Glu Glu Trp
            20                  25                  30
```

-continued

```
Met Leu Glu Met Pro Thr Leu Leu Ala Asp Met Ala Glu Gly Met Leu
        35                  40                  45

Leu


<210> SEQ ID NO 210
<211> LENGTH: 49
<212> TYPE: PRT
<213> ORGANISM: Brassica napus

<400> SEQUENCE: 210

Gln Ser Glu Gly Phe Asn Met Ala Lys Glu Ser Thr Val Glu Ala Ala
 1               5                  10                  15

Val Val Thr Glu Glu Pro Ser Lys Gly Ser Tyr Met Asp Glu Glu Trp
            20                  25                  30

Met Leu Glu Met Pro Thr Leu Leu Ala Asp Met Ala Glu Gly Met Leu
        35                  40                  45

Leu


<210> SEQ ID NO 211
<211> LENGTH: 49
<212> TYPE: PRT
<213> ORGANISM: Brassica rapa

<400> SEQUENCE: 211

Gln Ser Glu Gly Phe Asn Met Ala Lys Glu Ser Thr Val Glu Ala Ala
 1               5                  10                  15

Val Val Thr Glu Glu Pro Ser Lys Gly Ser Tyr Met Asp Glu Glu Trp
            20                  25                  30

Met Leu Glu Met Pro Thr Leu Leu Ala Asp Met Ala Glu Gly Met Leu
        35                  40                  45

Leu


<210> SEQ ID NO 212
<211> LENGTH: 49
<212> TYPE: PRT
<213> ORGANISM: Brassica napus

<400> SEQUENCE: 212

Gln Ser Glu Gly Phe Asn Met Ala Lys Glu Ser Thr Val Glu Ala Ala
 1               5                  10                  15

Val Val Thr Glu Glu Pro Ser Lys Gly Ser Tyr Met Asp Glu Glu Trp
            20                  25                  30

Met Leu Glu Met Pro Thr Leu Leu Ala Asp Met Ala Glu Gly Met Leu
        35                  40                  45

Leu


<210> SEQ ID NO 213
<211> LENGTH: 49
<212> TYPE: PRT
<213> ORGANISM: Brassica napus

<400> SEQUENCE: 213

Gln Ser Glu Gly Phe Asn Met Ala Lys Glu Ser Thr Val Glu Ala Ala
 1               5                  10                  15

Val Val Thr Glu Glu Pro Ser Lys Gly Ser Tyr Met Asp Glu Glu Trp
            20                  25                  30
```

-continued

```
Met Leu Glu Met Pro Thr Leu Leu Ala Asp Met Ala Glu Gly Met Leu
        35                  40                  45

Leu
```

<210> SEQ ID NO 214
<211> LENGTH: 49
<212> TYPE: PRT
<213> ORGANISM: Brassica napus

<400> SEQUENCE: 214

```
Gln Ser Glu Gly Phe Asn Met Ala Glu Glu Ser Thr Val Glu Ala Ala
 1               5                  10                  15

Val Val Thr Asp Glu Leu Ser Lys Gly Phe Tyr Met Asp Glu Glu Trp
            20                  25                  30

Thr Tyr Glu Met Pro Thr Leu Leu Ala Asp Met Ala Ala Gly Met Leu
        35                  40                  45

Leu
```

<210> SEQ ID NO 215
<211> LENGTH: 49
<212> TYPE: PRT
<213> ORGANISM: Brassica oleracea

<400> SEQUENCE: 215

```
Gln Ser Glu Gly Phe Asn Met Ala Glu Glu Ser Thr Val Glu Ala Ala
 1               5                  10                  15

Val Val Thr Asp Glu Leu Ser Lys Gly Phe Tyr Met Asp Glu Glu Trp
            20                  25                  30

Thr Tyr Glu Met Pro Thr Leu Leu Ala Asp Met Ala Ala Gly Met Leu
        35                  40                  45

Leu
```

<210> SEQ ID NO 216
<211> LENGTH: 49
<212> TYPE: PRT
<213> ORGANISM: Brassica napus

<400> SEQUENCE: 216

```
Gln Ser Glu Gly Phe Asn Met Ala Glu Glu Ser Thr Val Glu Ala Ala
 1               5                  10                  15

Val Val Thr Asp Glu Leu Ser Lys Gly Phe Tyr Met Asp Glu Glu Trp
            20                  25                  30

Thr Tyr Glu Met Pro Thr Leu Leu Ala Asp Met Ala Ala Gly Met Leu
        35                  40                  45

Leu
```

<210> SEQ ID NO 217
<211> LENGTH: 49
<212> TYPE: PRT
<213> ORGANISM: Brassica oleracea

<400> SEQUENCE: 217

```
Gln Ser Glu Gly Phe Asn Met Ala Lys Glu Ser Thr Ala Glu Ala Ala
 1               5                  10                  15

Val Val Thr Glu Glu Leu Ser Lys Gly Val Tyr Met Asp Glu Glu Trp
            20                  25                  30
```

-continued

```
Thr Tyr Glu Met Pro Thr Leu Leu Ala Asp Met Ala Ala Gly Met Leu
        35                  40                  45

Leu


<210> SEQ ID NO 218
<211> LENGTH: 48
<212> TYPE: PRT
<213> ORGANISM: Brassica rapa

<400> SEQUENCE: 218

Gln Arg Glu Gly Phe Tyr Met Thr Glu Glu Thr Arg Val Glu Gly Val
 1               5                  10                  15

Val Thr Glu Glu Gln Asn Asn Trp Phe Tyr Met Asp Glu Glu Trp Met
            20                  25                  30

Phe Gly Met Pro Thr Leu Leu Val Asp Met Ala Glu Gly Met Leu Ile
        35                  40                  45


<210> SEQ ID NO 219
<211> LENGTH: 48
<212> TYPE: PRT
<213> ORGANISM: Raphanus sativus

<400> SEQUENCE: 219

Gln Arg Glu Gly Phe Tyr Met Thr Glu Glu Thr Arg Val Glu Gly Val
 1               5                  10                  15

Val Thr Glu Glu Gln Asn Asn Trp Phe Tyr Met Asp Glu Glu Trp Met
            20                  25                  30

Phe Gly Met Pro Thr Leu Leu Val Asp Met Ala Glu Gly Met Leu Leu
        35                  40                  45


<210> SEQ ID NO 220
<211> LENGTH: 49
<212> TYPE: PRT
<213> ORGANISM: Brassica napus

<400> SEQUENCE: 220

Gln Arg Asp Gly Phe Tyr Met Ala Glu Glu Thr Thr Val Glu Gly Val
 1               5                  10                  15

Val Pro Glu Glu Gln Met Ser Lys Gly Phe Tyr Met Asp Glu Glu Trp
            20                  25                  30

Met Phe Gly Met Pro Thr Leu Leu Ala Asp Met Ala Ala Gly Met Leu
        35                  40                  45

Leu


<210> SEQ ID NO 221
<211> LENGTH: 49
<212> TYPE: PRT
<213> ORGANISM: Brassica oleracea

<400> SEQUENCE: 221

Gln Arg Asp Gly Phe Tyr Met Ala Glu Glu Thr Thr Val Glu Gly Val
 1               5                  10                  15

Val Pro Glu Glu Gln Met Ser Lys Gly Phe Tyr Met Asp Glu Glu Trp
            20                  25                  30

Met Phe Gly Met Pro Thr Leu Leu Ala Asp Met Ala Ala Gly Met Leu
        35                  40                  45

Leu
```

-continued

<210> SEQ ID NO 222
<211> LENGTH: 49
<212> TYPE: PRT
<213> ORGANISM: Brassica napus

<400> SEQUENCE: 222

```
Gln Arg Glu Gly Phe Tyr Met Ala Glu Glu Thr Thr Val Val Gly Val
 1               5                  10                  15

Val Pro Glu Glu Gln Met Ser Lys Gly Phe Tyr Met Asp Glu Glu Trp
            20                  25                  30

Met Phe Gly Met Pro Thr Leu Leu Ala Asp Met Ala Ala Gly Met Leu
        35                  40                  45

Leu
```

<210> SEQ ID NO 223
<211> LENGTH: 49
<212> TYPE: PRT
<213> ORGANISM: Brassica rapa

<400> SEQUENCE: 223

```
Gln Arg Glu Gly Phe Tyr Met Ala Glu Glu Thr Thr Val Glu Gly Ile
 1               5                  10                  15

Val Pro Glu Glu Gln Met Ser Lys Gly Phe Tyr Met Asp Glu Glu Trp
            20                  25                  30

Met Phe Gly Met Pro Thr Leu Leu Ala Asp Met Ala Ala Gly Met Leu
        35                  40                  45

Leu
```

<210> SEQ ID NO 224
<211> LENGTH: 49
<212> TYPE: PRT
<213> ORGANISM: Brassica rapa

<400> SEQUENCE: 224

```
Gln Arg Glu Gly Phe Tyr Met Ala Glu Glu Thr Thr Val Glu Gly Val
 1               5                  10                  15

Val Pro Glu Glu Gln Met Ser Lys Gly Phe Tyr Met Asp Glu Glu Trp
            20                  25                  30

Thr Phe Glu Met Pro Arg Leu Leu Ala Asp Met Ala Glu Gly Met Leu
        35                  40                  45

Leu
```

<210> SEQ ID NO 225
<211> LENGTH: 48
<212> TYPE: PRT
<213> ORGANISM: Brassica oleracea

<400> SEQUENCE: 225

```
Gln Arg Glu Gly Phe Tyr Leu Ala Glu Glu Thr Thr Val Glu Gly Val
 1               5                  10                  15

Val Thr Glu Glu Gln Ser Lys Gly Phe Tyr Met Asp Glu Glu Trp Thr
            20                  25                  30

Phe Gly Met Gln Ser Phe Leu Ala Asp Met Ala Glu Gly Met Leu Phe
        35                  40                  45
```

<210> SEQ ID NO 226
<211> LENGTH: 29
<212> TYPE: PRT
<213> ORGANISM: Brassica juncea -continued

<400> SEQUENCE: 226

```
Glu Ser Ser Glu Gly Phe Tyr Met Asp Glu Glu Phe Met Phe Gly Met
 1               5                  10                  15

Pro Thr Leu Trp Ala Ser Met Ala Glu Gly Met Leu Leu
            20                  25
```

<210> SEQ ID NO 227
<211> LENGTH: 29
<212> TYPE: PRT
<213> ORGANISM: Brassica juncea

<400> SEQUENCE: 227

```
Glu Ser Ser Glu Gly Phe Tyr Met Ala Glu Glu Phe Met Phe Gly Met
 1               5                  10                  15

Pro Thr Leu Trp Ala Ser Val Ala Glu Gly Met Leu Leu
            20                  25
```

<210> SEQ ID NO 228
<211> LENGTH: 30
<212> TYPE: PRT
<213> ORGANISM: Brassica napus

<400> SEQUENCE: 228

```
Glu Asn Asn Asp Gly Phe Tyr Met Asp Glu Glu Glu Ser Met Phe Gly
 1               5                  10                  15

Met Pro Ala Leu Leu Ala Ser Met Ala Glu Gly Met Leu Leu
            20                  25                  30
```

<210> SEQ ID NO 229
<211> LENGTH: 29
<212> TYPE: PRT
<213> ORGANISM: Raphanus sativus

<400> SEQUENCE: 229

```
Val Asn Asn Asp Glu Phe Tyr Met Asp Glu Glu Ser Met Phe Gly Met
 1               5                  10                  15

Pro Ser Leu Leu Ala Ser Met Ala Glu Gly Met Leu Leu
            20                  25
```

<210> SEQ ID NO 230
<211> LENGTH: 29
<212> TYPE: PRT
<213> ORGANISM: Arabidopsis thaliana

<400> SEQUENCE: 230

```
Gln Ser Glu Gly Ala Phe Tyr Met Asp Glu Glu Thr Met Phe Gly Met
 1               5                  10                  15

Pro Thr Leu Leu Asp Asn Met Ala Glu Gly Met Leu Leu
            20                  25
```

<210> SEQ ID NO 231
<211> LENGTH: 29
<212> TYPE: PRT
<213> ORGANISM: Arabidopsis thaliana

<400> SEQUENCE: 231

```
Gln Ser Gln Asp Ala Phe Tyr Met Asp Glu Glu Ala Met Leu Gly Met
 1               5                  10                  15

Ser Ser Leu Leu Asp Asn Met Ala Glu Gly Met Leu Leu
            20                  25
```

-continued

```
<210> SEQ ID NO 232
<211> LENGTH: 29
<212> TYPE: PRT
<213> ORGANISM: Arabidopsis thaliana

<400> SEQUENCE: 232

Gln Ser Glu Asn Ala Phe Tyr Met His Asp Glu Ala Met Phe Glu Met
 1               5                  10                  15

Pro Ser Leu Leu Ala Asn Met Ala Glu Gly Met Leu Leu
            20                  25


<210> SEQ ID NO 233
<211> LENGTH: 50
<212> TYPE: PRT
<213> ORGANISM: Brassica napus

<400> SEQUENCE: 233

Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Gln Asn Gly Leu Asn Met Glu Glu Thr Thr Ala Val Ala
        35                  40                  45

Ser Gln
    50


<210> SEQ ID NO 234
<211> LENGTH: 50
<212> TYPE: PRT
<213> ORGANISM: Brassica napus

<400> SEQUENCE: 234

Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Gln Asn Gly Leu Asn Met Glu Glu Thr Thr Ala Val Ala
        35                  40                  45

Ser Gln
    50


<210> SEQ ID NO 235
<211> LENGTH: 50
<212> TYPE: PRT
<213> ORGANISM: Brassica rapa

<400> SEQUENCE: 235

Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Val Thr Met Gln Asn Gly Leu Asn Met Glu Glu Met Thr Ala Val Ala
        35                  40                  45

Ser Gln
    50


<210> SEQ ID NO 236
<211> LENGTH: 50
<212> TYPE: PRT
<213> ORGANISM: Brassica napus
```

-continued

<400> SEQUENCE: 236

Ala Trp Arg Leu Arg Ile Pro Glu Thr Thr Cys His Lys Asp Ile Gln
1 5 10 15

Lys Ala Ala Ala Glu Ala Ala Leu Ala Phe Glu Ala Glu Lys Ser Asp
20 25 30

Val Thr Met Gln Asn Gly Gln Asn Met Glu Glu Thr Thr Ala Val Ala
35 40 45

Ser Gln
50

<210> SEQ ID NO 237
<211> LENGTH: 44
<212> TYPE: PRT
<213> ORGANISM: Brassica napus

<400> SEQUENCE: 237

Ala Ser Arg Leu Arg Ile Pro Glu Thr Thr Cys His Lys Asp Ile Gln
1 5 10 15

Lys Ala Ala Ala Glu Ala Ala Leu Ala Phe Glu Ala Glu Lys Ser Asp
20 25 30

Val Thr Met Glu Glu Thr Met Ala Val Ala Ser Gln
35 40

<210> SEQ ID NO 238
<211> LENGTH: 44
<212> TYPE: PRT
<213> ORGANISM: Brassica napus

<400> SEQUENCE: 238

Ala Ser Arg Leu Arg Ile Pro Glu Thr Thr Cys His Lys Asp Ile Gln
1 5 10 15

Lys Ala Ala Ala Glu Ala Ala Leu Ala Phe Glu Ala Glu Lys Ser Asp
20 25 30

Val Thr Met Glu Glu Thr Met Ala Val Ala Ser Gln
35 40

<210> SEQ ID NO 239
<211> LENGTH: 44
<212> TYPE: PRT
<213> ORGANISM: Brassica oleracea

<400> SEQUENCE: 239

Ala Trp Arg Leu Arg Ile Pro Glu Thr Thr Cys His Lys Asp Ile Gln
1 5 10 15

Lys Ala Ala Ala Glu Ala Ala Leu Ala Phe Glu Ala Glu Lys Ser Asp
20 25 30

Val Thr Met Glu Glu Thr Met Ala Val Ala Ser Gln
35 40

<210> SEQ ID NO 240
<211> LENGTH: 50
<212> TYPE: PRT
<213> ORGANISM: Brassica napus

<400> SEQUENCE: 240

Ala Trp Arg Leu Arg Ile Pro Glu Thr Thr Cys His Lys Asp Ile Gln
1 5 10 15

Lys Ala Ala Ala Glu Ala Ala Leu Ala Phe Glu Ala Glu Lys Ser Asp
20 25 30

-continued

```
Val Thr Met Gln Asn Gly Leu Asn Met Glu Glu Thr Thr Ala Val Ala
        35                  40                  45

Ser Gln
    50


<210> SEQ ID NO 241
<211> LENGTH: 50
<212> TYPE: PRT
<213> ORGANISM: Brassica oleracea

<400> SEQUENCE: 241

Ala Trp Arg Leu Arg Ile Pro Glu Thr Thr Cys His Lys Asp Ile Gln
 1               5                  10                  15

Lys Ala Ala Ala Glu Ala Ala Leu Ala Phe Glu Ala Glu Lys Ser Asp
            20                  25                  30

Ala Thr Met Gln Asn Gly Leu Asn Met Glu Glu Thr Thr Ala Ala Ala
        35                  40                  45

Ser Gln
    50


<210> SEQ ID NO 242
<211> LENGTH: 50
<212> TYPE: PRT
<213> ORGANISM: Brassica napus

<400> SEQUENCE: 242

Ala Glu Val Asn Asp Thr Thr Thr Glu His Gly Met Asn Met Glu Glu
 1               5                  10                  15

Ala Thr Ala Val Ala Ser Gln Ala Glu Val Asn Asp Thr Thr Thr Asp
            20                  25                  30

His Gly Val Asp Met Glu Glu Thr Met Val Glu Ala Val Phe Thr Gly
        35                  40                  45

Glu Gln
    50


<210> SEQ ID NO 243
<211> LENGTH: 50
<212> TYPE: PRT
<213> ORGANISM: Brassica napus

<400> SEQUENCE: 243

Ala Glu Val Asn Asp Thr Thr Thr Glu His Gly Met Asn Met Glu Glu
 1               5                  10                  15

Ala Thr Ala Val Ala Ser Gln Ala Glu Val Asn Asp Thr Thr Thr Asp
            20                  25                  30

His Gly Val Asp Met Glu Glu Thr Met Val Glu Ala Val Phe Thr Gly
        35                  40                  45

Glu Gln
    50


<210> SEQ ID NO 244
<211> LENGTH: 50
<212> TYPE: PRT
<213> ORGANISM: Brassica rapa

<400> SEQUENCE: 244

Ala Glu Val Asn Asp Thr Thr Thr Glu His Gly Met Asn Met Glu Glu
 1               5                  10                  15

Ala Thr Ala Val Ala Ser Gln Ala Glu Val Asn Asp Thr Thr Thr Asp
            20                  25                  30
```

-continued

His Gly Val Asp Met Glu Glu Thr Met Val Glu Ala Val Phe Thr Glu
35 40 45

Glu Gln
50

<210> SEQ ID NO 245
<211> LENGTH: 50
<212> TYPE: PRT
<213> ORGANISM: Brassica napus

<400> SEQUENCE: 245

Ala Glu Val Asn Asp Thr Thr Thr Glu His Gly Met Asn Met Glu Glu
1 5 10 15

Ala Thr Ala Val Ala Ser Gln Ala Glu Val Asn Asp Thr Thr Thr Asp
20 25 30

His Gly Val Asp Met Glu Glu Thr Met Val Glu Ala Val Phe Thr Gly
35 40 45

Glu Gln
50

<210> SEQ ID NO 246
<211> LENGTH: 50
<212> TYPE: PRT
<213> ORGANISM: Brassica napus

<400> SEQUENCE: 246

Ala Glu Val Asn Asp Thr Thr Thr Asp His Gly Met Asn Met Glu Glu
1 5 10 15

Ala Thr Ala Val Ala Ser Gln Ala Glu Val Asn Asp Thr Thr Thr Asp
20 25 30

His Gly Val Asp Met Glu Glu Thr Met Val Glu Ala Val Phe Thr Gly
35 40 45

Glu Gln
50

<210> SEQ ID NO 247
<211> LENGTH: 50
<212> TYPE: PRT
<213> ORGANISM: Brassica napus

<400> SEQUENCE: 247

Ala Glu Val Asn Asp Thr Thr Thr Asp His Gly Met Asn Met Glu Glu
1 5 10 15

Ala Thr Ala Val Ala Ser Gln Ala Glu Val Asn Asp Thr Thr Thr Asp
20 25 30

His Gly Val Asp Met Glu Glu Thr Met Val Glu Ala Val Phe Thr Glu
35 40 45

Glu Gln
50

<210> SEQ ID NO 248
<211> LENGTH: 50
<212> TYPE: PRT
<213> ORGANISM: Brassica oleracea

<400> SEQUENCE: 248

Ala Glu Val Asn Asp Thr Thr Thr Asp His Gly Met Asn Met Glu Glu
1 5 10 15

Ala Thr Ala Val Ala Ser Gln Ala Glu Val Asn Asp Thr Thr Thr Asp
20 25 30

-continued

```
His Gly Val Asp Met Glu Glu Thr Met Val Glu Ala Val Phe Thr Glu
        35                  40                  45

Glu Gln
    50


<210> SEQ ID NO 249
<211> LENGTH: 50
<212> TYPE: PRT
<213> ORGANISM: Brassica napus

<400> SEQUENCE: 249

Ala Glu Val Asn Asp Thr Thr Thr Glu His Gly Met Asn Met Glu Glu
 1               5                  10                  15

Ala Thr Ala Val Ala Ser Gln Ala Glu Val Asn Asp Thr Thr Thr Asp
            20                  25                  30

His Gly Val Asp Met Glu Glu Thr Met Val Glu Ala Val Phe Thr Glu
        35                  40                  45

Glu Gln
    50


<210> SEQ ID NO 250
<211> LENGTH: 50
<212> TYPE: PRT
<213> ORGANISM: Brassica oleracea

<400> SEQUENCE: 250

Thr Glu Val Ser Asp Thr Thr Thr Asp His Gly Met Asn Met Glu Glu
 1               5                  10                  15

Thr Thr Ala Val Ala Ser Gln Ala Glu Val Asn Asp Thr Thr Thr Asp
            20                  25                  30

His Gly Val Asp Met Glu Glu Thr Met Val Glu Ala Val Phe Thr Glu
        35                  40                  45

Glu Gln
    50


<210> SEQ ID NO 251
<211> LENGTH: 50
<212> TYPE: PRT
<213> ORGANISM: Brassica napus

<400> SEQUENCE: 251

Ser Glu Gly Phe Asn Met Ala Lys Glu Ser Thr Val Glu Ala Ala Val
 1               5                  10                  15

Val Thr Glu Glu Pro Ser Lys Gly Ser Tyr Met Asp Glu Glu Trp Met
            20                  25                  30

Leu Glu Met Pro Thr Leu Leu Ala Asp Met Ala Glu Gly Met Leu Leu
        35                  40                  45

Pro Pro
    50


<210> SEQ ID NO 252
<211> LENGTH: 50
<212> TYPE: PRT
<213> ORGANISM: Brassica rapa

<400> SEQUENCE: 252

Ser Glu Gly Phe Asn Met Ala Lys Glu Ser Thr Val Glu Ala Ala Val
 1               5                  10                  15

Val Thr Glu Glu Pro Ser Lys Gly Ser Tyr Met Asp Glu Glu Trp Met
            20                  25                  30
```

-continued

```
Leu Glu Met Pro Thr Leu Leu Ala Asp Met Ala Glu Gly Met Leu Leu
        35                  40                  45

Pro Pro
    50


<210> SEQ ID NO 253
<211> LENGTH: 50
<212> TYPE: PRT
<213> ORGANISM: Brassica napus

<400> SEQUENCE: 253

Ser Glu Gly Phe Asn Met Ala Lys Glu Ser Thr Val Glu Ala Ala Val
 1               5                  10                  15

Val Thr Glu Glu Pro Ser Lys Gly Ser Tyr Met Asp Glu Glu Trp Met
            20                  25                  30

Leu Glu Met Pro Thr Leu Leu Ala Asp Met Ala Glu Gly Met Leu Leu
        35                  40                  45

Pro Pro
    50


<210> SEQ ID NO 254
<211> LENGTH: 48
<212> TYPE: PRT
<213> ORGANISM: Brassica napus

<400> SEQUENCE: 254

Ser Glu Gly Phe Asn Met Ala Lys Glu Ser Thr Val Glu Ala Ala Val
 1               5                  10                  15

Val Thr Glu Glu Pro Ser Lys Gly Ser Tyr Met Asp Glu Glu Trp Met
            20                  25                  30

Leu Glu Met Pro Thr Leu Leu Ala Asp Met Ala Glu Gly Met Leu Leu
        35                  40                  45


<210> SEQ ID NO 255
<211> LENGTH: 50
<212> TYPE: PRT
<213> ORGANISM: Brassica napus

<400> SEQUENCE: 255

Ser Glu Gly Phe Asn Met Ala Lys Glu Ser Thr Val Glu Ala Ala Val
 1               5                  10                  15

Val Thr Glu Glu Pro Ser Lys Gly Ser Tyr Met Asp Glu Glu Trp Met
            20                  25                  30

Leu Glu Met Pro Thr Leu Leu Ala Asp Met Ala Glu Gly Met Leu Leu
        35                  40                  45

Pro Pro
    50


<210> SEQ ID NO 256
<211> LENGTH: 50
<212> TYPE: PRT
<213> ORGANISM: Brassica napus

<400> SEQUENCE: 256

Ser Glu Gly Phe Asn Met Ala Glu Glu Ser Thr Val Glu Ala Ala Val
 1               5                  10                  15

Val Thr Asp Glu Leu Ser Lys Gly Phe Tyr Met Asp Glu Glu Trp Thr
            20                  25                  30
```

-continued

```
Tyr Glu Met Pro Thr Leu Leu Ala Asp Met Ala Ala Gly Met Leu Leu
        35                  40                  45

Pro Pro
    50


<210> SEQ ID NO 257
<211> LENGTH: 50
<212> TYPE: PRT
<213> ORGANISM: Brassica oleracea

<400> SEQUENCE: 257

Ser Glu Gly Phe Asn Met Ala Glu Glu Ser Thr Val Glu Ala Ala Val
 1               5                  10                  15

Val Thr Asp Glu Leu Ser Lys Gly Phe Tyr Met Asp Glu Glu Trp Thr
            20                  25                  30

Tyr Glu Met Pro Thr Leu Leu Ala Asp Met Ala Ala Gly Met Leu Leu
        35                  40                  45

Pro Pro
    50


<210> SEQ ID NO 258
<211> LENGTH: 50
<212> TYPE: PRT
<213> ORGANISM: Brassica napus

<400> SEQUENCE: 258

Ser Glu Gly Phe Asn Met Ala Glu Glu Ser Thr Val Glu Ala Ala Val
 1               5                  10                  15

Val Thr Asp Glu Leu Ser Lys Gly Phe Tyr Met Asp Glu Glu Trp Thr
            20                  25                  30

Tyr Glu Met Pro Thr Leu Leu Ala Asp Met Ala Ala Gly Met Leu Leu
        35                  40                  45

Pro Pro
    50


<210> SEQ ID NO 259
<211> LENGTH: 50
<212> TYPE: PRT
<213> ORGANISM: Brassica oleracea

<400> SEQUENCE: 259

Ser Glu Gly Phe Asn Met Ala Lys Glu Ser Thr Ala Glu Ala Ala Val
 1               5                  10                  15

Val Thr Glu Glu Leu Ser Lys Gly Val Tyr Met Asp Glu Glu Trp Thr
            20                  25                  30

Tyr Glu Met Pro Thr Leu Leu Ala Asp Met Ala Ala Gly Met Leu Leu
        35                  40                  45

Pro Pro
    50
```